(12) United States Patent
Hermanson et al.

(10) Patent No.: US 10,730,857 B2
(45) Date of Patent: Aug. 4, 2020

(54) BENZOCYANINE COMPOUNDS

(71) Applicants: Pierce Biotechnology, Inc., Rockford, IL (US); Dyomics GmbH, Jena (DE)

(72) Inventors: Greg Hermanson, Loves Park, IL (US); Peter T. Czerney, Weimar (DE); Surbhi Desai, Rockford, IL (US); Matthias S. Wenzel, Jena (DE); Boguslawa Dworecki, Rockford, IL (US); Frank G. Lehmann, Jena (DE); Marie Christine Nlend, Rockford, IL (US)

(73) Assignees: Pierce Biotechnology, Inc., Rockford, IL (US); Dyomics GmbH, Jena (DE)

( * ) Notice: Subject to any disclaimer, the term of this patent is extended or adjusted under 35 U.S.C. 154(b) by 0 days.

(21) Appl. No.: 16/141,534

(22) Filed: Sep. 25, 2018

(65) Prior Publication Data

US 2019/0084964 A1 Mar. 21, 2019

Related U.S. Application Data

(62) Division of application No. 14/966,437, filed on Dec. 11, 2015, now Pat. No. 10,125,120, which is a division of application No. 13/571,858, filed on Aug. 10, 2012, now Pat. No. 9,249,307.

(60) Provisional application No. 61/607,737, filed on Mar. 7, 2012, provisional application No. 61/604,232, filed on Feb. 28, 2012, provisional application No. 61/524,167, filed on Aug. 16, 2011.

(51) Int. Cl.

| | |
|---|---|
| *C07D 403/06* | (2006.01) |
| *C07D 495/04* | (2006.01) |
| *G01N 33/53* | (2006.01) |
| *A61K 49/00* | (2006.01) |
| *C09B 23/08* | (2006.01) |
| *C07H 3/00* | (2006.01) |
| *C07H 21/00* | (2006.01) |
| *C07K 14/00* | (2006.01) |
| *C07K 14/475* | (2006.01) |
| *C07K 14/575* | (2006.01) |
| *C07K 16/00* | (2006.01) |

(52) U.S. Cl.
CPC ........ *C07D 403/06* (2013.01); *A61K 49/0034* (2013.01); *A61K 49/0058* (2013.01); *C07D 495/04* (2013.01); *C07H 3/00* (2013.01); *C07H 21/00* (2013.01); *C07K 14/00* (2013.01); *C07K 14/475* (2013.01); *C07K 14/575* (2013.01); *C07K 16/00* (2013.01); *C09B 23/083* (2013.01); *G01N 33/5308* (2013.01)

(58) Field of Classification Search
CPC ........ C07H 3/00; C07H 21/00; C07K 14/575; C07K 14/475; C07K 14/00; C07K 16/00; G01N 33/5308; C07D 403/06; C07D 495/04; A61K 49/0058; A61K 49/0034; C09B 23/083

See application file for complete search history.

(56) References Cited

U.S. PATENT DOCUMENTS

| | | | |
|---|---|---|---|
| 1,524,791 | A | 2/1925 | Konig |
| 4,839,265 | A | 6/1989 | Ohno et al. |
| 4,981,977 | A | 1/1991 | Southwick et al. |
| 5,268,486 | A | 12/1993 | Waggoner et al. |
| 5,486,616 | A | 1/1996 | Waggoner et al. |
| 5,556,959 | A | 9/1996 | Brush et al. |
| 5,569,587 | A | 10/1996 | Waggoner |
| 5,569,766 | A | 10/1996 | Waggoner et al. |
| 5,627,027 | A | 5/1997 | Waggoner |
| 5,846,737 | A | 12/1998 | Kang |
| 5,972,838 | A | 10/1999 | Pearce et al. |
| 5,986,086 | A | 11/1999 | Brush et al. |
| 6,048,982 | A | 4/2000 | Waggoner |
| 6,083,485 | A | 7/2000 | Licha et al. |
| 6,136,612 | A | 10/2000 | Della Ciana et al. |
| 6,225,050 | B1 | 5/2001 | Waggoner |
| 6,258,340 | B1 | 7/2001 | Licha et al. |
| 6,342,326 | B1 | 1/2002 | Milton |
| 6,534,041 | B1 | 3/2003 | Licha et al. |
| 6,641,093 | B2 | 11/2003 | Coudrais |
| 6,761,878 | B2 | 7/2004 | Achilefu et al. |
| 6,924,372 | B2 | 8/2005 | Czerney et al. |
| 6,939,532 | B2 | 9/2005 | Achilefu et al. |
| 6,974,873 | B2 | 12/2005 | Leung et al. |
| 6,977,305 | B2 | 12/2005 | Leung et al. |

(Continued)

FOREIGN PATENT DOCUMENTS

| | | |
|---|---|---|
| AU | 2006200511 | 2/2006 |
| DE | 4445065 A1 | 6/1996 |

(Continued)

OTHER PUBLICATIONS

Search Report issued by the German Patent Office regarding App #10 2006 029 454.8 dated Oct. 10, 2006 (with English language summary).

Search Report issued by the German Patent Office regarding App #10 2006 057 345.5 dated May 21, 2007 (with English language summary).

Alvarez-Maubecin, V. et al. Functional Coupling Between Neurons and Glia. The Journal of Neuroscience. Jun. 1, 2000, 20(11):4091-4098.

Bharaj, B.S. et al. Rapid sequencing of the p53 gene with a new automated DNA sequencer. Clinical Chemistry. 44:7 1397-1403 1998.

(Continued)

*Primary Examiner* — Shafiqul Haq
(74) *Attorney, Agent, or Firm* — McNeill Baur PLLC

(57) ABSTRACT

Compounds useful as labels with properties comparable to known fluorescent compounds. The compounds are conjugated to proteins and nucleic acids for biological imaging and analysis. Synthesis of the compounds, formation and use of the conjugated compounds, and specific non-limiting examples of each are provided.

6 Claims, 22 Drawing Sheets
(14 of 22 Drawing Sheet(s) Filed in Color)

(56) References Cited

U.S. PATENT DOCUMENTS

| | | |
|---|---|---|
| 7,172,907 B2 | 2/2007 | Chen et al. |
| 7,175,831 B2 | 2/2007 | Achilefu et al. |
| 7,566,790 B2 | 7/2009 | Leung et al. |
| 7,671,214 B2 | 3/2010 | Leung et al. |
| 7,745,640 B2 | 6/2010 | Czerney et al. |
| 7,750,163 B2 | 7/2010 | West et al. |
| 7,790,893 B2 | 9/2010 | Leung et al. |
| 7,820,824 B2 | 10/2010 | Leung et al. |
| 7,855,293 B2 | 12/2010 | Haalck et al. |
| 7,927,830 B2 | 4/2011 | Cheung et al. |
| 7,951,959 B2 | 5/2011 | Brush et al. |
| 8,431,111 B2 | 4/2013 | Nairne et al. |
| 8,889,884 B1 | 11/2014 | Hermanson et al. |
| 9,097,667 B2 | 8/2015 | Mao et al. |
| 9,249,307 B2 | 2/2016 | Hermanson et al. |
| 9,365,598 B2 | 6/2016 | Hermanson et al. |
| 9,676,787 B2 | 6/2017 | Hermanson et al. |
| 9,751,868 B2 * | 9/2017 | Hermanson ........ A61K 49/0058 |
| 9,791,450 B2 | 10/2017 | Mao et al. |
| 10,000,467 B2 | 6/2018 | Hermanson et al. |
| 10,053,447 B2 | 8/2018 | Hermanson et al. |
| 10,125,120 B2 | 11/2018 | Hermanson et al. |
| 2001/0055567 A1 | 12/2001 | Licha et al. |
| 2002/0064794 A1 | 5/2002 | Leung et al. |
| 2002/0077487 A1 | 6/2002 | Leung et al. |
| 2004/0166515 A1 | 8/2004 | Terpetschnig et al. |
| 2004/0241095 A1 | 12/2004 | Achilefu et al. |
| 2006/0004188 A1 | 1/2006 | Leung et al. |
| 2006/0099638 A1 | 5/2006 | Leung et al. |
| 2007/0128659 A1 | 6/2007 | Czerney et al. |
| 2007/0178512 A1 | 8/2007 | Leung et al. |
| 2007/0203343 A1 | 8/2007 | West et al. |
| 2008/0233050 A1 | 9/2008 | Achilefu et al. |
| 2009/0035809 A1 | 2/2009 | Leung et al. |
| 2009/0305410 A1 | 12/2009 | Mao et al. |
| 2010/0040547 A1 | 2/2010 | Frangioni |
| 2010/0196282 A1 | 8/2010 | Nairne |
| 2010/0215585 A1 | 8/2010 | Frangioni |
| 2010/0267937 A1 | 10/2010 | West et al. |
| 2010/0303732 A1 | 12/2010 | Bahner |
| 2011/0065876 A1 | 3/2011 | Licha et al. |
| 2011/0065896 A1 | 3/2011 | Licha et al. |
| 2011/0171678 A1 | 7/2011 | Leung et al. |
| 2011/0178397 A1 | 7/2011 | Bahner |
| 2012/0114563 A1 | 5/2012 | Carter et al. |
| 2012/0156140 A1 | 6/2012 | Hermanson et al. |
| 2013/0045488 A1 | 2/2013 | Hermanson et al. |
| 2013/0230465 A1 | 9/2013 | Hermanson et al. |
| 2013/0230466 A1 | 9/2013 | Hermanson et al. |
| 2014/0106349 A1 | 4/2014 | Mao et al. |
| 2014/0255312 A1 | 9/2014 | Hermanson et al. |
| 2015/0119281 A1 | 4/2015 | Hermanson et al. |
| 2015/0322078 A1 | 11/2015 | Hermanson et al. |
| 2016/0176852 A1 | 6/2016 | Hermanson et al. |
| 2016/0176853 A1 | 6/2016 | Hermanson et al. |
| 2018/0002340 A1 | 1/2018 | Hermanson et al. |
| 2018/0118723 A1 | 5/2018 | Hermanson et al. |
| 2018/0134689 A1 | 5/2018 | Hermanson et al. |
| 2018/0327387 A1 | 11/2018 | Hermanson et al. |

FOREIGN PATENT DOCUMENTS

| | | |
|---|---|---|
| DE | 19717904 A1 | 10/1998 |
| DE | 19926460 A1 | 12/1999 |
| DE | 10046215 A1 | 4/2002 |
| EP | 1152008 | 7/2001 |
| EP | 1181940 | 2/2002 |
| EP | 1322710 | 7/2003 |
| EP | 1770129 | 4/2007 |
| EP | 1792949 | 6/2007 |
| EP | 1801165 | 6/2007 |
| EP | 2325263 | 7/2010 |
| GB | 434875 | 9/1935 |
| JP | 03217837 | 9/1991 |
| JP | 5-313304 | 11/1993 |
| WO | 96/17628 | 6/1996 |
| WO | 98/48838 | 11/1998 |
| WO | 00/075237 | 12/2000 |
| WO | 02/26891 | 4/2002 |
| WO | 02/32466 A1 | 4/2002 |
| WO | 2004/065491 A1 | 8/2004 |
| WO | 05/044923 | 5/2005 |
| WO | 05/103162 | 11/2005 |
| WO | 06/020947 | 2/2006 |
| WO | 2009/016180 | 2/2009 |
| WO | 2009/016181 | 2/2009 |
| WO | 09/078970 | 6/2009 |
| WO | 2009/078970 A1 | 6/2009 |
| WO | 10/091126 | 8/2010 |
| WO | 2010/106169 | 9/2010 |
| WO | 2012/088007 A1 | 6/2012 |
| WO | 2012/129128 A1 | 9/2012 |

OTHER PUBLICATIONS

Biotium. Product brochure titled CF™ Dyes The next-generation dyes for protein labeling. Apr. 6, 2009.

Burns, M.A. et al. An Integrated Nanoliter DNA Analysis Device. Science. vol. 282, pp. 484-487, Oct. 16, 1998.

DeRisi, J.L. et al. Exploring the Metabolic and Genetic Control of Gene Expression on a Genomic Scale. Science. vol. 278, pp. 680-686, Oct. 24, 1997.

Fradelizi, J. et al. Quantitative Measurement of Proteins by Western Blotting with Cy5™-Coupled Secondary Antibodies. BioTechniques. 26:484-494 Mar. 1999.

Gragg, J. L. Synthesis of Near-Infrared Heptamethine Cyanine Dyes. Chemistry Theses. Paper 28 (2010). http://digitalarchive.gsu.edu/chemistry_theses/28.

MacBeath, G. and S.L. Schreiber. Printing Proteins as Microarrays for High-Throughput Function Determination. Science. vol. 289, pp. 1760-1763, Sep. 8, 2000.

Manders, E.M.M. et al. Direct Imaging of DNA in Living Cells Reveals the Dynamics of Chromosome Formation. The Journal of Cell Biology. vol. 144, No. 5, Mar. 8, 1999 813-821.

Mank, A.J.G. et al., Visible Diode Laser-Induced Fluorescence Detection in Liquid Chromatography after Precolumn Derivatization of Amines. Anal. Chem. vol. 67, pp. 1742-1748, 1995.

Mujumdar, R.B. et al. Cyanine Dye Labeling Reagents: Sulfoindocyanine Succinimidyl Esters. Bioconjug Chem. vol. 4, No. 2, pp. 105-111, Mar./Apr. 1993.

Patonay, G., et al. Noncovalent Labeling of Biomolecules with Red and Near-Infrared Dyes. Molecules. 9, 40-49, 2004.

Pharmacia Biotech. Table of Contents p. 294 and p. 295 of the Pharmacia Biotech Catalogue. 1994.

Roman, B.L. et al. Non-Radioisotopic AFLP Method Using PCR Primers Fluorescently Labeled with Cy™ 5. BioTechniques. vol. 26, No. 2, pp. 236-238, Feb. 1999.

Schena, M. et al. Parallel human genome analysis: Microarray-based expression monitoring of 1000 genes. Proc. Natl. Acad. Sci. USA. vol. 93, pp. 10614-10619, Oct. 1996.

Shao, F. et al. Monofunctional Carbocyanine Dyes for Bio- and Bioorthogonal Conjugation. Bioconjugate Chemistry. 19(12): 2487-2491, Dec. 2008.

Voss, H. et al. Automated Cycle Sequencing with Taquenase™: Protocols for Internal Labeling, Dye Primer and "Doublex" Simultaneous Sequencing. BioTechniques. vol. 23, No. 2, pp. 312-318, Aug. 1997.

Wilchek, M. and Miron, T. Activation of Sepharose with N,N'-disuccinimidyl carbonate. Applied Biochemistry and Biotechnology, vol. 11, pp. 191-193 (1985).

International Search Report of the World Intellectual Property Bureau for PCT/US2011/065975, dated Mar. 15, 2012. (12 pages).

Written Opinion of the World Intellectual Property Bureau for PCT/US2011/065975, dated Mar. 15, 2012, 7 pages.

United Kingdom Search and Examination Report GB1214580.1, dated Nov. 22, 2012, 4 pages.

International Search Report and Written Opinion PCT/US2013/028252, issued by the European Patent Office, and dated Apr. 25, 2013 (12 pages).

(56) References Cited

OTHER PUBLICATIONS

International Search Report and Written Opinion for PCT/US2011/065975, dated Mar. 15, 2012 (12 pages).
Examination Report, Great Britain Application No. 1214580.1, dated May 31, 2013 (4 pages).
Hermanson, Bioconjugate Techniques, 2nd Ed., London, Elsevier Inc. 2008, pp. 464-474; 690-697.
Strekowski (ed.), Heterocyclic Polymethine Dyes: Synthesis, Properties and Applications, (2008) Springer-Verlag, Berlin Heidelberg, pp. 1-241.
International Preliminary Report on Patentability, PCT/US/2011/065975, dated Jul. 4, 2013 (8 pages).
Licha et al. Synthesis and Characterization of Cyanine Dye-Poly(ethylene Glycol) Conjugates as Contrast Agents for In Vivo Fluorescence Imaging. SPIE 3196 (1998) 98-102.
Riefke et al. Tumor Detection with Cyanine Dye-Poly(ethylene Glycol) Conjugates as Contrast Agents for Near-Infrared Imaging. SPIE 3196 (1998) 103-110.
Second Office Action with English translation issued in Chinese Patent Application No. 201380005497.X (dated Apr. 28, 2016, 21 pages).
Extended European Search Report and Written Opinion issued in European Patent Application No. 16169172.0 (dated Jul. 14, 2016, 7 pages).
Extended European Search Report, European Patent Application No. 15198169.3 (dated Mar. 29, 2016, 8 pages).
Rejection Decision with English translation issued in Chinese Patent Application No. 201380005497.X (dated Nov. 2, 2016, 11 pages).
Knop et al., "Poly(ethylene glycol) in Drug Delivery: Pros and Cons as Well as Potential Alternatives," Agnew. Chem. Int. Ed, 2010, 49:6288-6308.
File History of U.S. Appl. No. 13/571,858, filed Aug. 10, 2012.
File History of U.S. Appl. No. 14/966,437, filed Dec. 11, 2015.

\* cited by examiner

679 Compound 1
▲ 7.5X molar excess
■ 15X molar excess
▲ 22.5 molar excess

Company A Compound
✕ 7.5X molar excess
✱ 15X molar excess
● 22.5X molar excess ▲ 679 Compound 1/1
■ Company A Compound
■ V08-15173

FIG. 11

| Signal/Background | @ 125ng/well |
|---|---|
| V08-15173-2.5X | 2.2 |
| V08-15173-5X | 2.1 |
| V08-15173-10X | 2.4 |
| V08-15173-15X | 2.0 |
| COMPANY A-680-2.5X | 2.8 |
| COMPANY A-5X | 2.8 |
| COMPANY A-7.5X | 2.3 |
| COMPANY A-15X | 2.4 |
| 679 Compound 1/1-2.5X | 1.2 |
| 679 Compound 1/1-5X | 1.9 |
| 679 Compound 1/1-10X | 1.8 |
| 679 Compound 1/1-15X | 3.9 |

FIG. 13

| Signal/ Background | @ 125ng/well |
|---|---|
| V08-15173-5X | 2.1 |
| V08-15173-15X | 1.8 |
| V08-15173-25X | 2.2 |
| COMPANY A-5X | 1.9 |
| COMPANY A-15X | 1.8 |
| COMPANY A-25X | 1.9 |
| V10-04152-5X | 1.4 |
| V10-04152-15X | 1.3 |
| V10-04152-25X | 1.3 |
| 679 Compound 1/1-5X | 1.6 |
| 679 Compound 1/1-15X | 1.8 |
| 679 Compound 1/1-25X | 1.7 |

2X 3X 4X 1  2

1 2

BENZOCYANINE COMPOUNDS

This application claims priority to U.S. Ser. No. 14/966,437, filed Dec. 11, 2015, which claims priority to U.S. Ser. No. 13/571,858 filed Aug. 10, 2012, now U.S. Pat. No. 9,249,307, which claims priority to U.S. Ser. Nos. 61/524,167 filed Aug. 16, 2011; 61/604,232 filed Feb. 28, 2012; and 61/607,737 filed Mar. 7, 2012, each of which is expressly incorporated by reference herein in its entirety.

Compounds useful as labels with properties comparable to known fluorescent compounds are disclosed. The compounds can be conjugated to proteins and nucleic acids for biological imaging and analysis. Synthesis of the compounds, formation and use of the conjugated compounds, and specific non-limiting examples of each are disclosed.

Compounds that react with biomolecules (e.g., antigens, antibodies, DNA-segments with the corresponding complimentary species for measuring enzyme kinetics, receptor-ligand interactions, nucleic acid hybridization kinetics in vitro as well as in vivo, etc.), termed labels or dyes, are useful for, e.g., pharmacological characterization of receptors and drugs, binding data, etc. Compounds such as xanthylium salts (U.S. Pat. No. 5,846,737) and/or cyanines (U.S. Pat. No. 5,627,027) are used for such applications, but aggregate and form dimers, especially in aqueous solution, due to planarity of their t-system. Compounds that have insufficient hydrophilicity undergo non-specific interactions with various surfaces, resulting in problems when attempting to purify the corresponding conjugate, and an unsatisfactory signal to noise ratio.

Efforts are directed to reducing undesirable properties by introducing substituents that increase the hydrophilicity of the compounds. For example, sulfonic acid function substituents have been introduced into the cyanine chromophore. U.S. Pat. No. 6,083,485 (Licha) and U.S. Pat. Nos. 6,977,305 and 6,974,873 (Molecular Probes) disclose cyanine compounds having one of the common methyl groups in the 3-position of the terminal indole heterocycle substituted by an ω-carboxyalkyl function, and in which the previously present (e.g. in Cy3 or Cy5) N-alkyl or N-ω-carboxyalkyl functions are replaced by N-ω-alkyl sulfonic acid functions. WO 05/044923 discloses cyanine compounds having the common methyl substituent in the 3-position of the terminal indole heterocycle substituted by a N-ω-alkyl sulfonic acid function. In these publications, cyanine compounds having more than two sulfonic acid function substituents exhibited higher solubility and correspondingly a lower tendency to dimer formation, in comparison to cyanine compounds (Cy3, Cy5) described in U.S. Pat. No. 5,627,027.

The disclosed benzocyanine compounds are useful as labels in optical, e.g., fluorescence optical, determination and detection methods. The compounds have high hydrophilicity, high molar absorbance, high photo-stability, and high storage stability. These compounds were excited by monochromatic (e.g., lasers, laser diodes) or polychromatic (e.g., white light sources) light in the ultraviolet (UV), visible, and near infrared (NIR) spectral region to generate emission of fluorescence light.

Typical application methods are based on the reaction of the compounds with biomolecules, e.g., proteins (e.g., antigens, antibodies, etc.), DNA and/or RNA segments, etc. with the corresponding complimentary species. Thus, among other embodiments, the compounds are used to measure enzyme kinetics, receptor-ligand interactions, and nucleic acid hybridization kinetics in vitro and/or in vivo. The compounds are used for the pharmacological characterization of receptors and/or drugs. Applications include, but are not limited to, uses in medicine, pharmacy, biological sciences, materials sciences, environmental control, detection of organic and inorganic micro samples occurring in nature, etc.

The following nomenclature is used to describe the embodiments of the compounds having either a single PEG or multiple PEGs:
The following nomenclature is used for compounds having one ethylene glycol or one (poly)ethylene glycol, which is always at the indole N on the left side of the cyanine: (the first compound is explained in detail, and all other compounds follow this same nomenclature format):
579 Compound 1 ((ethylene glycol) (e.g., is a 579 compound, 1 is the length of the ethylene glycol))
579 Compound 2 (diethylene glycol)
579 Compound 3 (polyethylene glycol (3))
579 Compound 4 (polyethylene glycol (4))
579 Compound 5 (polyethylene glycol (5))
579 Compound 6 (polyethylene glycol (6))
679 Compound 1 (ethylene glycol)
679 Compound 2 (diethylene glycol)
679 Compound 3 (polyethylene glycol (3))
679 Compound 4 (polyethylene glycol (4))
679 Compound 5 (polyethylene glycol (5))
679 Compound 6 (polyethylene glycol (6))
779 Compound 1 (ethylene glycol)
779 Compound 2 (diethylene glycol)
779 Compound 3 (polyethylene glycol (3))
779 Compound 4 (polyethylene glycol (4))
779 Compound 5 (polyethylene glycol (5))
779 Compound 6 (polyethylene glycol (6))
The following nomenclature is used for compounds having more than one ethylene glycol or more than one (poly)ethylene glycol; i.e., one is always at the indole N on the left side of the cyanine, and at least 1 more (2 total) at a site(s) other than the indole N on the left side of the cyanine (the first compound is explained in detail, and all other compounds follow this same nomenclature format):
579 Compound 1/X (e.g., compound 1 is the length of the PEG at the left portion on the cyanine; X is the total number of PEGs on the entire compound).
579 Compound 2/X
579 Compound 3/X
579 Compound 4/X
579 Compound 5/X
579 Compound 6/X
679 Compound 1/X
679 Compound 2/X
679 Compound 3/X
679 Compound 4/X
679 Compound 5/X
679 Compound 6/X
779 Compound 1/X
779 Compound 2/X
779 Compound 3/X
779 Compound 4/X
779 Compound 5/X
779 Compound 6/X
Thus, 579, 679, and 779 compounds comprise a polymethine chain of 3 C, 5 C, and 7 C atoms, respectively, the first 1-6 number refers to the length of a PEG group on an indole N position, e.g., 1 is ethylene glycol ($PEG_1$), 2 is diethylene glycol ($PEG_2$), 3 is polyethylene glycol (3) ($PEG_3$), 4 is polyethylene glycol (4) ($PEG_4$), 5 is polyethylene glycol (5) ($PEG_5$), and 6 is polyethylene glycol (6) ($PEG_6$), and X refers to the number of PEG groups on the compound. For example, in one embodiment, 679 Compound 4/4 means a PEG$_4$ on an indole N and a total of four PEG groups on the compound.

In one embodiment, the benzocyanine compounds have, in an N-position of one heterocycle, an ethylene glycol group or an ethylene glycol polymer (i.e., poly(ethylene) glycol, collectively abbreviated as PEG), and the other heterocycle has, in an N-position, a function for conjugating the compound to a biomolecule. In one embodiment, the benzocyanine compound has, in any position of the compound, at least one sulfo (SO$_3^-$) and/or sulfoalkyl group. In one embodiment, the benzocyanine compound has, in any position of the compound, a sulfonamide and/or carboxamide group comprising an ethylene glycol group or an ethylene glycol polymer (i.e., poly(ethylene) glycol, collectively abbreviated as PEG), either directly or indirectly attached to the compound. Indirect attachment indicates use of a linker, direct attachment indicates lack of such a linker. A linker can be any moiety.

In one embodiment, the benzocyanine compounds have, in an N-position of one heterocycle, an ethylene glycol group or an ethylene glycol polymer (i.e., poly(ethylene) glycol, collectively abbreviated as PEG), and the other heterocycle has, in a N-position, an ethylene glycol group or an ethylene glycol polymer (i.e., poly(ethylene) glycol, collectively abbreviated as PEG) and a function for conjugating the compound to a biomolecule. In one embodiment, the benzocyanine compounds have an ethylene glycol group or an ethylene glycol polymer (i.e., poly(ethylene) glycol, collectively abbreviated as PEG) in another position of the benzocyanine compound. In one embodiment, the benzocyanine compound has, in any position of the compound, at least one sulfo and/or sulfoalkyl group. In one embodiment, the benzocyanine compound has, in any position of the compound, a sulfonamide and/or carboxamide group comprising an ethylene glycol group or an ethylene glycol polymer (i.e., poly(ethylene) glycol, collectively abbreviated as PEG), either directly or indirectly attached to the compound.

In one embodiment, the compound is general formula Ia

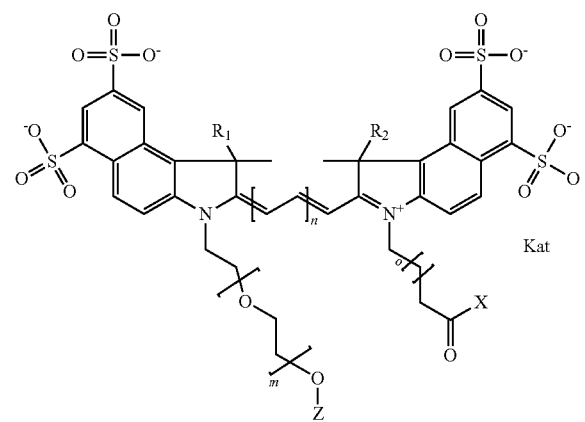

or general formula Ib

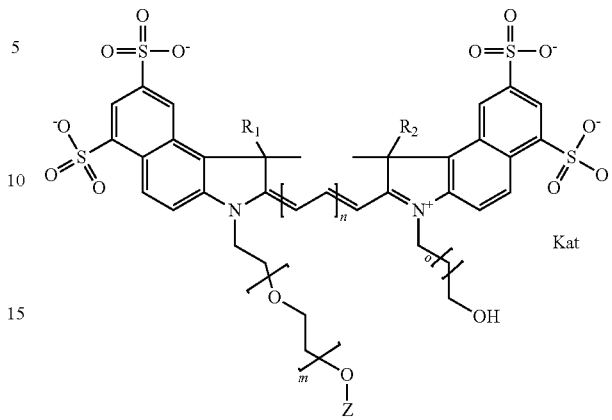

where each of $R^1$ and $R^2$ is the same or different and is independently selected from the group consisting of an aliphatic, heteroaliphatic, sulfoalkyl group, heteroaliphatic with terminal SO$_3$, a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, a sulfonamide group -L-SO$_2$NH—P—Z, and a carboxamide group -L-CONH—P—Z, and Z is selected from H, a CH$_3$, a CH$_3$ group, an alkyl group, a heteroalkyl group, or —CO—NHS; X is selected from the group consisting of —OH, —SH, —NH$_2$, —NH—NH$_2$, —F, —Cl, —Br, I, —NHS hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH$_2$—, imidazole, azide, —NR-L-O—NH$_2$, and —NR-L-O—CO—NHS, where R is —H or an aliphatic or heteroaliphatic group, and L is selected from the group consisting of a divalent linear (—(CH$_2$)$_t$—, t=0 to 15), crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive. In one embodiment, at least one of $R^1$ and $R^2$ contains a PEG group.

In one embodiment, the PEG group P is selected from the group consisting of —C—C—O—C (ethylene glycol with terminal methyl), —C—C—O—C—C—O—C (diethylene glycol with terminal methyl), —C—C—O—C—C—O—C—C—O—C(polyethylene glycol (3) with terminal methyl), —C—C—O—C—C—O—C—C—O—C—C—O—C (polyethylene glycol (4) with terminal methyl), —C—C—O—C—C—O—C—C—O—C—C—O—C—C—O—C(polyethylene glycol (5) with terminal methyl), and C—C—O—C—C—O—C—C—O—C—C—O—C—C—O—C—C—O—C(polyethylene glycol (6) with terminal methyl). In one embodiment, the PEG group P may be either uncapped, e.g., lack a terminal methyl, or may be capped with an atom or group other than a methyl. In one embodiment, the PEG group P terminates with a Z group, where Z is selected from H, CH$_3$, a CH$_3$ group, an alkyl group, or a heteroalkyl group.

In one embodiment, the compound is general formula Ia or general formula Ib, collectively referred to as general formula I, where R1 is methyl and R2 is sulfoalkyl; X is —OH, —NHS, —O-TFP, or —NR-L-maleimide; m is 0; o is 3; and n is 1. In one embodiment, the compound is general formula I, where R1 is methyl and R2 is sulfoalkyl; X is —OH, —NHS, —O-TFP, or —NR-L-maleimide; m is 1; o is 3; and n is 1. In one embodiment, the compound is general formula I, where R1 is methyl and R2 is sulfoalkyl; X is —OH, —NHS, —O-TFP, or —NR-L-maleimide; m is 2; o is 3; and n is 1. In one embodiment, the compound is general formula I, where R1 is methyl and R2 is sulfoalkyl; X is —OH, —NHS, —O-TFP, or —NR-L-maleimide; m is 3; o is 3; and n is 1. In one embodiment, the compound is general formula I, where R1 is methyl and R2 is sulfoalkyl; X is —OH, —NHS, —O-TFP, or —NR-L-maleimide; m is 4; o is 3; and n is 1. In one embodiment, the compound is general formula I, where R1 is methyl and R2 is sulfoalkyl; X is —OH, —NHS, —O-TFP, or —NR-L-maleimide; m is 5; o is 3; and n is 1.

In one embodiment, the compound is general formula I, where R1 is methyl and R2 is sulfoalkyl; X is —OH, —NHS, —O-TFP, or —NR-L-maleimide; m is 0; o is 3; and n is 2. In one embodiment, the compound is general formula I, where R1 is methyl and R2 is sulfoalkyl; X is —OH, —NHS, —O-TFP, or —NR-L-maleimide; m is 1; o is 3; and n is 2. In one embodiment, the compound is general formula I, where R1 is methyl and R2 is sulfoalkyl; X is —OH, —NHS, —O-TFP, or —NR-L-maleimide; m is 2; o is 3; and n is 2. In one embodiment, the compound is general formula I, where R1 is methyl and R2 is sulfoalkyl; X is —OH, —NHS, —O-TFP, or —NR-L-maleimide; m is 3; o is 3; and n is 2. In one embodiment, the compound is general formula I, where R1 is methyl and R2 is sulfoalkyl; X is —OH, —NHS, —O-TFP, or —NR-L-maleimide; m is 4; o is 3; and n is 2. In one embodiment, the compound is general formula I, where R1 is methyl and R2 is sulfoalkyl; X is —OH, —NHS, —O-TFP, or —NR-L-maleimide; m is 5; o is 3; and n is 2.

In one embodiment, the compound is general formula I, where R1 is methyl and R2 is sulfoalkyl; X is —OH, —NHS, —O-TFP, or —NR-L-maleimide; m is 0; o is 3; and n is 3. In one embodiment, the compound is general formula I, where R1 is methyl and R2 is sulfoalkyl; X is —OH, —NHS, —O-TFP, or —NR-L-maleimide; m is 1; o is 3; and n is 3. In one embodiment, the compound is general formula I, where R1 is methyl and R2 is sulfoalkyl; X is —OH, —NHS, —O-TFP, or —NR-L-maleimide; m is 2; o is 3; and n is 3. In one embodiment, the compound is general formula I, where R1 is methyl and R2 is sulfoalkyl; X is —OH, —NHS, —O-TFP, or —NR-L-maleimide; m is 3; o is 3; and n is 3. In one embodiment, the compound is general formula I, where R1 is methyl and R2 is sulfoalkyl; X is —OH, —NHS, —O-TFP, or —NR-L-maleimide; m is 4; o is 3; and n is 3. In one embodiment, the compound is general formula I, where R1 is methyl and R2 is sulfoalkyl; X is —OH, —NHS, —O-TFP, or —NR-L-maleimide; m is 5; o is 3; and n is 3.

In one embodiment, the compound is general formula I, where R1 is sulfoalkyl and R2 is a PEG group; X is —OH, —NHS, —O-TFP, or —NR-L-maleimide; m is 0; o is 3; and n is 1. In one embodiment, the compound is general formula I, where R1 is sulfoalkyl and R2 is a PEG group; X is —OH, —NHS, —O-TFP, or —NR-L-maleimide; m is 1; o is 3; and n is 1. In one embodiment, the compound is general formula I, where R1 is sulfoalkyl and R2 is a PEG group; X is —OH, —NHS, —O-TFP, or —NR-L-maleimide; m is 2; o is 3; and n is 1. In one embodiment, the compound is general formula I, where R1 is sulfoalkyl and R2 is a PEG group; X is —OH, —NHS, —O-TFP, or —NR-L-maleimide; m is 3; o is 3; and n is 1. In one embodiment, the compound is general formula I, where R1 is sulfoalkyl and R2 is a PEG group; X is —OH, —NHS, —O-TFP, or —NR-L-maleimide; m is 4; o is 3; and n is 1. In one embodiment, the compound is general formula I, where R1 is sulfoalkyl and R2 is a PEG group; X is —OH, —NHS, —O-TFP, or —NR-L-maleimide; m is 5; o is 3; and n is 1.

In one embodiment, the compound is general formula I, where R1 is sulfoalkyl and R2 is a PEG group; X is —OH, —NHS, —O-TFP, or —NR-L-maleimide; m is 0; o is 3; and n is 2. In one embodiment, the compound is general formula I, where R1 is sulfoalkyl and R2 is a PEG group; X is —OH, —NHS, —O-TFP, or —NR-L-maleimide; m is 1; o is 3; and n is 2. In one embodiment, the compound is general formula I, where R1 is sulfoalkyl and R2 is a PEG group; X is —OH, —NHS, —O-TFP, or —NR-L-maleimide; m is 2; o is 3; and n is 2. In one embodiment, the compound is general formula I, where R1 is sulfoalkyl and R2 is a PEG group; X is —OH, —NHS, —O-TFP, or —NR-L-maleimide; m is 3; o is 3; and n is 2. In one embodiment, the compound is general formula I, where R1 is sulfoalkyl and R2 is a PEG group; X is —OH, —NHS, —O-TFP, or —NR-L-maleimide; m is 4; o is 3; and n is 2. In one embodiment, the compound is general formula I, where R1 is sulfoalkyl and R2 is a PEG group; X is —OH, —NHS, —O-TFP, or —NR-L-maleimide; m is 5; o is 3; and n is 2.

In one embodiment, the compound is general formula I, where R1 is sulfoalkyl and R2 is a PEG group; X is —OH, —NHS, —O-TFP, or —NR-L-maleimide; m is 0; o is 3; and n is 3. In one embodiment, the compound is general formula I, where R1 is sulfoalkyl and R2 is a PEG group; X is —OH, —NHS, —O-TFP, or —NR-L-maleimide; m is 1; o is 3; and n is 3. In one embodiment, the compound is general formula I, where R1 is sulfoalkyl and R2 is a PEG group; X is —OH, —NHS, —O-TFP, or —NR-L-maleimide; m is 2; o is 3; and n is 3. In one embodiment, the compound is general formula I, where R1 is sulfoalkyl and R2 is a PEG group; X is —OH, —NHS, —O-TFP, or —NR-L-maleimide; m is 3; o is 3; and n is 3. In one embodiment, the compound is general formula I, where R1 is sulfoalkyl and R2 is a PEG group; X is —OH, —NHS, —O-TFP, or —NR-L-maleimide; m is 4; o is 3; and n is 3. In one embodiment, the compound is general formula I, where R1 is sulfoalkyl and R2 is a PEG group; X is —OH, —NHS, —O-TFP, or —NR-L-maleimide; m is 5; o is 3; and n is 3.

In one embodiment, the compound is general formula I, where R1 is methyl and R2 is a PEG group; X is —OH, —NHS, —O-TFP, or —NR-L-maleimide; m is 0; o is 3; and n is 1. In one embodiment, the compound is general formula I, where R1 is methyl and R2 is a PEG group; X is —OH, —NHS, —O-TFP, or —NR-L-maleimide; m is 1; o is 3; and n is 1. In one embodiment, the compound is general formula I, where R1 is methyl and R2 is a PEG group; X is —OH, —NHS, —O-TFP, or —NR-L-maleimide; m is 2; o is 3; and n is 1. In one embodiment, the compound is general formula I, where R1 is methyl and R2 is a PEG group; X is —OH, —NHS, —O-TFP, or —NR-L-maleimide; m is 3; o is 3; and n is 1. In one embodiment, the compound is general formula I, where R1 is methyl and R2 is a PEG group; X is —OH, —NHS, —O-TFP, or —NR-L-maleimide; m is 4; o is 3; and n is 1. In one embodiment, the compound is general formula I, where R1 is methyl and R2 is a PEG group; X is —OH, —NHS, —O-TFP, or —NR-L-maleimide; m is 5; o is 3; and n is 1.

In one embodiment, the compound is general formula I, where R1 is methyl and R2 is a PEG group; X is —OH, —NHS, —O-TFP, or —NR-L-maleimide; m is 0; o is 3; and n is 2. In one embodiment, the compound is general formula I, where R1 is methyl and R2 is a PEG group; X is —OH, —NHS, —O-TFP, or —NR-L-maleimide; m is 1; o is 3; and n is 2. In one embodiment, the compound is general formula I, where R1 is methyl and R2 is a PEG group; X is —OH, —NHS, —O-TFP, or —NR-L-maleimide; m is 2; o is 3; and n is 2. In one embodiment, the compound is general formula I, where R1 is methyl and R2 is a PEG group; X is —OH, —NHS, —O-TFP, or —NR-L-maleimide; m is 3; o is 3; and n is 2. In one embodiment, the compound is general formula I, where R1 is methyl and R2 is a PEG group; X is —OH, —NHS, —O-TFP, or —NR-L-maleimide; m is 4; o is 3; and n is 2. In one embodiment, the compound is general formula I, where R1 is methyl and R2 is a PEG group; X is —OH, —NHS, —O-TFP, or —NR-L-maleimide; m is 5; o is 3; and n is 2.

In one embodiment, the compound is general formula I, where R1 is methyl and R2 is a PEG group; X is —OH, —NHS, —O-TFP, or —NR-L-maleimide; m is 0; o is 3; and n is 3. In one embodiment, the compound is general formula I, where R1 is methyl and R2 is a PEG group; X is —OH, —NHS, —O-TFP, or —NR-L-maleimide; m is 1; o is 3; and n is 3. In one embodiment, the compound is general formula I, where R1 is methyl and R2 is a PEG group; X is —OH, —NHS, —O-TFP, or —NR-L-maleimide; m is 2; o is 3; and n is 3. In one embodiment, the compound is general formula I, where R1 is methyl and R2 is a PEG group; X is —OH, —NHS, —O-TFP, or —NR-L-maleimide; m is 3; o is 3; and n is 3. In one embodiment, the compound is general formula I, where R1 is methyl and R2 is a PEG group; X is —OH, —NHS, —O-TFP, or —NR-L-maleimide; m is 4; o is 3; and n is 3. In one embodiment, the compound is general formula I, where R1 is methyl and R2 is a PEG group; X is —OH, —NHS, —O-TFP, or —NR-L-maleimide; m is 5; o is 3; and n is 3.

In one embodiment, the compound is general formula I, where each of R1 and R2 is a PEG group; X is —OH, —NHS, —O-TFP, or —NR-L-maleimide; m is 0; o is 3; and n is 1. In one embodiment, the compound is general formula I, where each of R1 and R2 is a PEG group; X is —OH, —NHS, —O-TFP, or —NR-L-maleimide; m is 1; o is 3; and n is 1. In one embodiment, the compound is general formula I, where each of R1 and R2 is a PEG group; X is —OH, —NHS, —O-TFP, or —NR-L-maleimide; m is 2; o is 3; and n is 1. In one embodiment, the compound is general formula I, where each of R1 and R2 is a PEG group; X is —OH, —NHS, —O-TFP, or —NR-L-maleimide; m is 3; o is 3; and n is 1. In one embodiment, the compound is general formula I, where each of R1 and R2 is a PEG group; X is —OH, —NHS, —O-TFP, or —NR-L-maleimide; m is 4; o is 3; and n is 1. In one embodiment, the compound is general formula I, where each of R1 and R2 is a PEG group; X is —OH, —NHS, —O-TFP, or —NR-L-maleimide; m is 5; o is 3; and n is 1.

In one embodiment, the compound is general formula I, where each of R1 and R2 is a PEG group; X is —OH, —NHS, —O-TFP, or —NR-L-maleimide; m is 0; o is 3; and n is 2. In one embodiment, the compound is general formula I, where each of R1 and R2 is a PEG group; X is —OH, —NHS, —O-TFP, or —NR-L-maleimide; m is 1; o is 3; and n is 2. In one embodiment, the compound is general formula I, where each of R1 and R2 is a PEG group; X is —OH, —NHS, —O-TFP, or —NR-L-maleimide; m is 2; o is 3; and n is 2. In one embodiment, the compound is general formula I, where each of R1 and R2 is a PEG group; X is —OH, —NHS, —O-TFP, or —NR-L-maleimide; m is 3; o is 3; and n is 2. In one embodiment, the compound is general formula I, where each of R1 and R2 is a PEG group; X is —OH, —NHS, —O-TFP, or —NR-L-maleimide; m is 4; o is 3; and n is 2. In one embodiment, the compound is general formula I, where each of R1 and R2 is a PEG group; X is —OH, —NHS, —O-TFP, or —NR-L-maleimide; m is 5; o is 3; and n is 2.

In one embodiment, the compound is general formula I, where each of R1 and R2 is a PEG group; X is —OH, —NHS, —O-TFP, or —NR-L-maleimide; m is 0; o is 3; and n is 3. In one embodiment, the compound is general formula I, where each of R1 and R2 is a PEG group; X is —OH, —NHS, —O-TFP, or —NR-L-maleimide; m is 1; o is 3; and n is 3. In one embodiment, the compound is general formula I, where each of R1 and R2 is a PEG group; X is —OH, —NHS, —O-TFP, or —NR-L-maleimide; m is 2; o is 3; and n is 3. In one embodiment, the compound is general formula I, where each of R1 and R2 is a PEG group; X is —OH, —NHS, —O-TFP, or —NR-L-maleimide; m is 3; o is 3; and n is 3. In one embodiment, the compound is general formula I, where each of R1 and R2 is a PEG group; X is —OH, —NHS, —O-TFP, or —NR-L-maleimide; m is 4; o is 3; and n is 3. In one embodiment, the compound is general formula I, where each of R1 and R2 is a PEG group; X is —OH, —NHS, —O-TFP, or —NR-L-maleimide; m is 5; o is 3; and n is 3.

In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 0; o is 3; and n is 1. In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 1; o is 3; and n is 1. In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 2; o is 3; and n is 1. In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 3; o is 3; and n is 1. In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 4; o is 3; and n is 1. In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 5; o is 3; and n is 1.

In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 0; o is 3; and n is 2. In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 1; o is 3; and n is 2. In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 2; o is 3; and n is 2. In one embodiment, the compound is general formula I, where R1 is sulfoalkyl and R2 is a sulfonamide group -L-$SO_2$NH—P where P is a PEG group; X is —OH, —NHS, —O-TFP, or —NR-L-maleimide; m is 3; o is 3; and n is 2. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 4; o is 3; and n is 2. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 5; o is 3; and n is 2.

In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 0; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 1; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 2; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 3; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 4; o is 3; and n is 3. In one embodiment, the compound is general formula I, where R1 is sulfoalkyl and R2 is a sulfonamide group -L-SO$_2$NH—P where P is a PEG group; X is —OH, —NHS, —O-TFP, or —NR-L-maleimide; m is 5; o is 3; and n is 3.

In one embodiment, the compound is general formula IIa

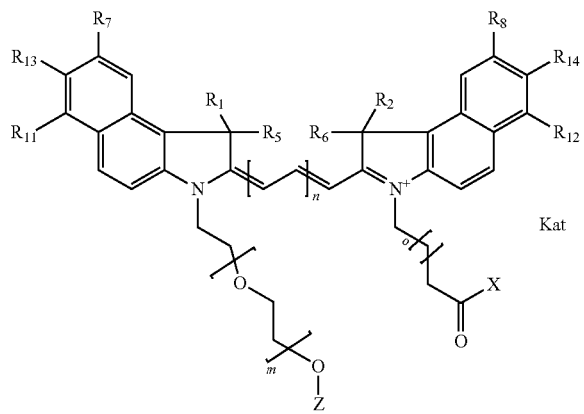

or general formula IIb

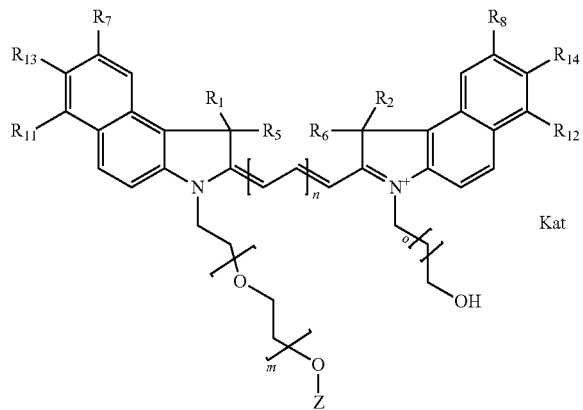

where each of $R^1$, $R^2$, $R^5$, and $R^6$ is the same or different and is independently selected from the group consisting of an aliphatic, heteroaliphatic, sulfoalkyl group, heteroaliphatic with terminal SO$_3$, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -L-SO$_2$NH—P—Z, and a caboxamide group -L-CONH—P—Z, and Z is selected from H, a CH$_3$ group, an alkyl group, a heteroalkyl group, or —CO—NHS; each of $R^7$, $R^8$, $R^{11}$, $R^{12}$, $R^{13}$, and $R^{14}$ is the same or different and is independently selected from the group consisting of H, SO$_3$, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -L-SO$_2$NH—P—Z, and a caboxamide group -L-CONH—P—Z, and Z is selected from H, a CH$_3$ group, an alkyl group, or a heteroalkyl group; X is selected from the group consisting of —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH$_2$-1, imidazole, azide, —NR-L-O—NH$_2$, and —NR-L-O—CO—NHS, where R is —H or an aliphatic or heteroaliphatic group, and L is selected from the group consisting of a divalent linear (—(CH$_2$)$_t$—, t=0 to 15), crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; and n is an integer from 1 to 3 inclusive.

In one embodiment, the compound is general formulas IIa or IIb, collectively general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 0; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 1; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 2; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 3; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 4; o is 3; and n is 1. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 5; o is 3; and n is 1.

In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 0; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 1; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 2; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 3; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 4; o is 3; and n is 2. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 5; o is 3; and n is 2.

In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 0; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 1; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 2; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 3; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 4; o is 3; and n is 3. In one embodiment, the compound is general formula II, where each of R1, R5, and R6 is methyl and R2 is a PEG group; each of R7, R8, R11, and R12 is H; each of R13 and R14 is sulfo; X is —OH, —NHS, —O-TFP, or —NR-L-maleimide; m is 5; o is 3; and n is 3.

In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; o is 3; and n is 1. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; o is 3; and n is 1.

In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; o is 3; and n is 2. In one embodiment, the compound is general formula II, where each of R5 and R6 is methyl; each of R1 and R2 is a PEG group; each of R7, R8, R11, and R12 is H; each of R13 and R14 is sulfo; X4 is —OH, —NHS, —O-TFP, or —NR-L-maleimide; m is 5; o is 3; and n is 2.

In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; o is 3; and n is 3. In one embodiment, the compound is general formula II, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; o is 3; and n is 3.

In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; o is 3; and n is 1. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; o is 3; and n is 1.

In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; o is 3; and n is 2. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; o is 3; and n is 2.

In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; o is 3; and n is 3. In one embodiment, the compound is general formula II, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; o is 3; and n is 3.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; o is 3; and n is 1. In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; o is 3; and n is 1.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; o is 3; and n is 2.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; o is 3; and n is 2.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; o is 3; and n is 2.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; o is 3; and n is 2.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; o is 3; and n is 2.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; o is 3; and n is 2.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; o is 3; and n is 3.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; o is 3; and n is 3.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; o is 3; and n is 3.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; o is 3; and n is 3.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; o is 3; and n is 3.

In one embodiment, the compound is general formula II, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; o is 3; and n is 3.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 0; o is 3; and n is 1.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 1; o is 3; and n is 1.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 2; o is 3; and n is 1.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 3; o is 3; and n is 1.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 4; o is 3; and n is 1.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 5; o is 3; and n is 1.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 0; o is 3; and n is 2.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 1; o is 3; and n is 2.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 2; o is 3; and n is 2.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 3; o is 3; and n is 2.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 4; o is 3; and n is 2. In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 5; o is 3; and n is 2.

In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 0; o is 3; and n is 3. In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 1; o is 3; and n is 3. In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 2; o is 3; and n is 3. In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 3; o is 3; and n is 3. In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 4; o is 3; and n is 3. In one embodiment, the compound is general formula II, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 5; o is 3; and n is 3.

In one embodiment, the compound is general formula IIIa

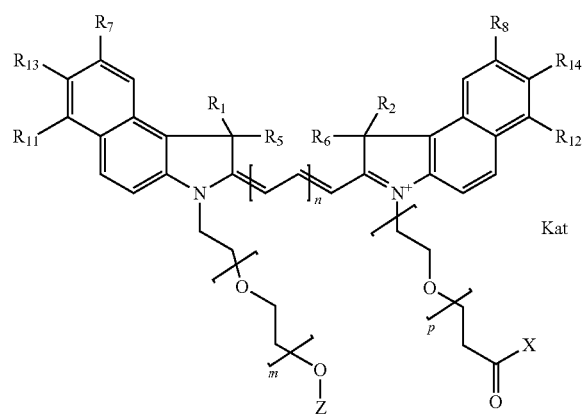

or general formula IIIb

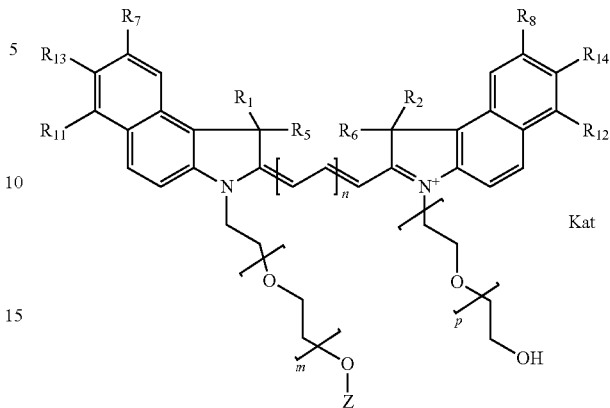

where each of R1, R2, R5, and R6 is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -L-$SO_2$NH—P—Z, and a caboxamide group -L-CONH—P—Z, and Z is selected from H, a $CH_3$ group, an alkyl group, or a heteroalkyl group; each of $R^7$, $R^8$, $R^{11}$, $R^{12}$, $R^{13}$, and $R^{14}$ is the same or different and is independently selected from the group consisting of H, $SO_3$, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group —$SO_2$NH—P—Z, and a caboxamide group —CONH—P—Z, and Z is selected from H, a $CH_3$ group, an alkyl group, a heteroalkyl group, or —CO—NHS; X is selected from the group consisting of —OH, —SH, —$NH_2$, —NH—$NH_2$, —F, —Cl, —Br, I, —NHS hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$-1, imidazole, azide, —NR-L-O—$NH_2$, and —NR-L-O—CO—NHS, where R is —H or an aliphatic or heteroaliphatic group, and L is selected from the group consisting of a divalent linear (—$(CH_2)_t$—, t=0 to 15), crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; p is an integer from 1 to 6 inclusive; and n is an integer from 1 to 3 inclusive.

In one embodiment, the compound is general formulas IIIa or IIIb, collectively termed general formula III where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 0; p is 1; and n is 1. In one embodiment, the compound is general formula III where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 1; p is 2; and n is 1. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 2; p is 3; and n is 1. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 3; p is 4; and n is 1. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 4; p is 5; and n is 1. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 5; p is 6; and n is 1.

In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 0; p is 1; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 1; p is 2; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 2; p is 3; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 3; p is 4; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 4; p is 5; and n is 2. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 5; p is 6; and n is 2.

In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 0; p is 1; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 1; p is 2; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 2; p is 3; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 3; p is 4; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 4; p is 5; and n is 3. In one embodiment, the compound is general formula III, where each of R1, R5, and R6 is methyl; R2 is a PEG group; each of R7, R8, R11, and R12 is H; each of R13 and R14 is sulfo; X is —OH, —NHS, —O-TFP, or —NR-L-maleimide; m is 5; p is 6; and n is 3.

In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 0; p is 1; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 1; p is 2; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 2; p is 3; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 3; p is 4; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 4; p is 5; and n is 1. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 5; p is 6; and n is 1.

In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 0; p is 1; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 1; p is 2; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 2; p is 3; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 3; p is 4; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 4; p is 5; and n is 2. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 5; p is 6; and n is 2.

In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 0; p is 1; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 1; p is 2; and n is 3.

In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 2; p is 3; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 3; p is 4; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 4; p is 5; and n is 3. In one embodiment, the compound is general formula III, where each of R1, R5, and R6 is methyl; R2 is a PEG group; each of R7, R8, R11, and R12 is sulfo; each of R13 and R14 is H; X is —OH, —NHS, —O-TFP, or —NR-L-maleimide; m is 5; p is 6; and n is 3.

In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; p is 1; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; p is 2; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; p is 3; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; p is 4; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; p is 5; and n is 1. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; p is 6; and n is 1.

In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 0; p is 1; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; p is 2; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; p is 3; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; p is 4; and n is 2.

In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; p is 5; and n is 2. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; p is 6; and n is 2.

In one embodiment, the compound is general formula III, where each of R5 and R6 is methyl; each of R1 and R2 is a PEG group; each of R7, R8, R11, and R12 is sulfo; each of R13 and R14 is H; X is —OH, NHS, —O-TFP, or —NR-L-maleimide; m is 0; p is 1; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 1; p is 2; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 2; p is 3; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 3; p is 4; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 4; p is 5; and n is 3. In one embodiment, the compound is general formula III, where each of R5 and R6 is methyl; each of R1 and R2 is a PEG group; each of R7, R8, R11, and R12 is sulfo; each of R13 and R14 is H; X is —OH, —NHS, —O-TFP, or —NR-L-maleimide; m is 5; p is 6; and n is 3.

In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; p is 1; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; p is 2; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; p is 3; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; p is 4; and n is 1. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; p is 5; and n is 1.

In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; p is 6; and n is 1.

In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; p is 1; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; p is 2; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; p is 3; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; p is 4; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; p is 5; and n is 2. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; p is 6; and n is 2.

In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 0; p is 1; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 1; p is 2; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 2; p is 3; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 3; p is 4; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 4; p is 5; and n is 3. In one embodiment, the compound is general formula III, where each of R5 and R6 is methyl; each of R1 and R2 is a PEG group; each of R7, R8, R11, and R12 is H; each of R13 and R14 is sulfo; X is —OH, —NHS, —O-TFP, or —NR-L-maleimide; m is 5; p is 6; and n is 3.

In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; p is 1; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; p is 2; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; p is 3; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; p is 4; and n is 1. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; p is 5; and n is 1. In one embodiment, the compound is general formula Ill, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; p is 6; and n is 1.

In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; p is 1; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; p is 2; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; p is 3; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; p is 4; and n is 2. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; p is 5; and n is 2. In one embodiment, the compound is general formula Ill, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; p is 6; and n is 2.

In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 0; p is 1; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 1; p is 2; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 2; p is 3; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 3; p is 4; and n is 3. In one embodiment, the compound is general formula III, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 4; p is 5; and n is 3. In one embodiment, the compound is general formula Ill, where each of R5 and R6 is methyl; each of R1 and R2 is a PEG group; each of R7 and R8 is sulfo; each of R11 and R12 is a sulfonamide group —SO$_2$NH—P where P is a PEG group; each of R13 and R14 is H; X is —OH, —NHS, —O-TFP, or —NR-L-maleimide; m is 5; p is 6; and n is 3. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 0; p is 1; and n is 1. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 1; p is 2; and n is 1. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 2; p is 3; and n is 1. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 3; p is 4; and n is 1. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 4; p is 5; and n is 1. In one embodiment, the compound is general formula Ill, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 5; p is 6; and n is 1. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 0; p is 1; and n is 2. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 1; p is 2; and n is 2. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 2; p is 3; and n is 2. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 3; p is 4; and n is 2. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 4; p is 5; and n is 2. In one embodiment, the compound is general formula Ill, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 5; p is 6; and n is 2. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 0; p is 1; and n is 3. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 1; p is 2; and n is 3. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 2; p is 3; and n is 3. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 3; p is 4; and n is 3. In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 4; p is 5; and n is 3.
In one embodiment, the compound is general formula III, where each of R5 and R6 is methyl; each of R1 and R2 is a PEG group; each of R7 and R8 is sulfo; each of R11 and R12 is a caboxamide group —CONH—P where P is a PEG group; each of R13 and R14 is H; X is —OH, —NHS, —O-TFP, or —NR-L-maleimide; m is 5; p is 6; and n is 3.

In one embodiment, the compound is 579 Compound 1

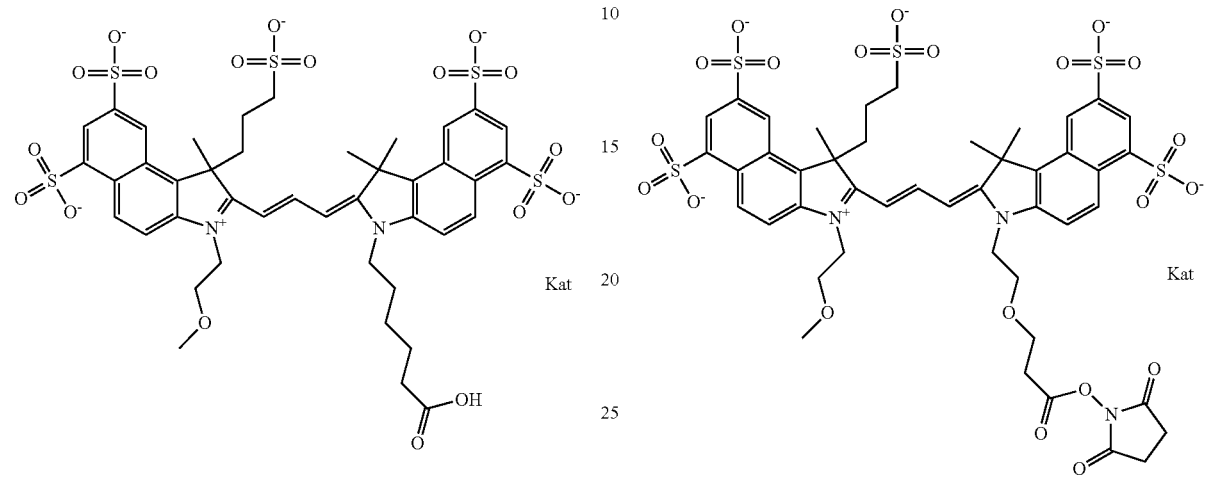

579 Compound 1 (6-((E)-2-((E)-3-(3-(2-methoxyethyl)-1-methyl-6,8-disulfonato-1-(3-sulfonatopropyl)-1H-benzo[e]indol-3-ium-2-yl)allylidene)-1,1-dimethyl-6,8-disulfonato-1H-benzo[e]indol-3(2H)-yl)hexanoate) contains an ethylene glycol on the indole N of the left heterocycle, i.e., a methylated ethylene glycol. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 579 Compound 1, but one skilled in the art appreciates that activation is not limited to these examples. One non-limiting example of an activated compound is the NHS-ester of 579 Compound 1, shown below:

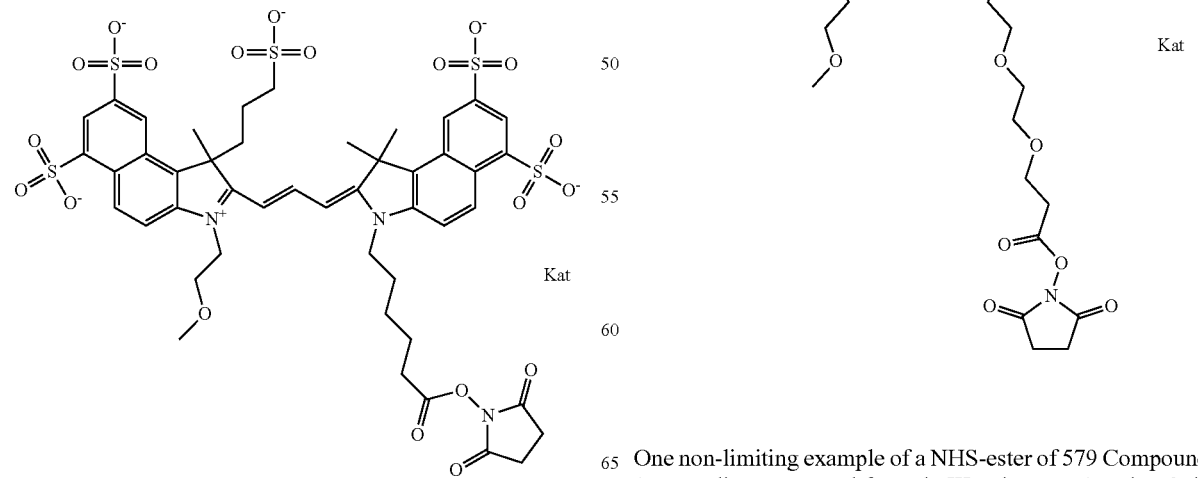

One non-limiting example of a NHS-ester of 579 Compound 1, according to general formula III, where m=1 and p=1, is shown below:

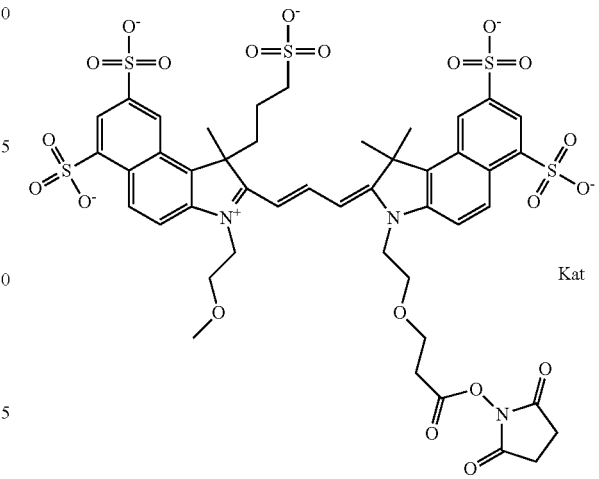

One non-limiting example of a NHS-ester of 579 Compound 1, according to general formula III, where m=1 and p=2, is shown below:

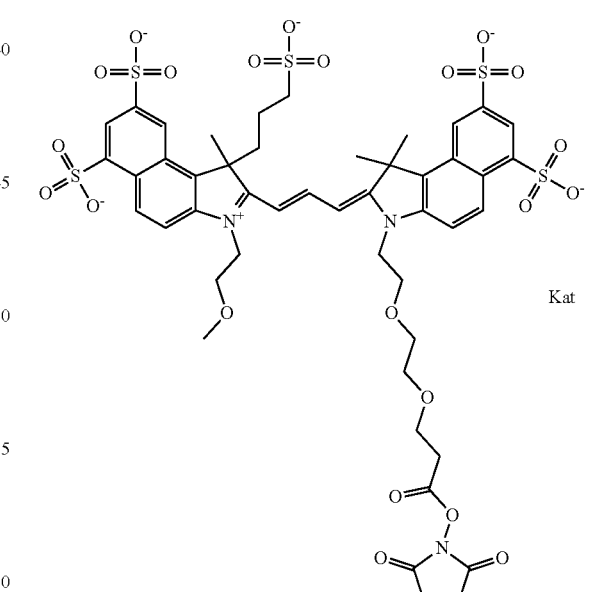

One non-limiting example of a NHS-ester of 579 Compound 1, according to general formula III, where m=1 and p=3, is shown below:

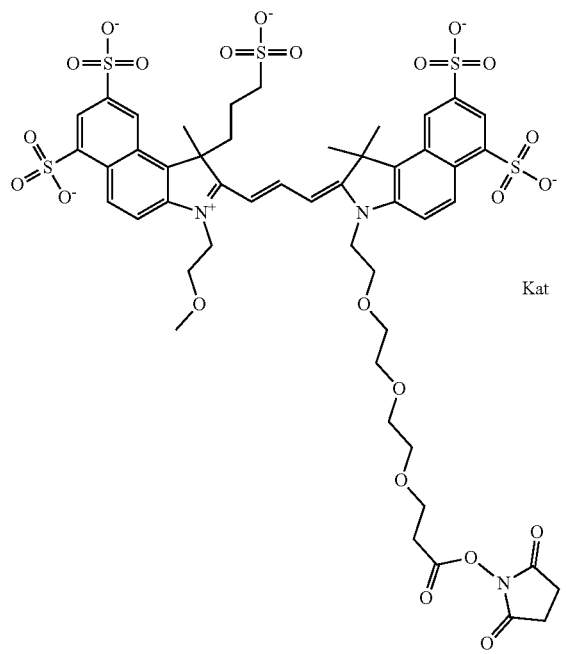

One non-limiting example of a NHS-ester of 579 Compound 1, according to general formula III, where m=1 and p=4, is shown below:

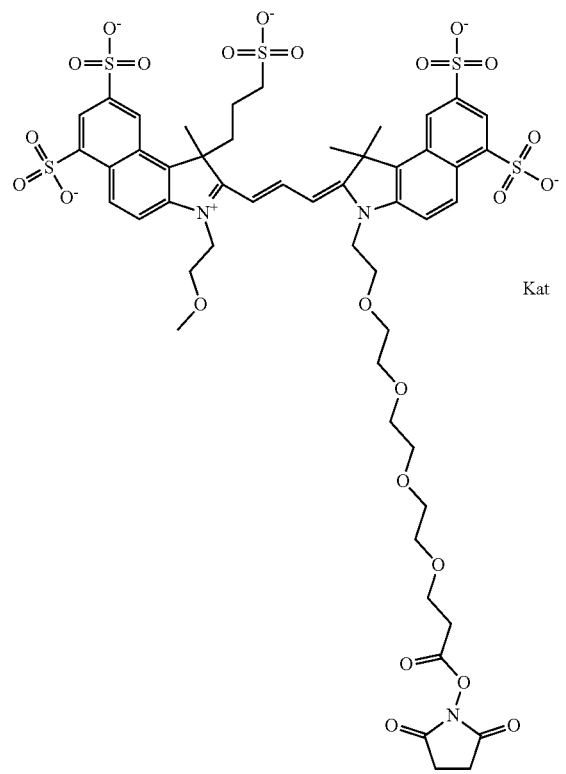

One non-limiting example of a NHS-ester of 579 Compound 1, according to general formula III, where m=1 and p=5, shown below:

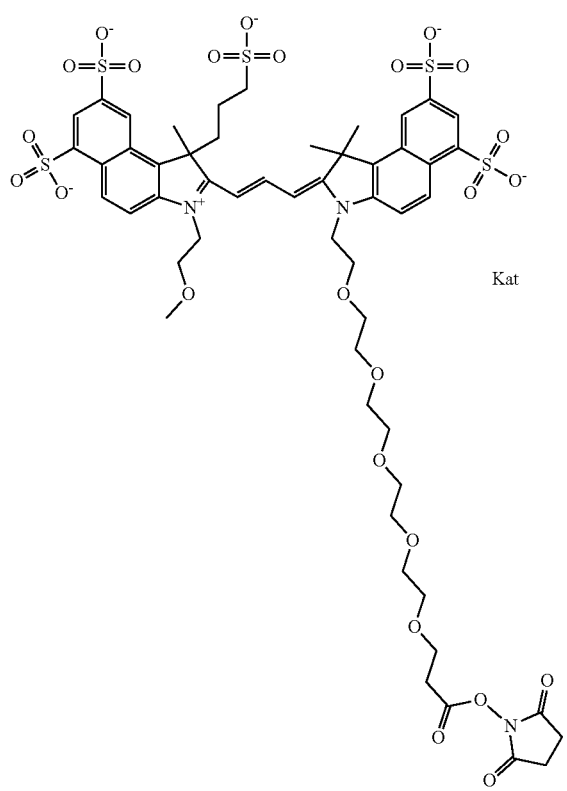

One non-limiting example of a NHS-ester of 579 Compound 1, according to general formula III, where m=1 and p=6, is shown below:

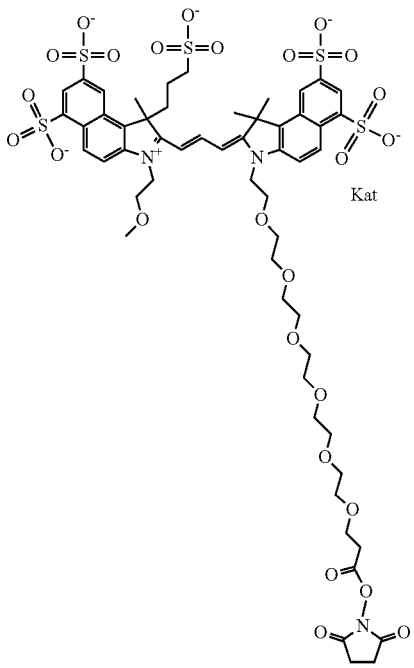

One non-limiting example of an activated 579 Compound 1 is a tetrafluorophenyl (TFP)-ester form of 579 Compound 1, shown below:

One non-limiting example of an activated 579 Compound 1 is a maleimide form of 579 Compound 1, shown below:
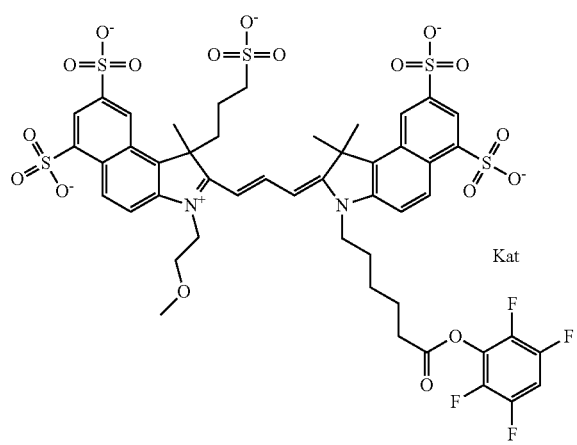 [SMILES: COCC[N+]1=C(/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]
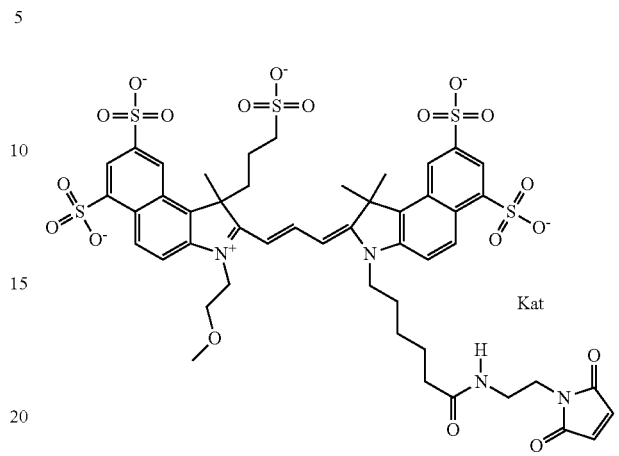
One non-limiting example of an activated 579 Compound 1 is a sulfotetrafluorophenyl (STP)-ester form of 579 Compound 1, shown below:
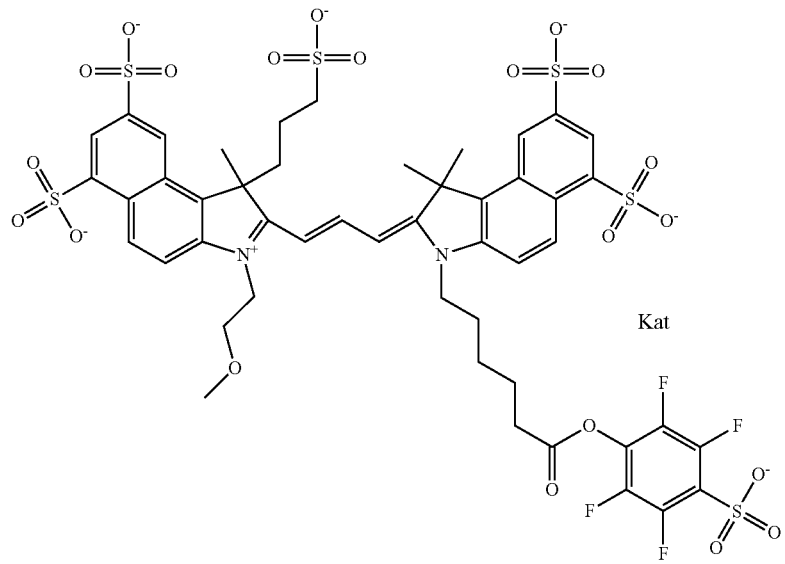 [SMILES: COCC[N+]1=C(/C=C/C=C2/N(CCCCCC(=O)Oc3c(F)c(F)c(S(=O)(=O)[O-])c(F)c3F)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]
One non-limiting example of an activated 579 Compound 1 is a hydrazide form of 579 Compound 1,
In one embodiment, the compound is 579 Compound 2
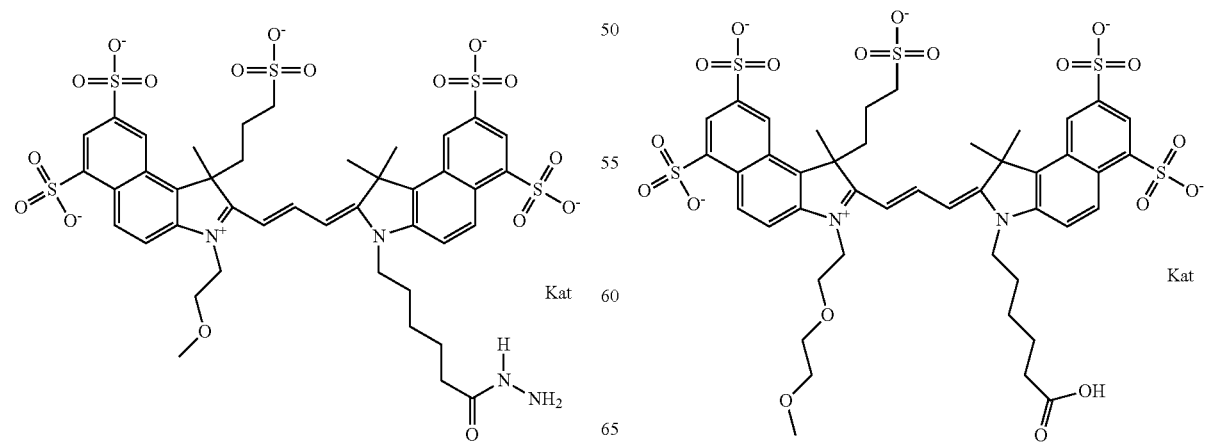

579 Compound 2 (6-((E)-2-((E)-3-(3-(2-(2-methoxyethoxy)ethyl)-1-methyl-6,8-disulfonato-1-(3-sulfonatopropyl)-1H-benzo[e]indol-3-ium-2-yl)allylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 2 is activated as described above.

In one embodiment, the compound is 579 Compound 3

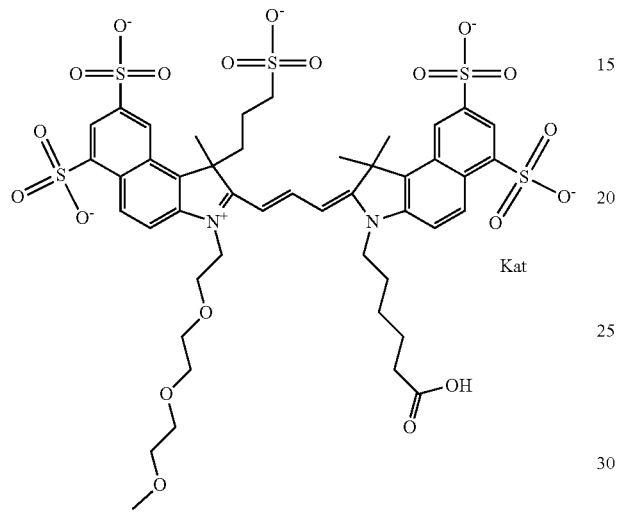

579 Compound 3 (6-((E)-2-((E)-3-(3-(2-(2-(2-methoxyethoxy)ethoxy)ethyl)-1-methyl-6,8-disulfonato-1-(3-sulfonatopropyl)-1H-benzo[e]indol-3-ium-2-yl)allylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 3 is activated as described above.

In one embodiment, the compound is 579 Compound 4

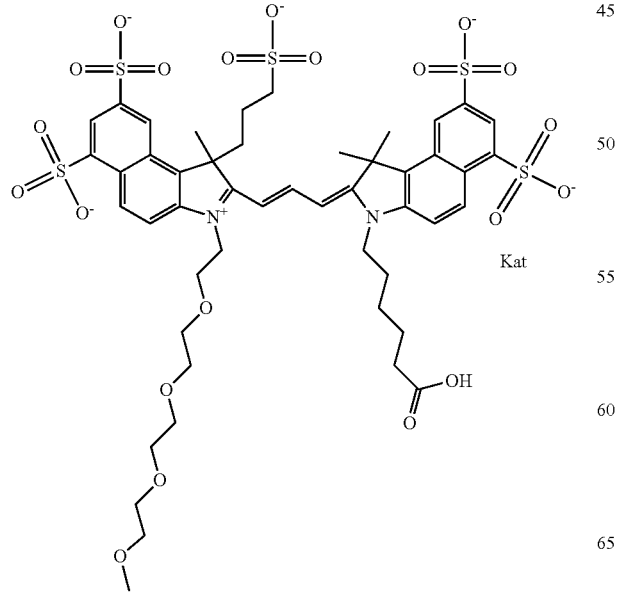

579 Compound 4 (6-((E)-1,1-dimethyl-2-((E)-3-(1-methyl-6,8-disulfonato-1-(3-sulfonatopropyl)-3-(2,5,8,11-tetraoxatridecan-13-yl)-1H-benzo[e]indol-3-ium-2-yl)allylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 579 Compound 4 is activated as described above.

In one embodiment, the compound is 579 Compound 5

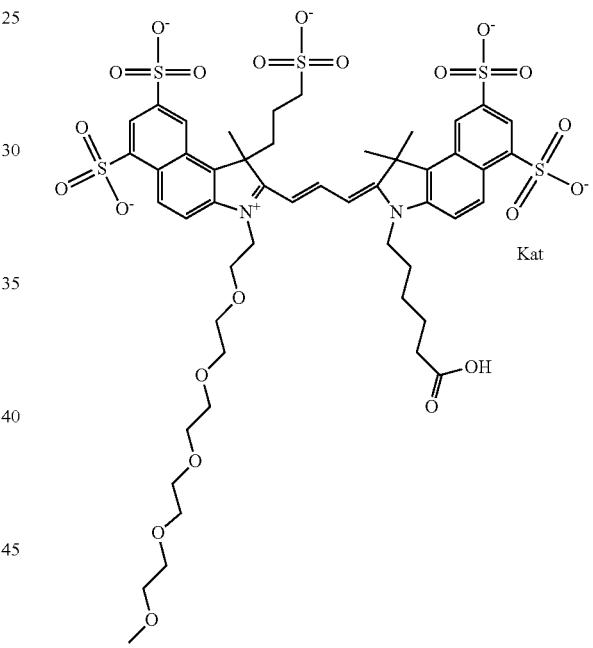

579 Compound 5 (6-((E)-2-((E)-3-(3-(2,5,8,11,14-pentaoxahexadecan-16-yl)-1-methyl-6,8-disulfonato-1-(3-sulfonatopropyl)-1H-benzo[e]indol-3-ium-2-yl)allylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 5 is activated as described above.

In one embodiment, the compound is 579 Compound 6

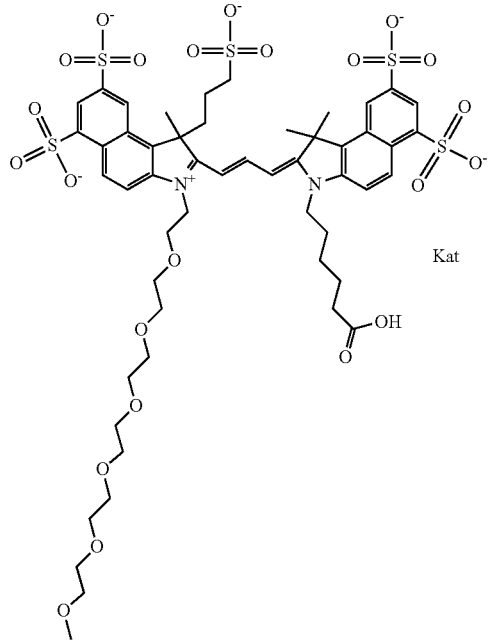 [SMILES: COCCOCCOCCOCCOCCOCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

579 Compound 6 (6-((E)-1,1-dimethyl-2-((E)-3-(1-methyl-3-(2,5,8,11,14,17-hexaoxanonadecan-19-yl)-6,8-disulfonato-1-(3-sulfonatopropyl)-1H-benzo[e]indol-3-ium-2-yl)allylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 579 Compound 6 is activated as described above.

In embodiments, the degree and/or location of sulfonation is varied to, e.g., vary the compound's degree of hydrophilicity or hydrophobicity. One non-limiting example is a monosulfonate form of 579 Compound 1, shown below:

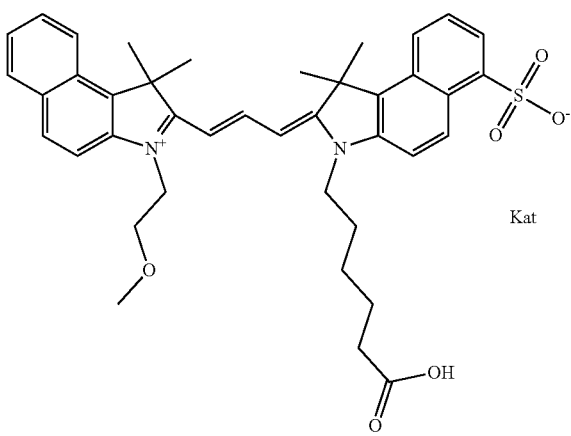 [SMILES: COCC[N+]1=C(/C=C/C=C2/N(CCCCCC(=O)O)c3ccc4c(S(=O)(=O)[O-])cccc4c3C2(C)C)C(C)(C)c2c1ccc1ccccc21]

One non-limiting example is a disulfonate form of 579 Compound 1, shown below:

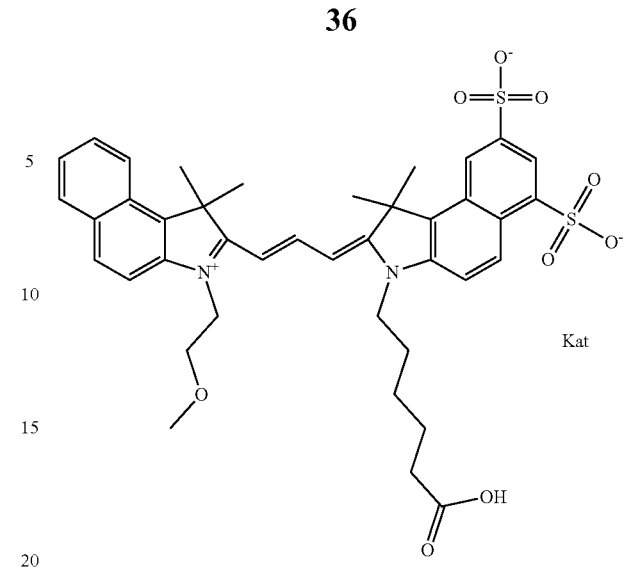

One non-limiting example is a trisulfonate form of 579 Compound 1, shown below:

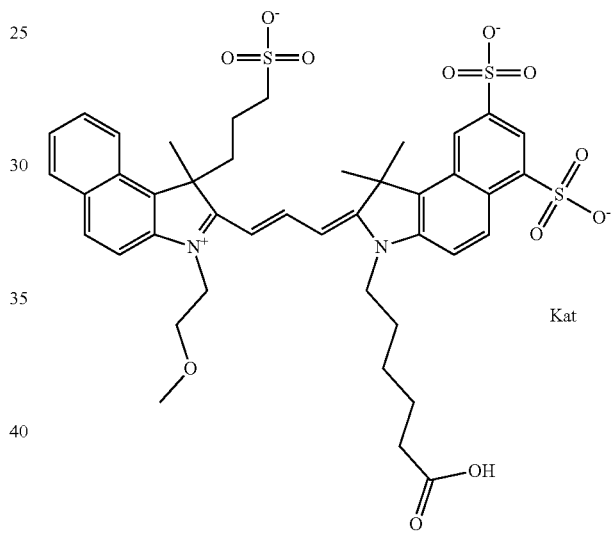

One non-limiting example is a tetrasulfonate form of 579 Compound 1, shown below:

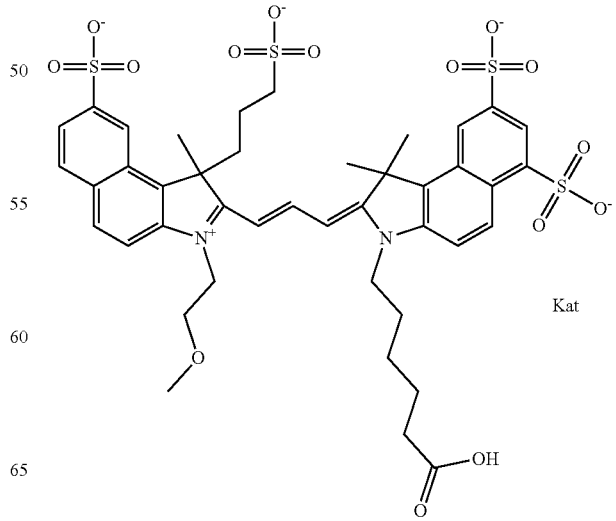

One non-limiting example is a pentasulfonate form of 579 Compound 1, shown below:

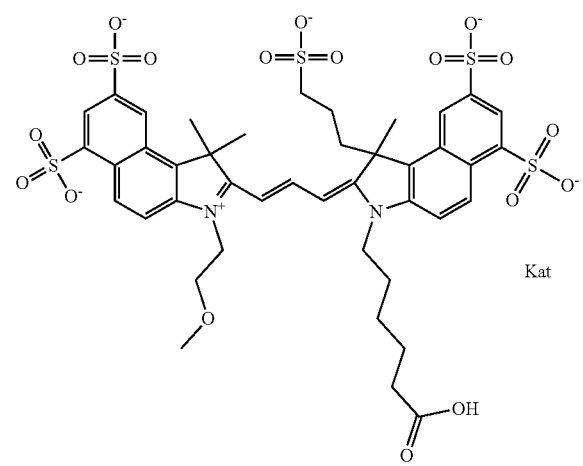 [SMILES: COCC[N+]1=C(/C=C/C=C2/N(CCCCCC(=O)O)c3ccc4c(S(=O)(=O)[O-])cc(S(=O)(=O)[O-])cc4c3C2(C)CCCS(=O)(=O)[O-])C(C)(C)c2c1ccc1c(S(=O)(=O)[O-])cc(S(=O)(=O)[O-])cc21]

In one embodiment, the compound is 579 Compound 1/2 (PEG$_4$)

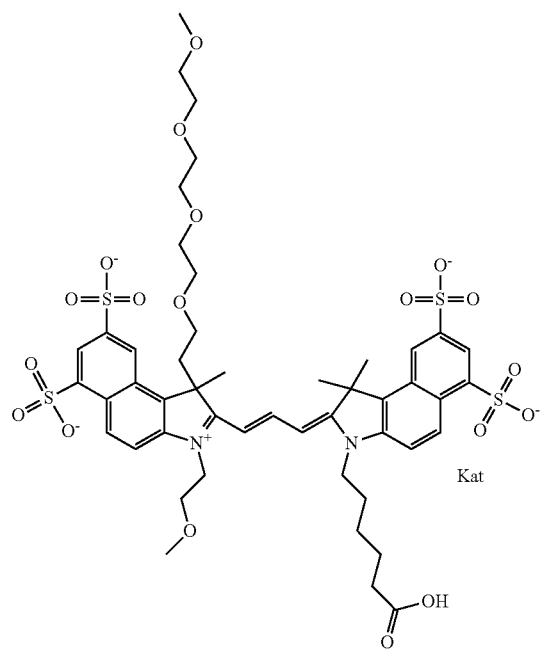 [SMILES: COCCOCCOCCOCCC1(C)C(/C=C/C=C2/N(CCCCCC(=O)O)c3ccc4c(S(=O)(=O)[O-])cc(S(=O)(=O)[O-])cc4c3C2(C)C)=[N+](CCOC)c2ccc3c(S(=O)(=O)[O-])cc(S(=O)(=O)[O-])cc3c21]

One non-limiting example of 579 Compound 1/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-3-(2-methoxyethyl)-1-methyl-1-(2,5,8,11-tetraoxatridecan-13-yl)-1H-benzo[e]indolium-6,8-disulfonate) contains an ethylene glycol on the indole N of the left heterocycle, i.e., a methylated ethylene glycol, and a methylated PEG$_4$ group. The methyl group on the ethylene glycol/PEG prevents the terminal —OH from oxidation. Oxidation is known to occur, over time, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 579 Compound 1/2 (PEG$_4$), but one skilled in the art appreciates that activation is not limited to these examples. One non-limiting example of an activated compound is the NHS-ester of 579 Compound 1/2 (PEG$_4$), shown below:

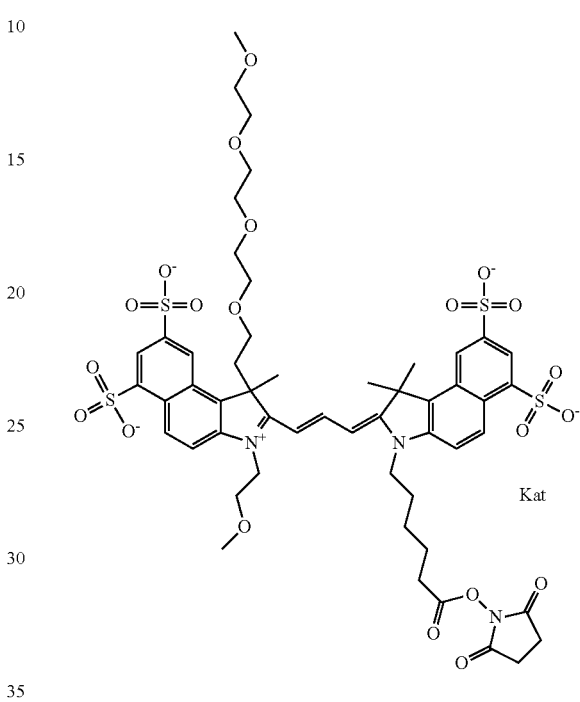

One non-limiting example of a NHS-ester of 579 Compound 1/3 (PEG$_4$), according to general formula III, where m=1 and p=1, is shown below:

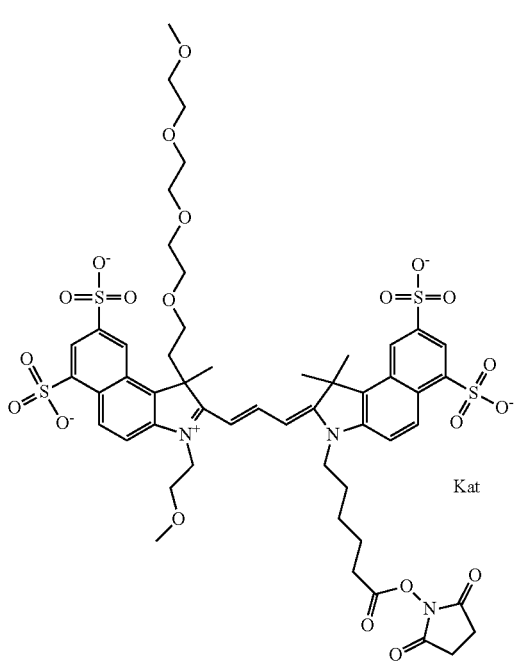

One non-limiting example of a NHS-ester of 579 Compound 1/3 (PEG$_4$), according to general formula III, where m=1 and p=2, is shown below:

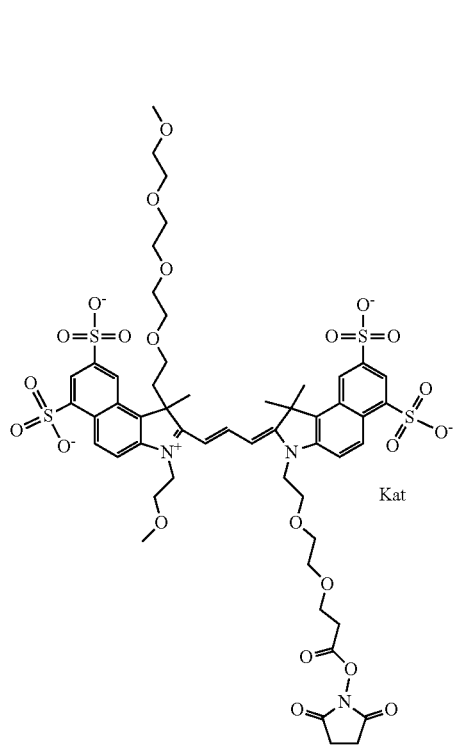

One non-limiting example of a NHS-ester of 579 Compound 1/3 (PEG$_4$), according to general formula III, where m=1 and p=3, is shown below:

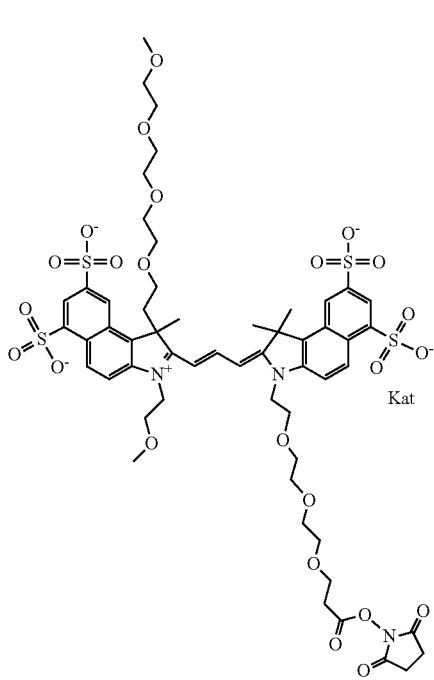

One non-limiting example of a NHS-ester of 579 Compound 1/3 (PEG$_4$), according to general formula III, where m=1 and p=4, is shown below:

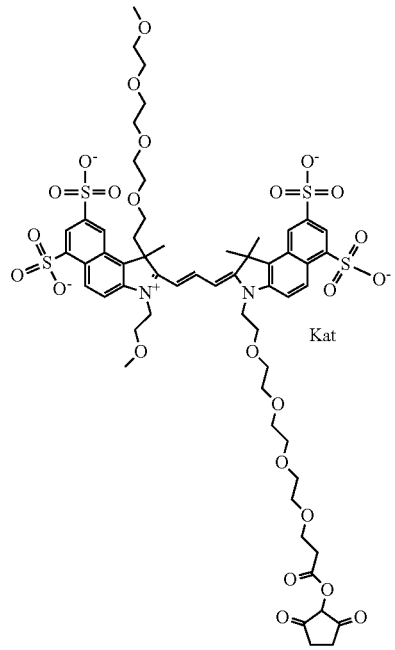

One non-limiting example of a NHS-ester of 579 Compound 1/3 (PEG$_4$), according to general formula III, where m=1 and p=5, is shown below:

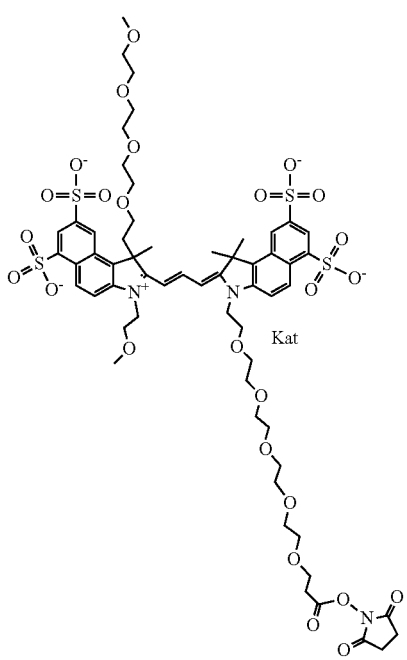

One non-limiting example of a NHS-ester of 579 Compound 1/3 (PEG$_4$), according to general formula III, where m=1 and p=6, is shown below:

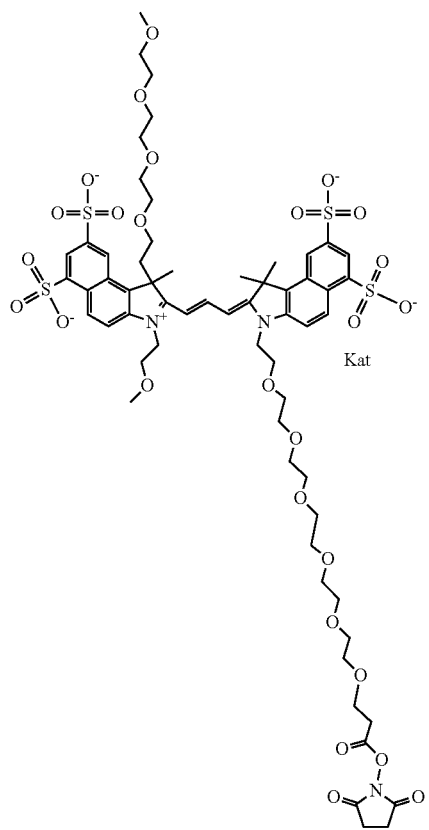

One non-limiting example of an activated 579 Compound 1/2 (PEG$_4$) is a sulfotetrafluorophenyl (STP)-ester form of 579 Compound 1, shown below:

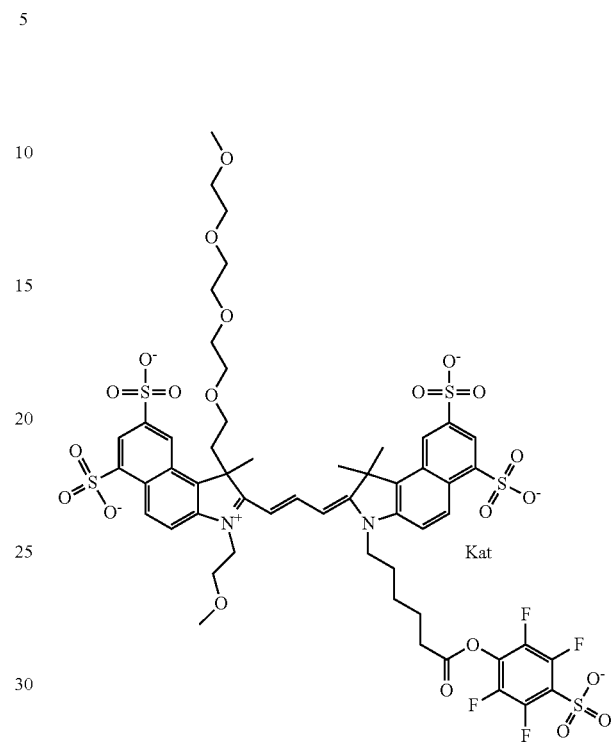

One non-limiting example of an activated 579 Compound 1/2 is a hydrazide form of 579 Compound 1 (PEG$_4$), shown below:

One non-limiting example of an activated 579 Compound 1/2 (PEG$_4$) is a tetrafluorophenyl (TFP)-ester form of 579 Compound 1, shown below:

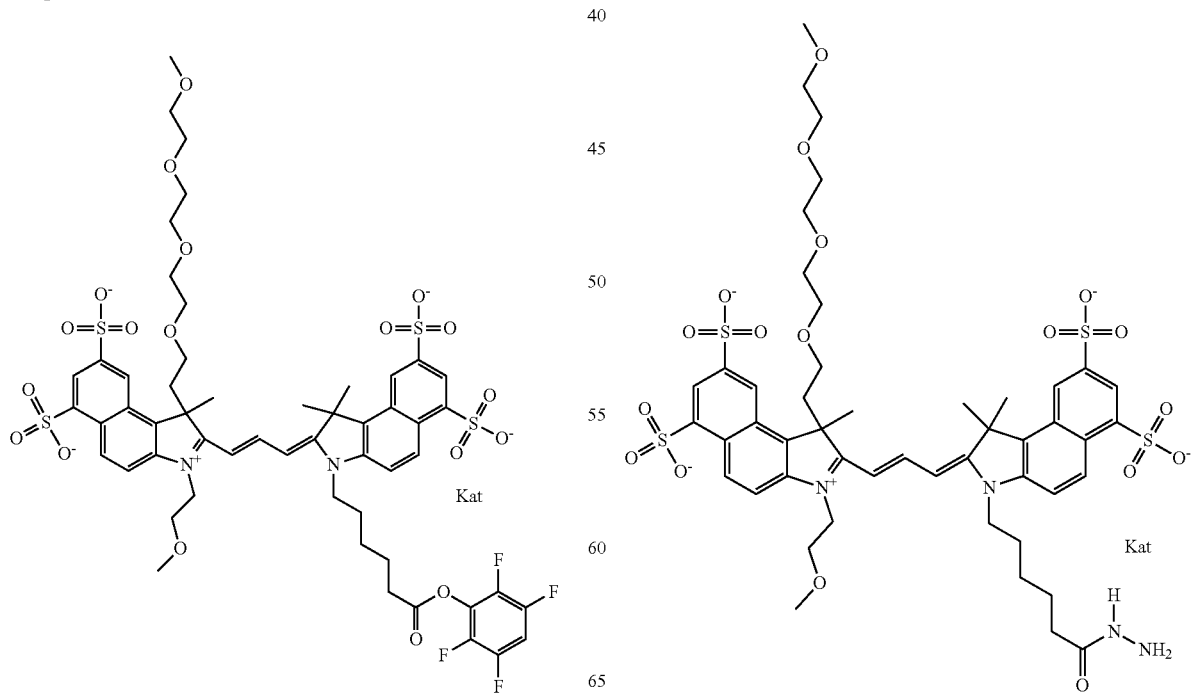

One non-limiting example of an activated 579 Compound 1/2 (PEG$_4$) is a maleimide form of 579 Compound 1, shown below:

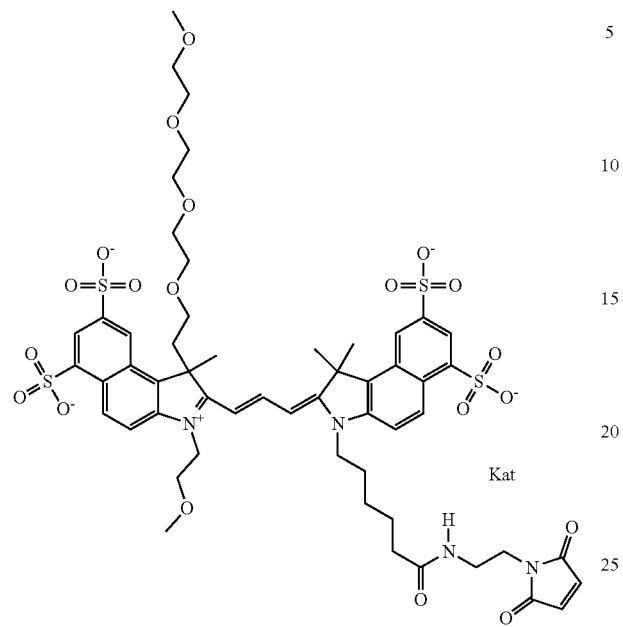

In one embodiment, the compound is 579 Compound 2/2 (PEG$_4$)

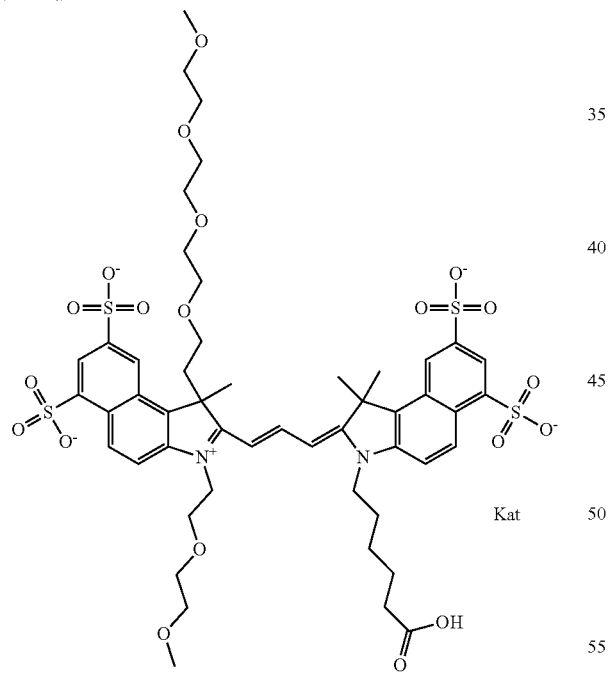

One non-limiting example of 579 Compound 2/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-3-(2-(2-methoxyethoxy)ethyl)-1-methyl-1-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the (poly)ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 2/2 (PEG$_4$) is activated as described above.

In one embodiment, the compound is 579 Compound 3/2 (PEG$_4$)

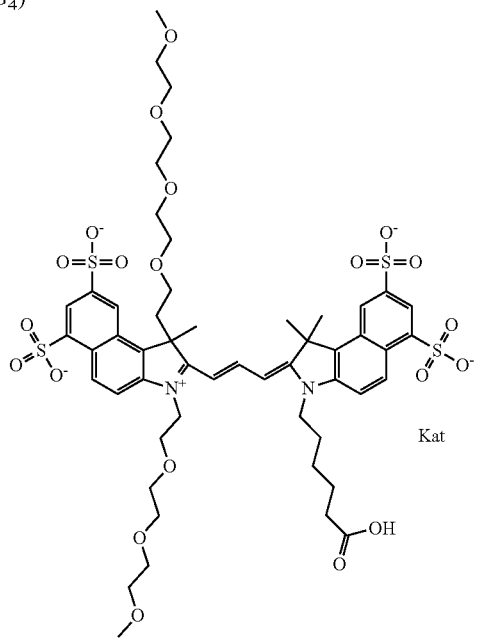

One non-limiting example of 579 Compound 3/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-3-(2-(2-(2-methoxyethoxy)ethoxy)ethyl)-1-methyl-1-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 3/2 (PEG$_4$) is activated as described above.

In one embodiment, the compound is 579 Compound 4/2 (PEG$_4$)

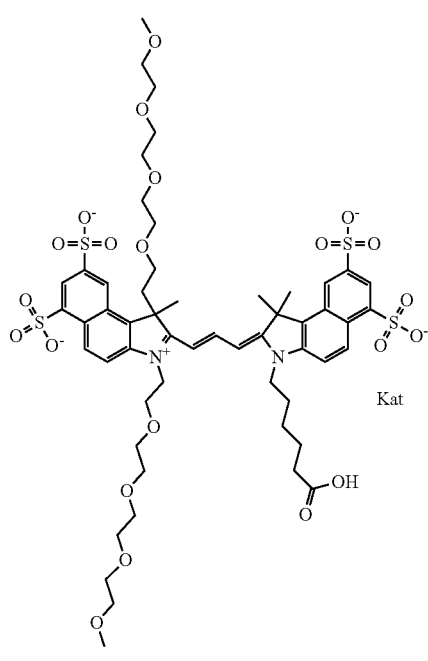 [SMILES: COCCOCCOCCOCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCOCCOCCOCCOC)c2c1ccc1c(S(=O)(=O)[O-])cc(S(=O)(=O)[O-])cc21]

One non-limiting example of 579 Compound 4/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-1-methyl-1,3-di(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 4/2 (PEG$_4$) is activated as described above.

In one embodiment, the compound is 579 Compound 5/2 (PEG$_4$)

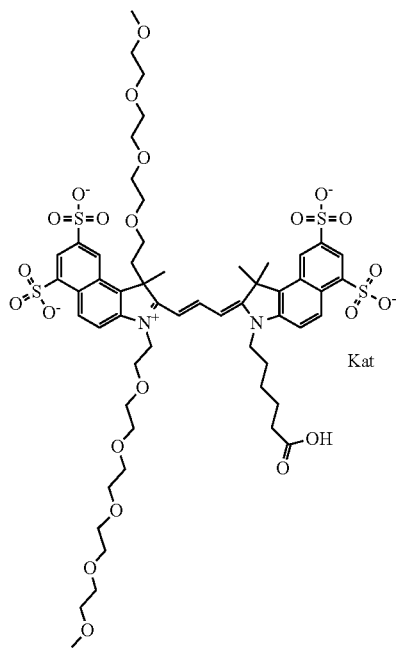 [SMILES: COCCOCCOCCOCCOCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCOCCOCCOCCOC)c2c1ccc1c(S(=O)(=O)[O-])cc(S(=O)(=O)[O-])cc21]

One non-limiting example of 579 Compound 5/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-3-(2,5,8,11,14-pentaoxahexadecan-16-yl)-1-methyl-1-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 5/2 (PEG$_4$) is activated as described above.

In one embodiment, the compound is 579 Compound 6/2 (PEG$_4$)

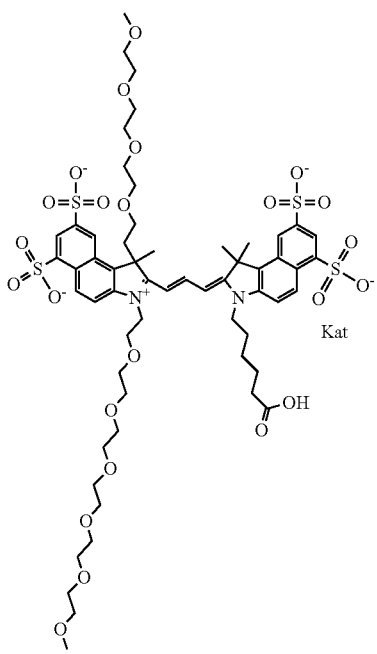 [SMILES: COCCOCCOCCOCCOCCOCC[N+]1=C(/C=C/C=C2/N(CCCCCC(=O)O)c3ccc4c(S(=O)(=O)[O-])cc(S(=O)(=O)[O-])cc4c3C2(C)C)C(C)(CCOCCOCCOCCOC)c2c1ccc1c(S(=O)(=O)[O-])cc(S(=O)(=O)[O-])cc21]

One non-limiting example of 579 Compound 6/2 (PEG$_4$) (2-((1E,3E)-3-(3-(5-carboxypentyl)-1,1-dimethyl-6,8-disulfonato-1H-benzo[e]indol-2(3H)-ylidene)prop-1-enyl)-1-methyl-3-(2,5,8,11,14,17-hexaoxanonadecan-19-yl)-1-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 579 Compound 6/2 (PEG$_4$) is activated as described above.

In embodiments, the degree and/or location of sulfonation is varied to, e.g., vary the compound's degree of hydrophilicity or hydrophobicity. One non-limiting example is a monosulfonate form of 579 Compound 1/2 (PEG$_4$), shown below:

One non-limiting example is a trisulfonate form of 579 Compound 1/2 (PEG$_4$), shown below:
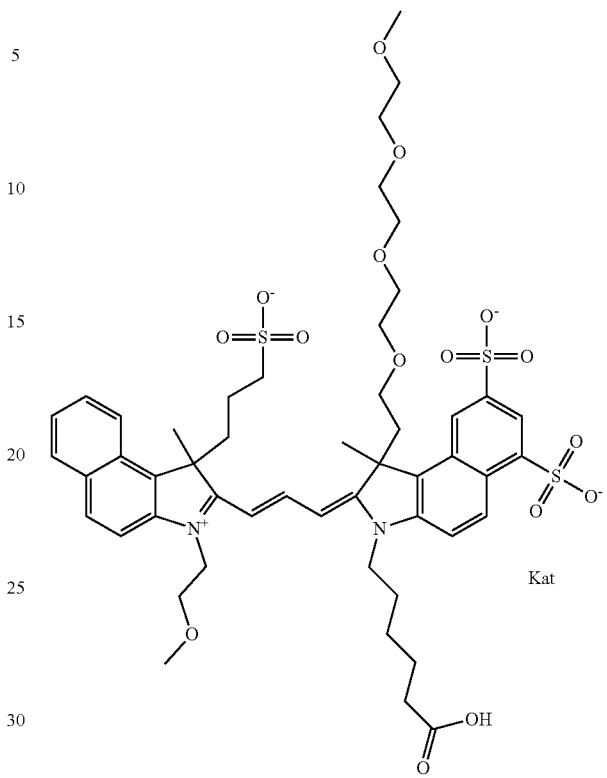
One non-limiting example is a disulfonate form of 579 Compound 1/2 (PEG$_4$), shown below:
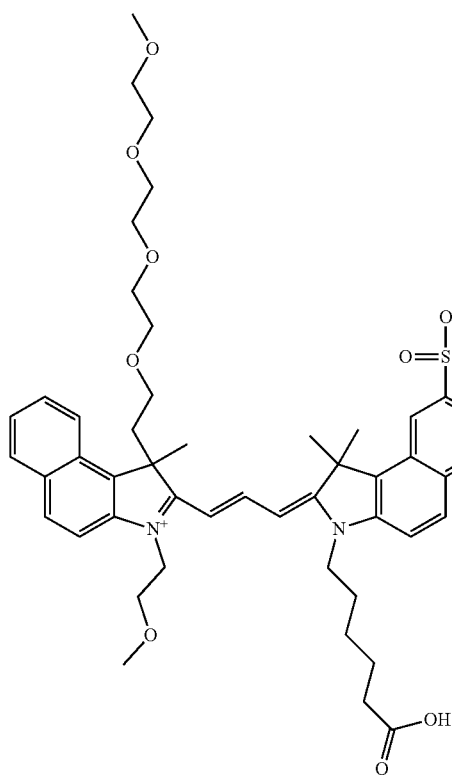
One non-limiting example is a tetrasulfonate form of 579 Compound 1/2 (PEG$_4$), shown below:
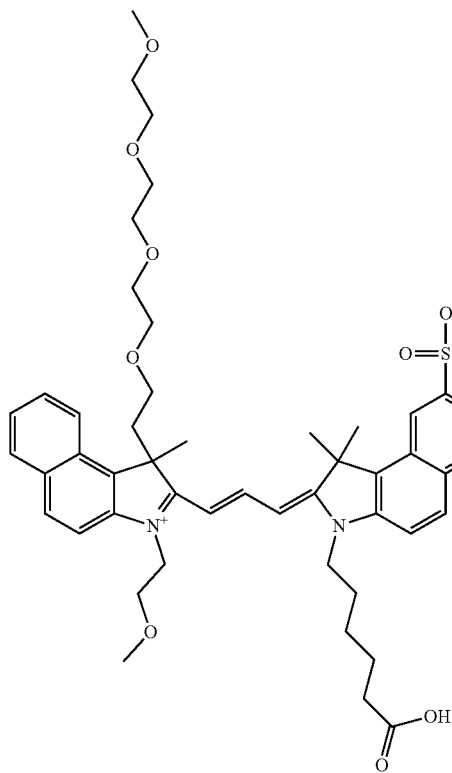
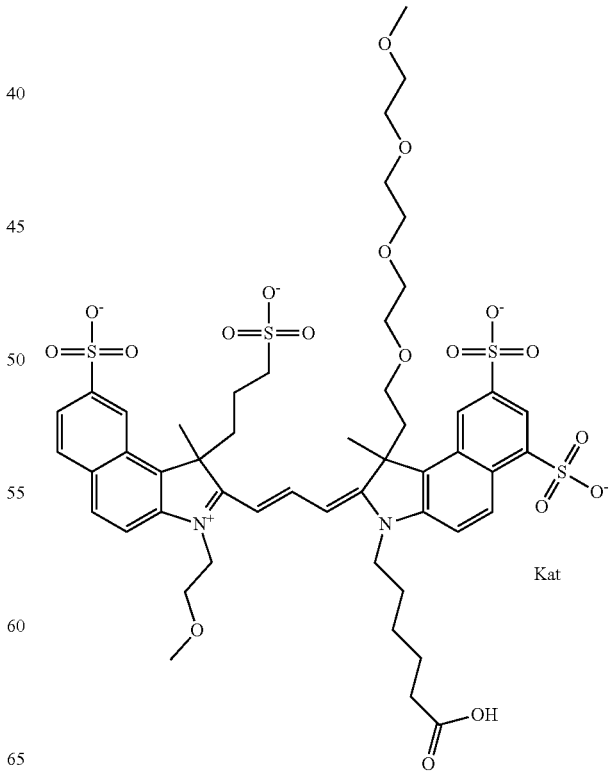

One non-limiting example is a pentasulfonate form of Compound 1/2 (PEG$_4$), shown below:

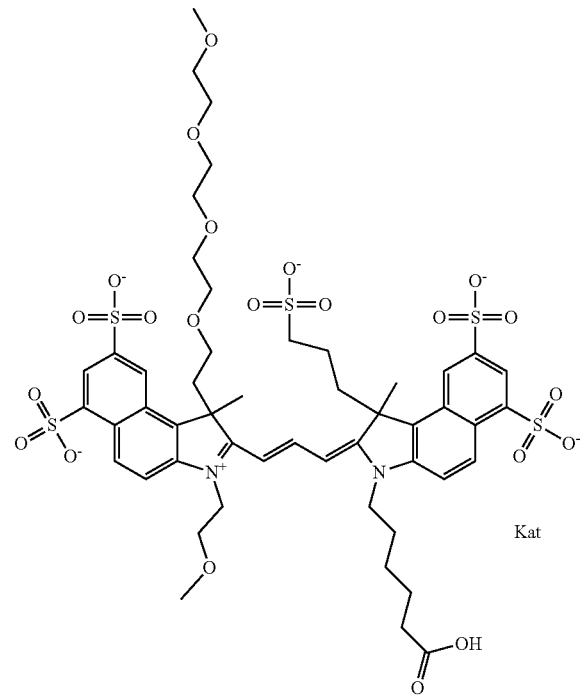 [SMILES: COCCOCCOCCOCCC1(C)C(/C=C/C=C2/N(CCCCCC(=O)O)c3ccc4c(S(=O)(=O)[O-])cc(S(=O)(=O)[O-])cc4c3C2(C)CCCS(=O)(=O)[O-])=[N+](CCOC)c2ccc3c(S(=O)(=O)[O-])cc(S(=O)(=O)[O-])cc3c21]

In embodiments, the compound contains one or more substitutions of the polymethine linker. In one embodiment, the compound has general formula IVa

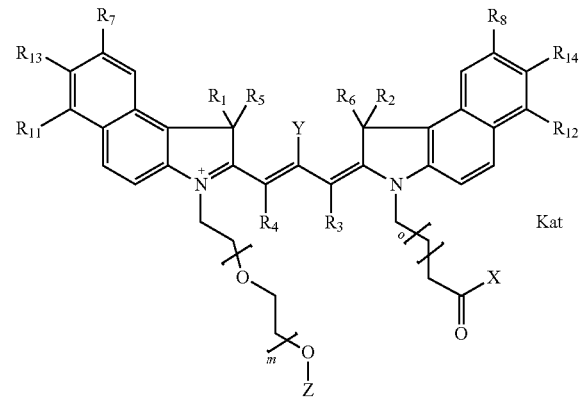

general formula IVb

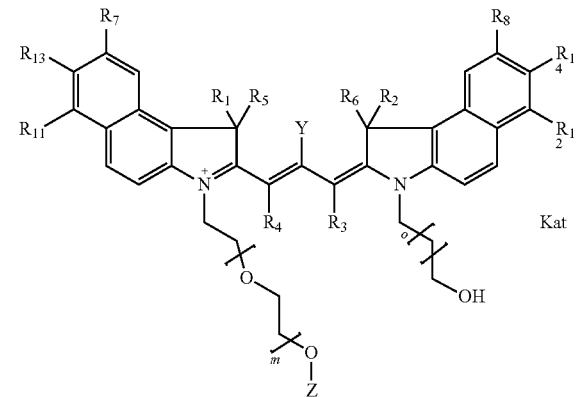

general formula IVc

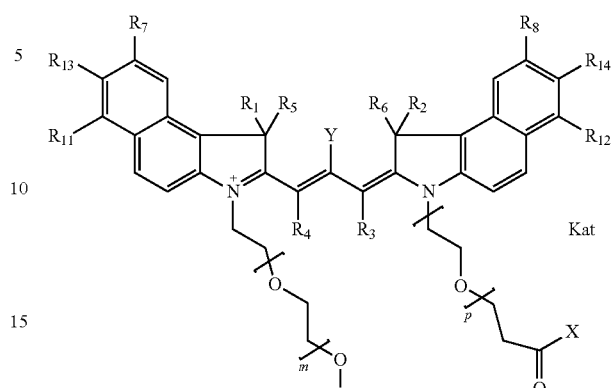

or general formula IVd

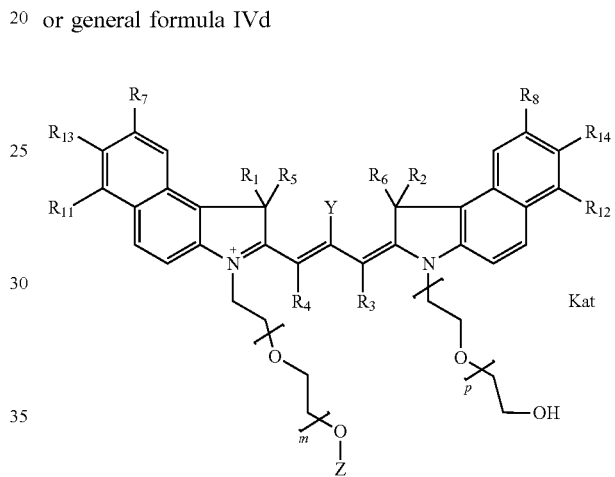

where each of $R^1$, $R^2$, $R^5$, and $R^6$ is the same or different and is independently selected from the group consisting of an aliphatic, heteroaliphatic, sulfoalkyl group, heteroaliphatic with terminal SO$_3$, a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, a sulfonamide group -L-SO$_2$NH—P—Z, and a caboxamide group -L-CONH—P—Z, and Z is selected from H, CH$_3$, a CH$_3$ group, an alkyl group, a heteroalkyl group, or —CO—NHS; each of $R^7$, $R^8$, $R^{11}$, $R^{12}$, $R^{13}$, and $R^{14}$ is the same or different and is independently selected from either H, SO$_3$, a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, a sulfonamide group -L-SO$_2$NH—P—Z, or a caboxamide group -L-CONH—P—Z, and Z is selected from H, a CH$_3$ group, an alkyl group, or a heteroalkyl group; X is selected from the group consisting of —OH, —SH, —NH$_2$, —NH—NH$_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—CH$_2$-1, imidazole, azide, —NR-L-O—NH$_2$, and —NR-L-O—CO—NHS, where R is —H or an aliphatic or heteroaliphatic group, and L is selected from the group consisting of a divalent linear (—(CH$_2$)$_t$—, t=0 to 15), crossed, or cyclic alkyl group optionally substituted by at least one oxygen atom and/or sulfur atom; Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive; p is an integer from 1 to 6 inclusive; each of R3 and R4 is the same or different and is independently hydrogen, an aliphatic group, a heteroaliphatic group, or a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, and Z is selected from H, a CH$_3$ group, an alkyl group, or a heteroalkyl group; or R3 and R4 together form a cyclic structure where R3 and R4 are joined using a divalent structural element selected from the group consisting of —(CH$_2$)$_q$—, —(CH$_2$)$_q$O(CH$_2$)$_{q'}$—, —(CH$_2$)$_q$S(CH$_2$)$_{q'}$—, —(CH$_2$)$_q$CH═CH—, and —OCH═CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy-, phenylmercapto function, and a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, and Z is selected from H, CH$_3$, a CH$_3$ group, an alkyl group, or a heteroalkyl group.

In one embodiment, the compound of general formula IV wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH$_2$)$_q$— and CH═CH, where q is an integer from 1 to 2 inclusive, to result in a 3-, 4-, or 5-membered ring.

In various embodiments, an ethylene glycol group, diethylene glycol group, and/or a polyethylene glycol group, which will collectively be referred to as a PEG group, unless specifically defined, may be present at position(s) in addition to such groups being present on the N atom(s) of the indole structure. One non-limiting example of an additionally PEG-substituted compound is a 579 Compound 1/2 according to general formula II where R1 is an ethylene glycol group (PEG$_1$) terminating with a methyl group, shown below:

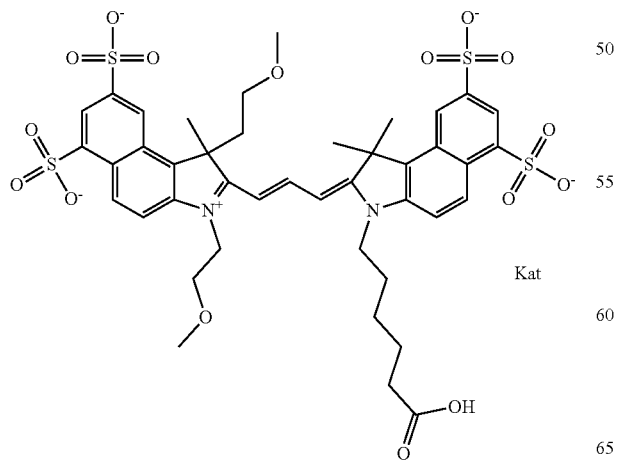

One non-limiting example of an additionally PEG-substituted compound is a 579 Compound 1/2 according to general formula II where R2 is an ethylene glycol group (PEG$_1$) terminating with a methyl group, shown below:

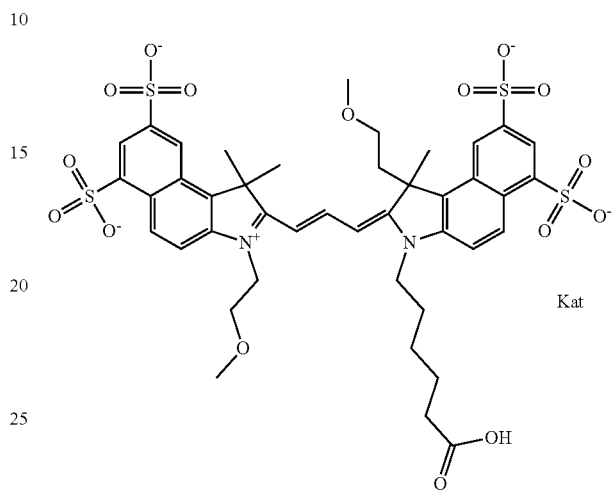

One non-limiting example of an additionally PEG-substituted compound is a 579 Compound 1/2 according to general formula II where R8 is an ethylene glycol group (PEG$_1$) terminating with a methyl group, shown below:

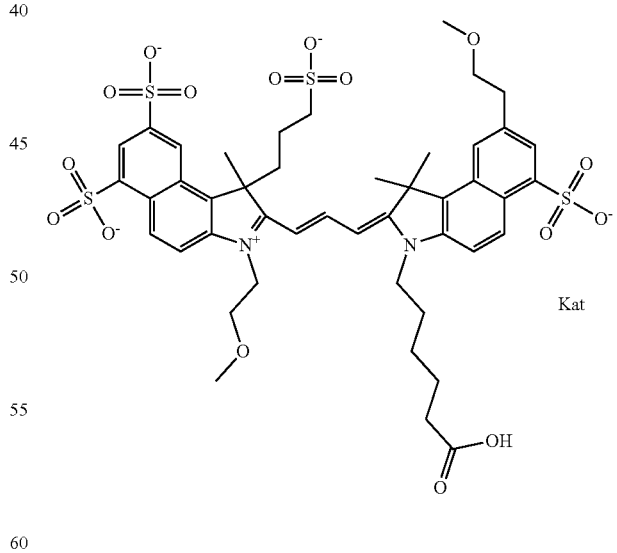

One non-limiting example of an additionally PEG-substituted compound is a 579 Compound 1/2 according to general formula II where R8 is a sulfonamide group with an ethylene glycol group (PEG$_1$) terminating with a methyl group, shown below:

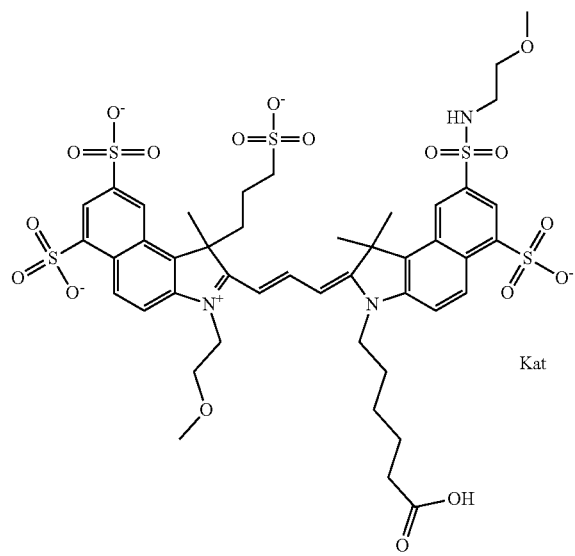

One non-limiting example of an additionally PEG-substituted compound is a 579 Compound 1/2 according to general formula II where R8 is a carboxamide group with an ethylene glycol group (PEG$_1$) terminating with a methyl group, shown below:

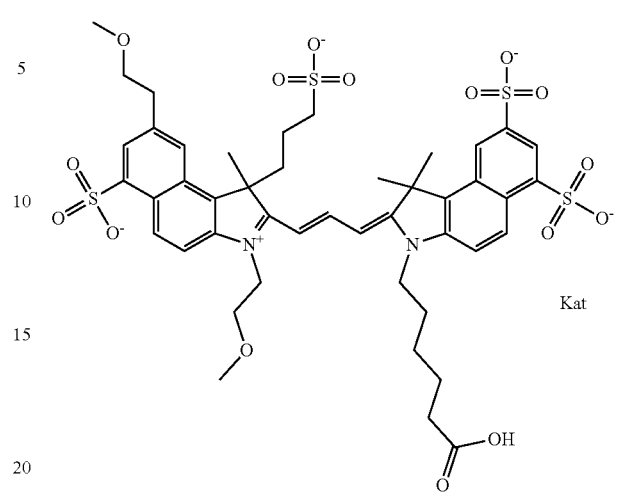

One non-limiting example of an additionally PEG-substituted compound is a 579 Compound 1/2 according to general formula II where R7 is a sulfonamide group with an ethylene glycol group (PEG$_1$) terminating with a methyl group, shown below:

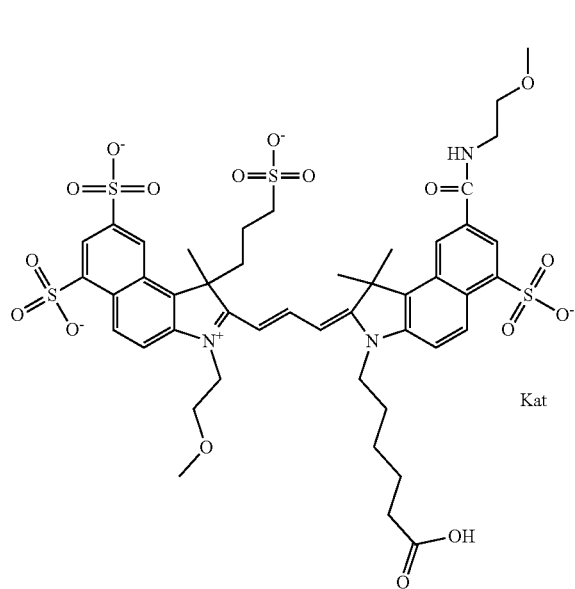

One non-limiting example of an additionally PEG-substituted compound is a 579 Compound 1/2 according to general formula II where R7 is an ethylene glycol group (PEG$_1$) terminating with a methyl group, shown below:

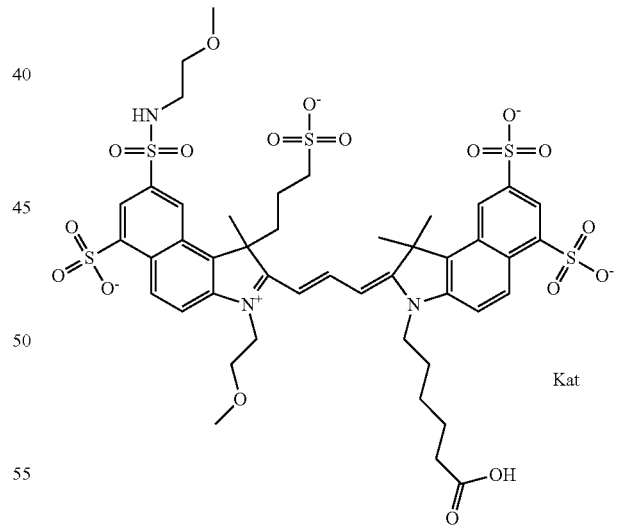

One non-limiting example of an additionally PEG-substituted compound is a 579 Compound 1/2 according to general formula II where R7 is a carboxamide group with an ethylene glycol group (PEG$_1$) terminating with a methyl group, shown below:

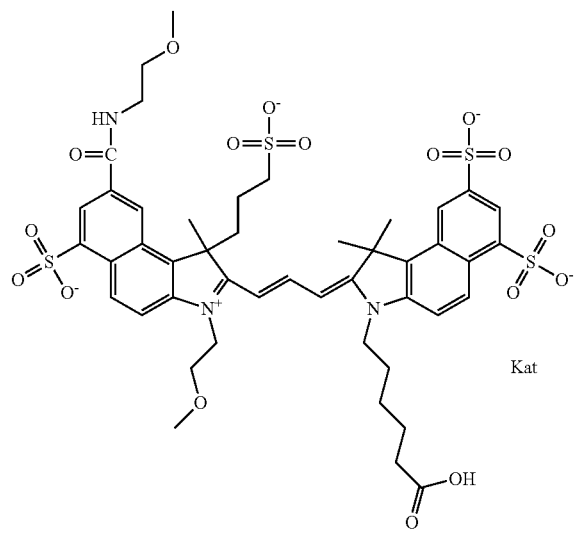

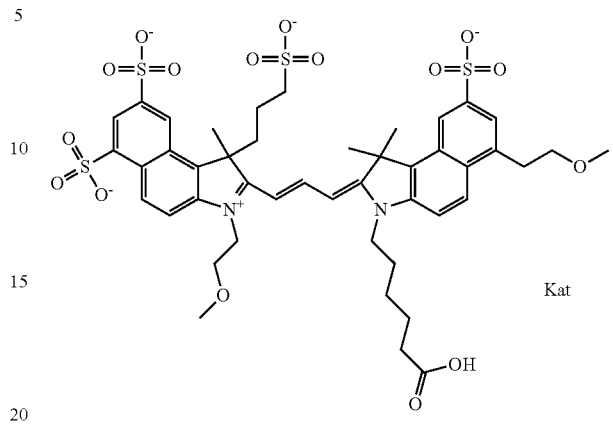

One non-limiting example of an additionally PEG-substituted compound is a 579 Compound 1/2 according to general formula II where R12 is an ethylene glycol group terminating with a methyl group, One non-limiting example of an additionally PEG-substituted compound is a 579 Compound 1/2 according to general formula II where R12 is a sulfonamide group with an ethylene glycol group (PEG$_1$) terminating with a methyl group, shown below:

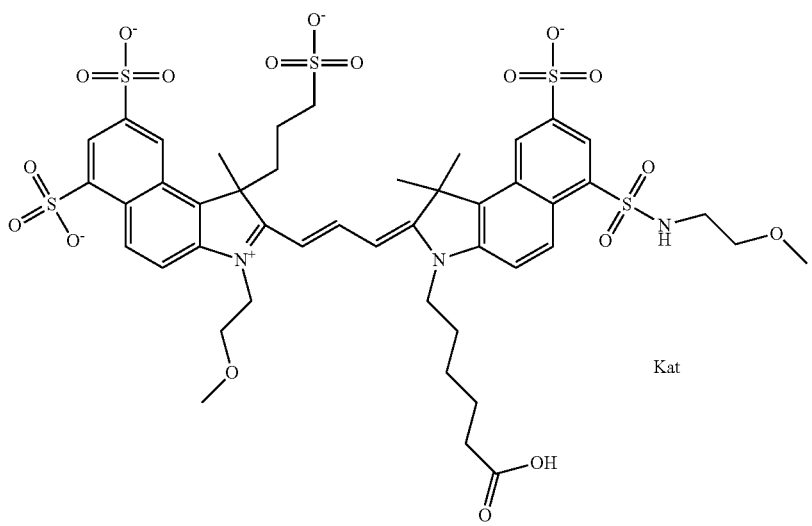

One non-limiting example of an additionally PEG-substituted compound is a 579 Compound 1/2 according to general formula II where R12 is a carboxamide group with an ethylene glycol group (PEG$_1$) terminating with a methyl group, shown below:

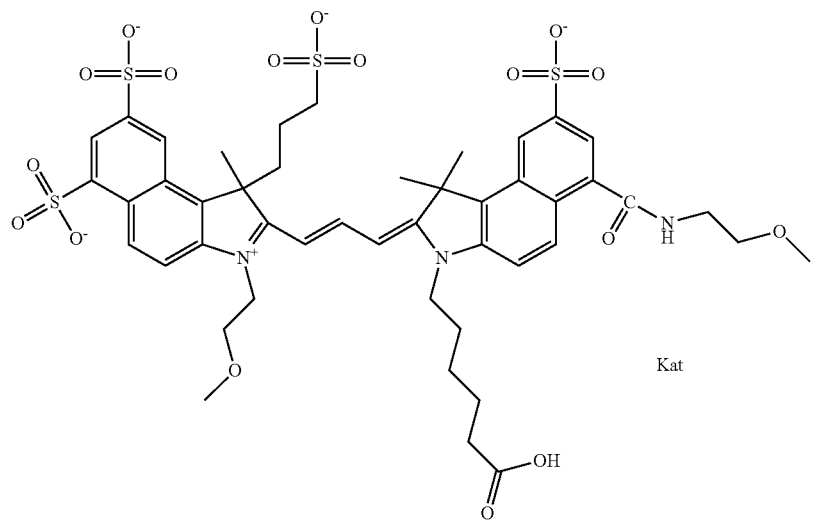

One non-limiting example of an additionally PEG-substituted compound is a 579 Compound 1/2 according to general formula II where R11 is an ethylene glycol group terminating with a methyl group, shown below:

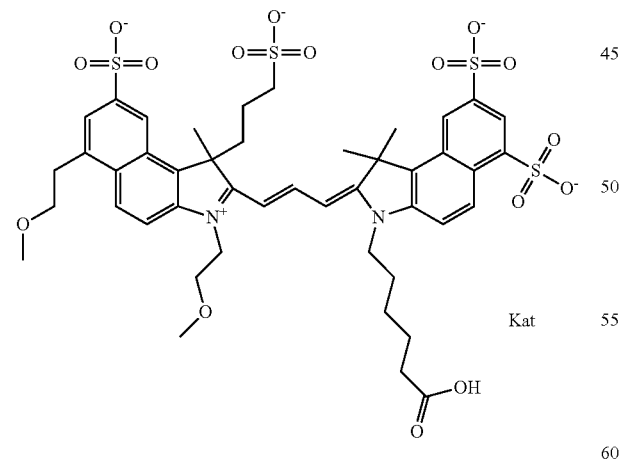

One non-limiting example of an additionally PEG-substituted compound is a 579 Compound 1/2 according to general formula II where R11 is a sulfonamide group with an ethylene glycol group (PEG$_1$) terminating with a methyl group, shown below:

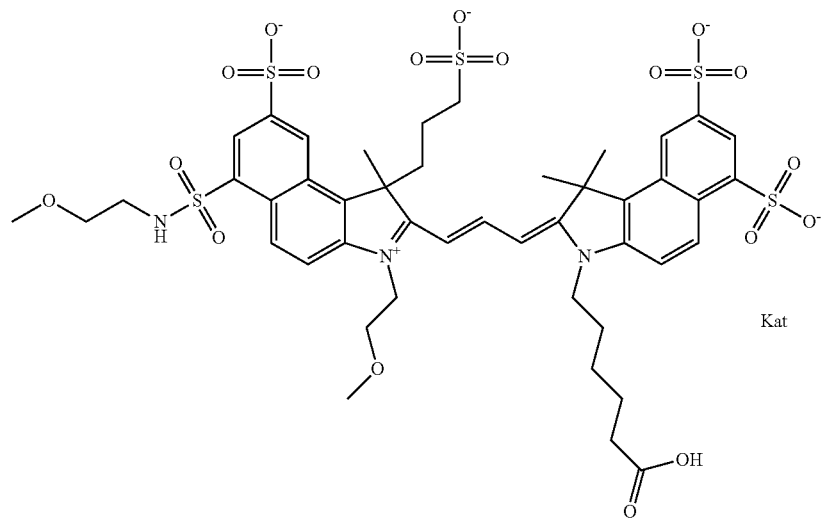
One non-limiting example of an additionally PEG-substituted compound is a 579 Compound 1/2 according to general formula II where R11 is a carboxamide group with an ethylene glycol group (PEG$_1$) terminating with a methyl group, shown below:
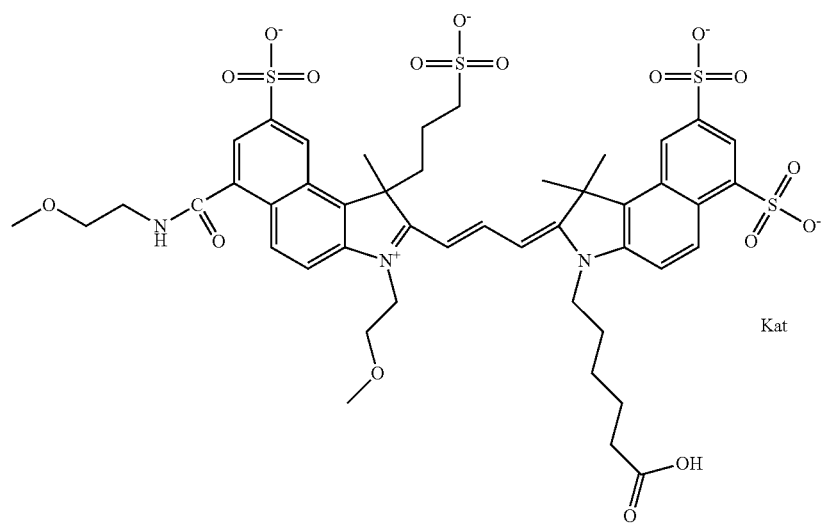

One non-limiting example of an additionally PEG-substituted compound is a 579 Compound 1/2 according to general formula II where R14 is an ethylene glycol group terminating with a methyl group,

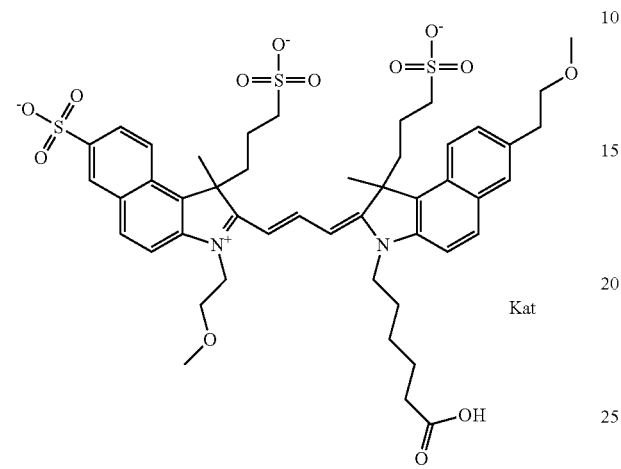

One non-limiting example of an additionally PEG-substituted compound is a 579 Compound 1/2 according to general formula II where R14 is a sulfonamide group with an ethylene glycol group (PEG$_1$) terminating with a methyl group, shown below:

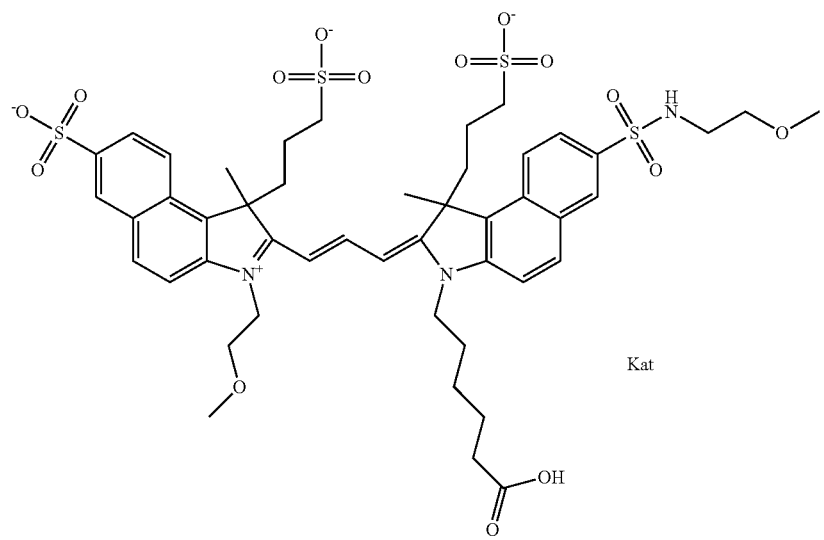

One non-limiting example of an additionally PEG-substituted compound is a 579 Compound 1/2 according to general formula II where R14 is a carboxamide group with an ethylene glycol group (PEG$_1$) terminating with a methyl group, shown below:

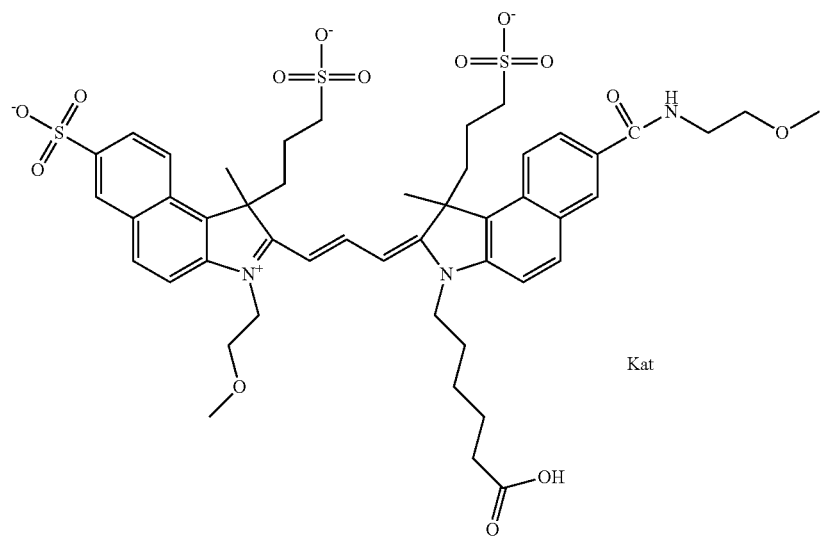

One non-limiting example of an additionally PEG-substituted compound is a 579 Compound 1/2 according to general formula II where R13 is an ethylene glycol group terminating with a methyl group, shown below:

One non-limiting example of an additionally PEG-substituted compound is a 579 Compound 1/2 according to general formula II where R13 is a sulfonamide group with an ethylene glycol group (PEG$_1$) terminating with a methyl group, shown below:

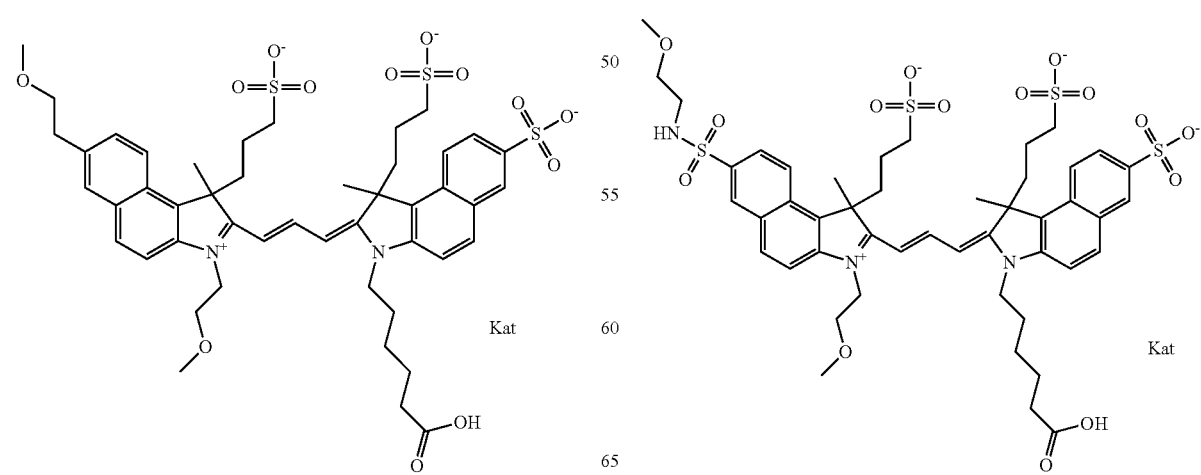

One non-limiting example of an additionally PEG-substituted compound is a 579 Compound 1/2 according to general formula II where R13 is a carboxamide group with an ethylene glycol group (PEG$_1$) terminating with a methyl group, shown below:

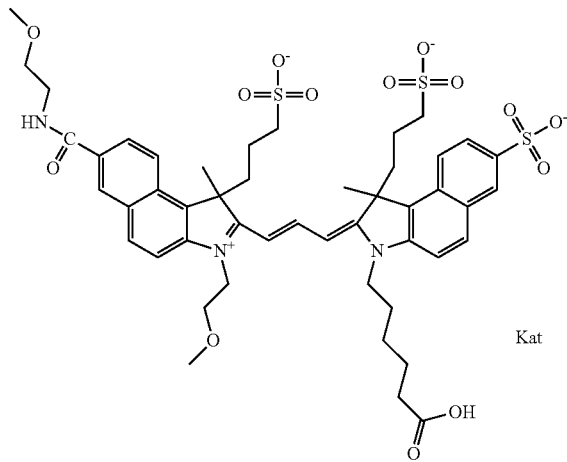

In one embodiment, the compound is 679 Compound 1

679 Compound 1 (6-((E)-2-((2E,4E)-5-(3-(2-methoxyethyl)-1-methyl-6,8-disulfonato-1-(3-sulfonatopropyl)-1H-benzo[e]indol-3-ium-2-yl)penta-2,4-dien-1-ylidene)-1,1-dimethyl-6,8-disulfonato-1H-benzo[e]indol-3(2H)-yl)hexanoate) contains an ethylene glycol on the indole N of the left heterocycle, i.e., a methylated ethylene glycol. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 679 Compound 1, but one skilled in the art appreciates that activation is not limited to these examples. One non-limiting example of an activated compound is the NHS-ester of 679 Compound 1, shown below:

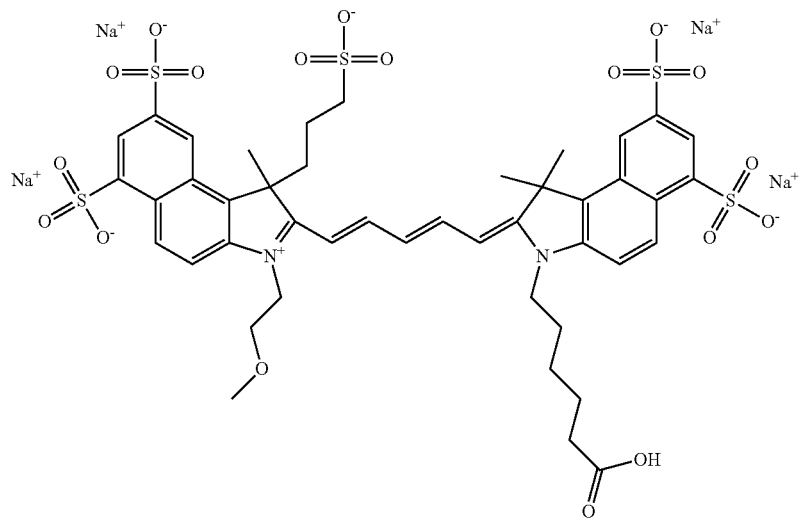 [SMILES: [Na+] ; COCC[N+]1=C(/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21 ; [Na+] ; [Na+] ; [Na+]]

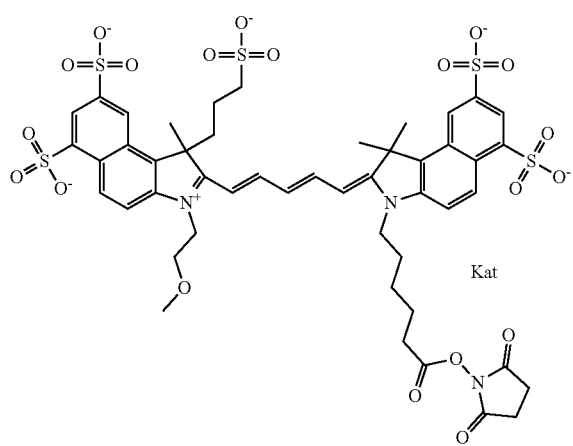 [SMILES: COCC[N+]1=C(/C=C/C=C/C=C2/N(CCOCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of a NHS-ester of 679 Compound 1, according to general formula III, where m=1 and p=1, is shown below:

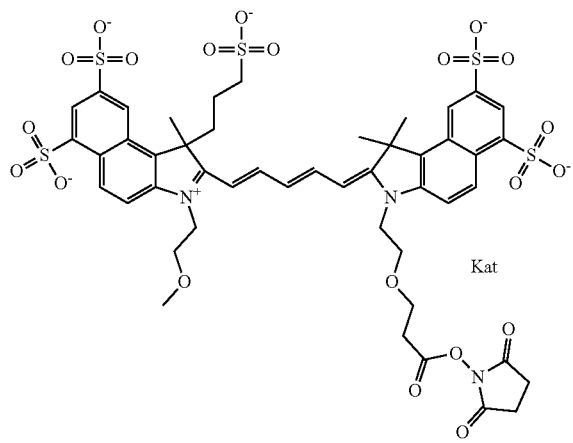

One non-limiting example of a NHS-ester of 679 Compound 1, according to general formula III, where m=1 and p=2, is shown below:

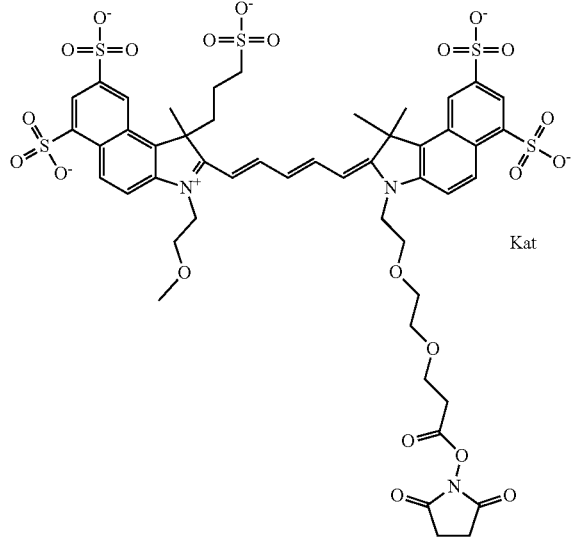

One non-limiting example of a NHS-ester of 679 Compound 1, according to general formula III, where m=1 and p=3, is shown below:

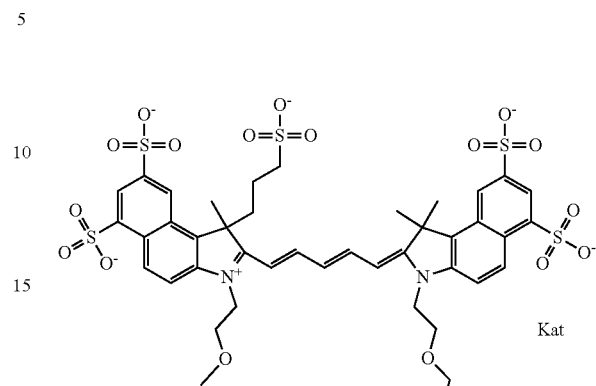

One non-limiting example of a NHS-ester of 679 Compound 1, according to general formula III, where m=1 and p=4, is shown below:

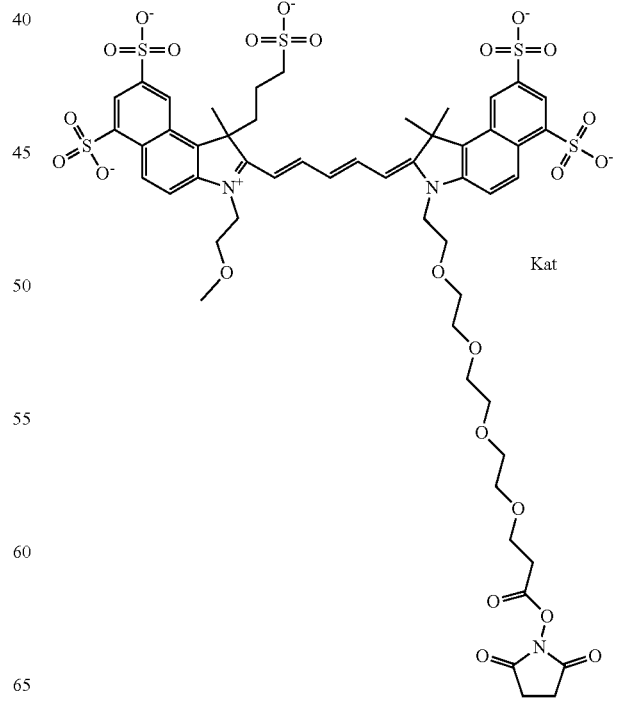

One non-limiting example of a NHS-ester of 679 Compound 1, according to general formula III, where m=1 and p=5, is shown below:
One non-limiting example of a NHS-ester of 679 Compound 1, according to general formula III, where m=1 and p=6, is shown below:
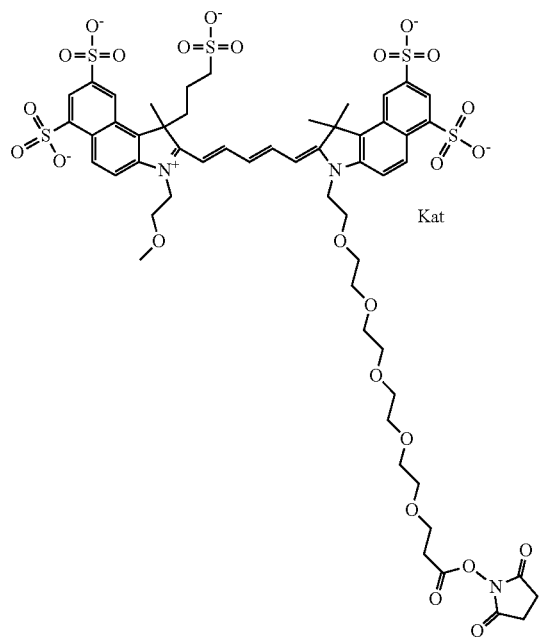
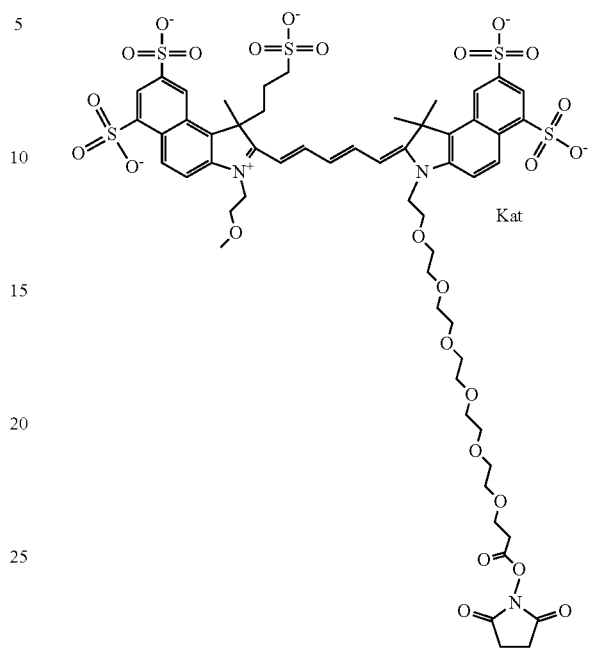
One non-limiting example of an activated 679 Compound 1 is a tetrafluorophenyl (TFP)-ester form of 679 Compound 1, shown below:
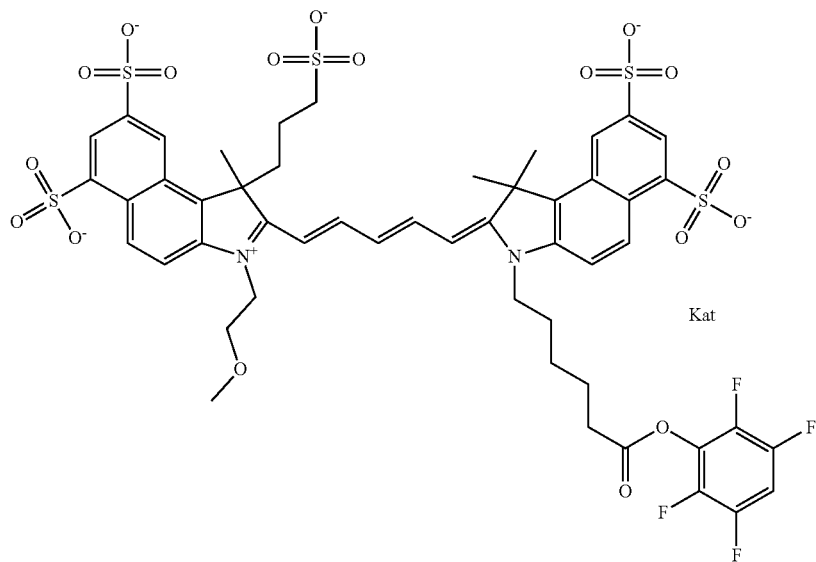 [SMILES: COCC[N+]1=C(/C=C/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of an activated 679 Compound 1 is a sulfotetrafluorophenyl (STP)-ester form of 679 Compound 1, shown below:
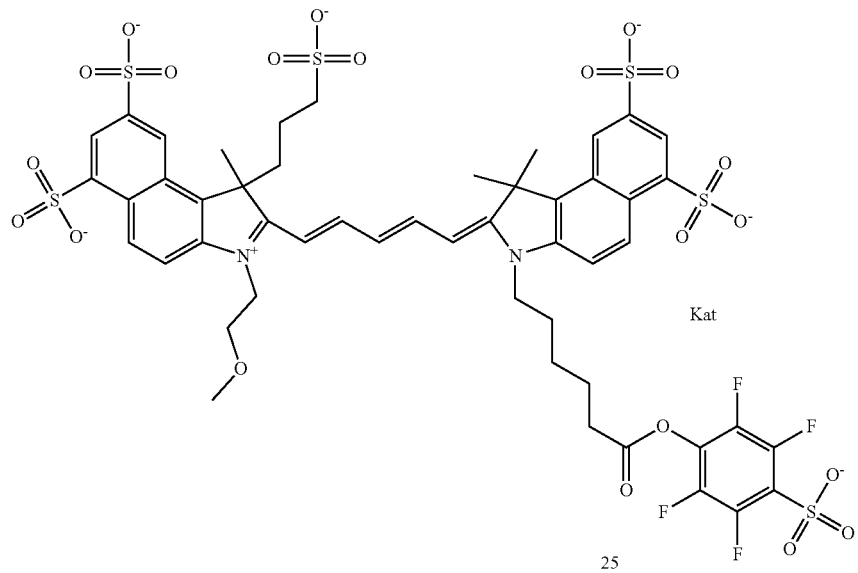
One non-limiting example of an activated 679 Compound 1 is a hydrazide form of 679 Compound 1,
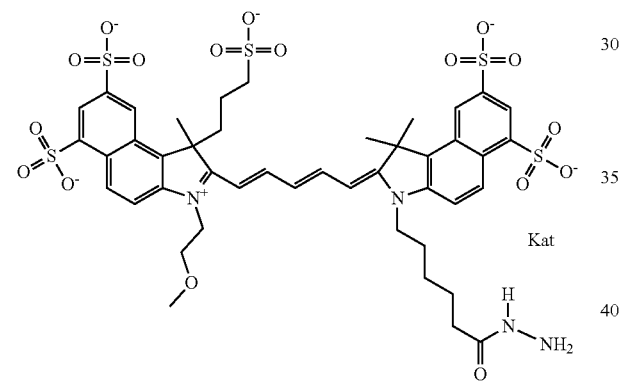
One non-limiting example of an activated 679 Compound 1 is a maleimide form of 679 Compound 1, shown below:
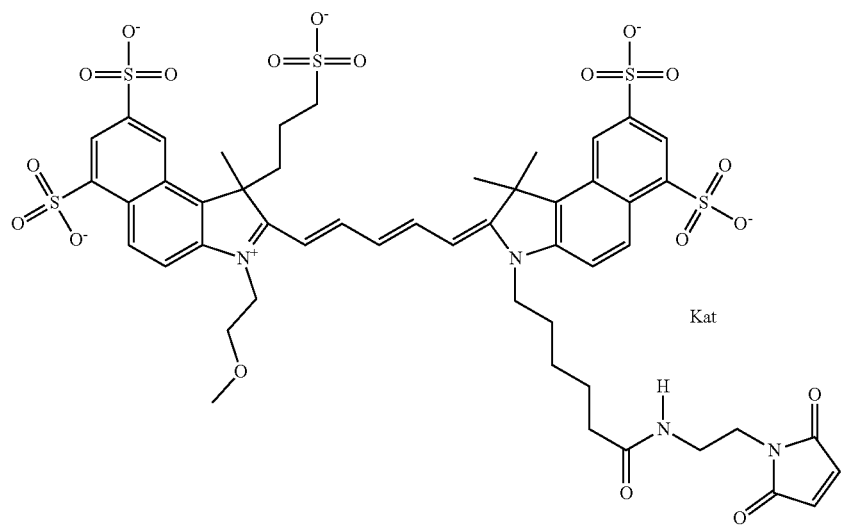 [SMILES: COCC[N+]1=C(/C=C/C=C/C=C2/N(CCCCCC(=O)NCCN3C(=O)C=CC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

In one embodiment, the compound is 679 Compound 2

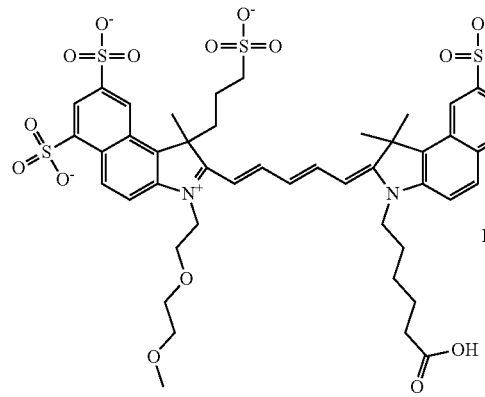

679 Compound 2 (6-((E)-2-((2E,4E)-5-(3-(2-(2-methoxyethoxy)ethyl)-1-methyl-6,8-disulfonato-1-(3-sulfonatopropyl)-1H-benzo[e]indol-3-ium-2-yl)penta-2,4-dien-1-ylidene)-1,1-dimethyl-6,8-disulfonato-1H-benzo[e]indol-3(2H)-yl)hexanoate) contains a diethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 2 is activated as described above.

In one embodiment, the compound is 679 Compound 3

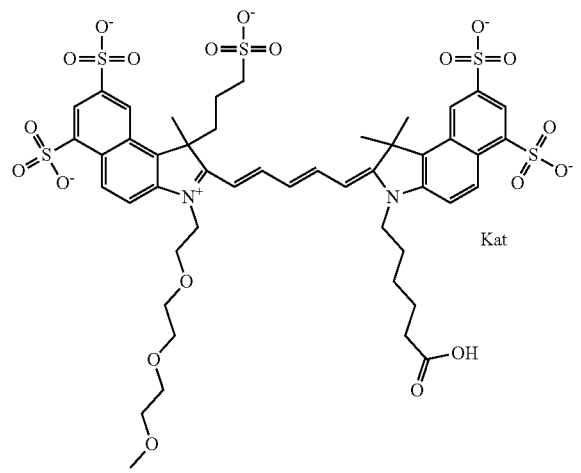 [SMILES: COCCOCCOCC[N+]1=C(/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

679 Compound 3 (6-((E)-2-((2E,4E)-5-(3-(2-(2-(2-methoxyethoxy)ethoxy)ethyl)-1-methyl-6,8-disulfonato-1-(3-sulfonatopropyl)-1H-benzo[e]indol-3-ium-2-yl)penta-2,4-dien-1-ylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 3 is activated as described above.

In one embodiment, the compound is 679 Compound 4

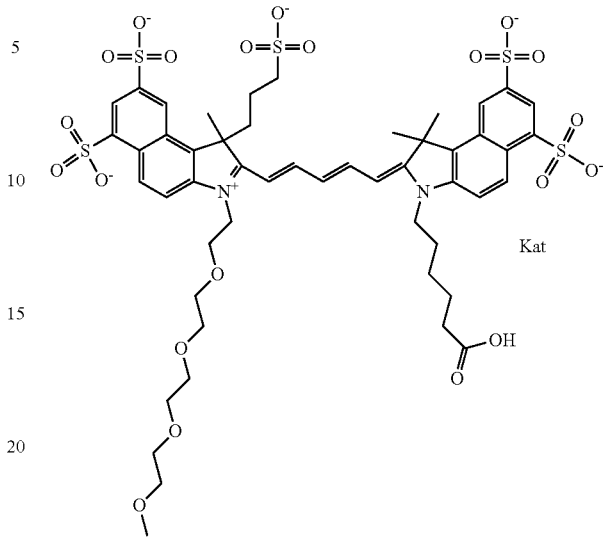

679 Compound 4 (6-((E)-1,1-dimethyl-2-((2E,4E)-5-(1-methyl-6,8-disulfonato-1-(3-sulfonatopropyl)-3-(2,5,8,11-tetraoxatridecan-13-yl)-1H-benzo[e]indol-3-ium-2-yl)penta-2,4-dien-1-ylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 679 Compound 4 is activated as described above.

In one embodiment, the compound is 679 Compound 5

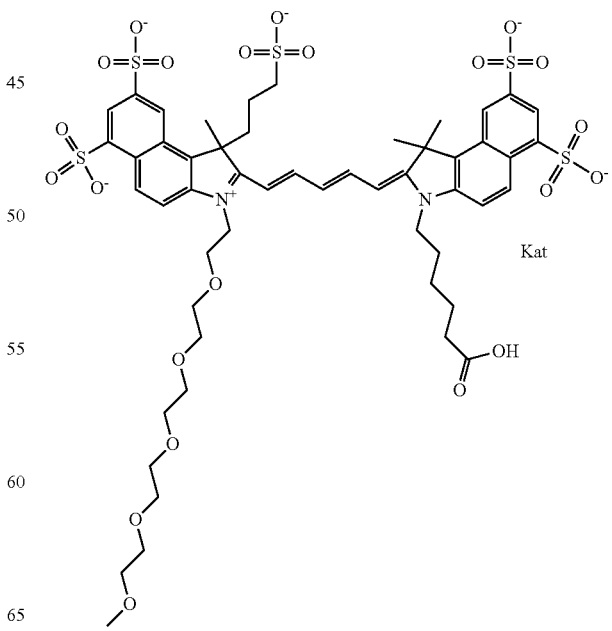

679 Compound 5 (6-((E)-2-((2E,4E)-5-(3-(2,5,8,11,14-pentaoxahexadecan-16-yl)-1-methyl-6,8-disulfonato-1-(3-sulfonatopropyl)-1H-benzo[e]indol-3-ium-2-yl)penta-2,4-dien-1-ylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 5 is activated as described above.

In one embodiment, the compound is 679 Compound 6

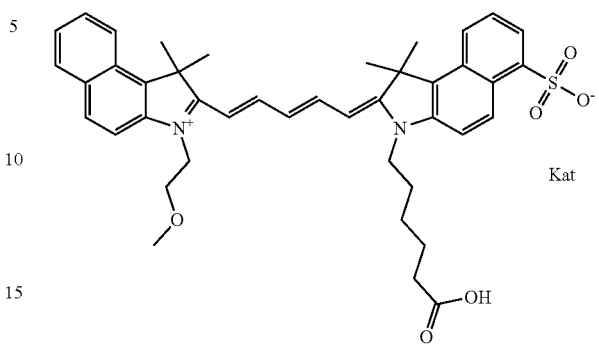

679 Compound 6 (6-((E)-1,1-dimethyl-2-((2E,4E)-5-(1-methyl-3-(2,5,8,11,14,17-hexaoxanonadecan-19-yl)-6,8-disulfonato-1-(3-sulfonatopropyl)-1H-benzo[e]indol-3-ium-2-yl)penta-2,4-dien-1-ylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 649 Compound 6 is activated as described above.

In embodiments, the degree and/or location of sulfonation is varied to, e.g., vary the compound's degree of hydrophilicity or hydrophobicity. One non-limiting example is a monosulfonate form of 679 Compound 1, shown below:

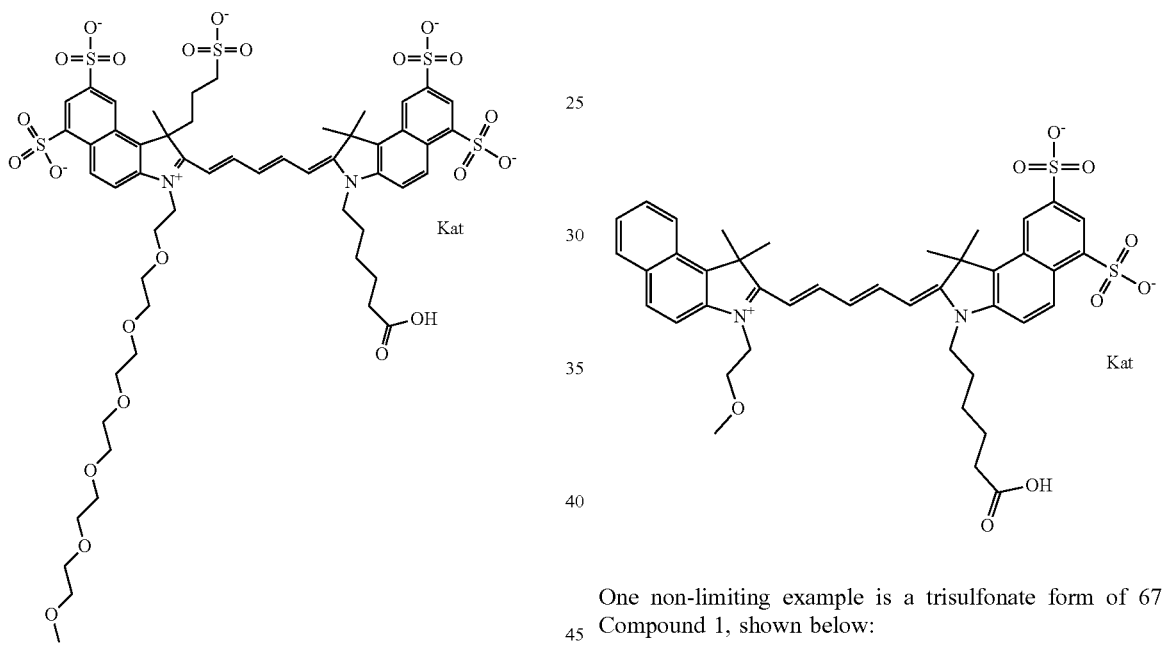

One non-limiting example is a disulfonate form of 679 Compound 1, shown below:

One non-limiting example is a trisulfonate form of 679 Compound 1, shown below:

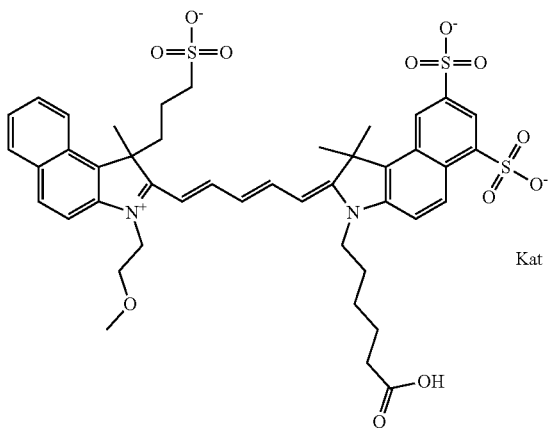 [SMILES: COCC[N+]1=C(/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1ccccc21]

One non-limiting example is a tetrasulfonate form of 679 Compound 1, shown below:
In one embodiment, the compound is 679 Compound 1/2 (PEG$_4$)
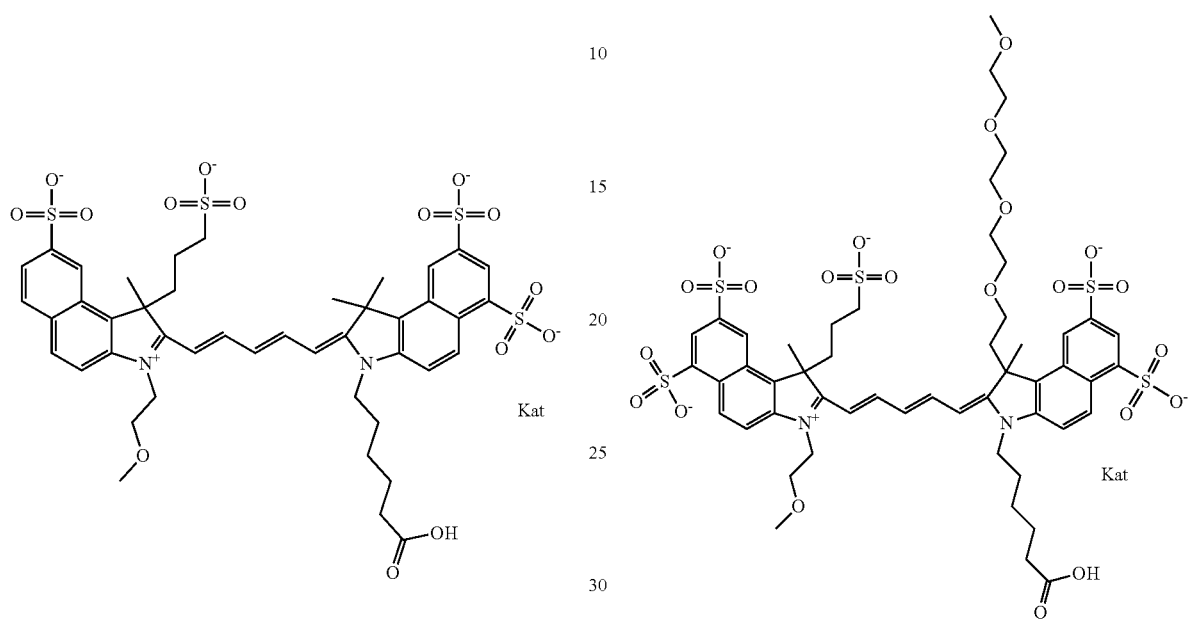
One non-limiting example is a pentasulfonate form of 679 Compound 1, shown below:
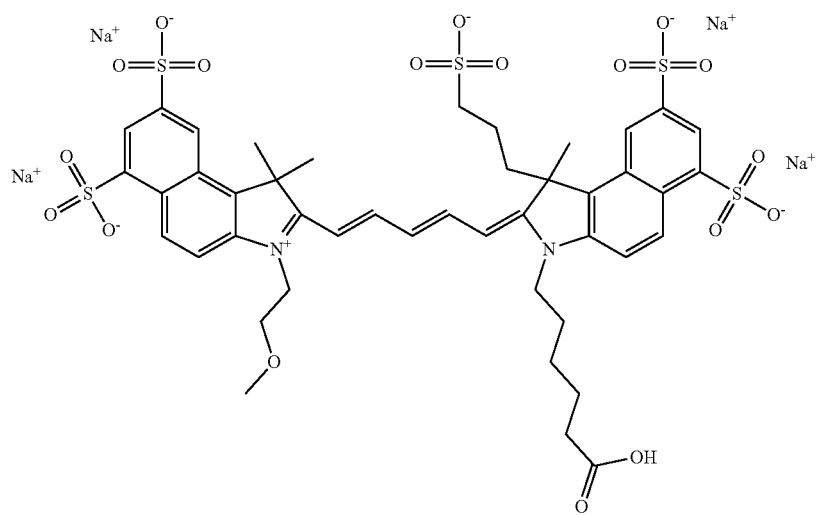 [SMILES: [Na+] ; COCC[N+]1=C(/C=C/C=C/C=C2/N(CCCCCC(=O)O)c3ccc4c(S(=O)(=O)[O-])cc(S(=O)(=O)[O-])cc4c3C2(C)CCCS(=O)(=O)[O-])C(C)(C)c2c1ccc1c(S(=O)(=O)[O-])cc(S(=O)(=O)[O-])cc21 ; [Na+] ; [Na+] ; [Na+]]

One non-limiting example of 679 Compound 1/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-(2-methoxyethyl)-1-methyl-1-(3-sulfonatopropyl)-1H-benzo[e]indolium-6,8-disulfonate) contains an ethylene glycol on the indole N of the left heterocycle, i.e., a methylated ethylene glycol, and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 679 Compound 1/2 (PEG$_4$), but one skilled in the art appreciates that activation is not limited to these examples. One non-limiting example of an activated compound is the NHS-ester of 679 Compound 1/2 (PEG$_4$), shown below:

One non-limiting example of a NHS-ester of 679 Compound 1/3 (PEG$_4$), according to general formula III, where m=1 and p=1, is shown below:

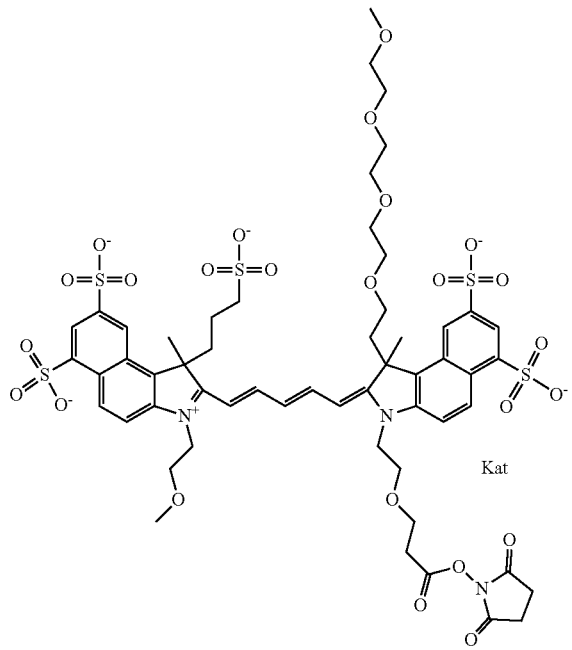

One non-limiting example of a NHS-ester of 679 Compound 1/3 (PEG$_4$), according to general formula III, where m=1 and p=2, is shown below:

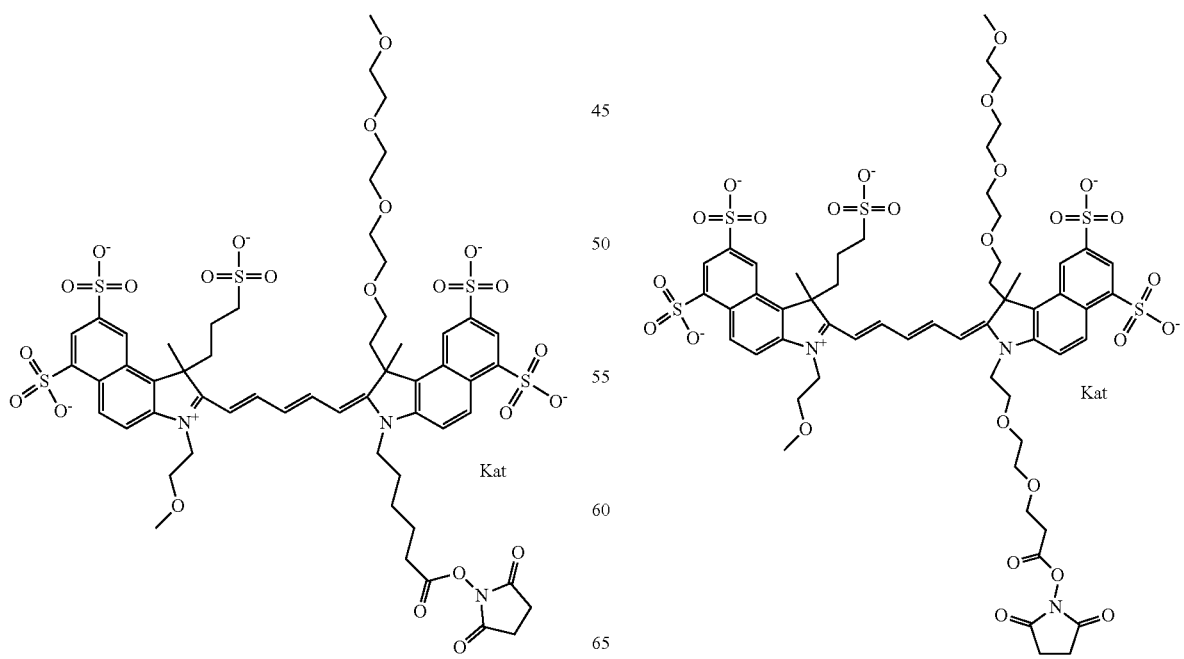

81

One non-limiting example of a NHS-ester of 679 Compound 1/3 (PEG$_4$), according to general formula III, where m=1 and p=3, is shown below:

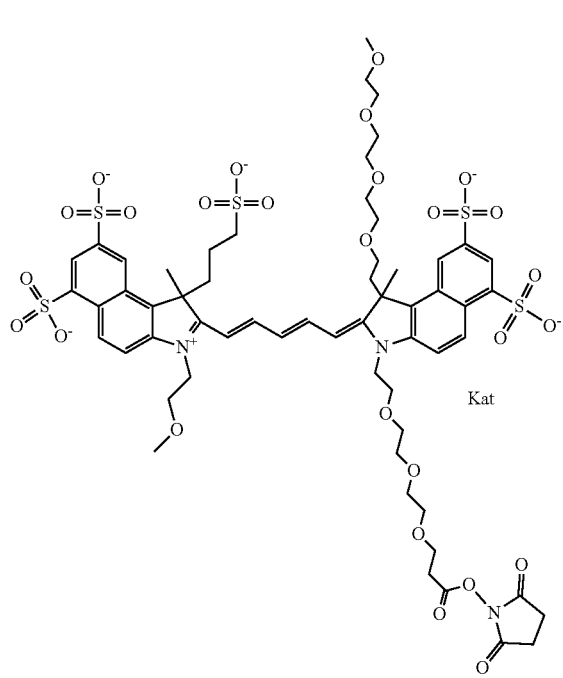

One non-limiting example of a NHS-ester of 679 Compound 1/3 (PEG$_4$), according to general formula III, where m=1 and p=4, is shown below:

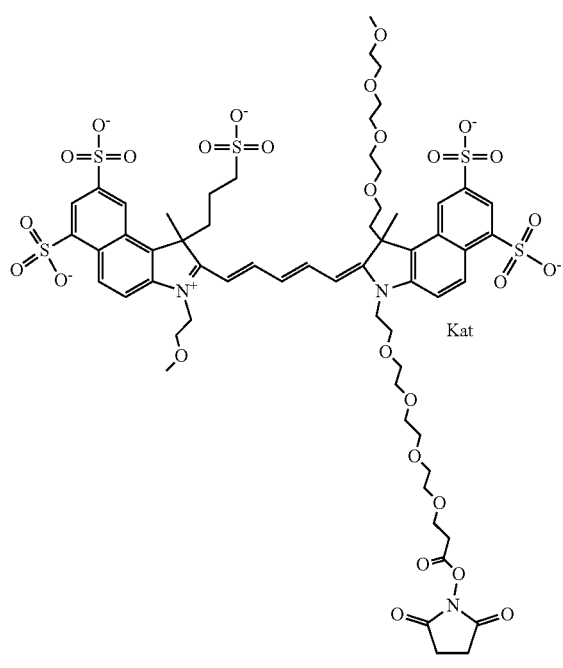

82

One non-limiting example of a NHS-ester of 679 Compound 1/3 (PEG$_4$), according to general formula III, where m=1 and p=5, is shown below:

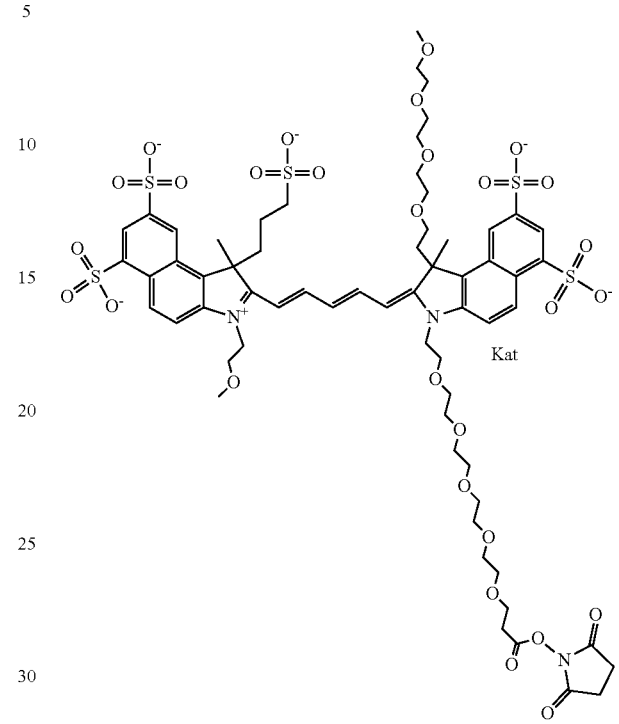

One non-limiting example of a NHS-ester of 679 Compound 1/3 (PEG$_4$), according to general formula III, where m=1 and p=6, is shown below:

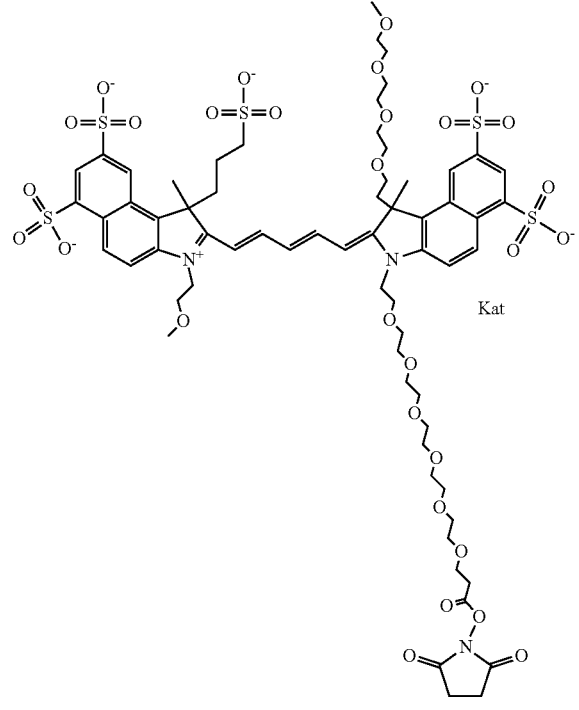

One non-limiting example of an activated 679 Compound 1/2 (PEG$_4$) is a tetrafluorophenyl (TFP)-ester form of 679 Compound 1, shown below:

One non-limiting example of an activated 679 Compound 1/2 (PEG$_4$) is a hydrazide form of 679 Compound 1, shown below:

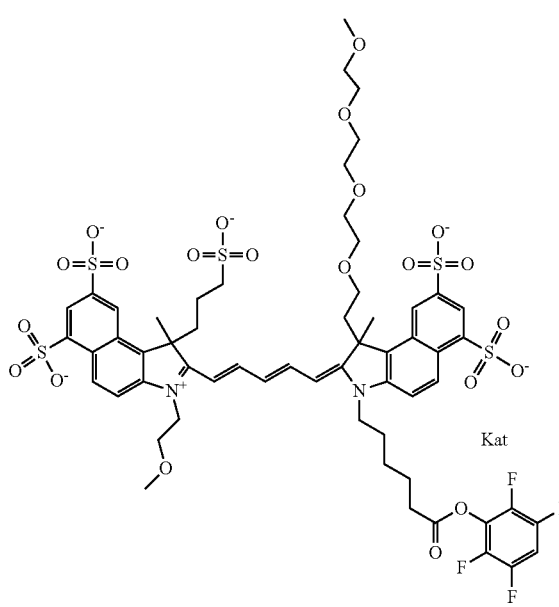

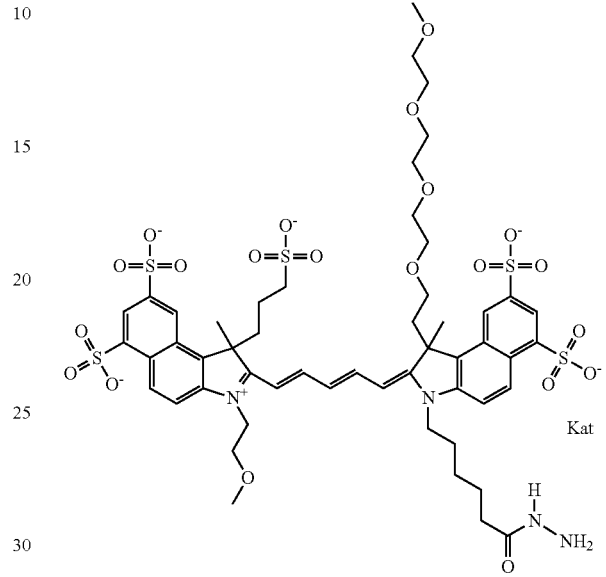

One non-limiting example of an activated 679 Compound 1/2 (PEG$_4$) is a sulfotetrafluorophenyl (STP)-ester form of 679 Compound 1, shown below:

One non-limiting example of an activated 679 Compound 1/2 (PEG$_4$) is a maleimide form of 679 Compound 1, shown below:

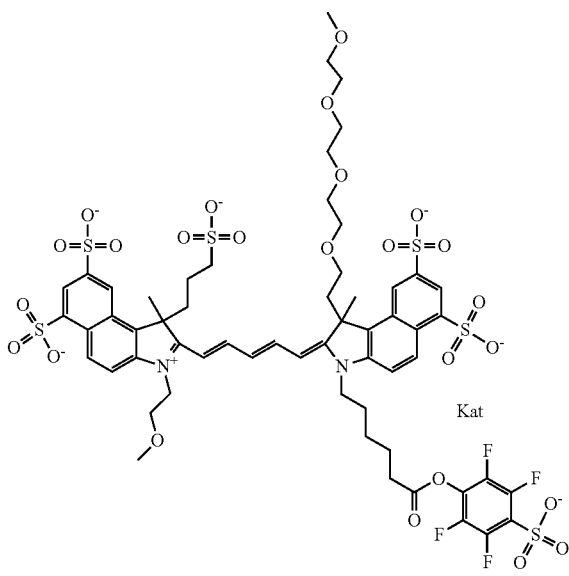 [SMILES: COCCOCCOCCOCCC1(C)\C(=C/C=C/C=C/C2=[N+](CCOC)c3ccc4c(S(=O)(=O)[O-])cc(S(=O)(=O)[O-])cc4c3C2(C)CCCS(=O)(=O)[O-])N(CCCCCC(=O)Oc2c(F)c(F)c(S(=O)(=O)[O-])c(F)c2F)c2ccc3c(S(=O)(=O)[O-])cc(S(=O)(=O)[O-])cc3c21]

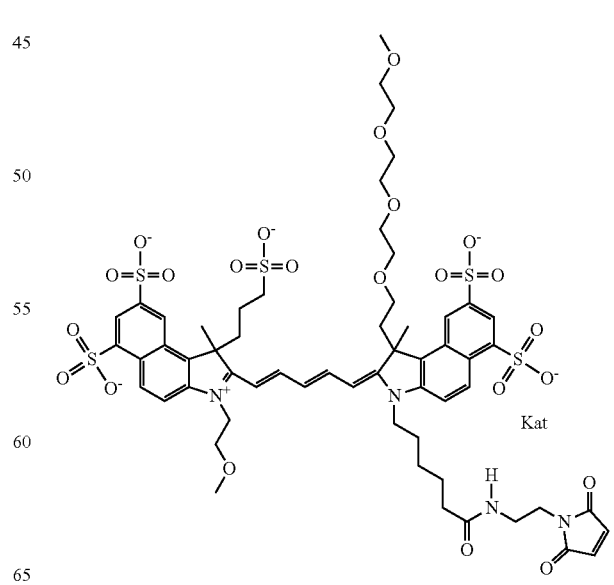

In one embodiment, the compound is 679 Compound 2/2 (PEG$_4$)

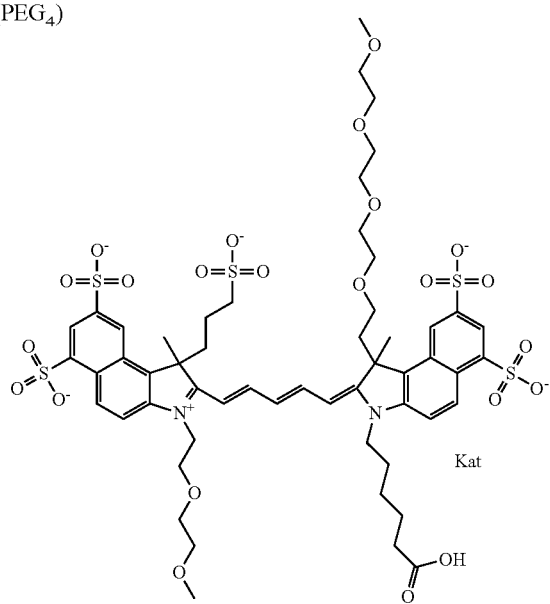

One non-limiting example of 679 Compound 2/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-(2-(2-methoxyethoxy)ethyl)-1-methyl-1-(3-sulfonatopropyl)-1H-benzo[e] indolium-6,8-disulfonate) contains a diethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 2/2 (PEG$_4$) is activated as described above.

In one embodiment, the compound is 679 Compound 3/2 (PEG$_4$)

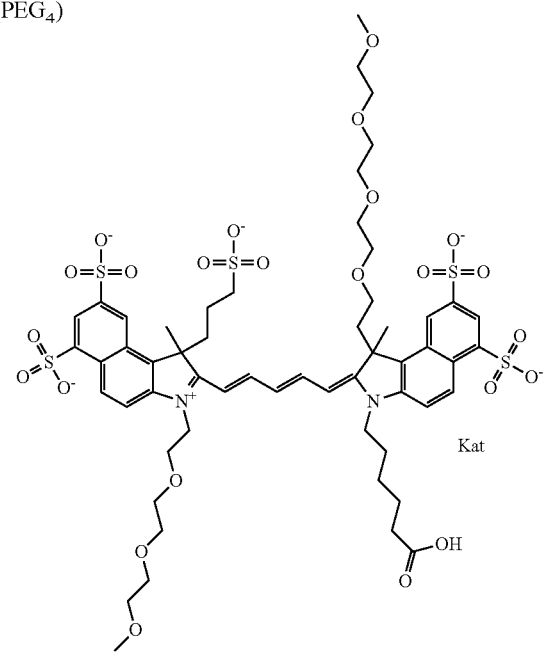

One non-limiting example of 679 Compound 3/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-(2-(2-(2-methoxyethoxy)ethoxy)ethyl)-1-methyl-1-(3-sulfonatopropyl)-1H-benzo[e]indolium-6,8-disulfonate) contains a (poly) ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 3/2 (PEG$_4$) is activated as described above.

In one embodiment, the compound is 679 Compound 4/2 (PEG$_4$)

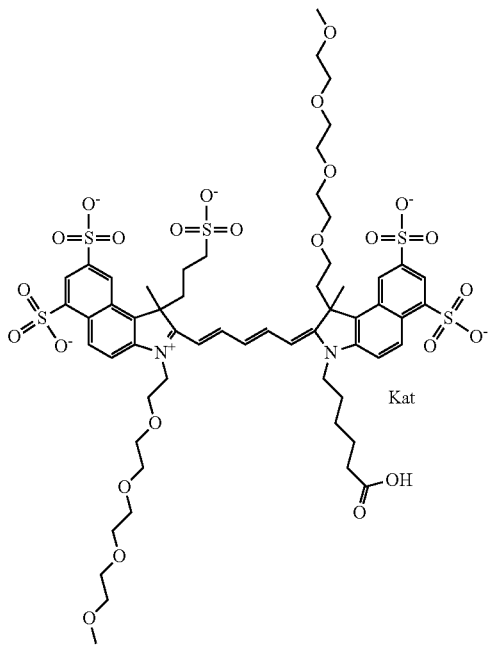 [SMILES: COCCOCCOCCOCC[N+]1=C(/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

One non-limiting example of 679 Compound 4/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-1-methyl-1-(3-sulfonatopropyl)-3-(2,5,8,11-tetraoxatridecan-13-yl)-1H-benzo[e]indolium-6,8-disulfonate) contains a (poly) ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 4/2 (PEG$_4$) is activated as described above.

In one embodiment, the compound is 679 Compound 5/2 (PEG$_4$)

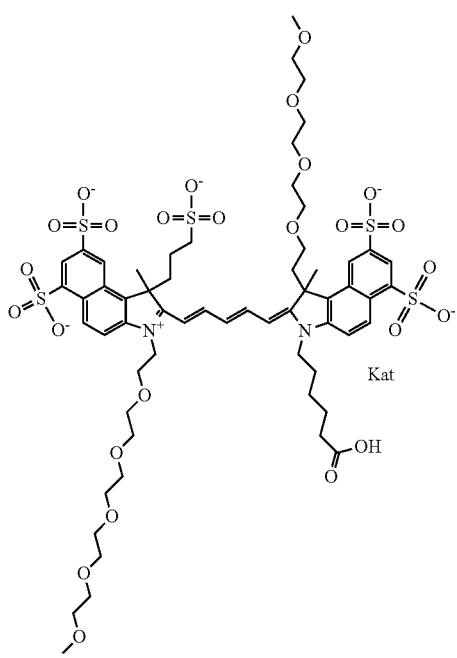 [SMILES: COCCOCCOCCOCCOCC[N+]1=C(/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

One non-limiting example of 679 Compound 5/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-3-(2,5,8,11,14-pentaoxahexadecan-16-yl)-1-methyl-1-(3-sulfonatopropyl)-1H-benzo[e]indolium-6,8-disulfonate) contains a (poly) ethylene glycol on the indole N of the left heterocycle and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 679 Compound 5/2 (PEG$_4$) is activated as described above.

In one embodiment, the compound is 679 Compound 6/2 (PEG$_4$)

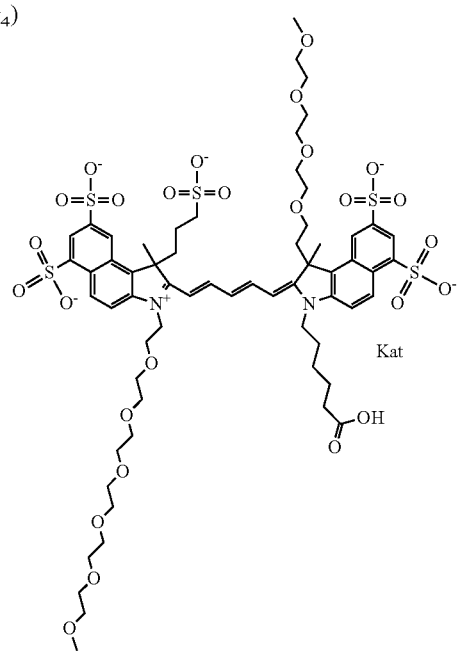

One non-limiting example of 679 Compound 6/2 (PEG$_4$) (2-((1E,3E,5E)-5-(3-(5-carboxypentyl)-1-methyl-6,8-disulfonato-1-(2,5,8,11-tetraoxatridecan-13-yl)-1H-benzo[e]indol-2(3H)-ylidene)penta-1,3-dienyl)-1-methyl-3-(2,5,8,11,14,17-hexaoxanonadecan-19-yl)-1-(3-sulfonatopropyl)-1H-benzo[e]indolium-6,8-disulfonate) contains a (poly) ethylene glycol on the indole N of the left heterocycle and a PEG$_4$ group on the indole C. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 649 Compound 6/2 (PEG$_4$) is activated as described above.

In embodiments, the degree and/or location of sulfonation is varied to, e.g., vary the compound's degree of hydrophilicity or hydrophobicity. One non-limiting example is a monosulfonate form of 679 Compound 1/2 (PEG$_4$), shown below:

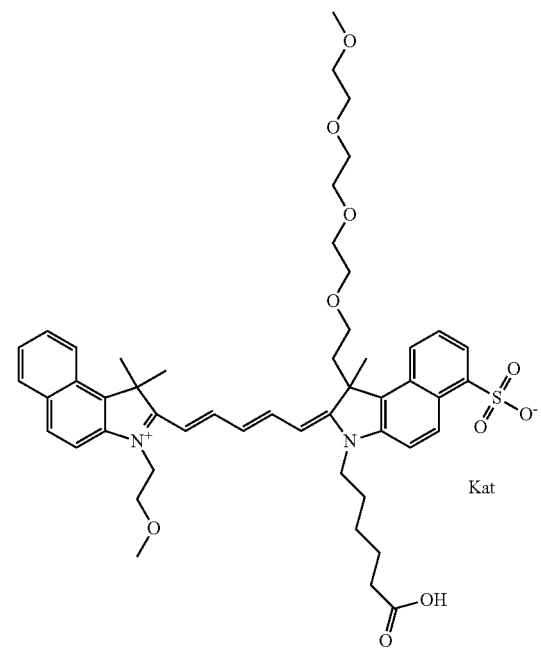 [SMILES: COCCOCCOCCOCCC1(C)\C(=C/C=C/C=C/C2=[N+](CCOC)c3ccc4ccccc4c3C2(C)C)N(CCCCCC(=O)O)c2ccc3c(S(=O)(=O)[O-])cccc3c21]

One non-limiting example is a disulfonate form of 679 Compound 1/2 (PEG$_4$), shown below:

One non-limiting example is a tetrasulfonate form of 679 Compound 1/2 (PEG₄), shown below:

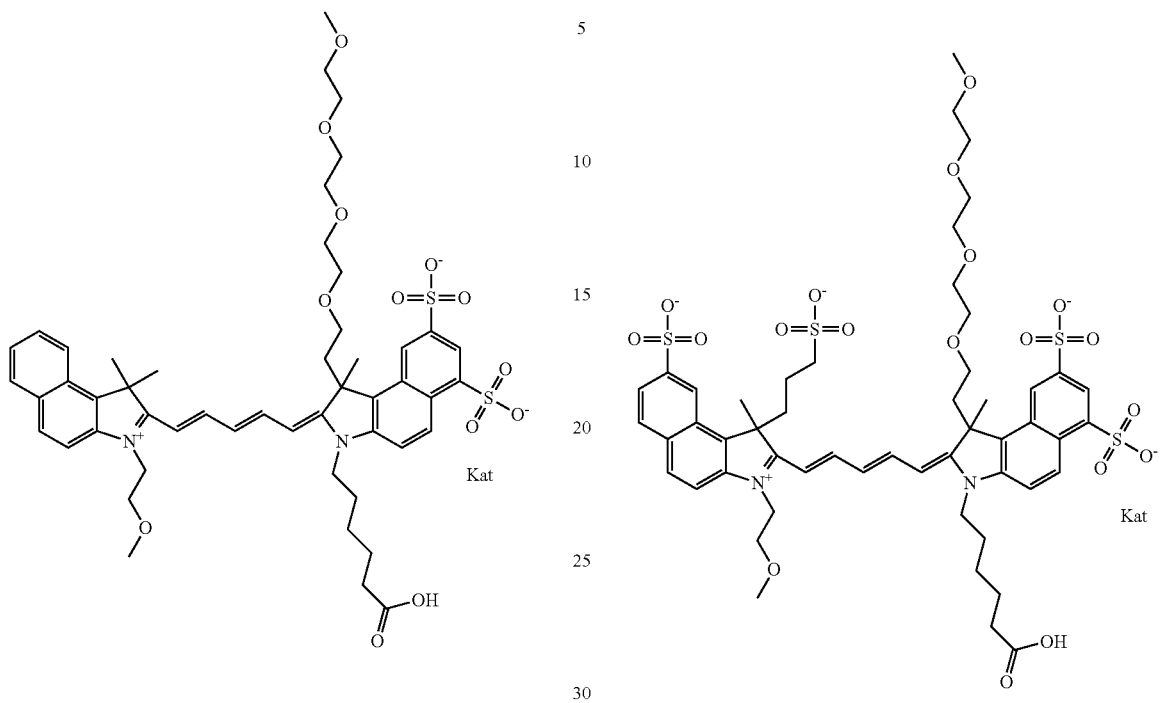

One non-limiting example is a trisulfonate form of 679 Compound 1/2 (PEG₄), shown below:

One non-limiting example is a tetrasulfonate form of 679 Compound 1/2 (PEG₄), shown below:

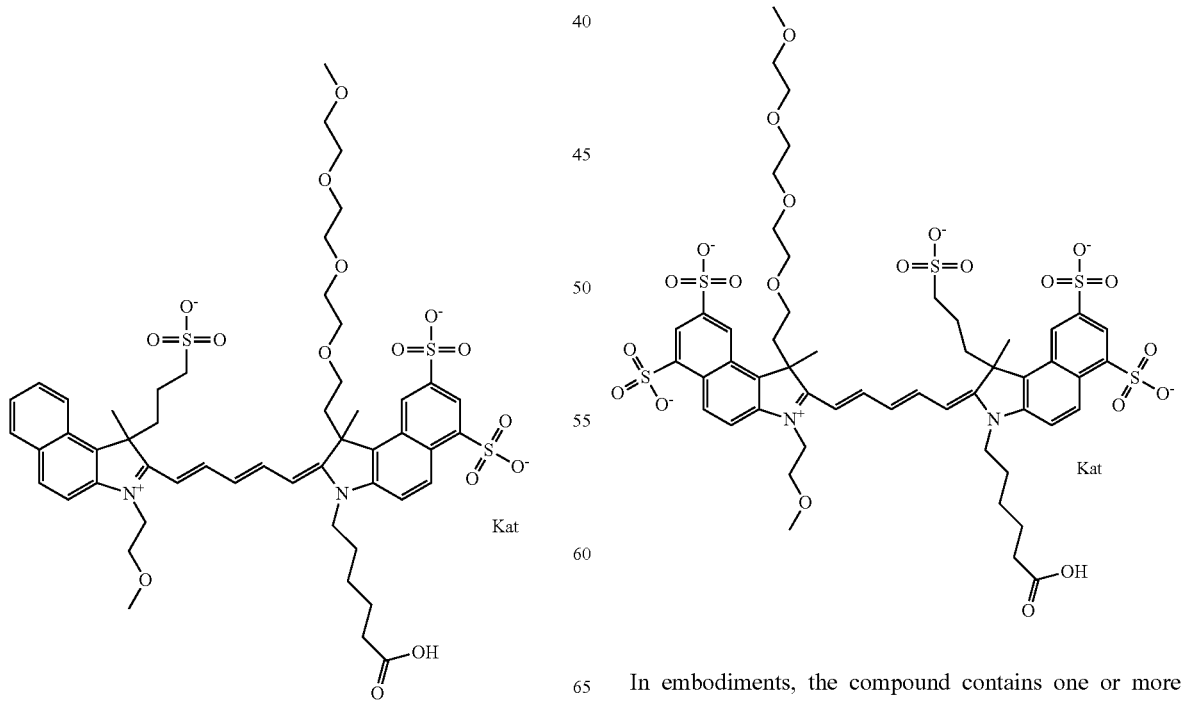

In embodiments, the compound contains one or more substitutions of the polymethine linker. In one embodiment, the compound has general formula Va

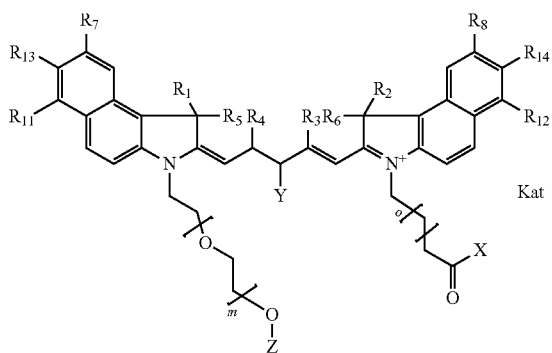

general formula Vb

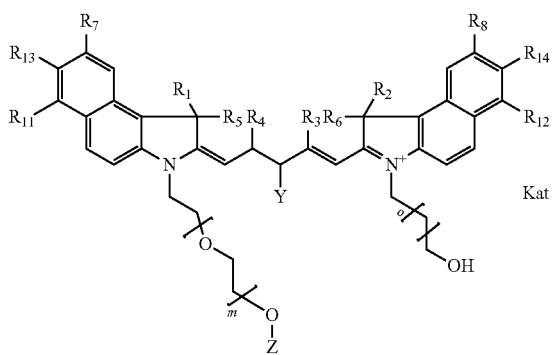

general formula Vc

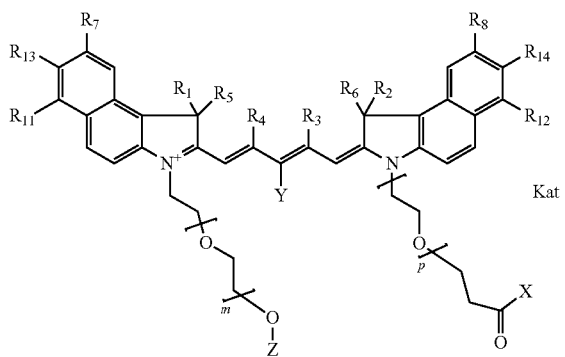

general formula Vd

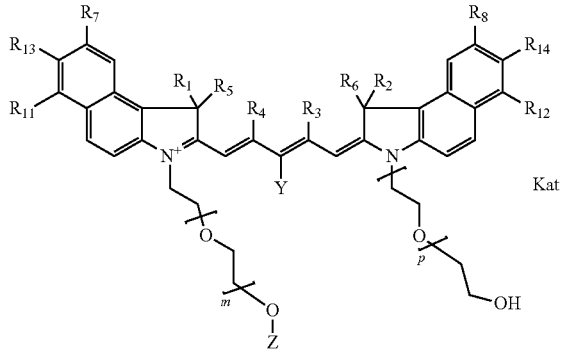

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -L-$SO_2$NH—P—Z, and a caboxamide group -L-CONH—P—Z, and Z is selected from H, a $CH_3$ group, an alkyl group, a heteroalkyl group, or —CO—NHS; each of $R^7$, $R^8$, $R^{11}$, $R^{12}$, $R^{13}$, and $R^{14}$ is the same or different and is independently selected from either H, $SO_3$, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group —$SO_2$NH—P—Z, or a caboxamide group —CONH—P—Z, and Z is selected from H, a $CH_3$ group, an alkyl group, a heteroalkyl group, or —CO—NHS; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$—I, imidazole, azide, —NR-L-O—$NH_2$, and —NR-L-O—CO—NHS, where R is —H or an aliphatic or heteroaliphatic group, and L is selected from the group consisting of a divalent linear (—$(CH_2)_t$—, t=0 to 15), crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; p is an integer from 1 to 6 inclusive; each of R3 and R4 is the same or different and is independently hydrogen, an aliphatic group, a heteroaliphatic group, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, and Z is selected from H, $CH_3$, a $CH_3$ group, an alkyl group, or a heteroalkyl group; or R3 and R4 together form a cyclic structure where R3 and R4 are joined using a divalent structural element selected from the group consisting of —$(CH_2)_q$—, —$(CH_2)_qO(CH_2)_{q'}$—, —$(CH_2)_q$ S$(CH_2)_{q'}$—, —$(CH_2)_q$CH=CH—, and —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy-, phenylmercapto function, and a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, and Z is selected from H, $CH_3$, a $CH_3$ group, an alkyl group, a heteroalkyl group, or —CO—NHS.

In one embodiment, the compound of general formula V wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —(CH$_2$)$_q$— and CH=CH, where q is an integer from 1 to 2 inclusive, to result in a 3-, 4-, or 5-membered ring.

One non-limiting example is a substituted polymethine form of 679 Compound 1, shown below:

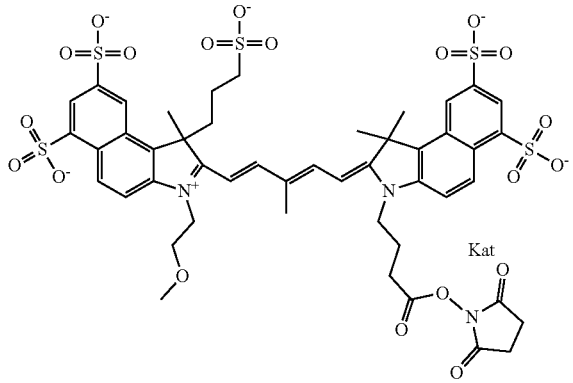 [SMILES: COCC[N+]1=C(/C=C/C(C)=C/C=C2/N(CCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 2, shown below:

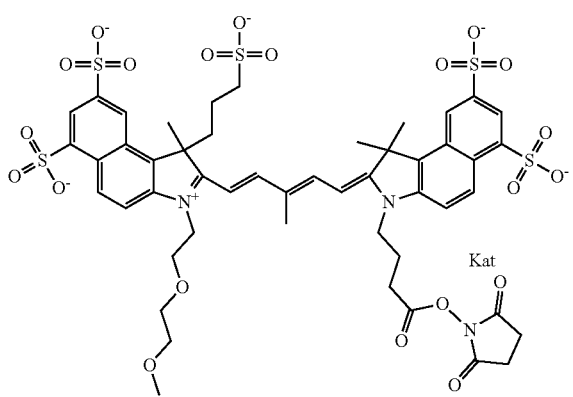 [SMILES: COCCOCC[N+]1=C(/C=C/C(C)=C/C=C2/N(CCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 3, shown below:

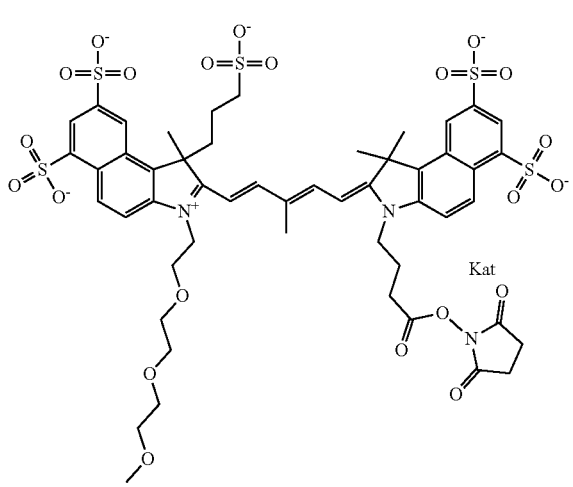 [SMILES: COCCOCCOCC[N+]1=C(/C=C/C(C)=C/C=C2/N(CCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 4, shown below:

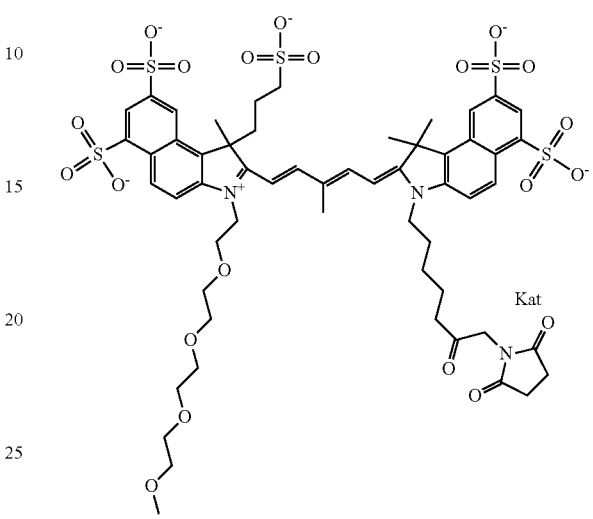

One non-limiting example is a substituted polymethine form of 679 Compound 5, shown below:

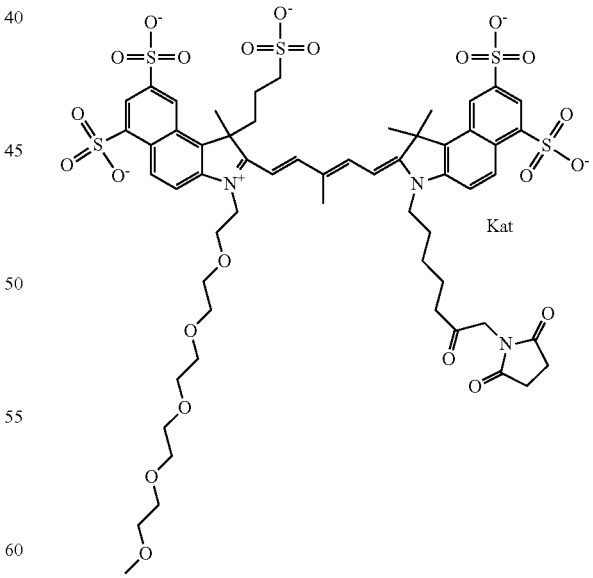

One non-limiting example is a substituted polymethine form of 679 Compound 6, shown below:

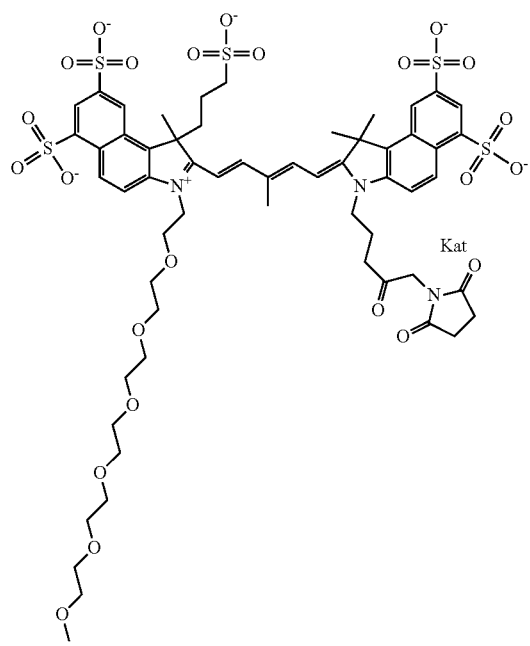 [SMILES: COCCOCCOCCOCCOCCOCC[N+]1=C(/C=C/C(C)=C/C=C2/N(CCCC(=O)CN3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 1, shown below:

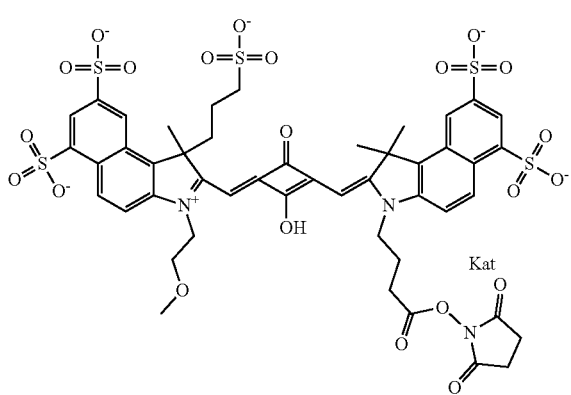 [SMILES: COCC[N+]1=C(/C=C2\C(=O)C(/C=C3/N(CCCC(=O)ON4C(=O)CCC4=O)c4ccc5c(S(=O)(=O)[O-])cc(S(=O)(=O)[O-])cc5c4C3(C)C)=C2O)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 2, shown below:

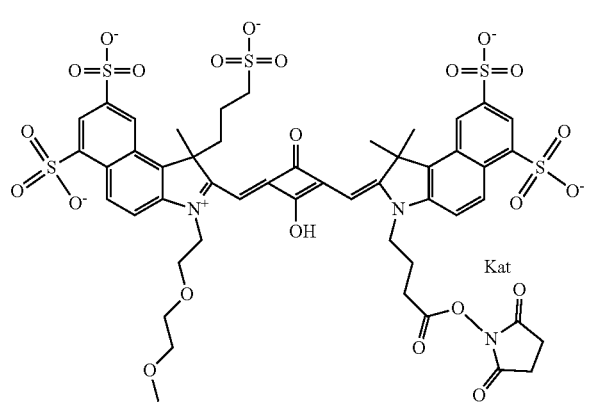 [SMILES: COCCOCC[N+]1=C(/C=C2\C(=O)C(/C=C3/N(CCCC(=O)ON4C(=O)CCC4=O)c4ccc5c(S(=O)(=O)[O-])cc(S(=O)(=O)[O-])cc5c4C3(C)C)=C2O)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 3, shown below:

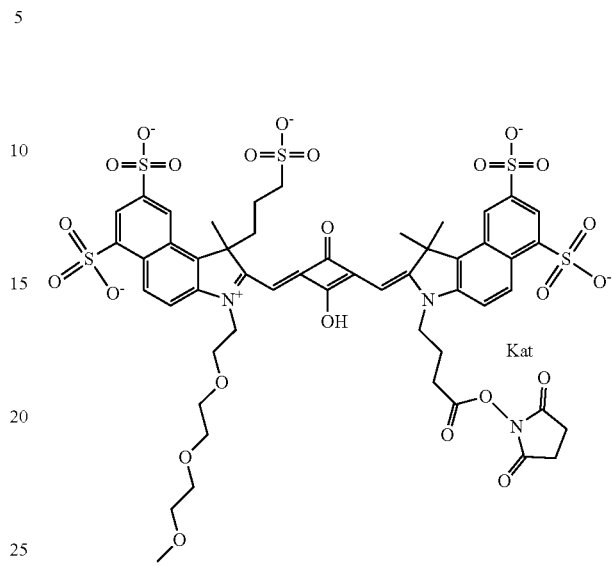

One non-limiting example is a substituted polymethine form of 679 Compound 4, shown below:

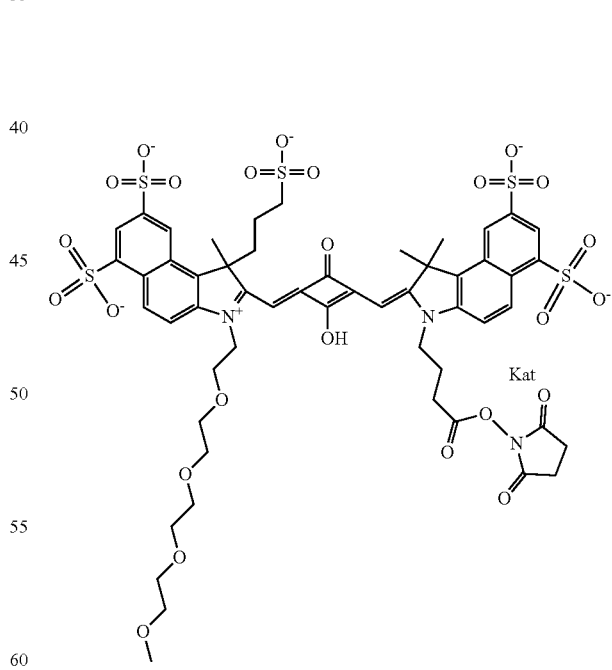

One non-limiting example is a substituted polymethine form of 679 Compound 5, shown below:

One non-limiting example is a substituted polymethine form of 679 Compound 1/2 (PEG$_4$), shown below:
One non-limiting example is a substituted polymethine form of 679 Compound 6, shown below:
One non-limiting example is a substituted polymethine form of 679 Compound 2/2 (PEG$_4$), shown below:
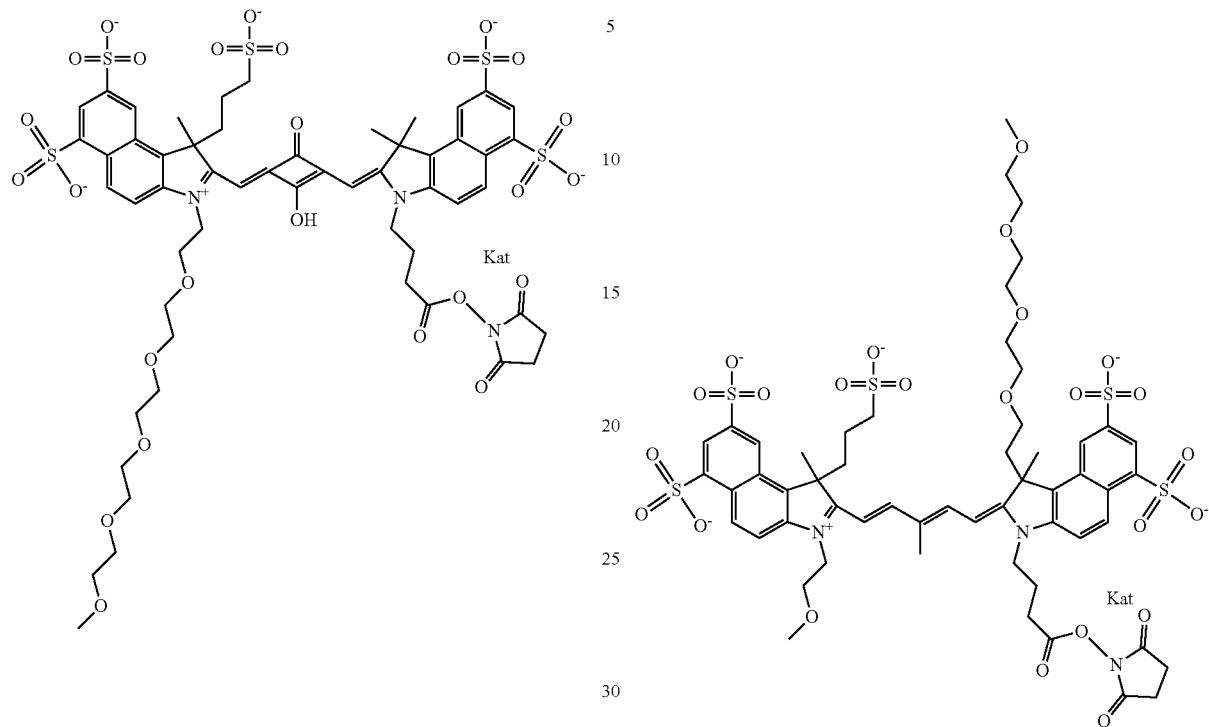
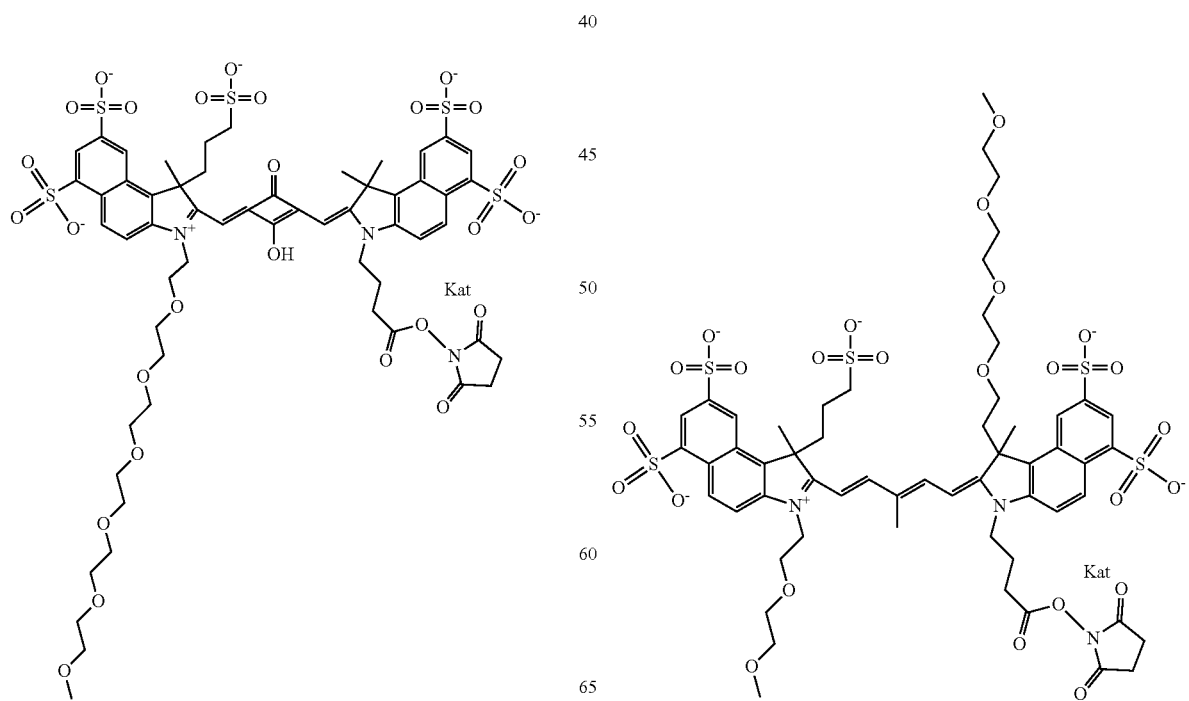

One non-limiting example is a substituted polymethine form of 679 Compound 3/2 (PEG$_4$), shown below:

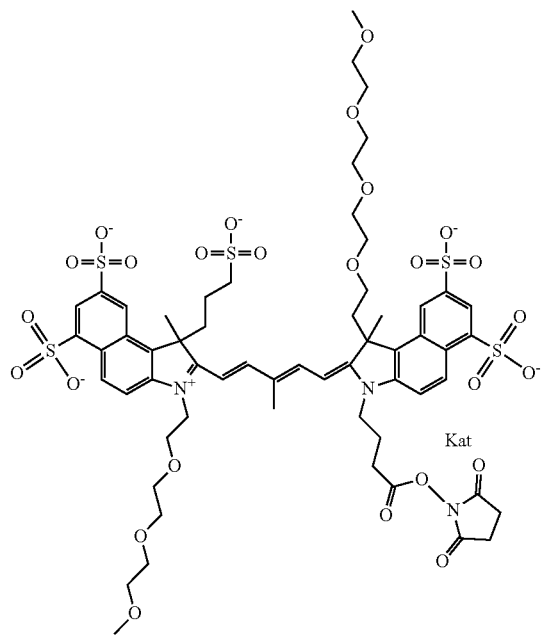 [SMILES: COCCOCCOCCOCCC1(C)\C(=C/C=C(C)/C=C/C2=[N+](CCOCCOCCOC)c3ccc4c(S(=O)(=O)[O-])cc(S(=O)(=O)[O-])cc4c3C2(C)CCCS(=O)(=O)[O-])N(CCCC(=O)ON2C(=O)CCC2=O)c2ccc3c(S(=O)(=O)[O-])cc(S(=O)(=O)[O-])cc3c21]

One non-limiting example is a substituted polymethine form of 679 Compound 5/2 (PEG$_4$), shown below:

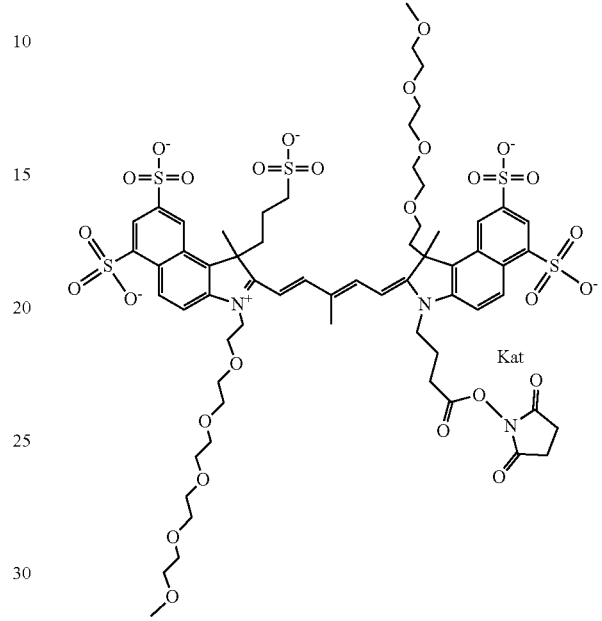

One non-limiting example is a substituted polymethine form of 679 Compound 4/2 (PEG$_4$), shown below:

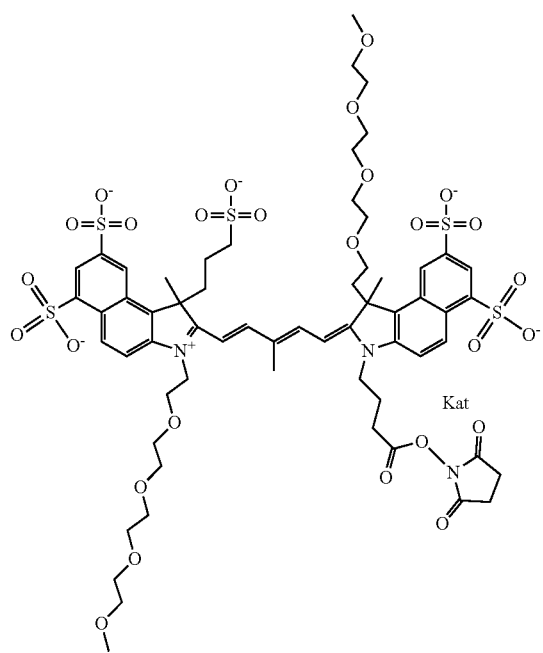 [SMILES: COCCOCCOCCOCC[N+]1=C(/C=C/C(C)=C/C=C2/N(CCCC(=O)ON3C(=O)CCC3=O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

One non-limiting example is a substituted polymethine form of 679 Compound 6/2 (PEG$_4$), Shown below:

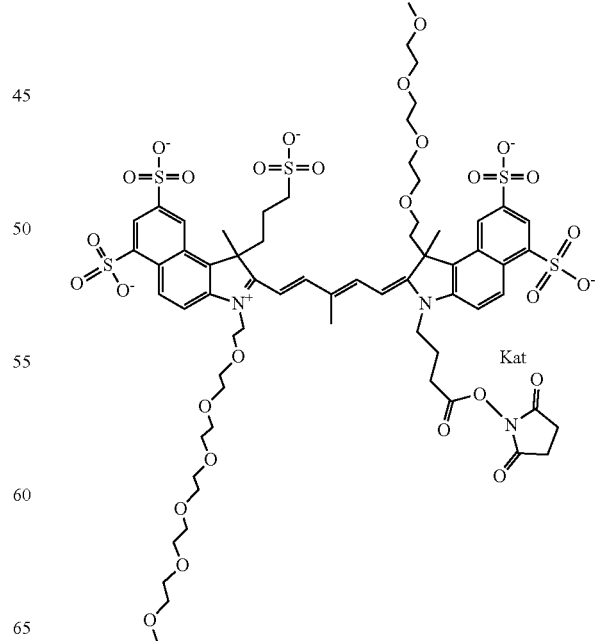

101

One non-limiting example is a substituted polymethine form of 679 Compound 1/2 (PEG$_4$), shown below:

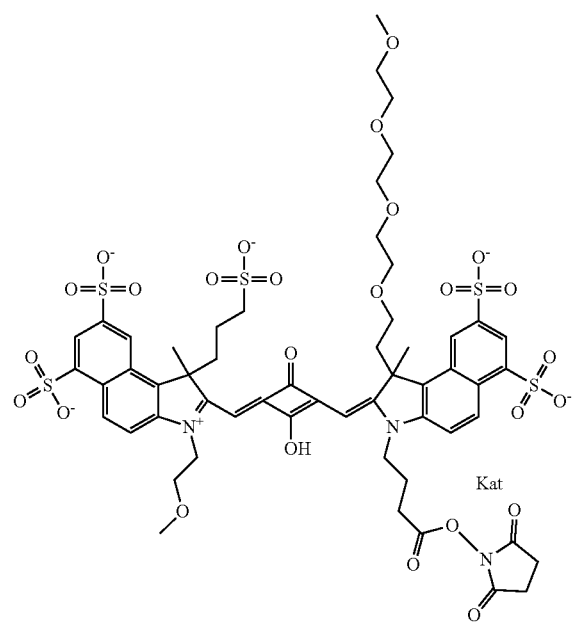 [SMILES: COCCOCCOCCOCCC1(C)/C(=C\C2=C(O)C(=C/C3=[N+](CCOC)c4ccc5c(S(=O)(=O)[O-])cc(S(=O)(=O)[O-])cc5c4C3(C)CCCS(=O)(=O)[O-])/C2=O)N(CCCC(=O)ON2C(=O)CCC2=O)c2ccc3c(S(=O)(=O)[O-])cc(S(=O)(=O)[O-])cc3c21]

102

One non-limiting example is a substituted polymethine form of 679 Compound 3/2 (PEG$_4$), shown below:

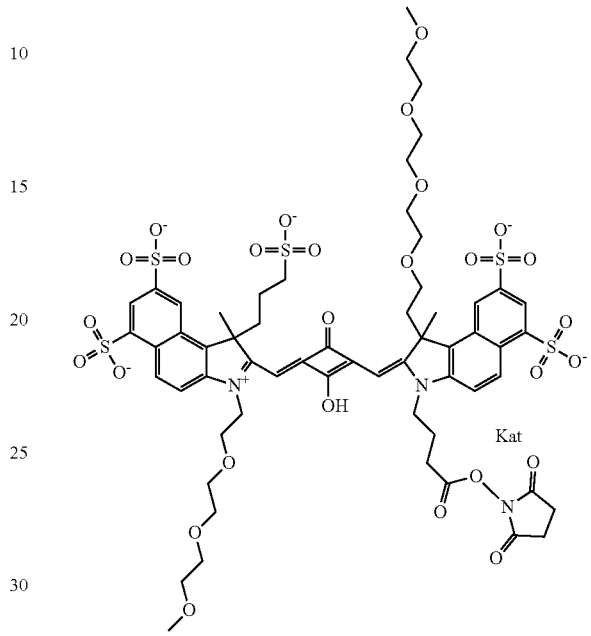

One non-limiting example is a substituted polymethine form of 679 Compound 2/2 (PEG$_4$), shown below:

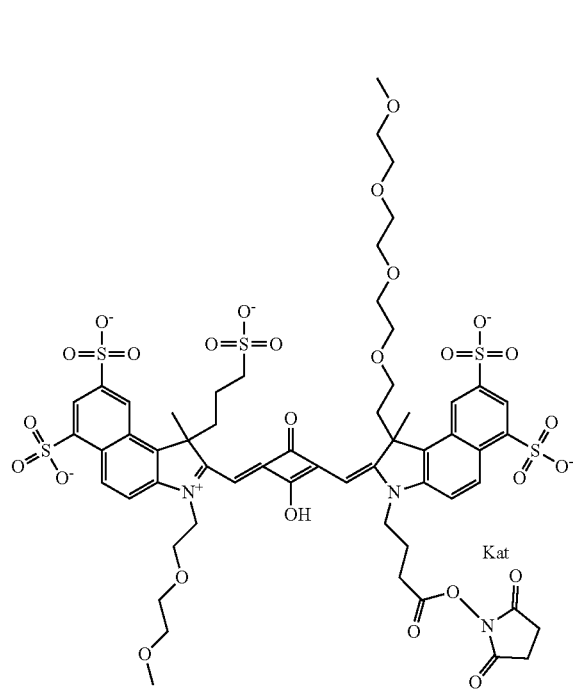 [SMILES: COCCOCCOCCOCCC1(C)/C(=C\C2=C(O)C(=C/C3=[N+](CCOCCOC)c4ccc5c(S(=O)(=O)[O-])cc(S(=O)(=O)[O-])cc5c4C3(C)CCCS(=O)(=O)[O-])/C2=O)N(CCCC(=O)ON2C(=O)CCC2=O)c2ccc3c(S(=O)(=O)[O-])cc(S(=O)(=O)[O-])cc3c21]

One non-limiting example is a substituted polymethine form of 679 Compound 4/2 (PEG$_4$), Shown below:

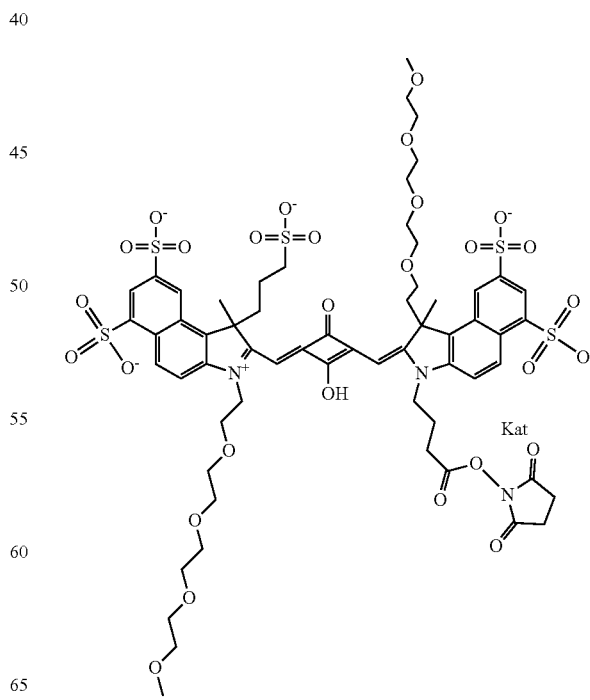

One non-limiting example is a substituted polymethine form of 679 Compound 5/2 (PEG$_4$), shown below:

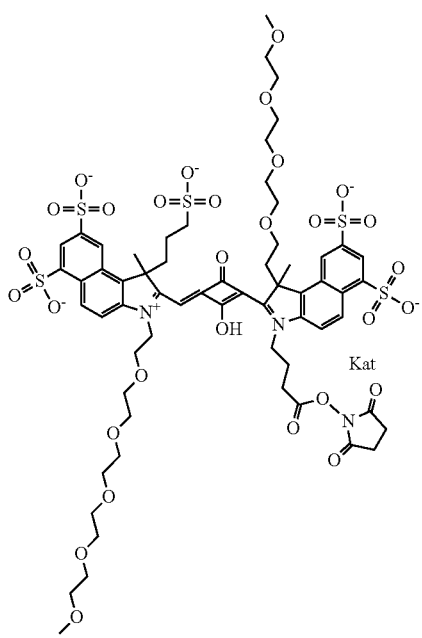

One non-limiting example is a substituted polymethine form of 679 Compound 6/2 (PEG$_4$), shown below:

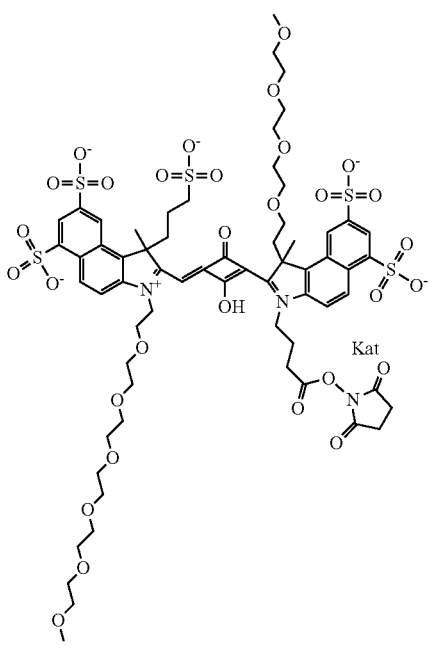

In various embodiments, an ethylene glycol group, diethylene glycol group, and/or a polyethylene glycol group, which will collectively be referred to as a PEG group, unless specifically defined, may be present at position(s) in addition to such groups being present on the N atom(s) of the indole structure. One non-limiting example of an additionally PEG-substituted compound is a 679 Compound 1/2 according to general formula II where R1 is an ethylene glycol group terminating with a methyl group,

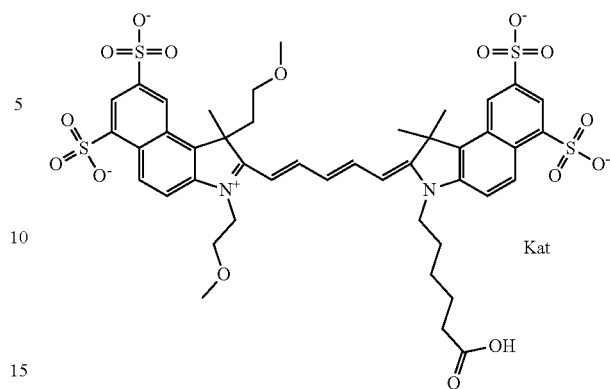

One non-limiting example of an additionally PEG-substituted compound is a 679 Compound 1/2 according to general formula II where R2 is an ethylene glycol group terminating with a methyl group, shown below:

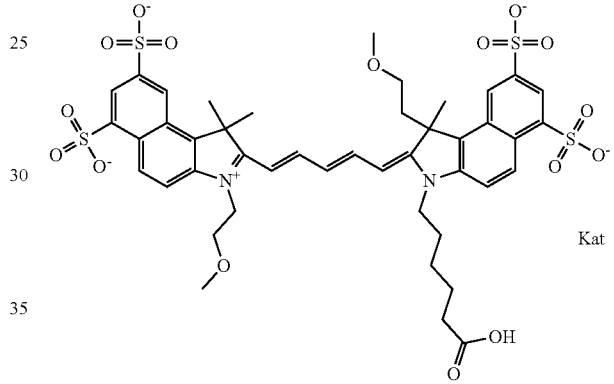

One non-limiting example of an additionally PEG-substituted compound is a 679 Compound 1/2 according to general formula II where R8 is an ethylene glycol group terminating with a methyl group,

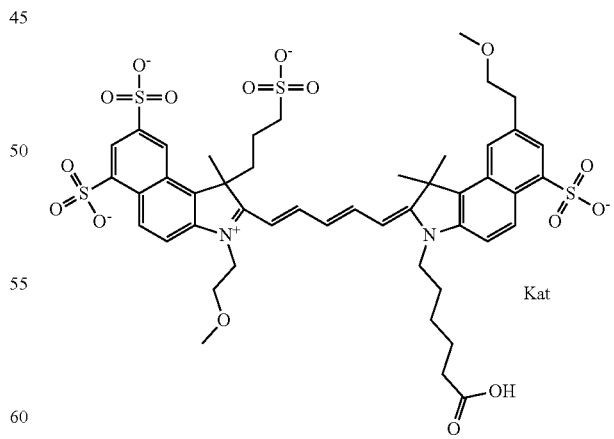

One non-limiting example of an additionally PEG-substituted compound is a 679 Compound 1/2 according to general formula II where R8 is a sulfonamide group with an ethylene glycol group (PEG$_1$) terminating with a methyl group, shown below:

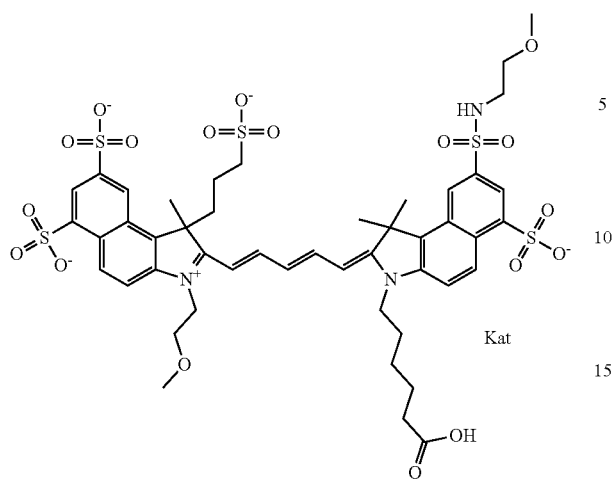

One non-limiting example of an additionally PEG-substituted compound is a 679 Compound 1/2 according to general general formula II where R8 is a carboxamide group with an ethylene glycol group (PEG$_1$) terminating with a methyl group, shown below:

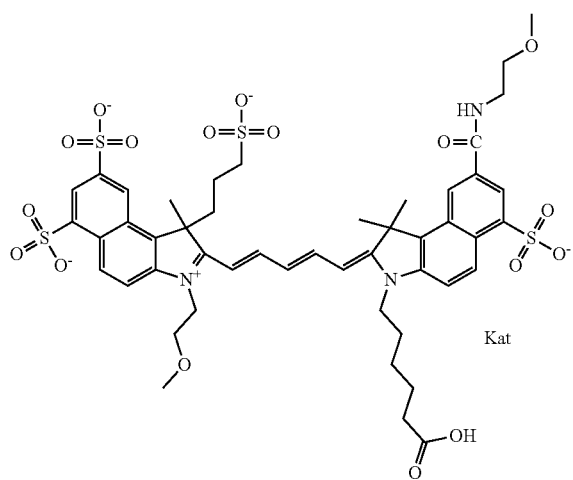

One non-limiting example of an additionally PEG-substituted compound is a 679 Compound 1/2 according to general formula II where R7 is an ethylene glycol group terminating with a methyl group, shown below:

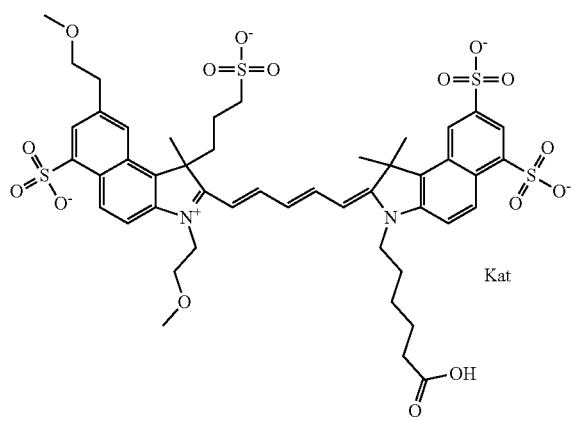

One non-limiting example of an additionally PEG-substituted compound is a 679 Compound 1/2 according to general formula II where R7 is a sulfonamide group with an ethylene glycol group (PEG$_1$) terminating with a methyl group, shown below:

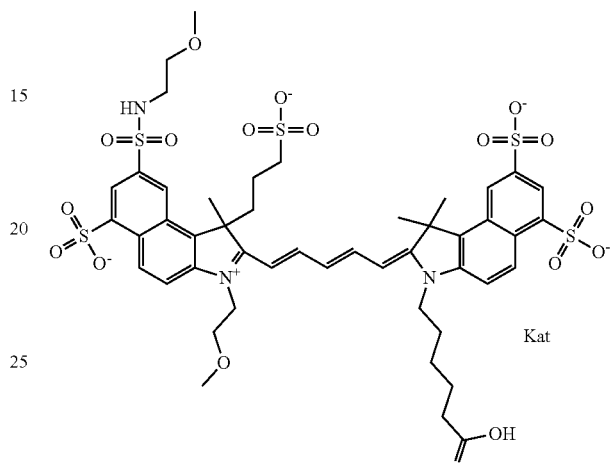

One non-limiting example of an additionally PEG-substituted compound is a 679 Compound 1/2 according to general formula II where R7 is a carboxamide group with an ethylene glycol group (PEG$_1$) terminating with a methyl group, shown below:

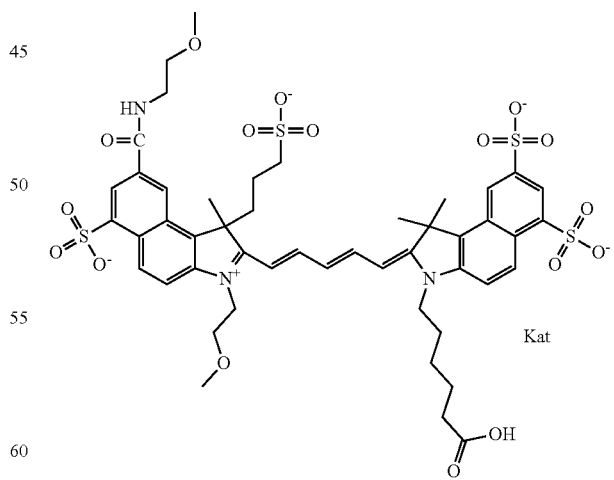

One non-limiting example of an additionally PEG-substituted compound is a 679 Compound 1/2 according to general formula II where R12 is an ethylene glycol group terminating with a methyl group,

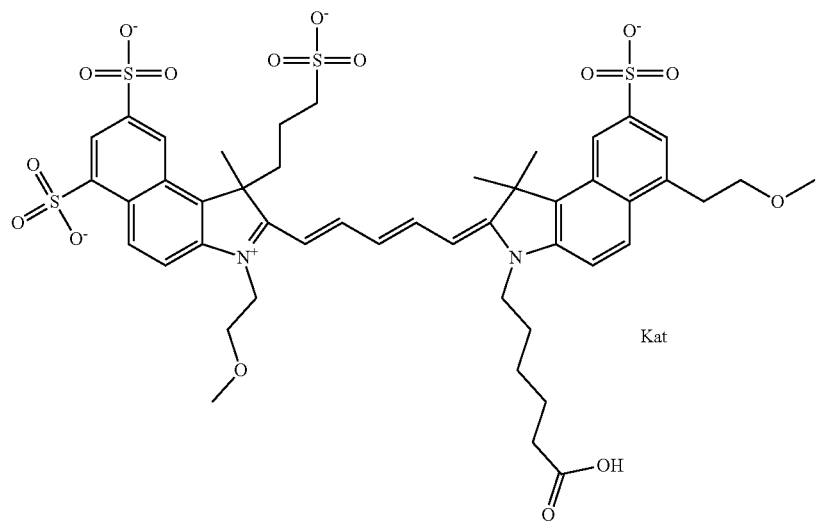

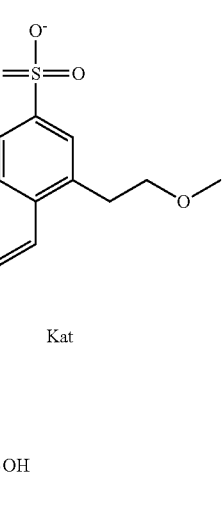

One non-limiting example of an additionally PEG-substituted compound is a 679 Compound 1/2 according to general formula II where R12 is a sulfonamide group with an ethylene glycol group (PEG$_1$) terminating with a methyl group, shown below:

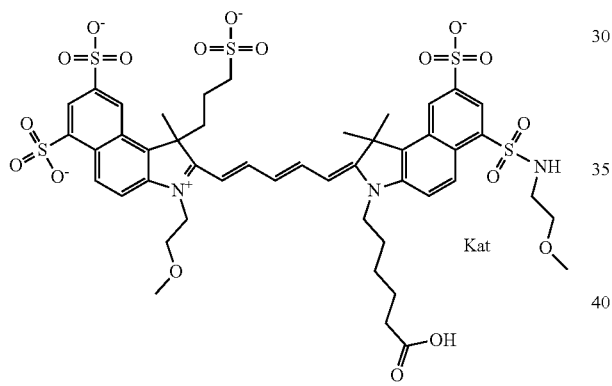

One non-limiting example of an additionally PEG-substituted compound is a 679 Compound 1/2 according to general formula II where R12 is a carboxamide group with an ethylene glycol group (PEG$_1$) terminating with a methyl group, shown below:

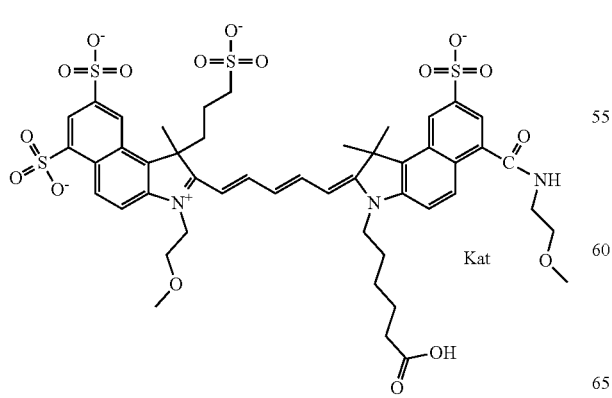

One non-limiting example of an additionally PEG-substituted compound is a 679 Compound 1/2 according to general formula II where R11 is an ethylene glycol group terminating with a methyl group, shown below:

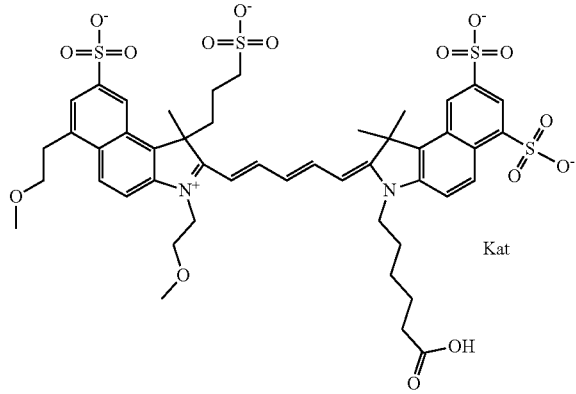

One non-limiting example of an additionally PEG-substituted compound is a 679 Compound 1/2 according to general formula II where R11 is a sulfonamide group with an ethylene glycol group (PEG$_1$) terminating with a methyl group, shown below:

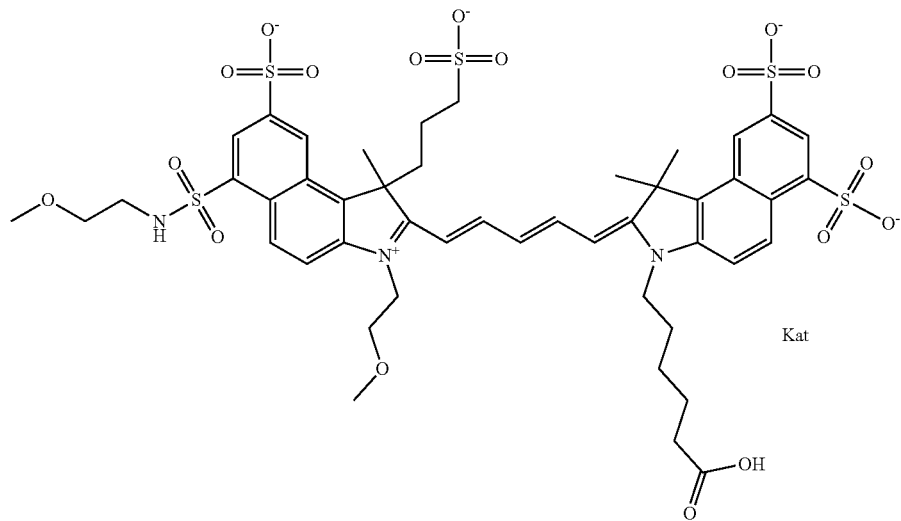
One non-limiting example of an additionally PEG-substituted compound is a 679 Compound 1/2 according to general formula II where R11 is a carboxamide group with an ethylene glycol group (PEG$_1$) terminating with a methyl group, shown below:
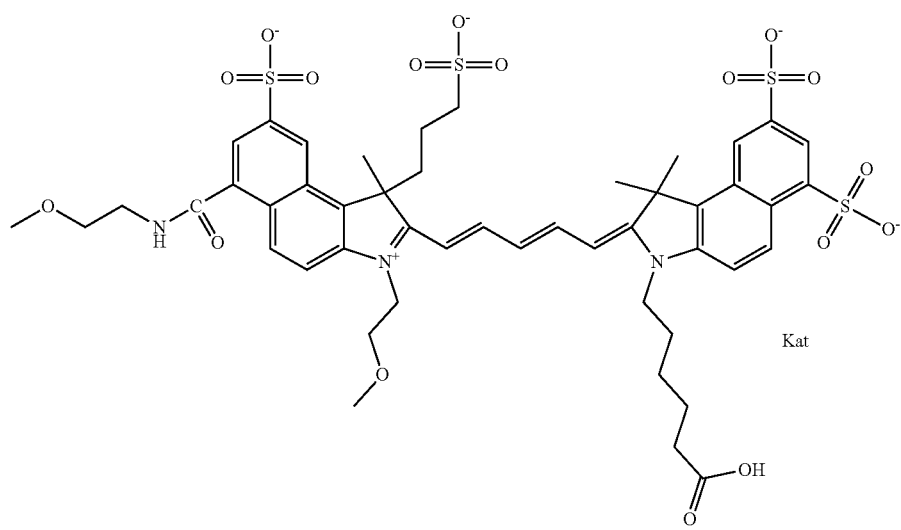

One non-limiting example of an additionally PEG-substituted compound is a 679 Compound 1/2 according to general formula II where R13 is an ethylene glycol group terminating with a methyl group,

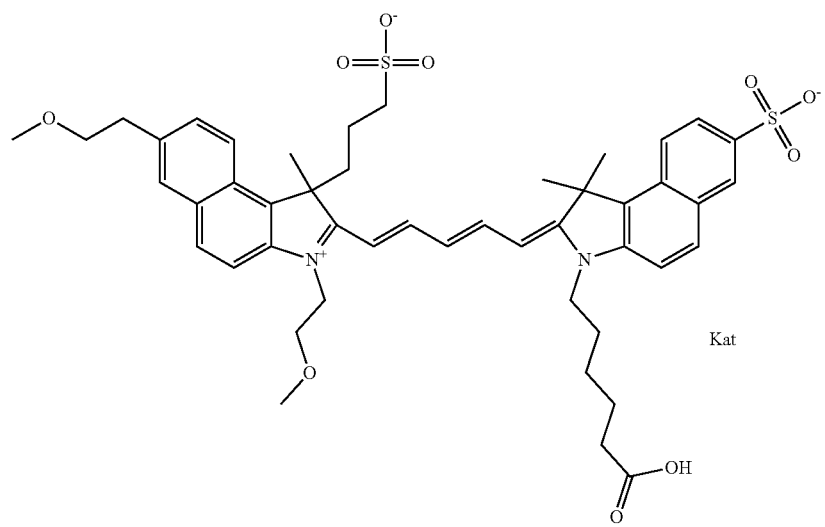

One non-limiting example of an additionally PEG-substituted compound is a 679 Compound 1/2 according to general formula II where R13 is a sulfonamide group with an ethylene glycol group (PEG$_1$) terminating with a methyl group, shown below:

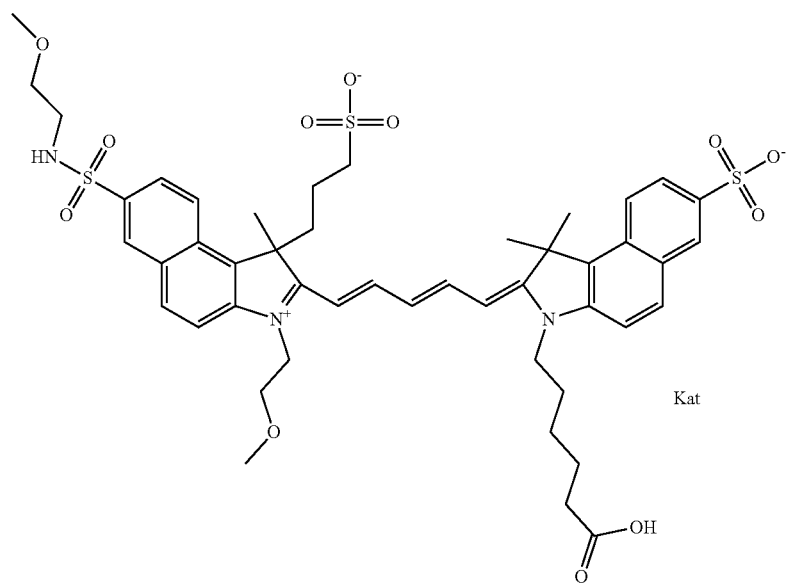

One non-limiting example of an additionally PEG-substituted compound is a 679 Compound 1/2 according to general formula II where R13 is a carboxamide group with an ethylene glycol group (PEG$_1$) terminating with a methyl group, shown below:

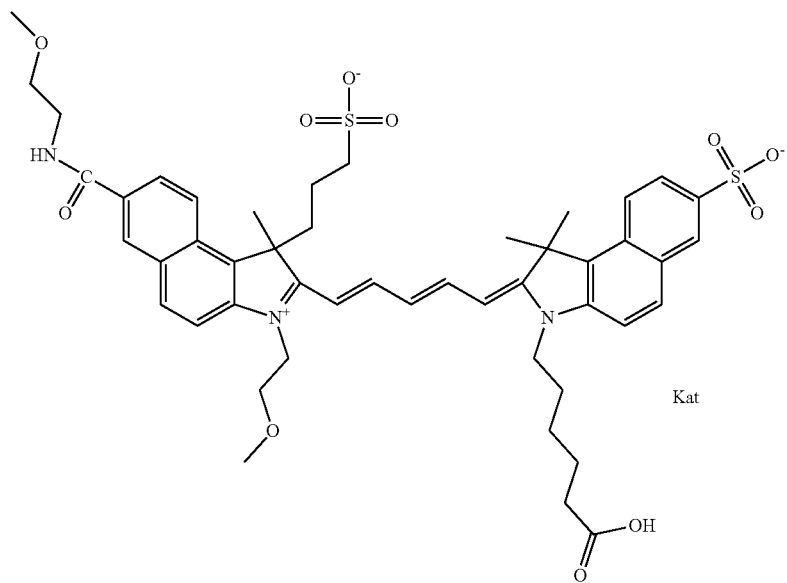

One non-limiting example of an additionally PEG-substituted compound is a 679 Compound 1/2 according to general formula II where R14 is an ethylene glycol group terminating with a methyl group, shown below:

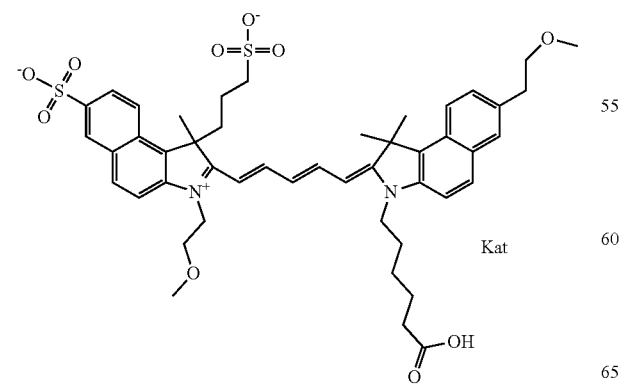

One non-limiting example of an additionally PEG-substituted compound is a 679 Compound 1/2 according to general formula II where R13 is a sulfonamide group with an ethylene glycol group (PEG$_1$) terminating with a methyl group, shown below:

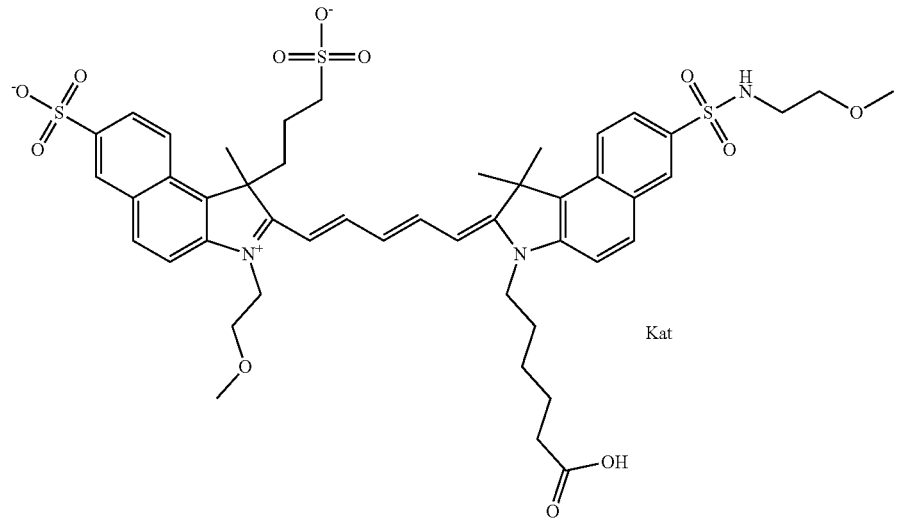

One non-limiting example of an additionally PEG-substituted compound is a 679 Compound 1/2 according to general formula II where R13 is a carboxamide group with an ethylene glycol group (PEG$_1$) terminating with a methyl group, shown below:

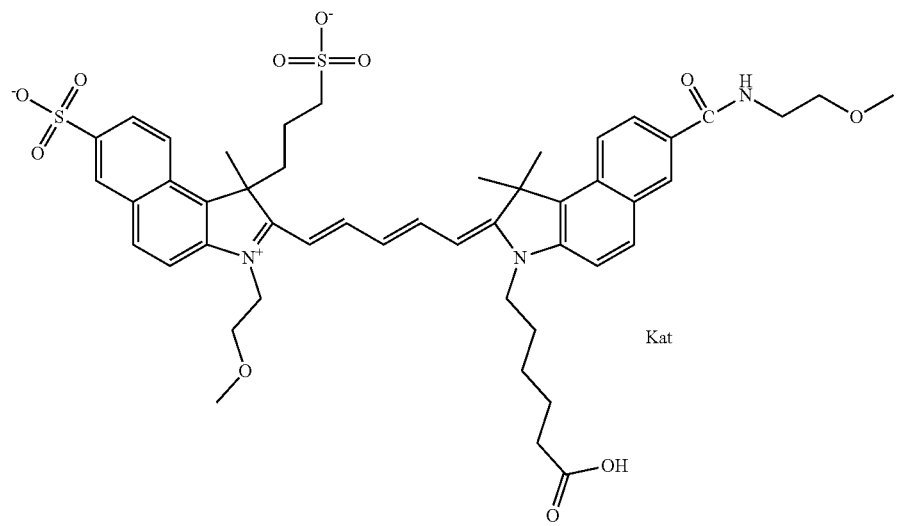

One non-limiting example of an additionally PEG-substituted compound is a 679 Compound 4/4 (V08-15173) according to general formula III where each of R1 and R2 is a polyethylene glycol (4) group terminating with a methyl group, p=4, X=NHS, and each of R7, R8, R11, and R12 are SO$_3$, shown below:

117
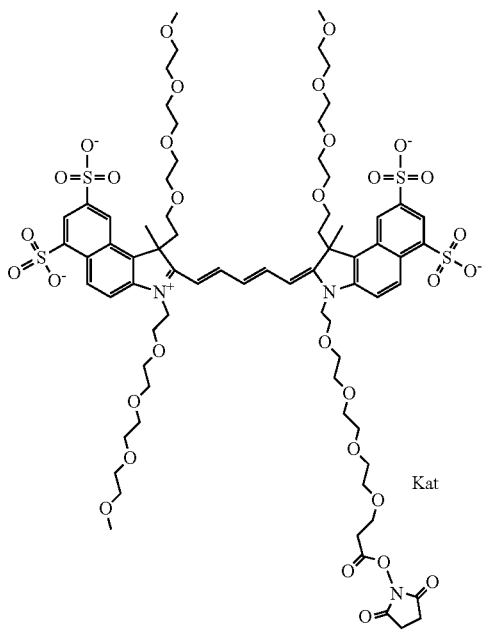 [SMILES: COCCOCCOCCOCC[N+]1=C(/C=C/C=C/C=C2/N(CCOCCOCCOCCOCCC(=O)ON3C(=O)CCC3=O)c3ccc4c(S(=O)(=O)[O-])cc(S(=O)(=O)[O-])cc4c3C2(C)CCOCCOCCOCCOC)C(C)(CCOCCOCCOCCOC)c2c1ccc1c(S(=O)(=O)[O-])cc(S(=O)(=O)[O-])cc21]
One non-limiting example of an additionally PEG-substituted compound is a 679 Compound 4/4 (V10-04152) according to general formula III where each of R1 and R2 is a polyethylene glycol (4) group terminating with a methyl
118
group, p=4, X=OH, and each of R13 and R14 are SO₃, shown below:
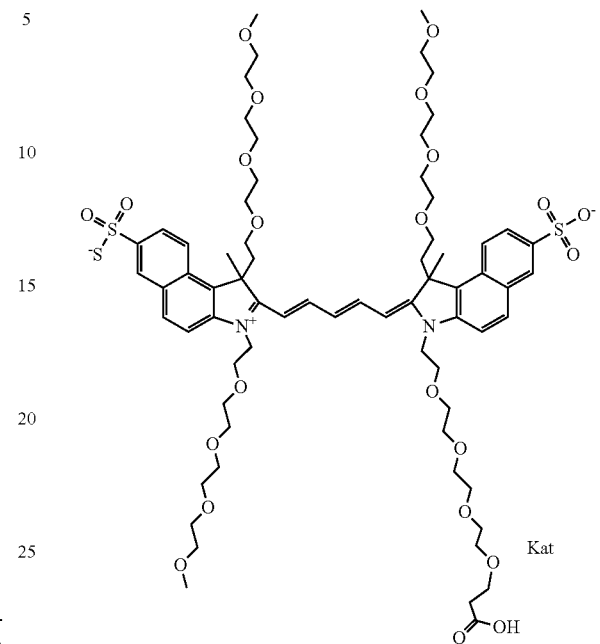
In one embodiment, the compound is 779 Compound 1
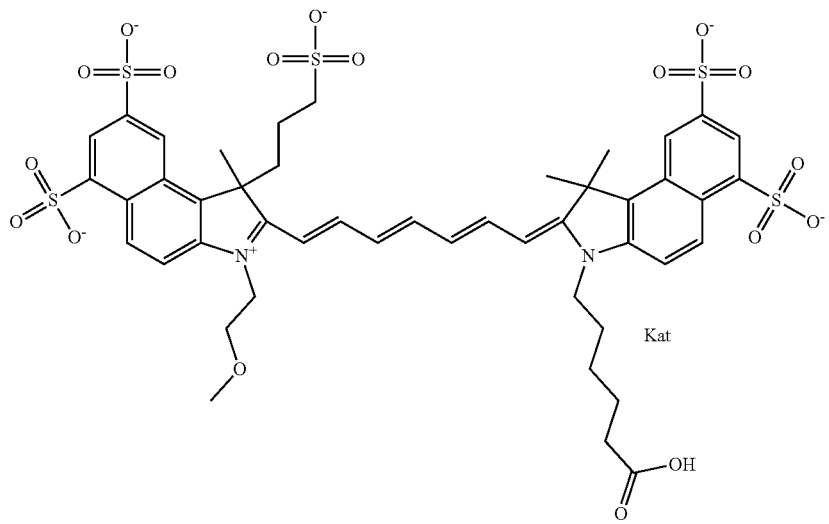 [SMILES: COCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 1 (6-((E)-2-((2E,4E,6E)-7-(3-(2-methoxyethyl)-1-methyl-6,8-disulfonato-1-(3-sulfonatopropyl)-1H-benzo[e]indol-3-ium-2-yl)hepta-2,4,6-trien-1-ylidene)-1,1-dimethyl-6,8-disulfonato-1H-benzo[e]indol-3(2H)-yl)hexanoate) contains an ethylene glycol on the indole N of the left heterocycle, i.e., a methylated ethylene glycol. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 779 Compound 1, but one skilled in the art appreciates that activation is not limited to these examples. One non-limiting example of an activated compound is the NHS-ester of 779 Compound 1, shown below:

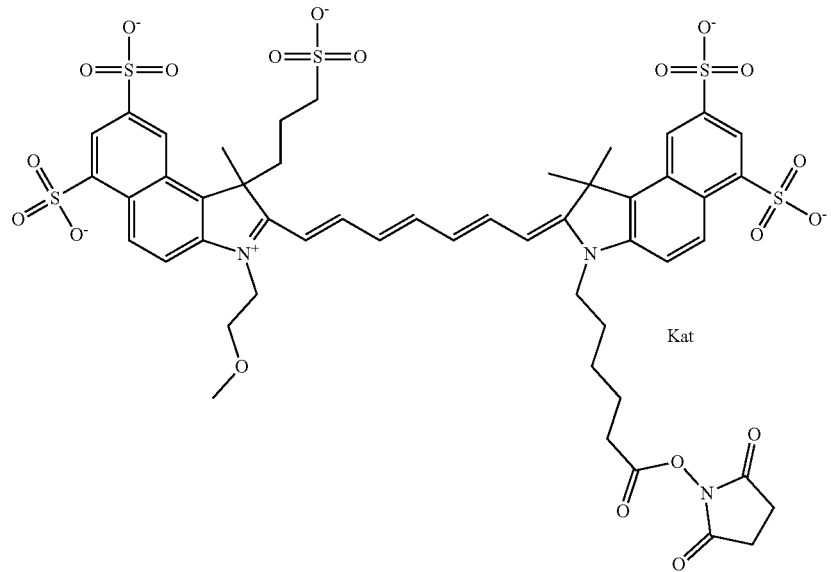 [SMILES: COCC[N+]1=C(/C=C/C=C/C=C/C=C2/N(CCCCCC(=O)ON3C(=O)CCC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of a NHS-ester of 779 Compound 1, according to general formula III, where m=1 and p=1, is shown below:

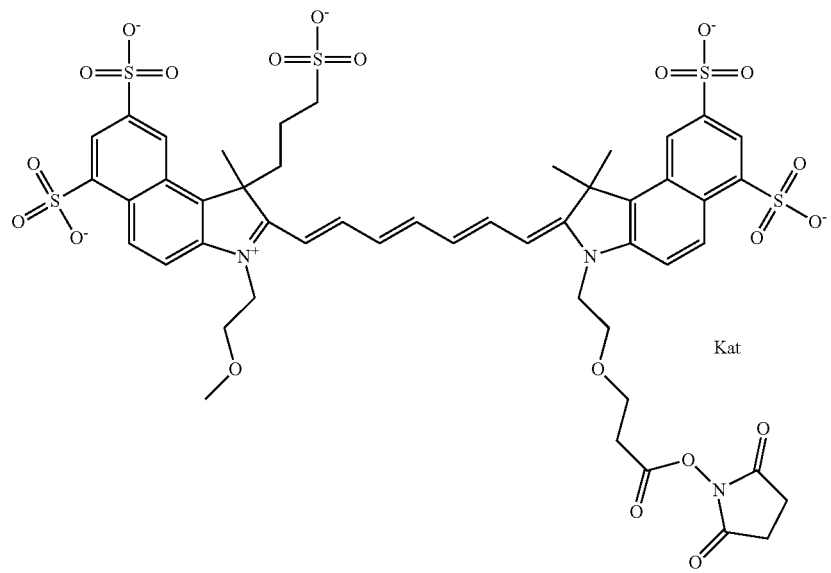

121

One non-limiting example of a NHS-ester of 779 Compound 1, according to general formula III, where m=1 and p=2, is shown below:

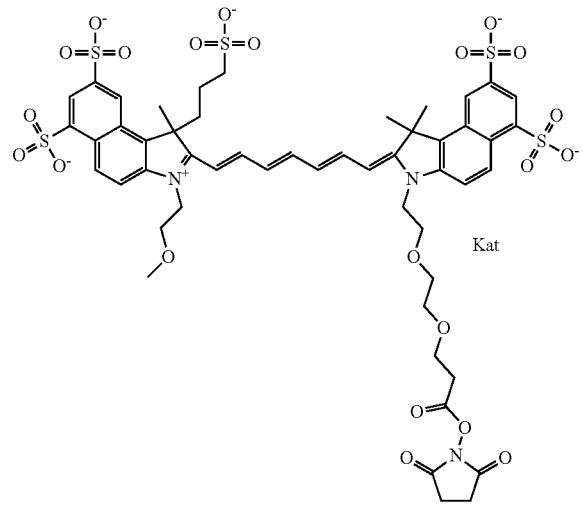

One non-limiting example of a NHS-ester of 779 Compound 1, according to general formula III, where m=1 and p=3, is shown below:

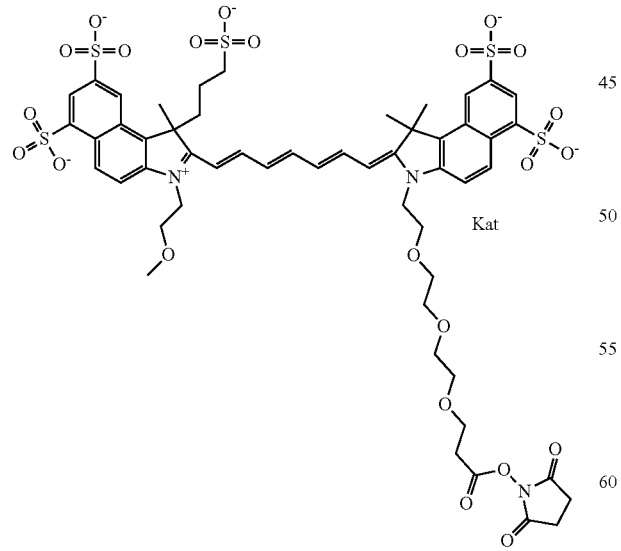

One non-limiting example of a NHS-ester of 779 Compound 1, according to general formula III, where m=1 and p=4, is shown below:

122

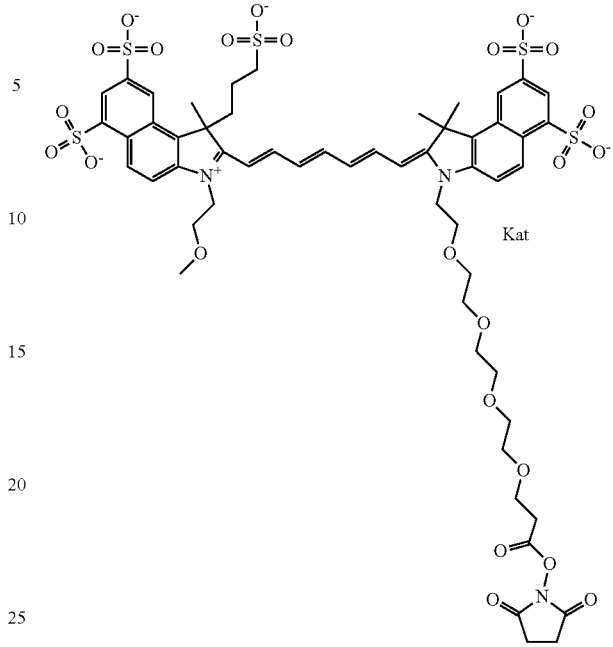

One non-limiting example of a NHS-ester of 779 Compound 1, according to general formula III, where m=1 and p=5, is shown below:

One non-limiting example of a NHS-ester of 779 Compound 1, according to general formula III, where m=1 and p=6, is shown below:

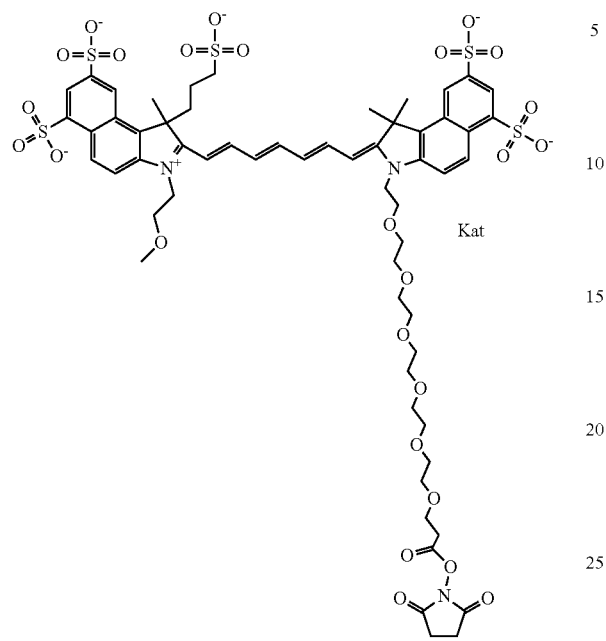
One non-limiting example of an activated 779 Compound 1 is a tetrafluorophenyl (TFP)-ester form of 779 Compound 1, shown below:
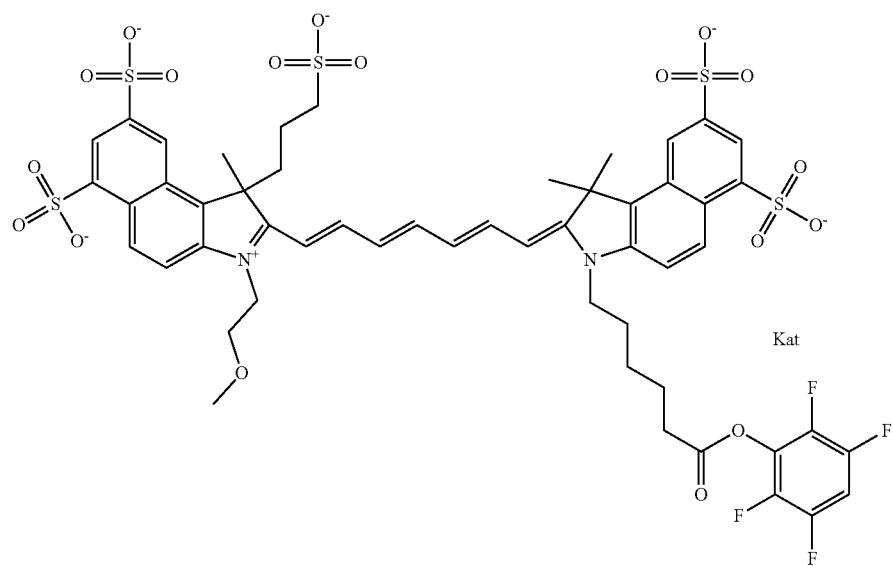 [SMILES: COCC[N+]1=C(/C=C/C=C/C=C/C=C2/N(CCCCCC(=O)Oc3c(F)c(F)cc(F)c3F)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of an activated 779 Compound 1 is a sulfotetrafluorophenyl (STP)-ester form of 779 Compound 1, shown below:
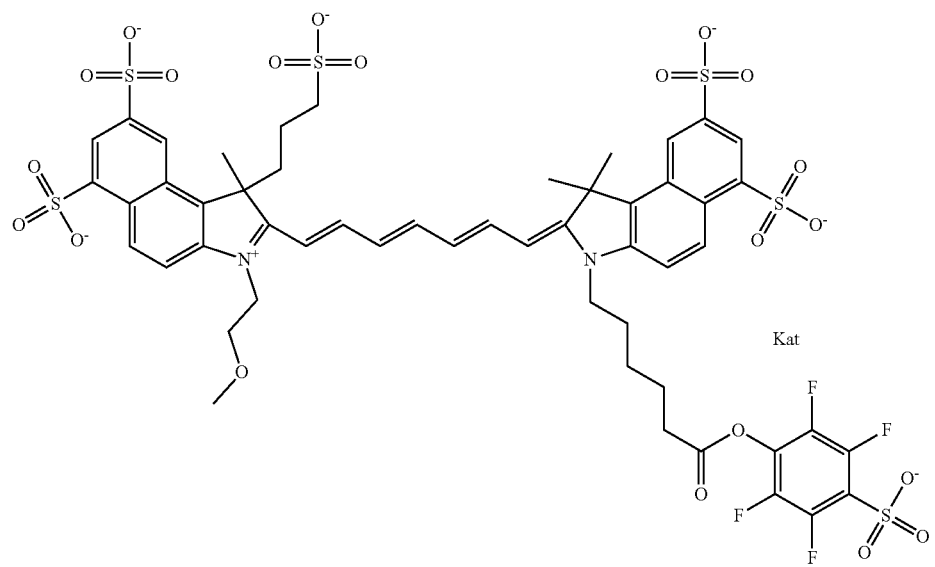 [SMILES: COCC[N+]1=C(/C=C/C=C/C=C/C=C2/N(CCCCCC(=O)Oc3c(F)c(F)c(S(=O)(=O)[O-])c(F)c3F)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]
One non-limiting example of an activated 779 Compound 1 is a hydrazide form of 779 Compound 1,
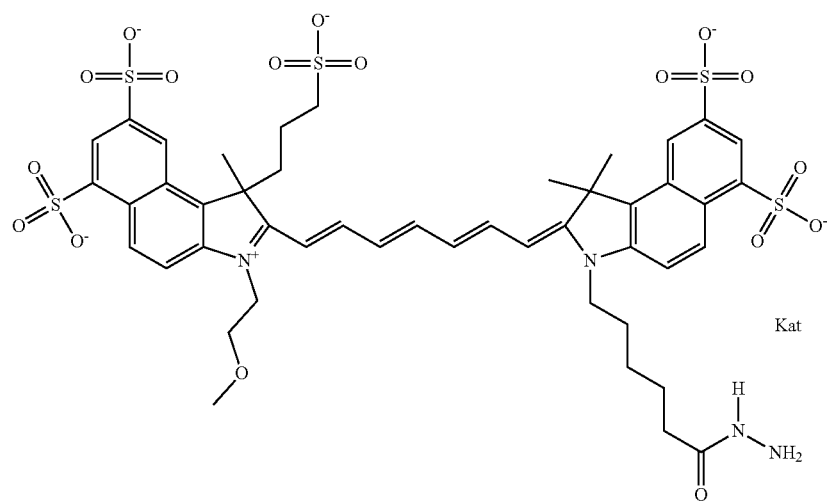 [SMILES: COCC[N+]1=C(/C=C/C=C/C=C/C=C2/N(CCCCCC(=O)NN)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

One non-limiting example of an activated 779 Compound 1 is a maleimide form of 779 Compound 1, shown below:

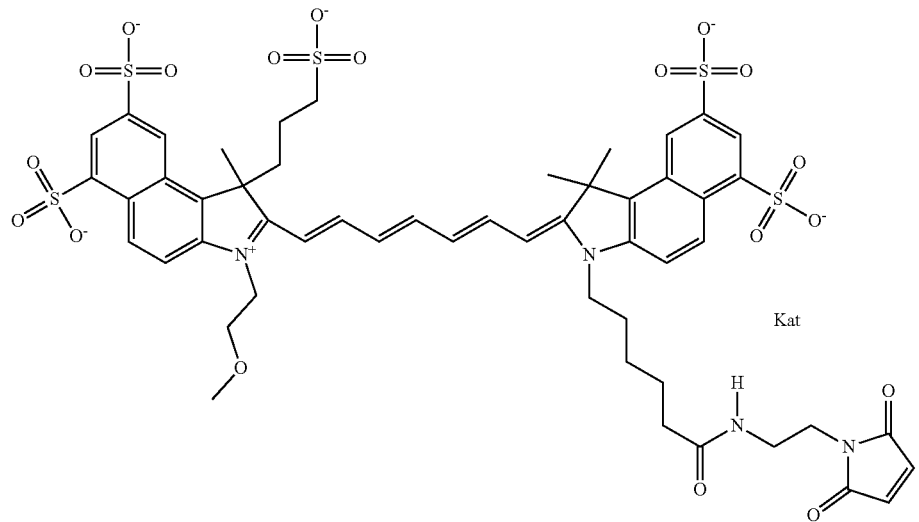 [SMILES: COCC[N+]1=C(/C=C/C=C/C=C/C=C2/N(CCCCCC(=O)NCCN3C(=O)C=CC3=O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

In one embodiment, the compound is 779 Compound 2

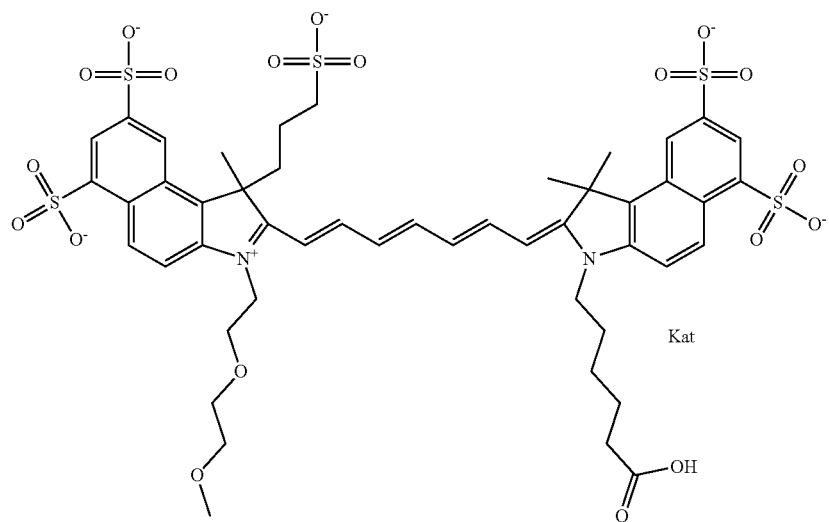 [SMILES: COCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 2 (6-((E)-2-((2E,4E,6E)-7-(3-(2-(2-methoxy)ethyl)-1-methyl-6,8-disulfonato-1-(3-sulfonatopropyl)-1H-benzo[e]indol-3-ium-2-yl)hepta-2,4,6-trien-1-ylidene)-1,1-dimethyl-6,8-disulfonato-1H-benzo[e]indol-3(2H)-yl)hexanoate) contains a diethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 2 is activated as described above.

In one embodiment, the compound is 779 Compound 3

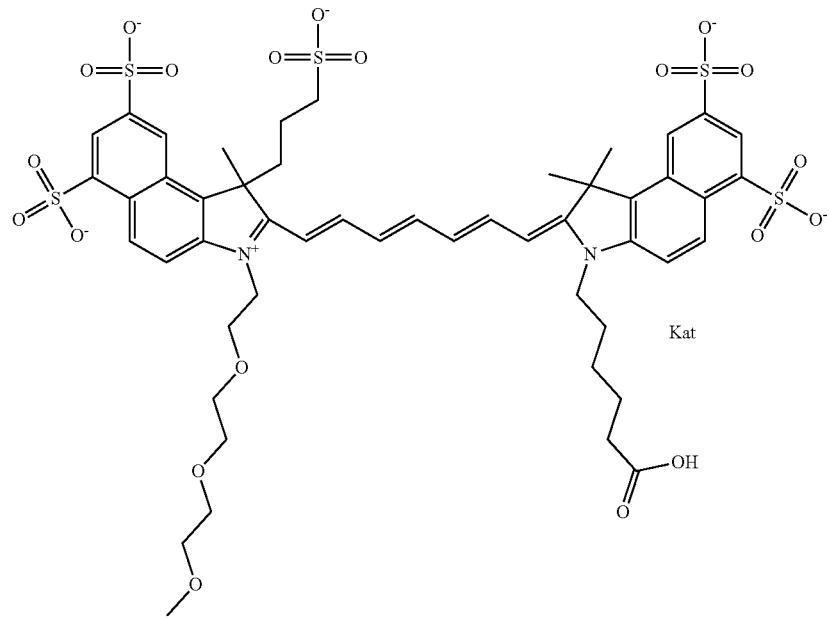 [SMILES: COCCOCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 3 (6-((E)-2-((2E,4E,6E)-7-(3-(2-(2-(2-methoxyethoxy)ethoxy)ethyl)-1-methyl-6,8-disulfonato-1-(3-sulfonatopropyl)-1H-benzo[e]indol-3-ium-2-yl)hepta-2,4,6-trien-1-ylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 3 is activated as described above.

In one embodiment, the compound is 779 Compound 4

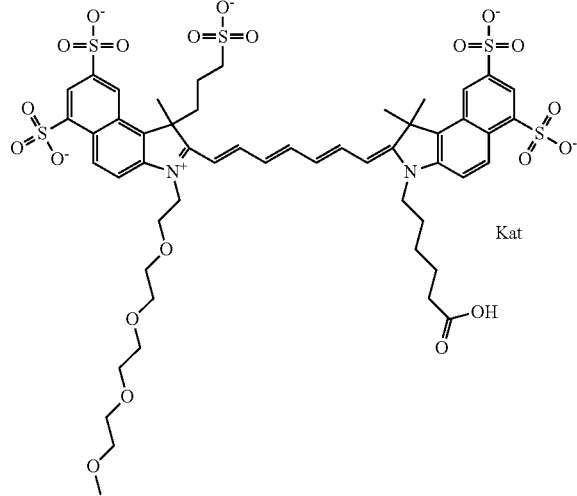 [SMILES: COCCOCCOCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(CCCS(=O)(=O)[O-])c2c1ccc1c(S(=O)(=O)[O-])cc(S(=O)(=O)[O-])cc21]

779 Compound 4 (6-((E)-1,1-dimethyl-2-((2E,4E,6E)-7-(1-methyl-6,8-disulfonato-1-(3-sulfonatopropyl)-3-(2,5,8,11-tetraoxatridecan-13-yl)-1H-benzo[e]indol-3-ium-2-yl)hepta-2,4,6-trien-1-ylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 4 is activated as described above.

In one embodiment, the compound is 779 Compound 5

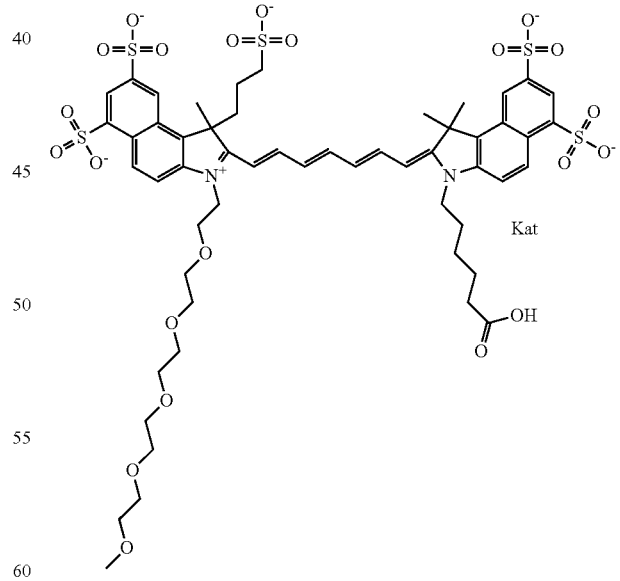

779 Compound 5 (6-((E)-2-((2E,4E,6E)-7-(3-(2,5,8,11,14-pentaoxahexadecan-16-yl)-1-methyl-6,8-disulfonato-1-(3-sulfonatopropyl)-1H-benzo[e]indol-3-ium-2-yl)hepta-2,4,6-trien-1-ylidene)-1,1-dimethyl-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over-time, on an unprotected PEG terminus. Adding a methyl ether provides this protection, and prevents reaction with electrophilic reactive groups. For functional assays, 779 Compound 5 is activated as described above.

In one embodiment, the compound is 779 Compound 6

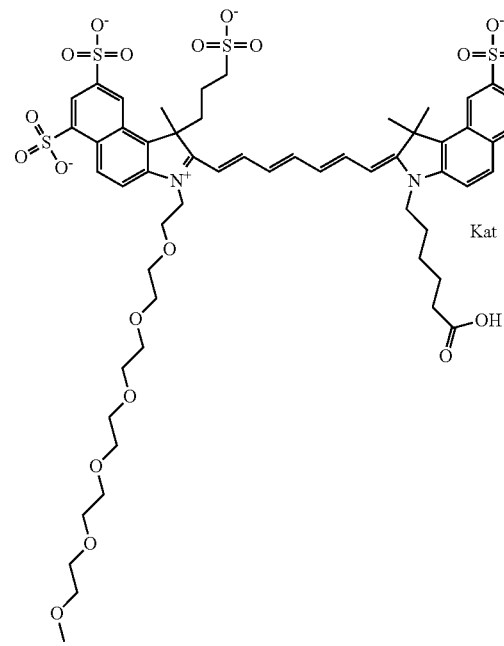

779 Compound 6 (6-((E)-1,1-dimethyl-2-((2E,4E,6E)-7-(1-methyl-3-(2,5,8,11,14,17-hexaoxanonadecan-19-yl)-6,8-disulfonato-1-(3-sulfonatopropyl)-1H-benzo[e]indol-3-ium-2-yl)hepta-2,4,6-trien-1-ylidene)-6,8-disulfonato-1H-benzo[e]indol-3(2H)-yl)hexanoate) contains a (poly)ethylene glycol on the indole N of the left heterocycle. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 6 is activated as described above.

In embodiments, the degree and/or location of sulfonation is varied to, e.g., vary the compound's degree of hydrophilicity or hydrophobicity. One non-limiting example is a monosulfonate form of 779 Compound 1, shown below:

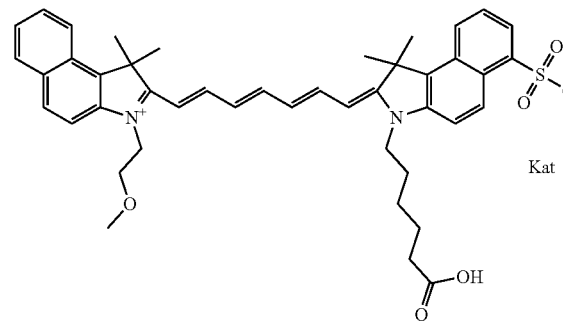

One non-limiting example is a disulfonate form of 779 Compound 1, shown below:

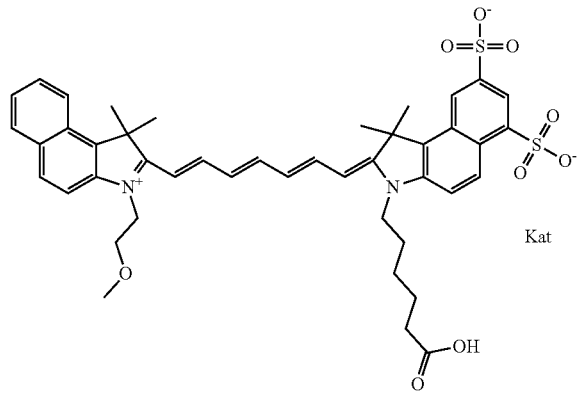 [SMILES: COCC[N+]1=C(/C=C/C=C/C=C/C=C2/N(CCCCCC(=O)O)c3ccc4c(S(=O)(=O)[O-])cc(S(=O)(=O)[O-])cc4c3C2(C)C)C(C)(C)c2c1ccc1ccccc21]

One non-limiting example is a trisulfonate form of 779 Compound 1, shown below:

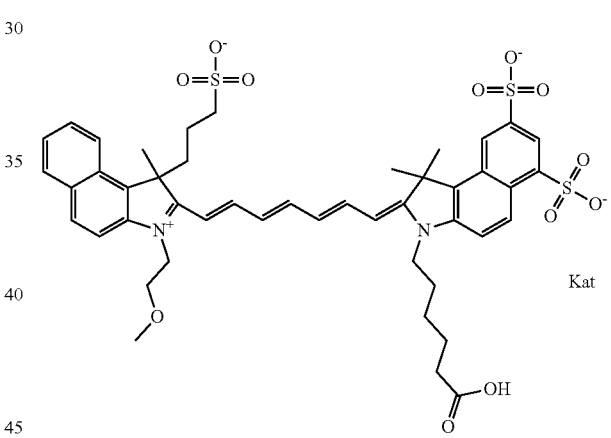

One non-limiting example is a tetrasulfonate form of 779 Compound 1, shown below:

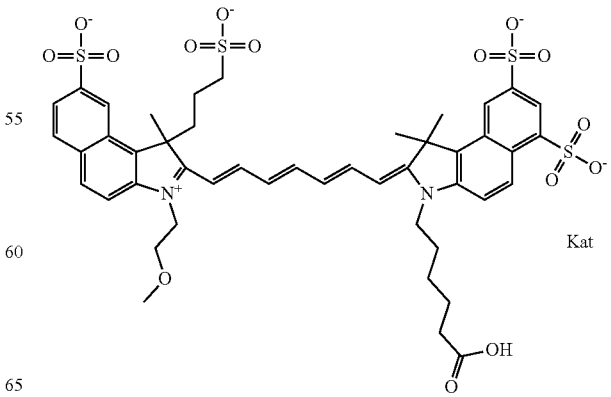

One non-limiting example is a pentasulfonate form of 779 Compound 1, shown below:

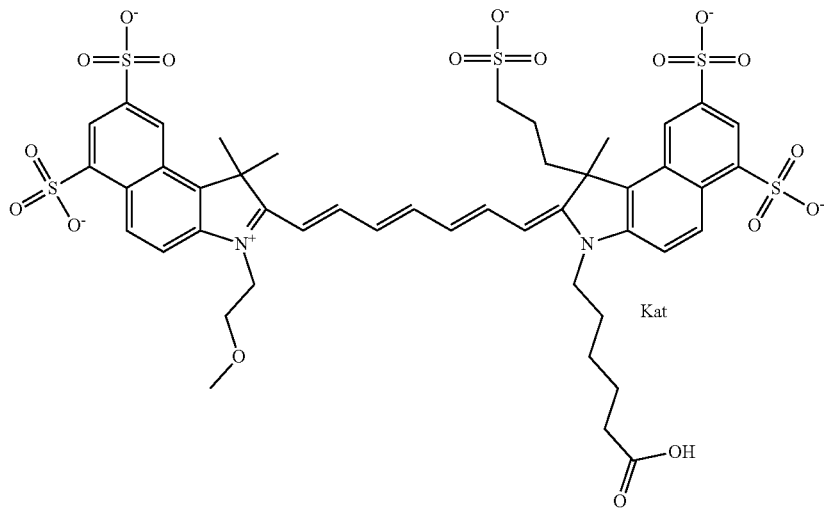 [SMILES: COCC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCCS(=O)(=O)[O-])C(C)(C)c2c1ccc1c(S(=O)(=O)[O-])cc(S(=O)(=O)[O-])cc21]

In one embodiment, the compound is 779 Compound 1/2 (PEG$_4$)

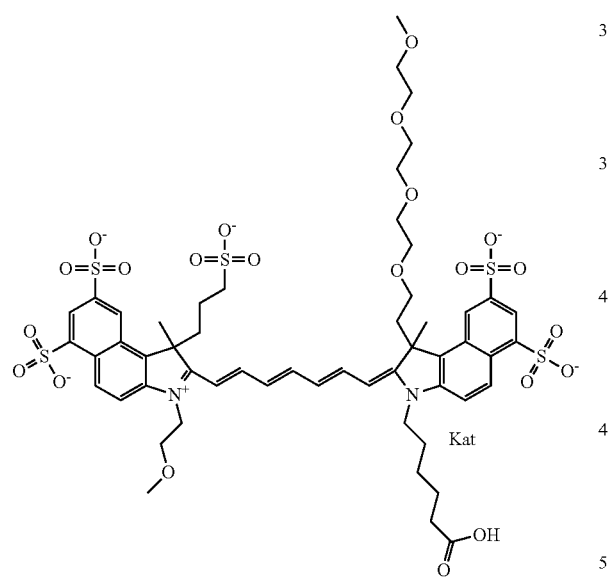

779 Compound 1/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene) hepta-1,3,5-trienyl)-3-(2-methoxyethyl)-1-methyl-1-(3-sulfonatopropyl)-1H-benzo[e]indolium-6,8-disulfonate) contains an ethylene glycol on the indole N of the left heterocycle, i.e., a methylated ethylene glycol and a PEG$_4$ group on the indole C. The methyl group on the ethylene glycol prevents the terminal —OH from oxidation. Oxidation is known to occur, over time, on an unprotected PEG terminus. Adding a methyl ether provides this protection, and prevents reaction with electrophilic reactive groups.

In embodiments, e.g., for functional assays, the inventive compounds are activated. Activation of the compound adds a chemical moiety such that the compound is in a form that can be conjugated to a biological moiety. Examples of chemical moieties for activation are described below with reference to activation of 779 Compound 1/2, but one skilled in the art appreciates that activation is not limited to these examples. One non-limiting example of an activated compound is the NHS-ester of 779 Compound 1/2 (PEG$_4$), shown below:

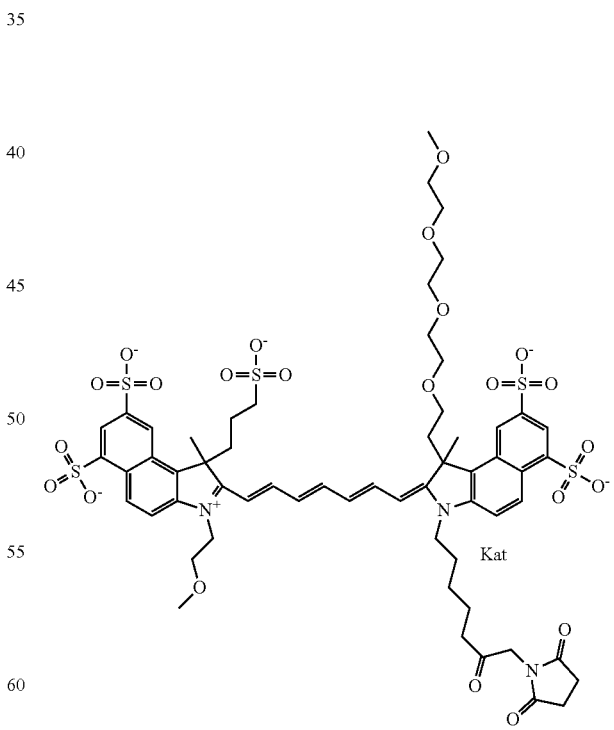

One non-limiting example of a NHS-ester of 779 Compound 1/3 (PEG$_4$), according to general formula III, where m=1 and p=1, is shown below:

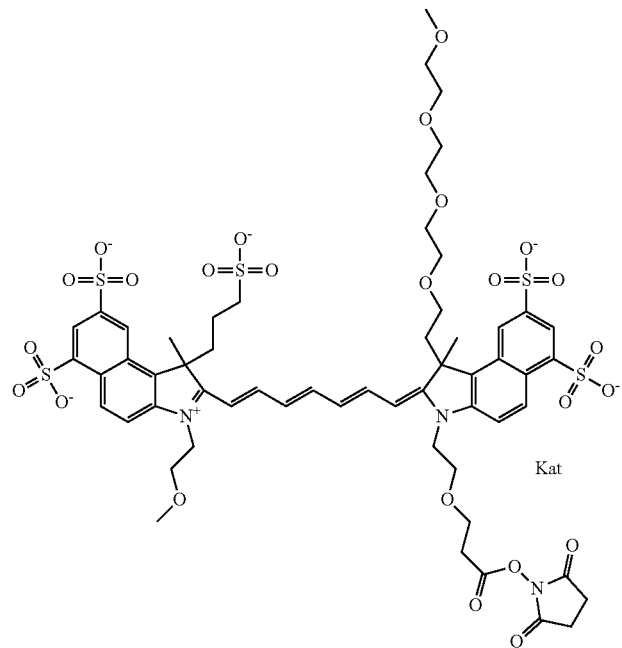
One non-limiting example of a NHS-ester of 779 Compound 1/3 (PEG$_4$), according to general formula III, where m=1 and p=2, is shown below:
One non-limiting example of a NHS-ester of 779 Compound 1/3 (PEG$_4$), according to general formula III, where m=1 and p=3, is shown below:
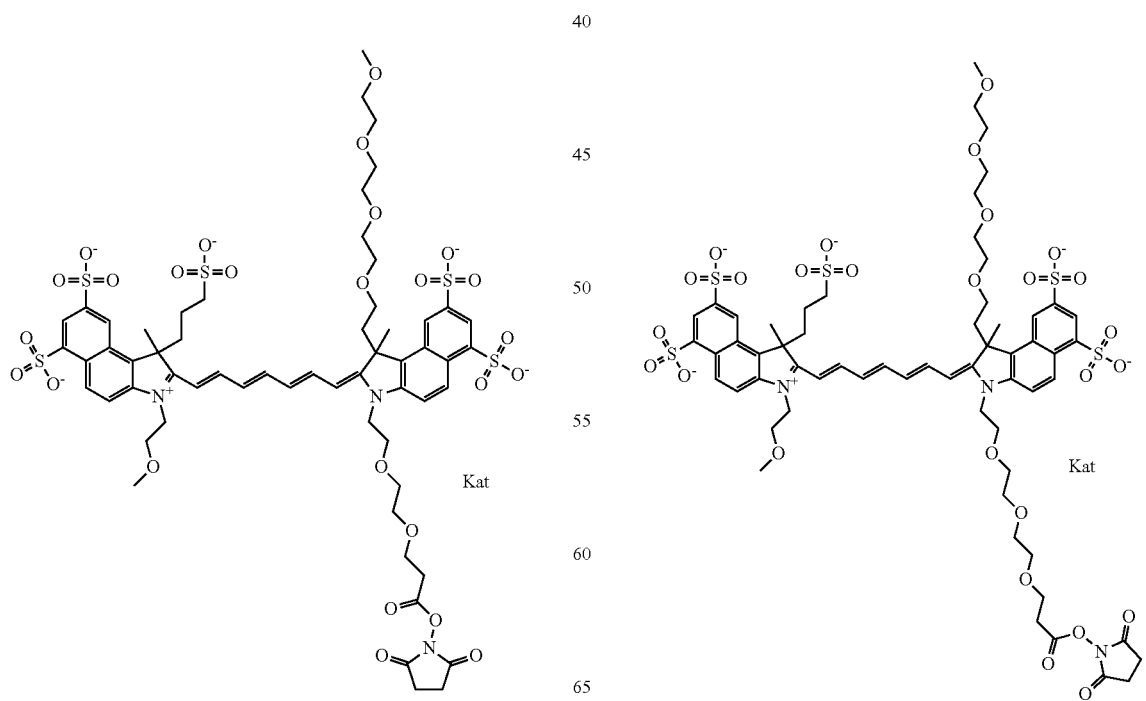

One non-limiting example of a NHS-ester of 779 Compound 1/3 (PEG$_4$), according to general formula III, where m=1 and p=4, is shown below:

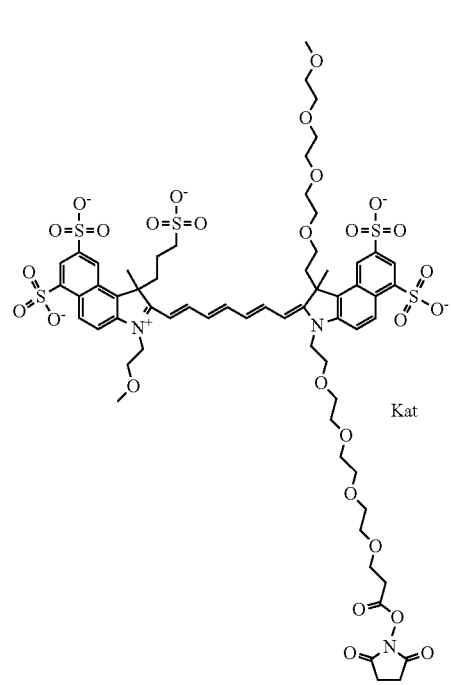

One non-limiting example of a NHS-ester of 779 Compound 1/3 (PEG$_4$), according to general formula III, where m=1 and p=6, is shown below:

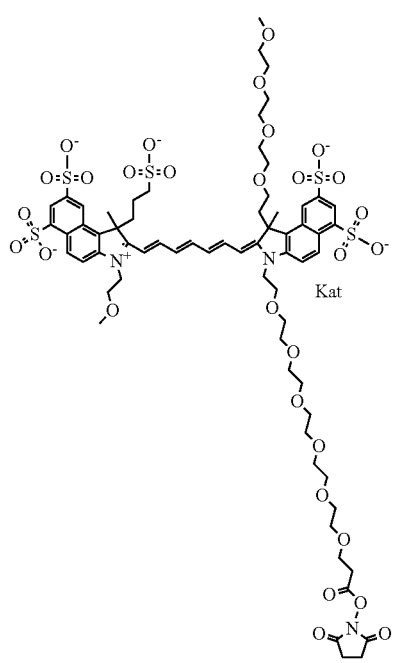

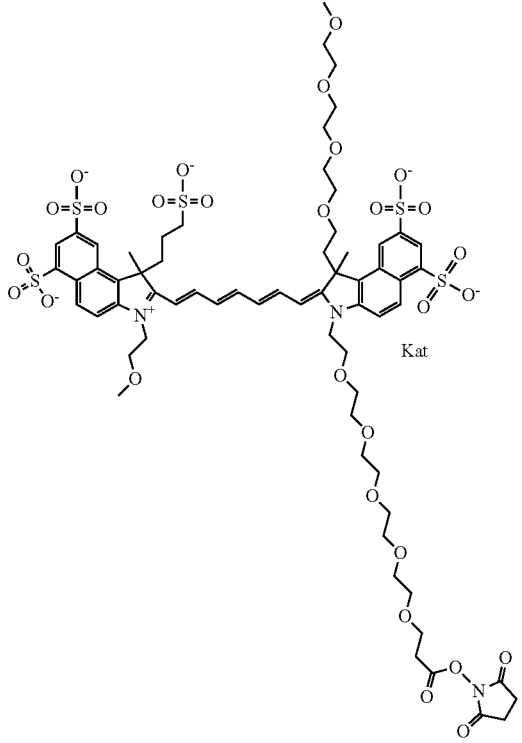

One non-limiting example of an activated 779 Compound 1/2 (PEG$_4$) is a tetrafluorophenyl (TFP)-ester form of 779 Compound 1, shown below:

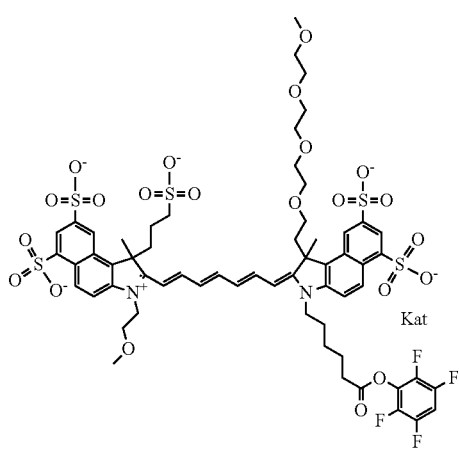 [SMILES: COCCOCCOCCOCCC1(C)\C(=C/C=C/C=C/C=C/C2=[N+](CCOC)c3ccc4c(S(=O)(=O)[O-])cc(S(=O)(=O)[O-])cc4c3C2(C)CCCS(=O)(=O)[O-])N(CCCCCC(=O)Oc2c(F)c(F)cc(F)c2F)c2ccc3c(S(=O)(=O)[O-])cc(S(=O)(=O)[O-])cc3c21]

One non-limiting example of an activated 779 Compound 1/2 (PEG$_4$) is a sulfotetrafluorophenyl (STP)-ester form of 779 Compound 1/2, shown below:

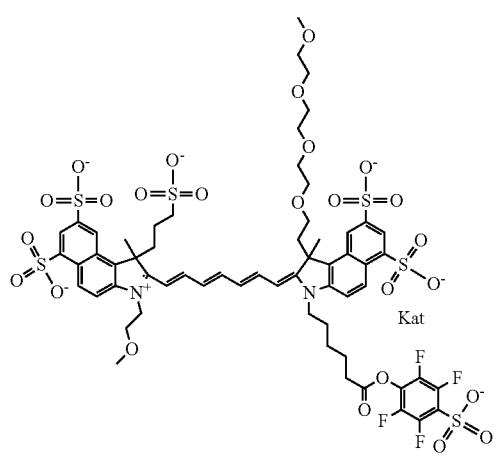 [SMILES: COCCOCCOCCOCCC1(C)\C(=C/C=C/C=C/C=C/C2=[N+](CCOC)c3ccc4c(S(=O)(=O)[O-])cc(S(=O)(=O)[O-])cc4c3C2(C)CCCS(=O)(=O)[O-])N(CCCCCC(=O)Oc2c(F)c(F)c(S(=O)(=O)[O-])c(F)c2F)c2ccc3c(S(=O)(=O)[O-])cc(S(=O)(=O)[O-])cc3c21]

One non-limiting example of an activated 779 Compound 1/2 (PEG$_4$) is a hydrazide form of 779 Compound 1/2, shown below:

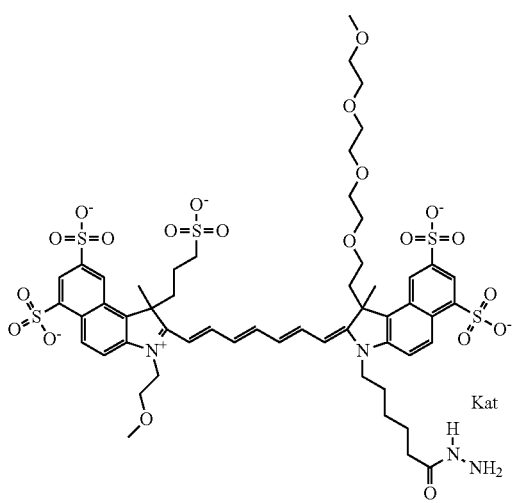 [SMILES: COCCOCCOCCOCCC1(C)\C(=C/C=C/C=C/C=C/C2=[N+](CCOC)c3ccc4c(S(=O)(=O)[O-])cc(S(=O)(=O)[O-])cc4c3C2(C)CCCS(=O)(=O)[O-])N(CCCCCC(=O)NN)c2ccc3c(S(=O)(=O)[O-])cc(S(=O)(=O)[O-])cc3c21]

One non-limiting example of an activated 779 Compound 1/2 (PEG$_4$) is a maleimide form of 779 Compound 1/2, shown below:

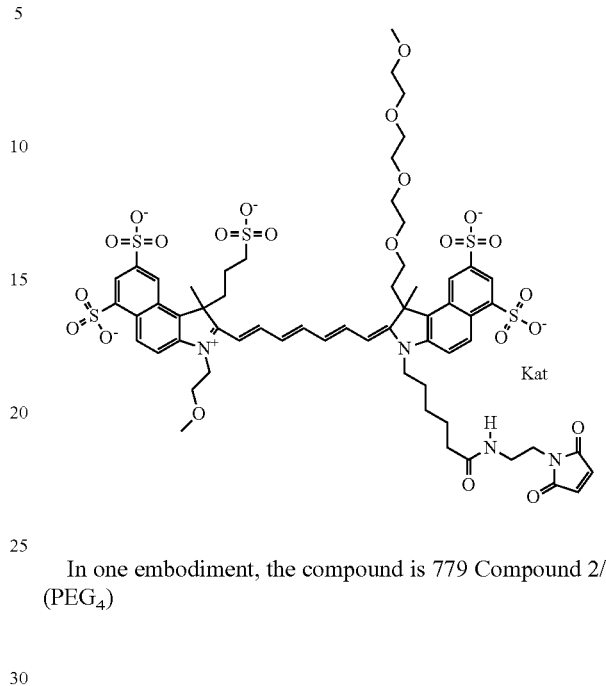

In one embodiment, the compound is 779 Compound 2/2 (PEG$_4$)

779 Compound 2/2 (PEG$_4$) (2-(((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene) hepta-1,3,5-trienyl)-3-(2-(2-methoxyethoxy)ethyl)-1-methyl-1-(3-sulfonatopropyl)-1H-benzo[e]indolium-6,8-disulfonate) contains a diethylene glycol on the indole N of the left heterocycle and a PEG$_4$ group on the indole C. The methyl group on the (poly)ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 2/2 (PEG$_4$) is activated as described above.

In one embodiment, the compound is 779 Compound 3/2 (PEG$_4$)

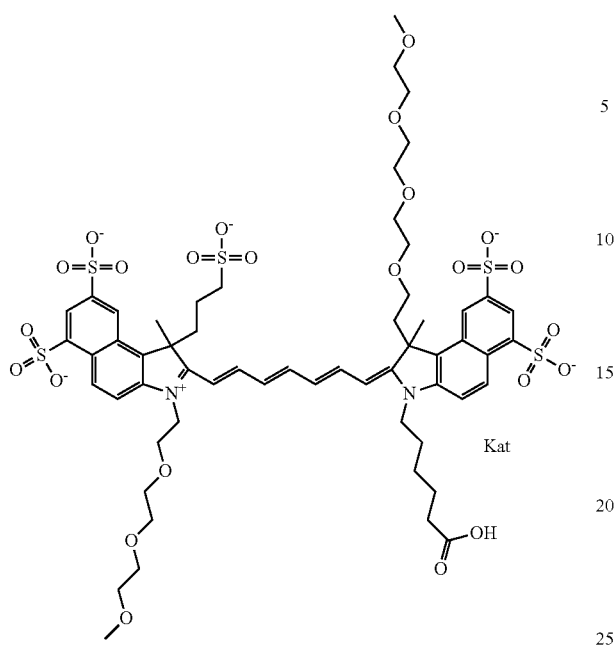

Kat

779 Compound 3/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-3-(2-(2-(2-methoxyethoxy)ethoxy)ethyl)-1-methyl-1-(3-sulfonatopropyl)-1H-benzo[e]indolium-6,8-disulfonate) contains a (poly)ethylene glycol on the indole N of the left heterocycle and a PEG$_4$ group on the indole C. The methyl group on the (poly)ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 3/2 (PEG$_4$) is activated as described above.

In one embodiment, the compound is 779 Compound 4/2 (PEG$_4$)

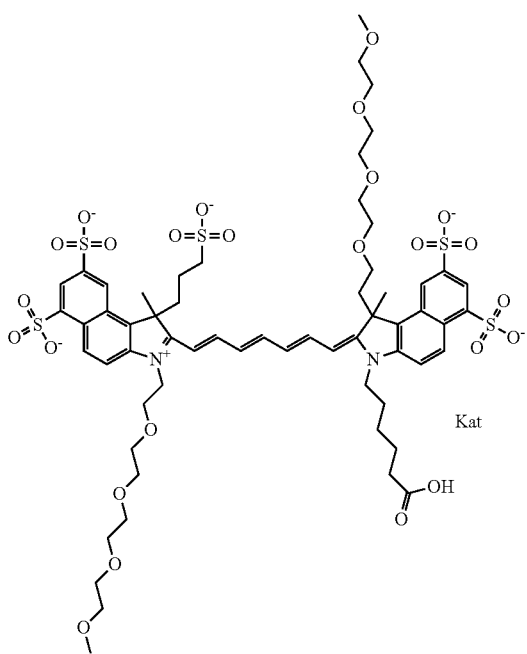 [SMILES: COCCOCCOCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

Kat

779 Compound 4/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-1-methyl-1-(3-sulfonatopropyl)-3-(2,5,8,11-tetraoxatridecan-13-yl)-1H-benzo[e]indolium-6,8-disulfonate) contains a (poly)ethylene glycol on the indole N of the left heterocycle and a PEG$_4$ group on the indole C. The methyl group on the (poly)ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 4/2 (PEG$_4$) is activated as described above.

In one embodiment, the compound is 779 Compound 5/2 (PEG$_4$)

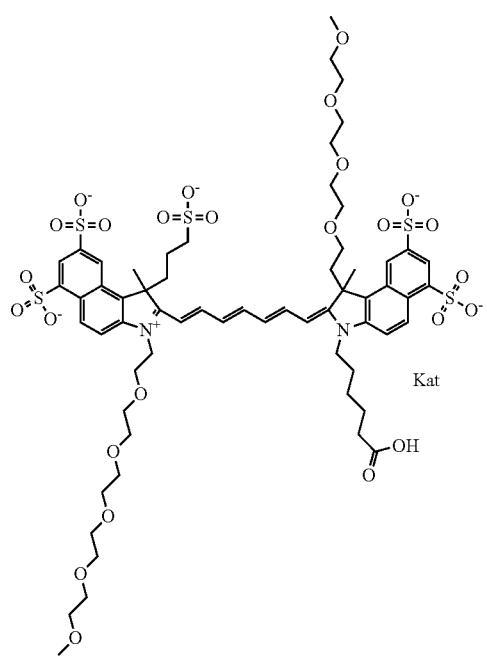 [SMILES: COCCOCCOCCOCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

Kat

779 Compound 5/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-3-(2,5,8,11,14-pentaoxahexadecan-16-yl)-1-methyl-1-(3-sulfonatopropyl)-1H-benzo[e]indolium-6,8-disulfonate) contains a (poly)ethylene glycol on the indole N of the left heterocycle and a PEG$_4$ group on the indole C. The methyl group on the (poly)ethylene glycol prevents the terminal —OH from oxidation. Oxidation is known to occur, overtime, on an unprotected PEG terminus. Adding a methyl ether provides this protection, and prevents reaction with electrophilic reactive groups. For functional assays, 779 Compound 5/2 (PEG$_4$) is activated as described above.

In one embodiment, the compound is 779 Compound 6/2 (PEG$_4$)

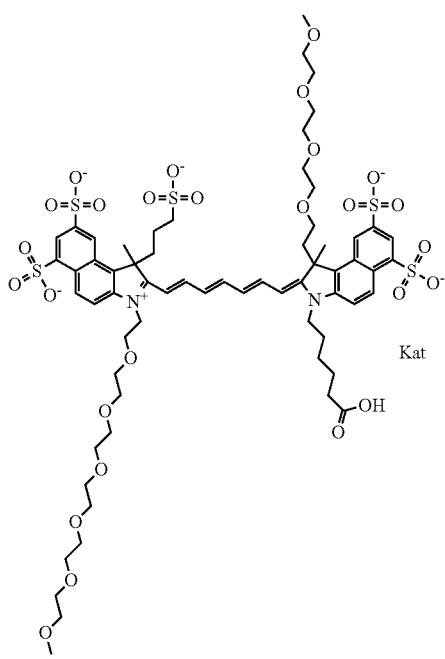 [SMILES: COCCOCCOCCOCCOCCOCC[N+]1=C(/C=C/C=C/C=C/C=C2/N(CCCCCC(=O)O)c3ccc4c(S(=O)(=O)[O-])cc(S(=O)(=O)[O-])cc4c3C2(C)CCOCCOCCOCCOC)C(C)(CCCS(=O)(=O)[O-])c2c1ccc1c(S(=O)(=O)[O-])cc(S(=O)(=O)[O-])cc21]

779 Compound 6/2 (PEG$_4$) (2-((1E,3E,5E,7E)-7-(3-(5-carboxypentyl)-1-methyl-6,8-disulfonato-1-(2,5,8,11-tetraoxatridecan-13-yl)-1H-benzo[e]indol-2(3H)-ylidene)hepta-1,3,5-trienyl)-1-methyl-3-(2,5,8,11,14,17-hexaoxanonadecan-19-yl)-1-(3-sulfonatopropyl)-1H-benzo[e]indolium-6,8-disulfonate) contains a (poly)ethylene glycol on the indole N of the left heterocycle. The methyl group on the (poly)ethylene glycol prevents the terminal —OH from oxidation. Oxidation is known to occur, over time, on an unprotected PEG terminus. Adding a methyl ether provides this protection, and prevents reaction with electrophilic reactive groups. For functional assays, 779 Compound 6/2 (PEG$_4$) is activated as described above.

In embodiments, the degree and/or location of sulfonation is varied to, e.g., vary the compound's degree of hydrophilicity or hydrophobicity. One non-limiting example is a monosulfonate form of 779 Compound 1/2 (PEG$_4$), shown below:

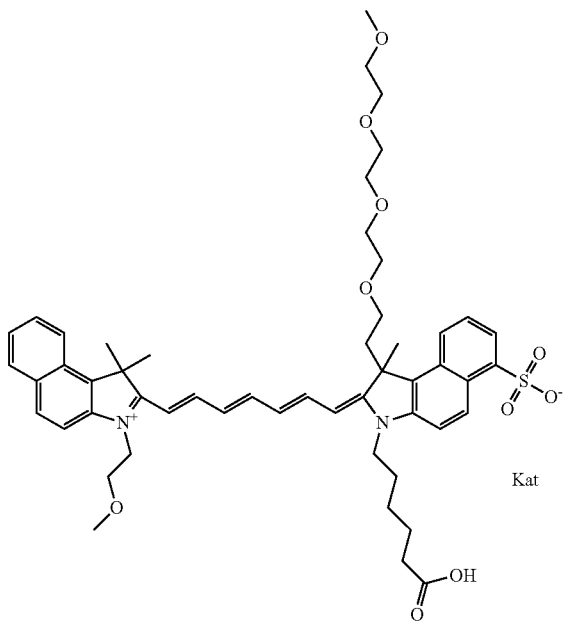 [SMILES: COCCOCCOCCOCCC1(C)\C(=C/C=C/C=C/C=C/C2=[N+](CCOC)c3ccc4ccccc4c3C2(C)C)N(CCCCCC(=O)O)c2ccc3c(S(=O)(=O)[O-])cccc3c21]

One non-limiting example is a disulfonate form of 779 Compound 1/2 (PEG$_4$), shown below:

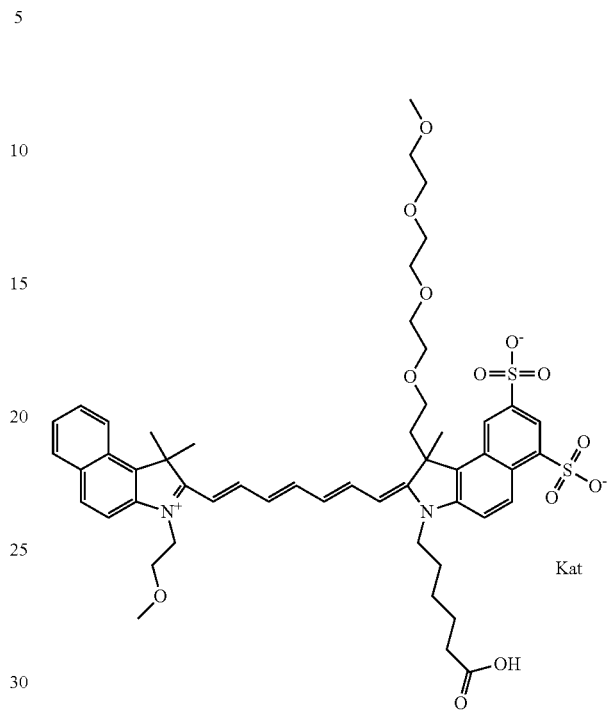

One non-limiting example is a trisulfonate form of 779 Compound 1/2 (PEG$_4$), shown below:

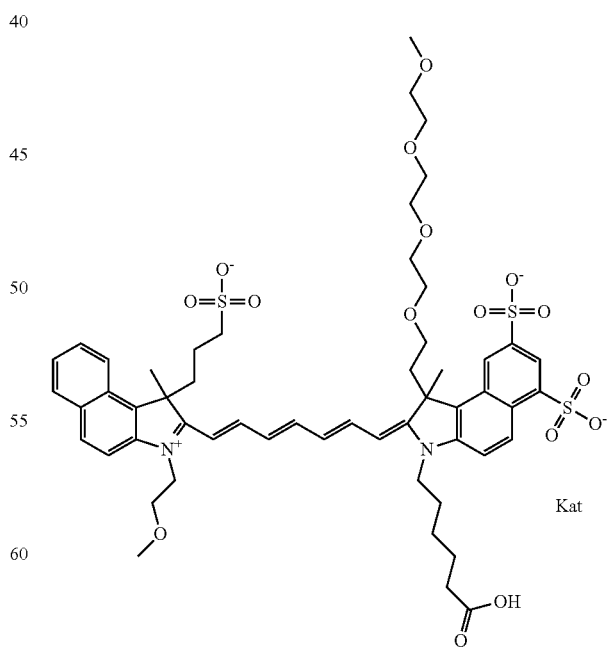

One non-limiting example is a tetrasulfonate form of 779 Compound 1/2 (PEG$_4$), shown below:

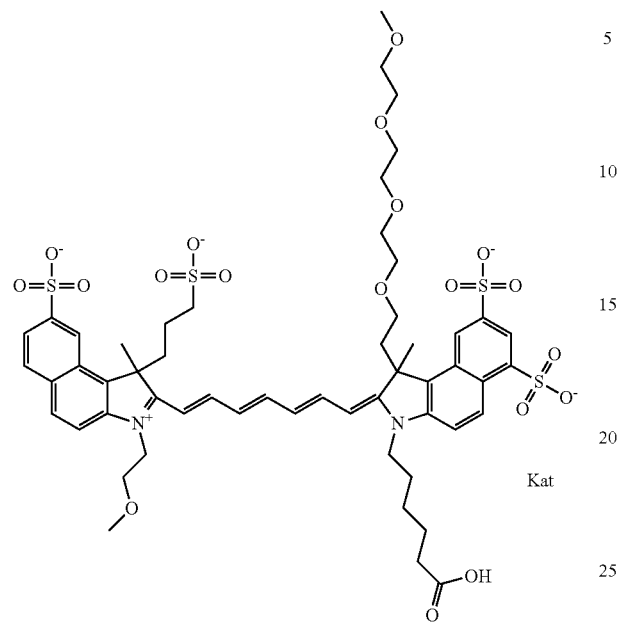
One non-limiting example is a pentasulfonate form of 779 Compound 1/2 (PEG$_4$), shown below:
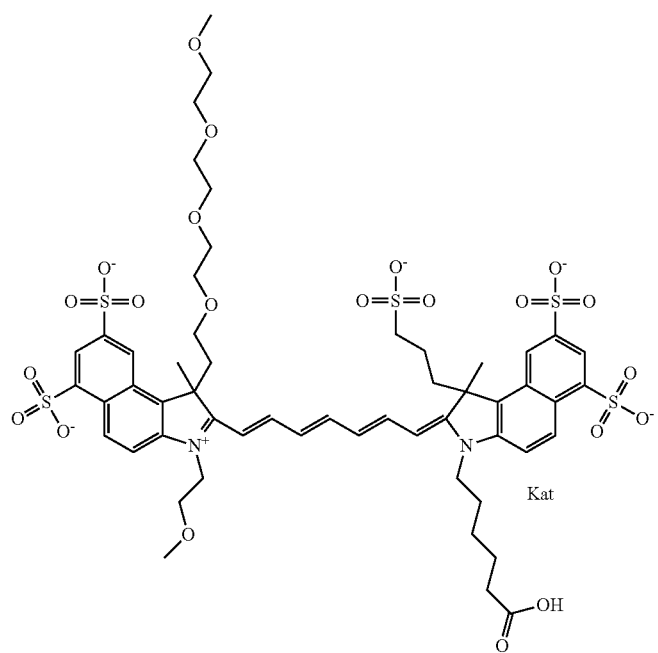 [SMILES: COCCOCCOCCOCCC1(C)C(/C=C/C=C/C=C/C=C2/N(CCCCCC(=O)O)c3ccc4c(S(=O)(=O)[O-])cc(S(=O)(=O)[O-])cc4c3C2(C)CCCS(=O)(=O)[O-])=[N+](CCOC)c2ccc3c(S(=O)(=O)[O-])cc(S(=O)(=O)[O-])cc3c21]

In embodiments, the compound contains one or more substitutions of the polymethine linker. In one embodiment, the compound has general formula VIa
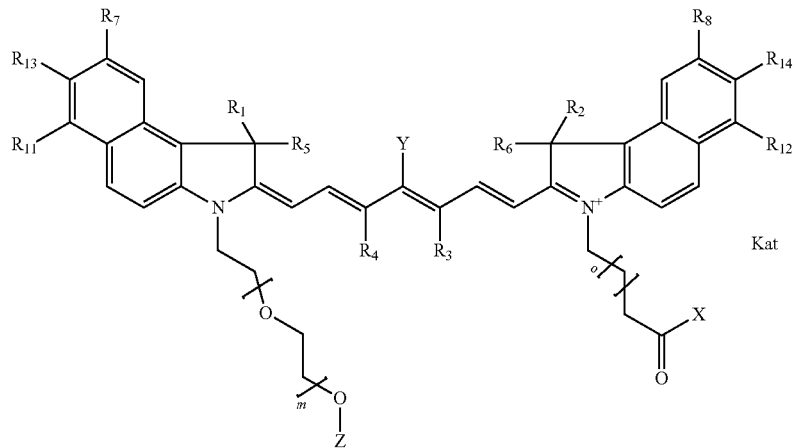
general formula VIb
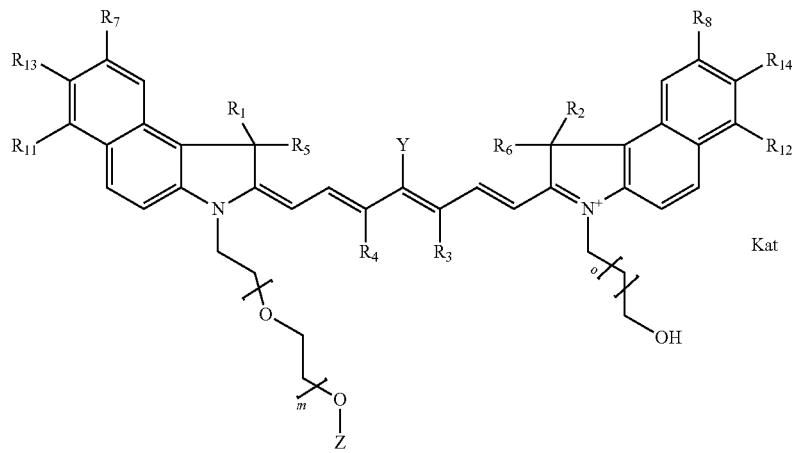
general formula VIc
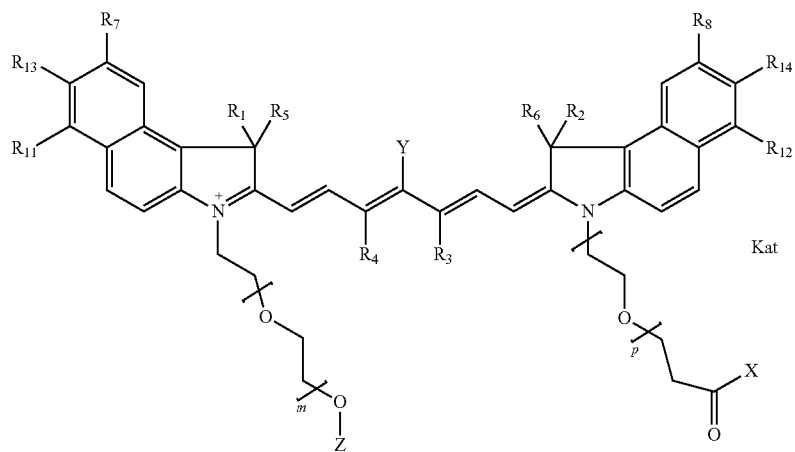

general formula VId

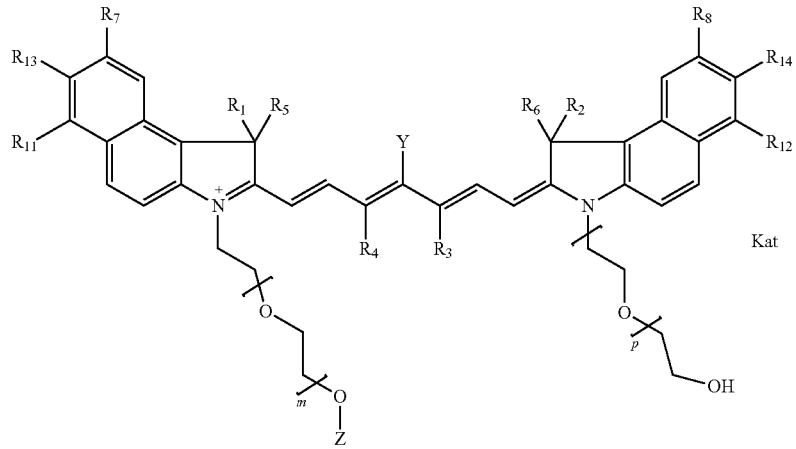

where each of $R^1$, $R^2$, $R^5$, and $R^6$ is the same or different and is independently selected from the group consisting of an aliphatic, heteroaliphatic, sulfoalkyl group, heteroaliphatic with terminal $SO_3$, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -L-$SO_2$NH—P—Z, and a caboxamide group -L-CONH—P—Z, and Z is selected from H, $CH_3$, a $CH_3$ group, an alkyl group, a heteroalkyl group, or —CO—NHS; each of $R^7$, $R^8$, $R^{11}$, $R^{12}$, $R^{13}$, and $R^{14}$ is the same or different and is independently selected from either H, $SO_3$, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -L-$SO_2$NH—P—Z, or a caboxamide group -L-CONH—P—Z, and Z is selected from H, a $CH_3$ group, an alkyl group, a heteroalkyl group, or —CO—NHS; X is selected from the group consisting of —OH, —SH, —$NH_2$, —NH—$NH_2$, —F, —Cl, —Br, I, —NHS (hydroxysuccinimidyl/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, —NR-L-OH, —NR-L-O-phosphoramidite, —NR-L-SH, —NR-L-$NH_2$, —NR-L-NH—$NH_2$, —NR-L-$CO_2$H, —NR-L-CO—NHS, —NR-L-CO-STP, —NR-L-CO-TFP, —NR-L-CO-benzotriazole, —NR-L-CHO, —NR-L-maleimide, —NR-L-NH—CO—$CH_2$-1, imidazole, azide, —NR-L-O—$NH_2$, and —NR-L-O—CO—NHS, where R is —H or an aliphatic or heteroaliphatic group, and L is selected from the group consisting of a divalent linear (—$(CH_2)_t$—, t=0 to 15), crossed, or cyclic alkyl group optionally substituted by at least one oxygen atom and/or sulfur atom; Kat is a number of $Na^+$, $K^+$, $Ca^{2+}$, ammonia, or other cation(s) needed to compensate the negative charge brought by the cyanine; m is an integer from 0 to 5 inclusive; o is an integer from 0 to 12 inclusive; p is an integer from 1 to 6 inclusive; each of R3 and R4 is the same or different and is independently hydrogen, an aliphatic group, a heteroaliphatic group, or a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, and Z is selected from H, $CH_3$, a $CH_3$ group, an alkyl group, a heteroalkyl group, or —CO—NHS; or R3 and R4 together form a cyclic structure where R3 and R4 are joined using a divalent structural element selected from the group consisting of —$(CH_2)_q$—, —$(CH_2)_qO(CH_2)_{q'}$—, —$(CH_2)_qS(CH_2)_{q'}$—, —$(CH_2)_q$CH=CH—, and —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl-, phenoxy-, phenylmercapto function, and a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, and Z is selected from H, $CH_3$, a $CH_3$ group, an alkyl group, a heteroalkyl group, or —CO—NHS.

In one embodiment, the compound of general formula VI wherein each of R3 and R4 is the same or different and is independently hydrogen, an aliphatic group, or a heteroaliphatic group, or R3 and R4 together form a cyclic structure where R3 and R4 are directly joined or joined using a divalent structural element selected from the group consisting of —$(CH_2)_q$— and CH=CH, where q is an integer from 1 to 2 inclusive, to result in a 3-, 4-, or 5-membered ring.

One non-limiting example is a substituted polymethine form of 779 Compound 1, shown below:

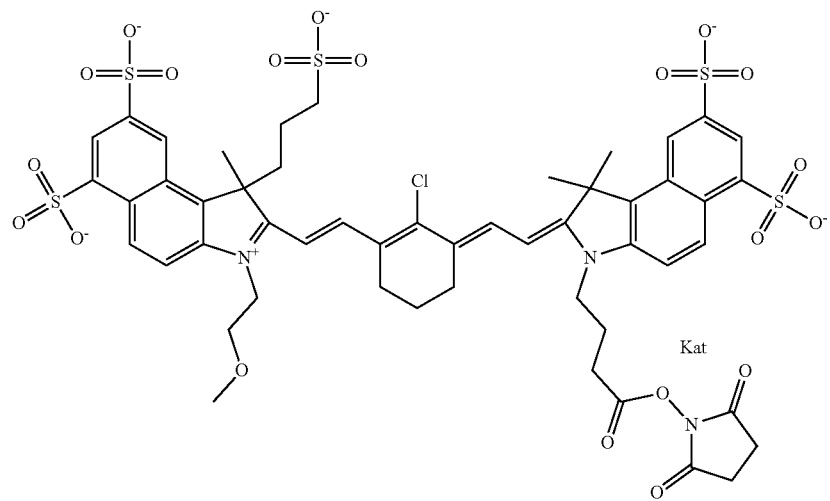 [SMILES: COCC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)C)/CCC2)C(C)(CCCS(=O)(=O)[O-])c2c1ccc1c(S(=O)(=O)[O-])cc(S(=O)(=O)[O-])cc21]
One non-limiting example is a substituted polymethine form of 779 Compound 2, shown below:
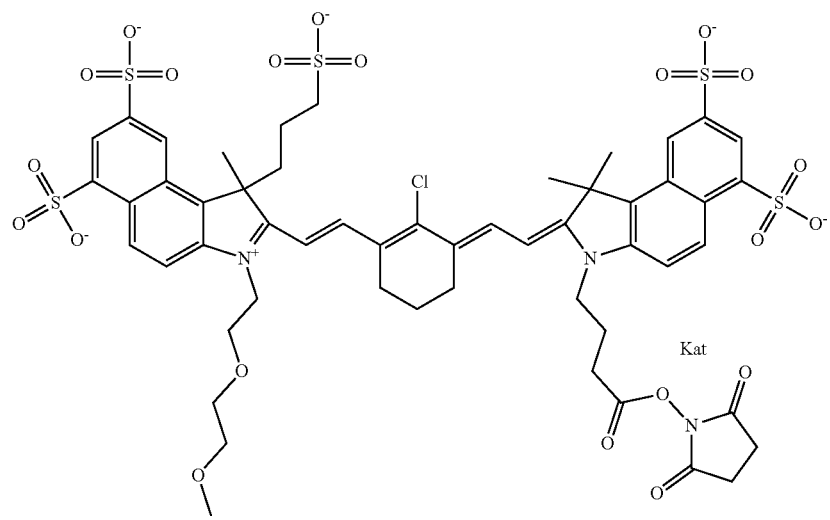 [SMILES: COCCOCC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)C)/CCC2)C(C)(CCCS(=O)(=O)[O-])c2c1ccc1c(S(=O)(=O)[O-])cc(S(=O)(=O)[O-])cc21]
One non-limiting example is a substituted polymethine form of 779 Compound 3, shown below:
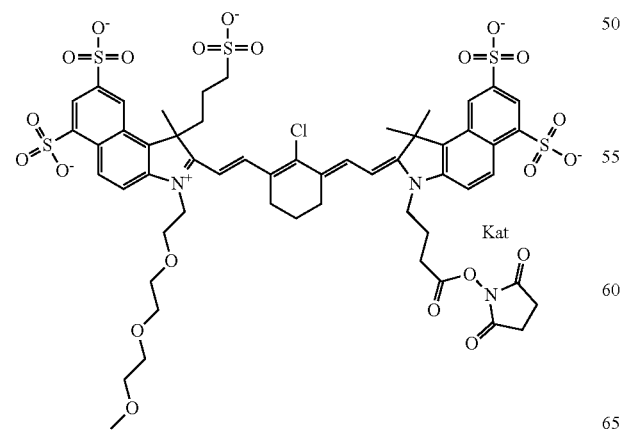

One non-limiting example is a substituted polymethine form of 779 Compound 4, shown below:
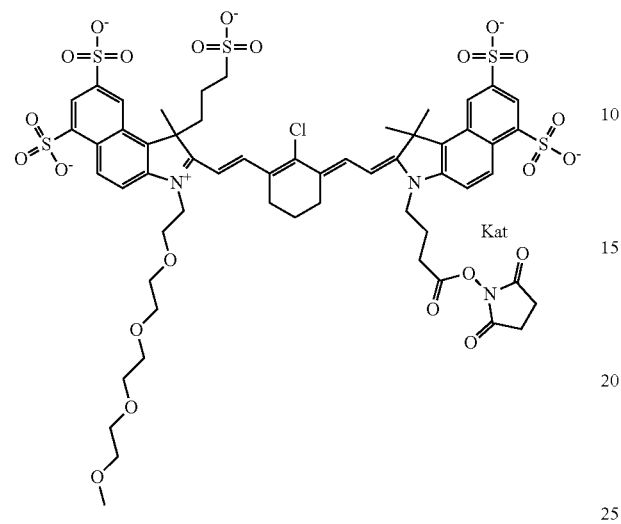
One non-limiting example is a substituted polymethine form of 779 Compound 5, shown below:
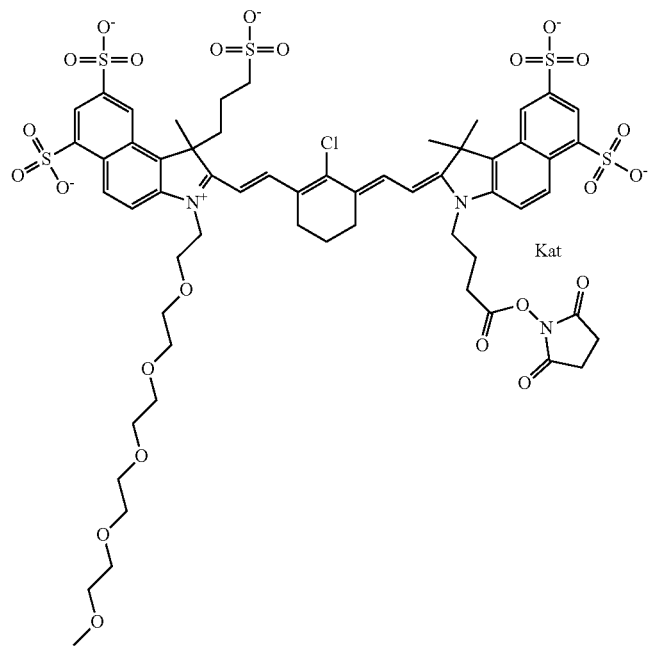 [SMILES: COCCOCCOCCOCCOCC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)C)/CCC2)C(C)(CCCS(=O)(=O)[O-])c2c1ccc1c(S(=O)(=O)[O-])cc(S(=O)(=O)[O-])cc21]

One non-limiting example is a substituted polymethine form of 779 Compound 6, shown below:
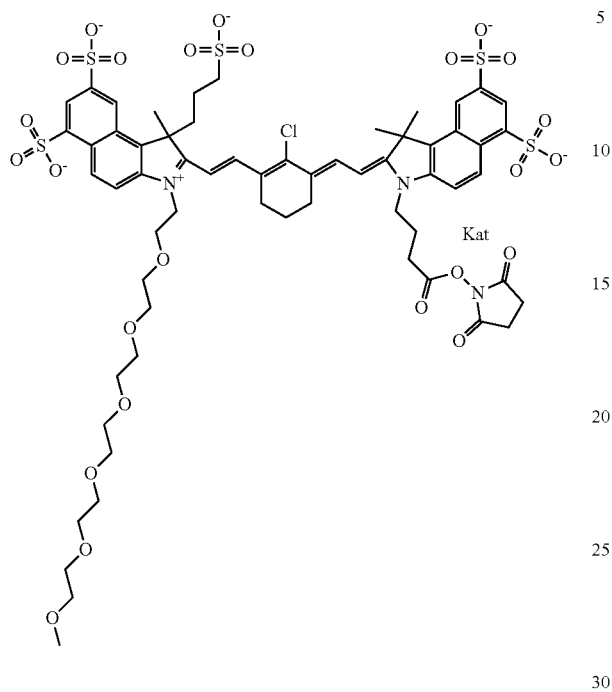
One non-limiting example is a substituted polymethine form of 779 Compound 1/2 (PEG$_4$), shown below:
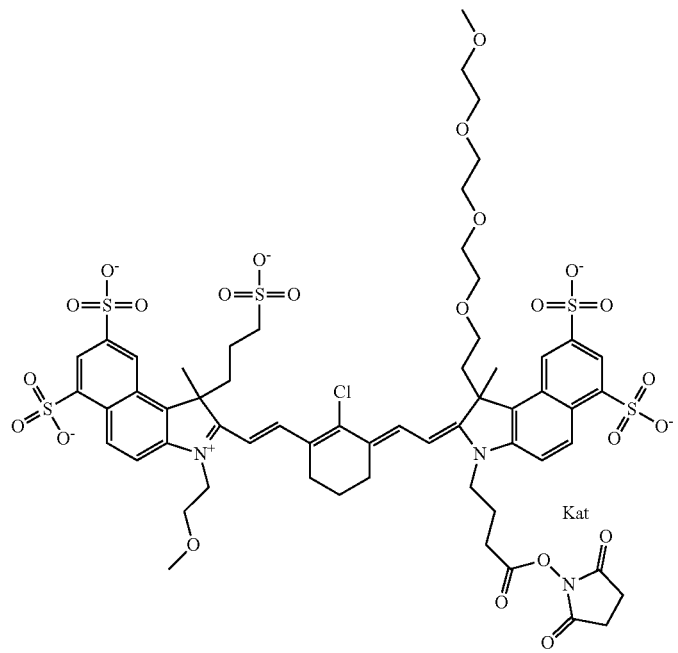 [SMILES: COCCOCCOCCOCCC1(C)/C(=C\C=C2/CCCC(/C=C/C3=[N+](CCOC)c4ccc5c(S(=O)(=O)[O-])cc(S(=O)(=O)[O-])cc5c4C3(C)CCCS(=O)(=O)[O-])=C2Cl)N(CCCC(=O)ON2C(=O)CCC2=O)c2ccc3c(S(=O)(=O)[O-])cc(S(=O)(=O)[O-])cc3c21]

One non-limiting example is a substituted polymethine form of 779 Compound 2/2 (PEG$_4$), shown below:
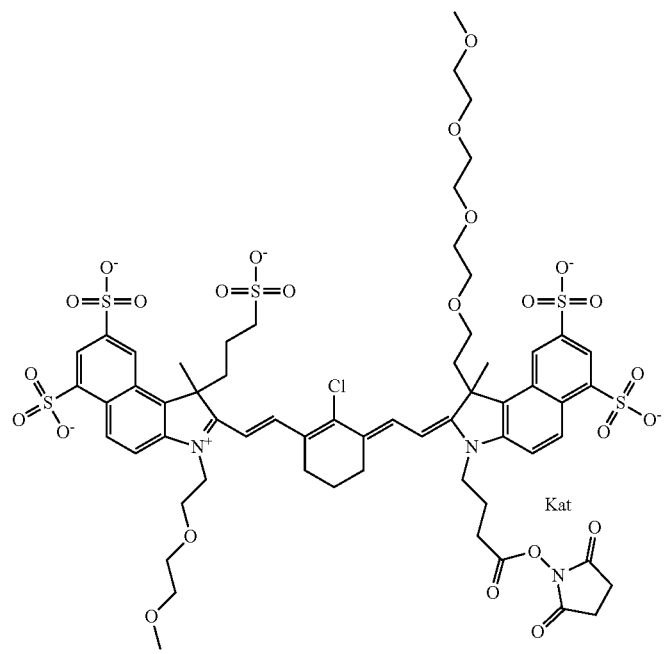 [SMILES: COCCOCCOCCOCCC1(C)/C(=C\C=C2/CCCC(/C=C/C3=[N+](CCOCCOC)c4ccc5c(S(=O)(=O)[O-])cc(S(=O)(=O)[O-])cc5c4C3(C)CCCS(=O)(=O)[O-])=C2Cl)N(CCCC(=O)ON2C(=O)CCC2=O)c2ccc3c(S(=O)(=O)[O-])cc(S(=O)(=O)[O-])cc3c21]
One non-limiting example is a substituted polymethine form of 779 Compound 3/2 (PEG$_4$), shown below:
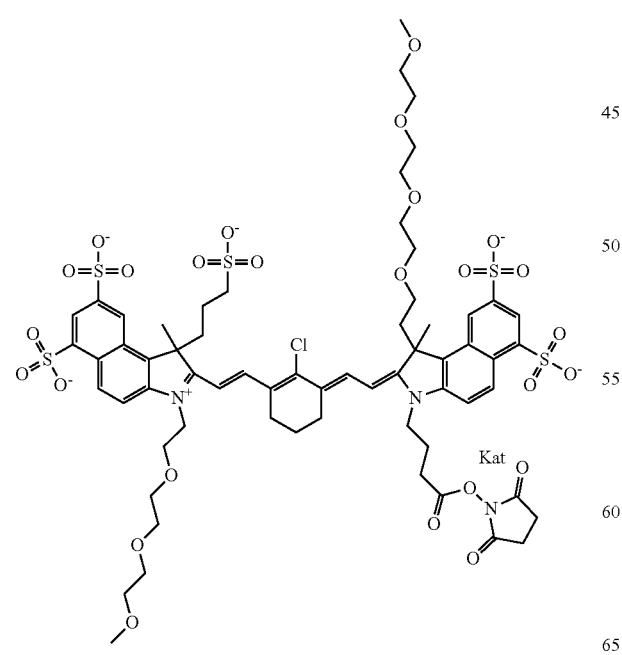
One non-limiting example is a substituted polymethine form of 779 Compound 4/2 (PEG$_4$), shown below:
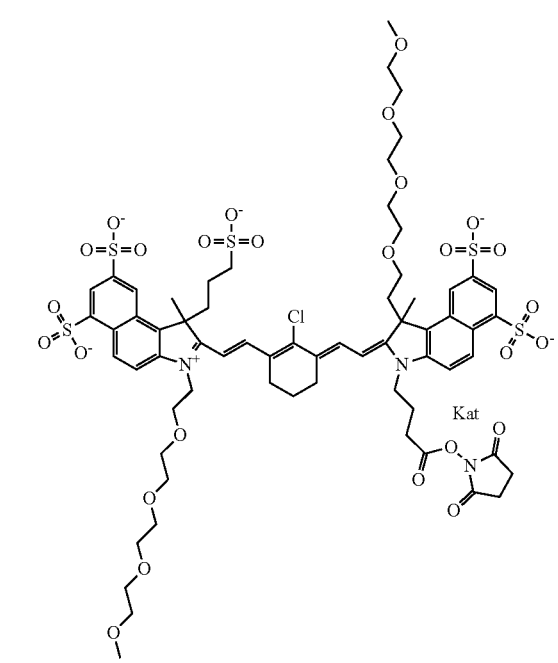 [SMILES: COCCOCCOCCOCC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)CCOCCOCCOCCOC)/CCC2)C(C)(CCCS(=O)(=O)[O-])c2c1ccc1c(S(=O)(=O)[O-])cc(S(=O)(=O)[O-])cc21]

One non-limiting example is a substituted polymethine form of 779 Compound 5/2 (PEG$_4$), shown below:

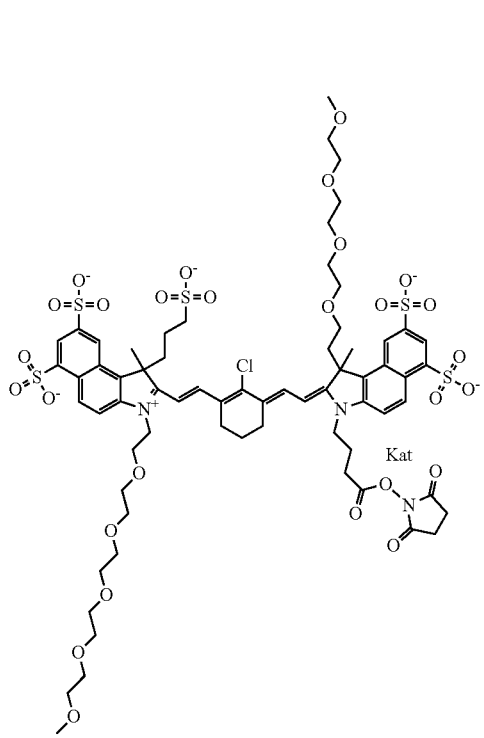 [SMILES: COCCOCCOCCOCCOCC[N+]1=C(/C=C/C2=C(Cl)C(=C/C=C3/N(CCCC(=O)ON4C(=O)CCC4=O)c4ccc5c(S(=O)(=O)[O-])cc(S(=O)(=O)[O-])cc5c4C3(C)CCOCCOCCOCCOC)/CCC2)C(C)(CCCS(=O)(=O)[O-])c2c1ccc1c(S(=O)(=O)[O-])cc(S(=O)(=O)[O-])cc21]

One non-limiting example is a substituted polymethine form of 779 Compound 6/2 (PEG$_4$), shown below:

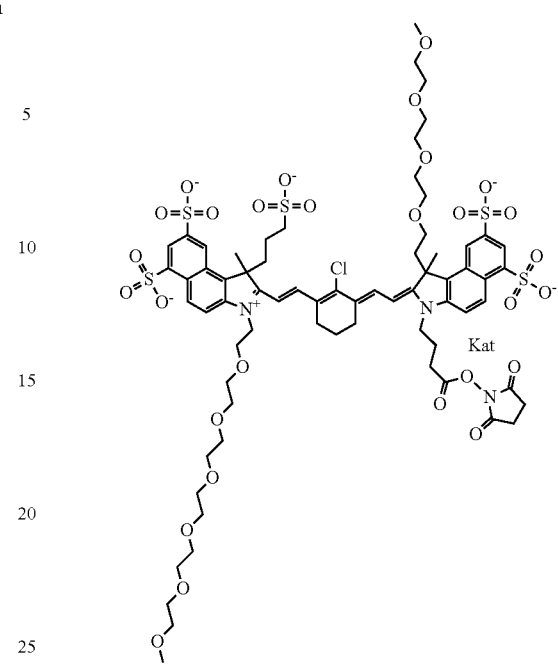

In embodiments, an ethylene glycol group, diethylene glycol group, and/or a polyethylene glycol group, collectively referred to as a PEG group unless specifically defined, may be present at position(s) in addition to such groups being present on the N atom(s) of the indole structure.

One non-limiting example of an additionally PEG-substituted compound is a 779 Compound 1/2 according to general formula II where R1 is an ethylene glycol group terminating with a methyl group,

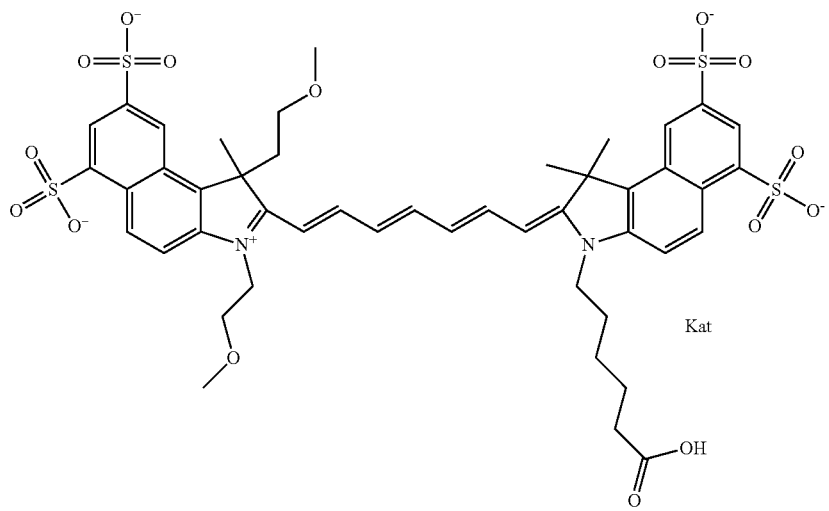

One non-limiting example of an additionally PEG-substituted compound is a 779 Compound 1/2 according to general formula II where R2 is an ethylene glycol group terminating with a methyl group, shown below:

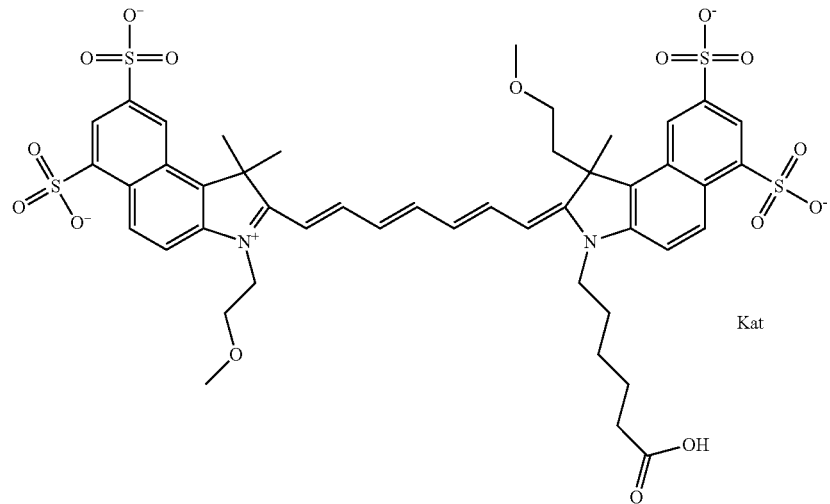

30

One non-limiting example of an additionally PEG-substituted compound is a 779 Compound 1/2 according to general formula II where R8 is an ethylene glycol group terminating with a methyl group,

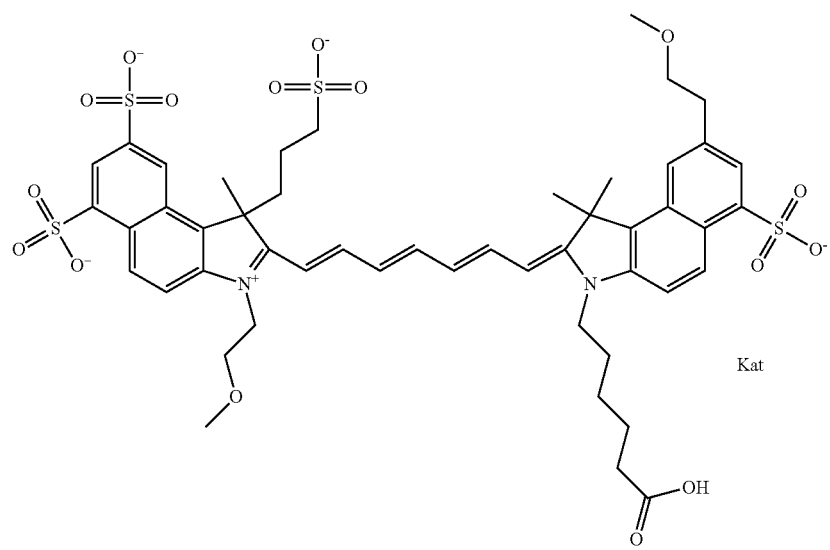

One non-limiting example of an additionally PEG-substituted compound is a 779 Compound 1/2 according to general formula II where R8 is a sulfonamide group with an ethylene glycol group (PEG$_1$) terminating with a methyl group, shown below:

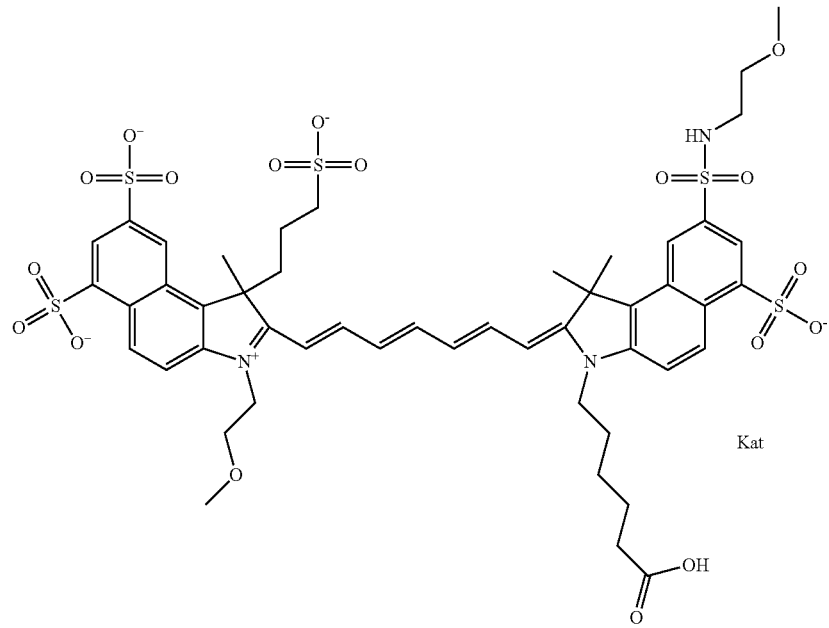

One non-limiting example of an additionally PEG-substituted compound is a 779 Compound 1/2 according to general formula II where R8 is a carboxamide group with an ethylene glycol group (PEG$_1$) terminating with a methyl group, shown below:

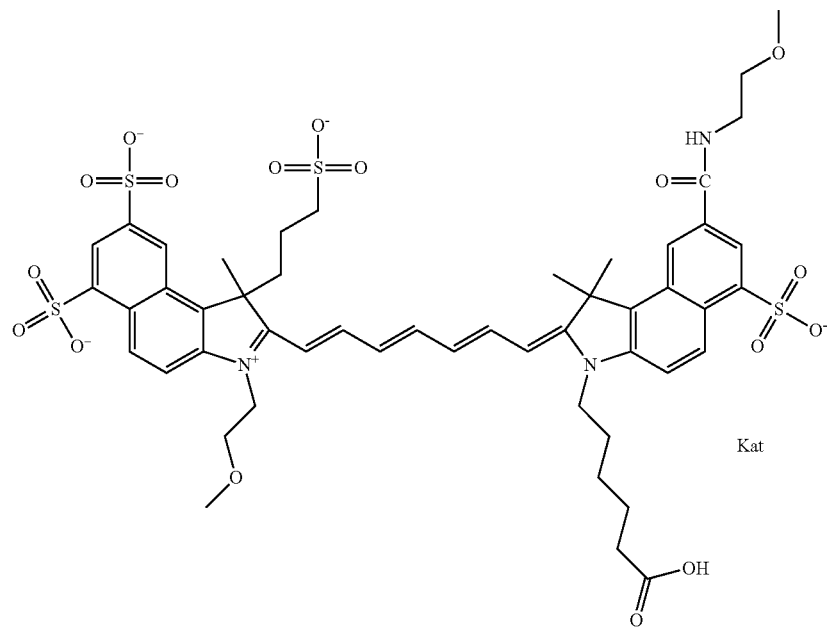

One non-limiting example of an additionally PEG-substituted compound is a 779 Compound 1/2 according to general formula II where R7 is an ethylene glycol group terminating with a methyl group, shown below:

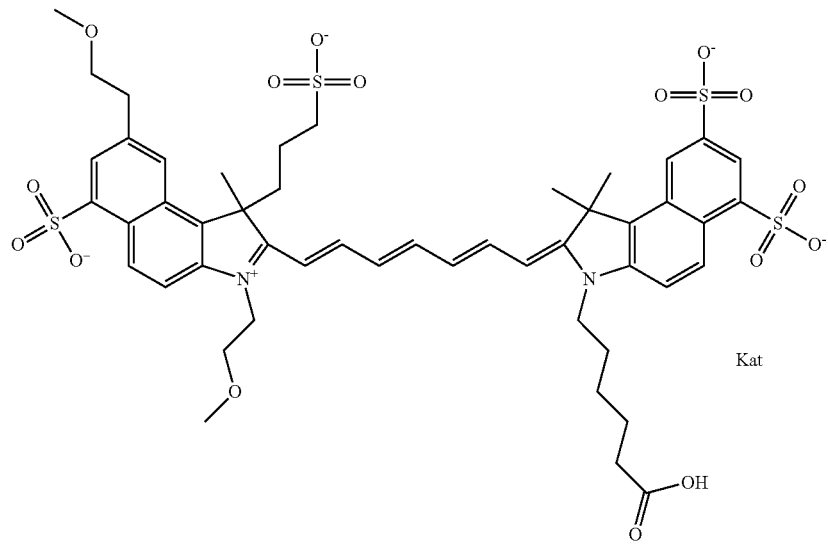

One non-limiting example of an additionally PEG-substituted compound is a 779 Compound 1/2 according to general formula II where R7 is a sulfonamide group with an ethylene glycol group (PEG$_1$) terminating with a methyl group, shown below:

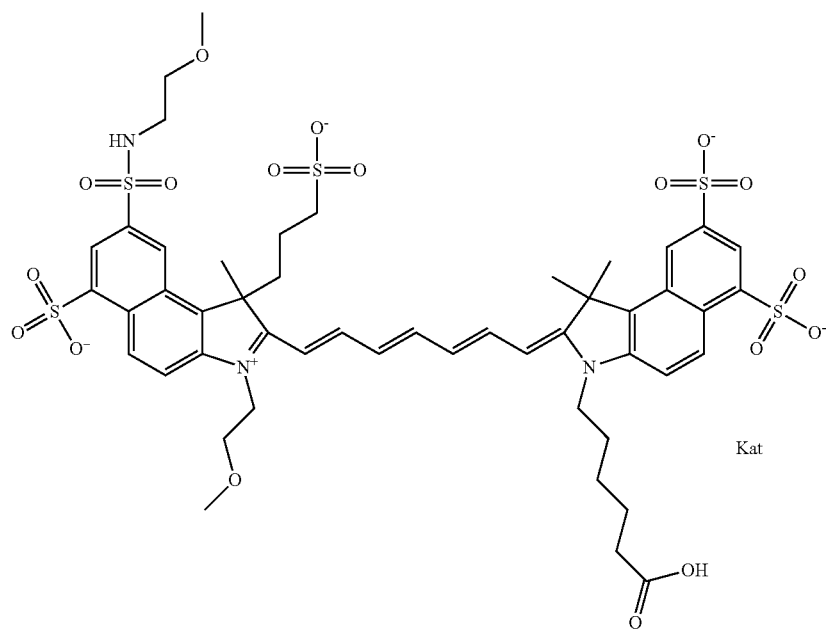

One non-limiting example of an additionally PEG-substituted compound is a 779 Compound 1/2 according to general formula II where R7 is a carboxamide group with an ethylene glycol group (PEG$_1$), terminating with a methyl group, shown below:

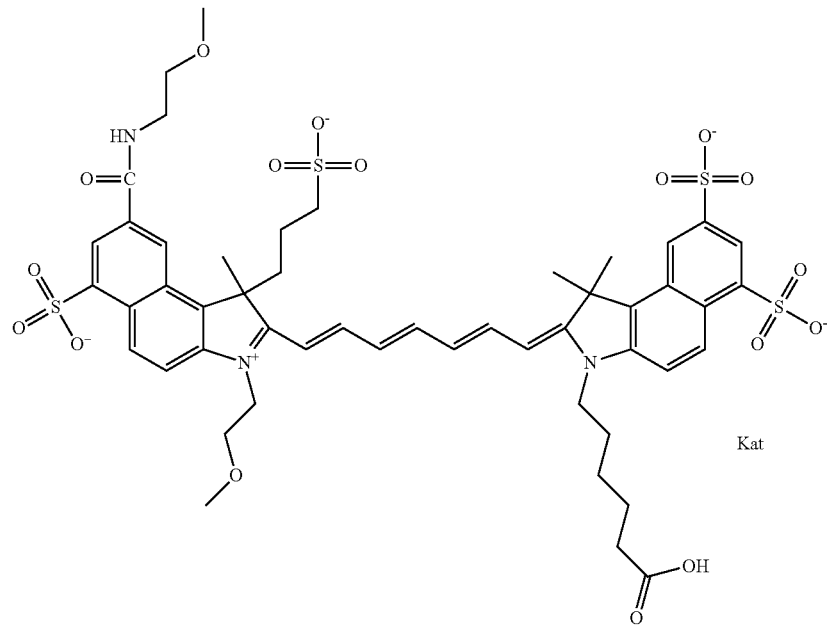

One non-limiting example of an additionally PEG-substituted compound is a 779 Compound 1/2 according to general formula II where R12 is an ethylene glycol group terminating with a methyl group, shown below:

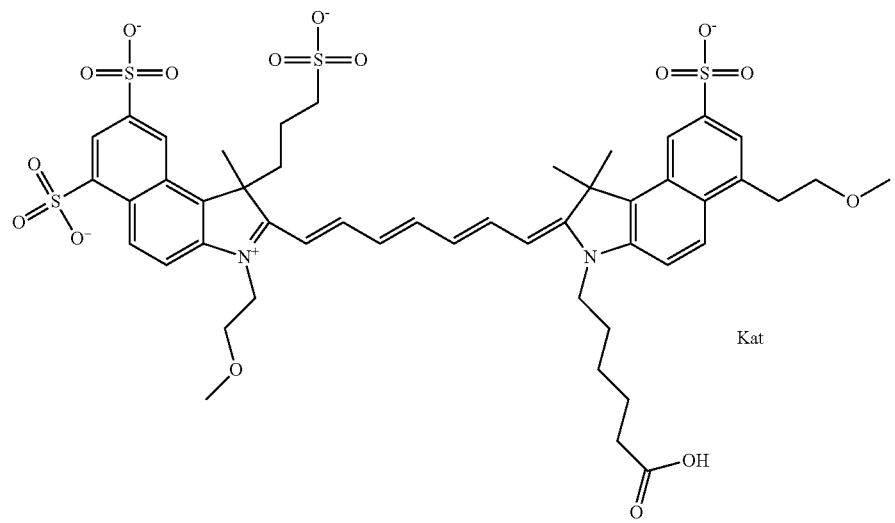

One non-limiting example of an additionally PEG-substituted compound is a 779 Compound 1/2 according to general formula II where R12 is a sulfonamide group with an ethylene glycol group (PEG$_1$) terminating with a methyl group, shown below:

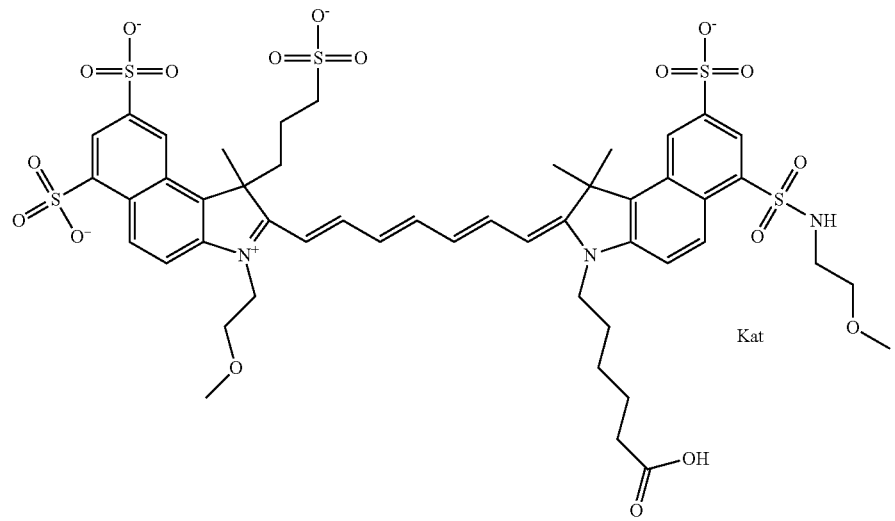

One non-limiting example of an additionally PEG-substituted compound is a 779 Compound 1/2 according to general formula II where R12 is a carboxamide group with an ethylene glycol group (PEG$_1$) terminating with a methyl group, shown below:

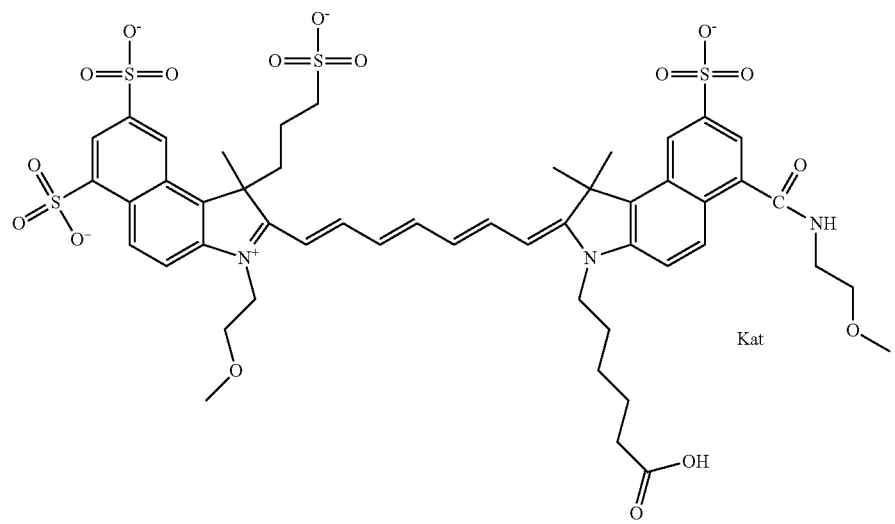

One non-limiting example of an additionally PEG-substituted compound is a 779 Compound 1/2 according to general formula II where R11 is an ethylene glycol group terminating with a methyl group, shown below:

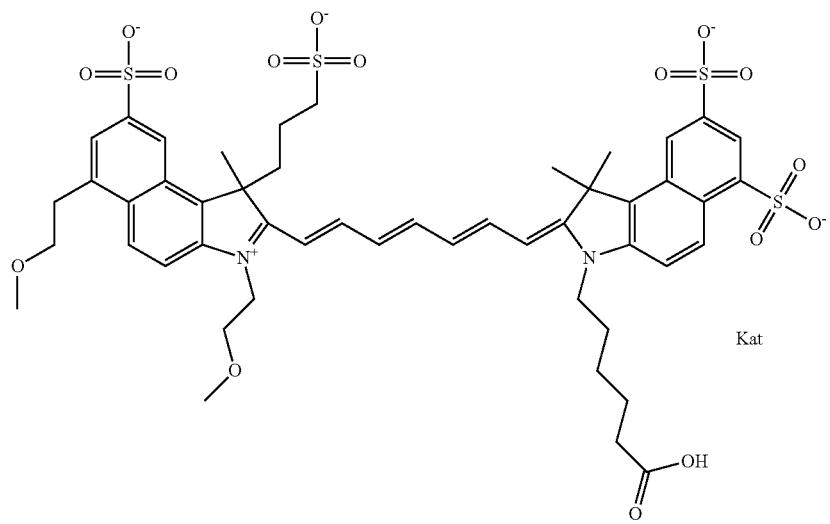

One non-limiting example of an additionally PEG-substituted compound is a 779 Compound 1/2 according to general formula II where R11 is a sulfonamide group with an ethylene glycol group (PEG$_1$) terminating with a methyl group, shown below:

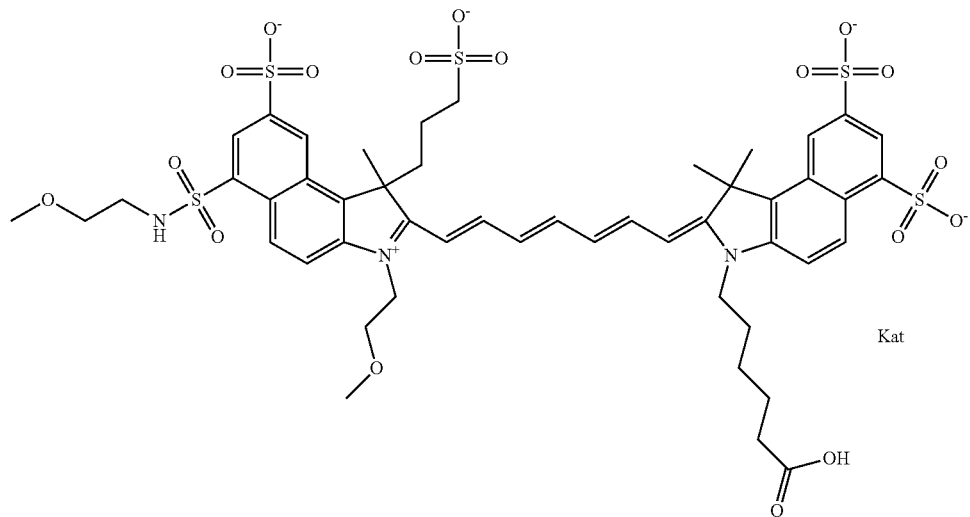

One non-limiting example of an additionally PEG-substituted compound is a 779 Compound 1/2 according to general formula II where R11 is a carboxamide group with an ethylene glycol group (PEG$_1$) terminating with a methyl group, shown below:

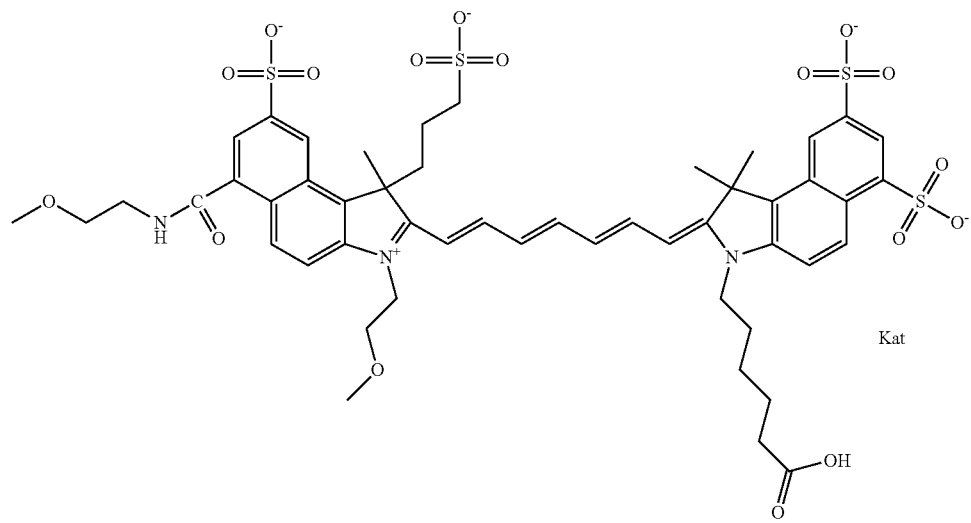

One non-limiting example of an additionally PEG-substituted compound is a 779 Compound 1/2 according to general formula II where R13 is an ethylene glycol group terminating with a methyl group,

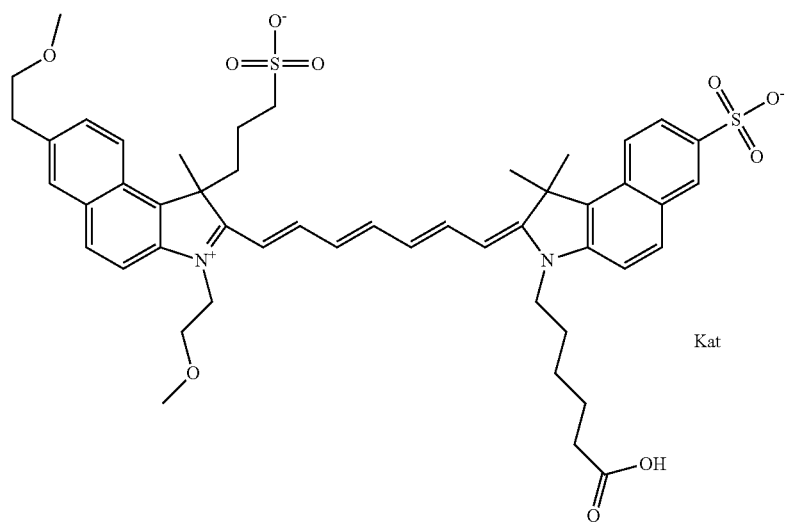

One non-limiting example of an additionally PEG-substituted compound is a 779 Compound 1/2 according to general formula II where R13 is a sulfonamide group with an ethylene glycol group (PEG$_1$) terminating with a methyl group, shown below:

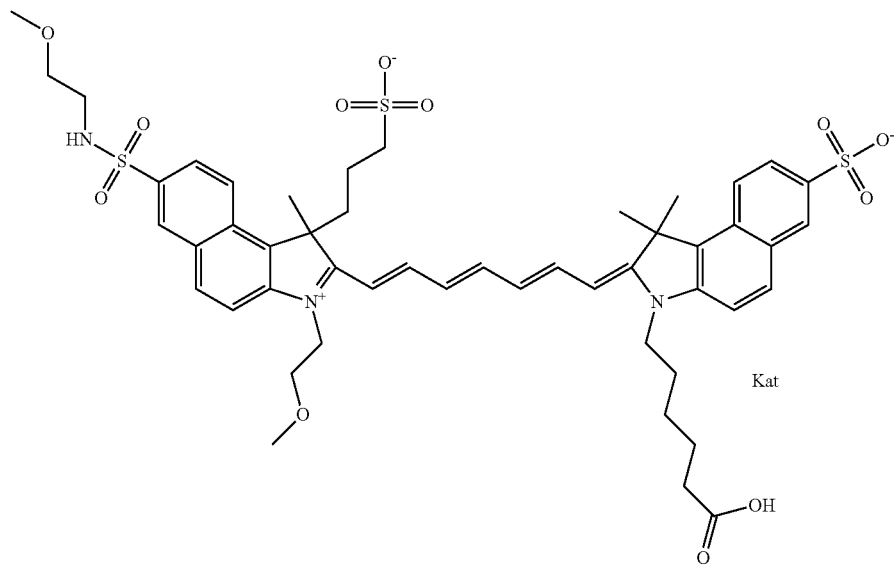

One non-limiting example of an additionally PEG-substituted compound is a 779 Compound 1/2 according to general formula II where R13 is a carboxamide group with an ethylene glycol group (PEG$_1$) terminating with a methyl group, shown below:

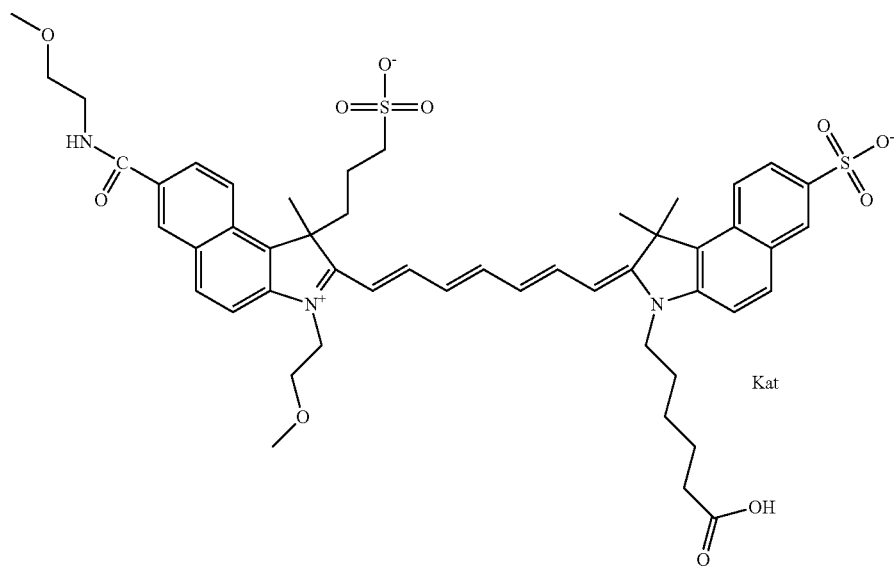

One non-limiting example of an additionally PEG-substituted compound is a 779 Compound 1/2 according to general formula II where R14 is an ethylene glycol group terminating with a methyl group, shown below:

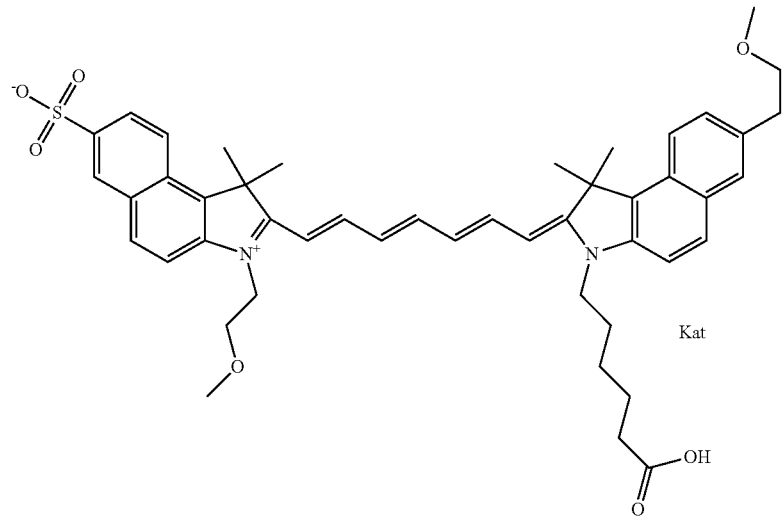

One non-limiting example of an additionally PEG-substituted compound is a 779 Compound 1/2 according to general formula II where R14 is a sulfonamide group with an ethylene glycol group (PEG$_1$) terminating with a methyl group, shown below:

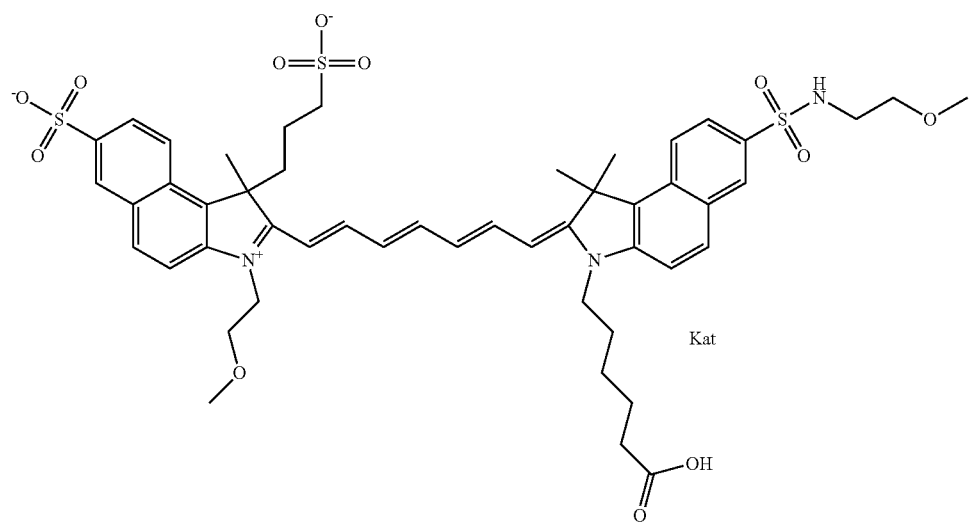

One non-limiting example of an additionally PEG-substituted compound is a 779 Compound 1/2 according to general formula II where R14 is a carboxamide group with an ethylene glycol group (PEG$_1$) terminating with a methyl group, shown below:

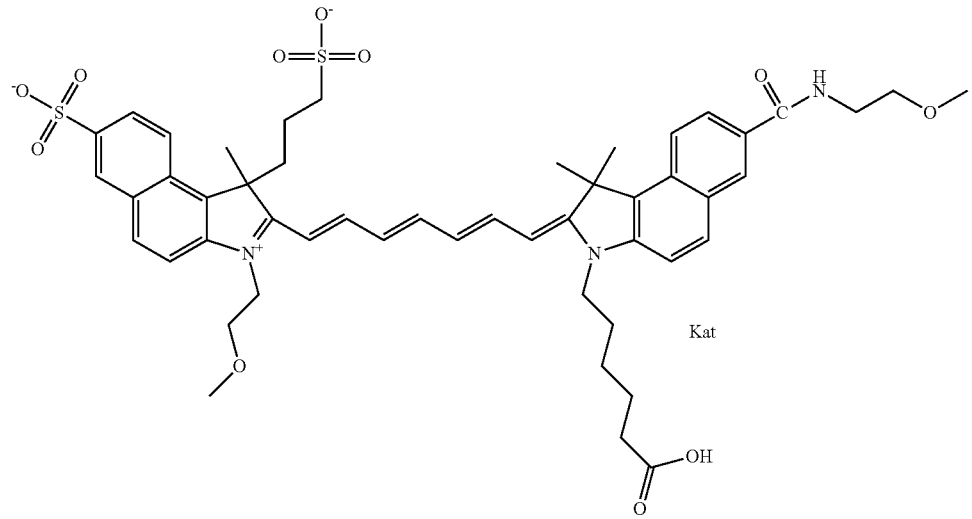

The disclosed compounds are useful as chromophores and/or fluorophores. For example, they are used for optical labelling and, therefore, for the qualitative and/or quantitative detection of proteins, nucleic acids, oligomers, DNA, RNA, biological cells, lipids, mono-, oligo- and polysaccharides, ligands, receptors, polymers, drugs, polymeric beads, etc.

The present compounds, containing the disclosed functionality or functionalities, may be synthesized using methods known in the art, e.g., as described as follows with all references expressly incorporated by reference herein in their entirety.

The core indocyanine structure without additional functionalities, along with its synthesis, was described by König in U.S. Pat. No. 1,524,791 and BP 434875, and included 3-, 5-, and 7-membered polymethine chains.

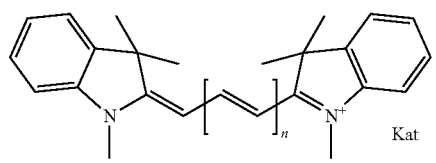

Synthesis of numerous modifications of the core indocyanine structure have been described. Such modifications provided various functionalities, e.g., synthesis of N-isothiocyanato-alkyl- and aromatic-carboxyalkyl-functionalized indocyanines were described in U.S. Pat. Nos. 5,627,027; 6,048,982; 4,981,977; U.S. Publication No. 2006/0199949; Southwick, Anal. Chem. 67 (1995)1742-48).

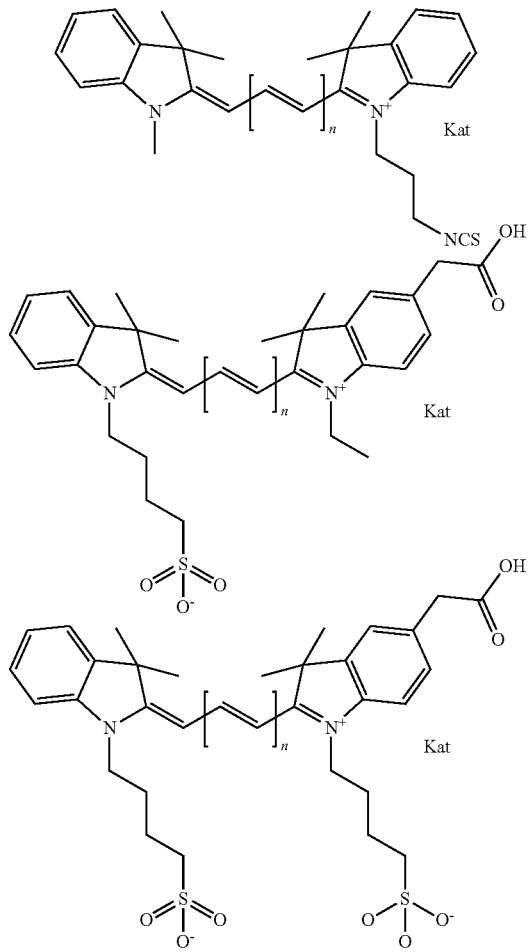

Synthesis of indocyanines with one or two N-carboxyalkyl functionalities were described in U.S. Pat. Nos. 5,268,486; 5,486,616; 5,569,587; 5,569,766; and JP 03217837.
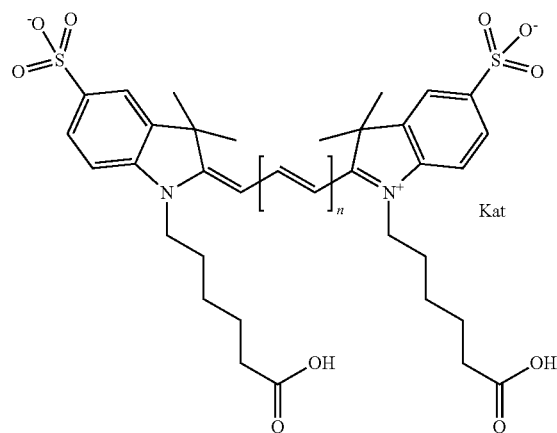
Synthesis of indocyanines containing C-carboxyalkyl groups were described in JP 05-313304; U.S. Publication Nos. 2006/0099638, 2006/0004188; 2002/0077487; 2002/0064794; U.S. Pat. Nos. 6,977,305 and 6,974,873.
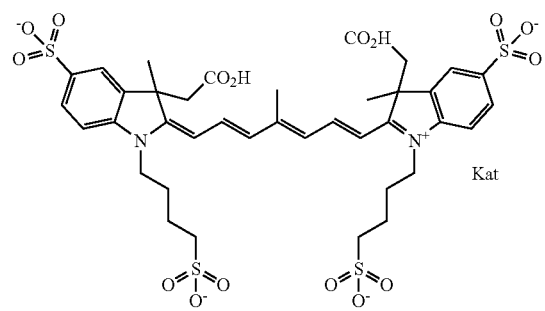
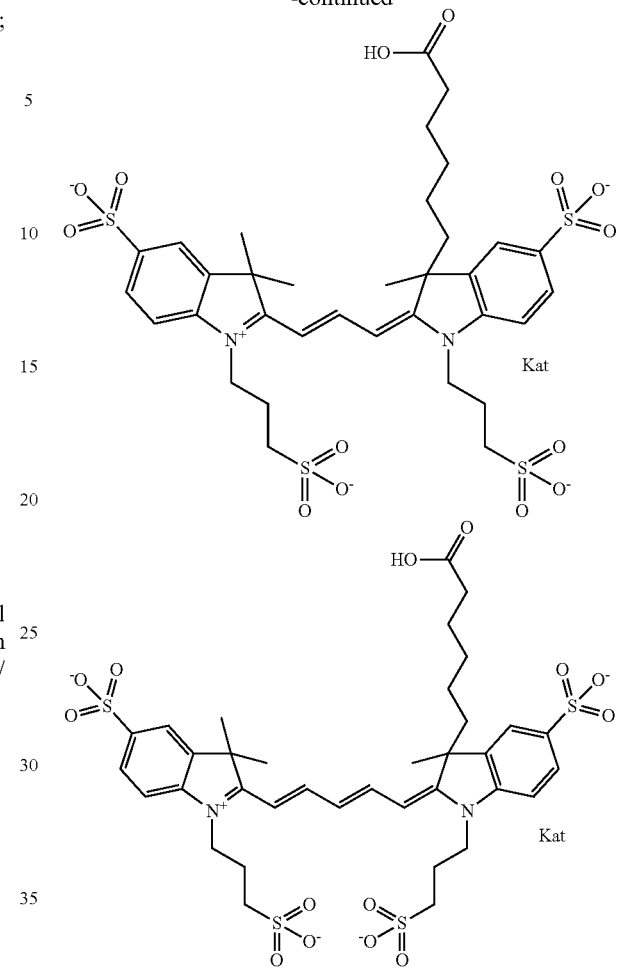
Synthesis of indocyanines with N- and C-sulfoalkyl groups were described in JP 05-313304; WO 2005/044923; U.S. Publication No. 2007/0203343.
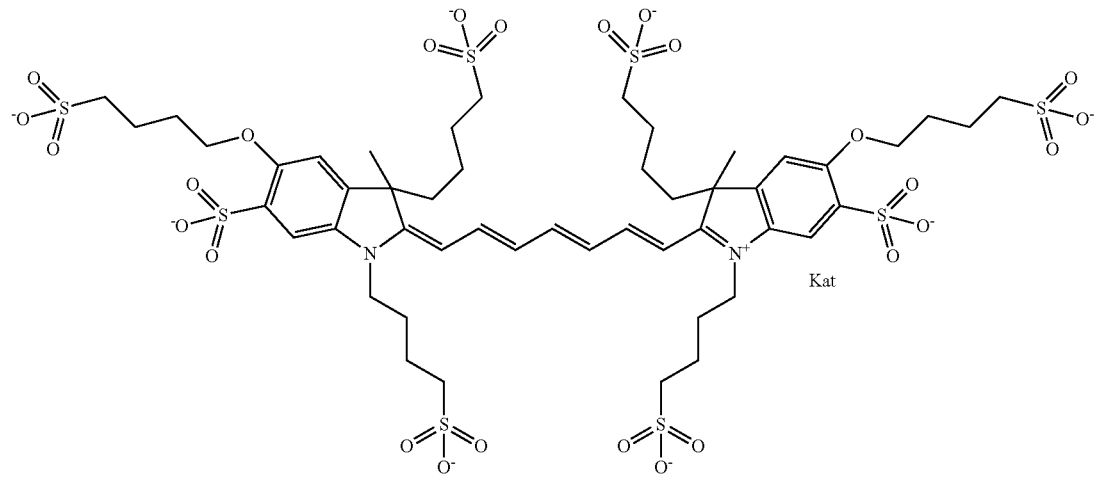

-continued
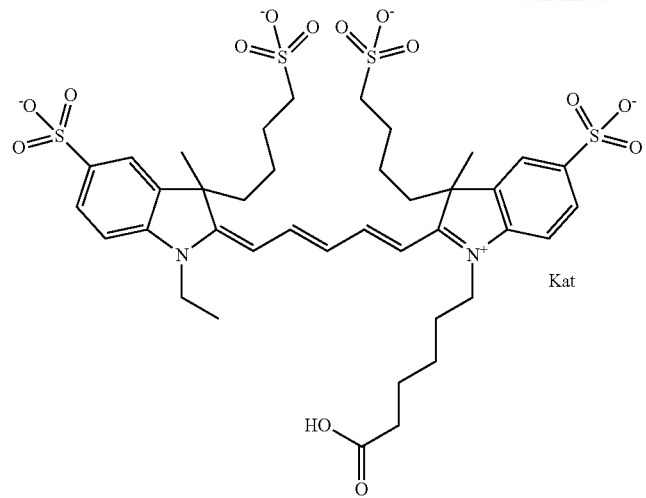
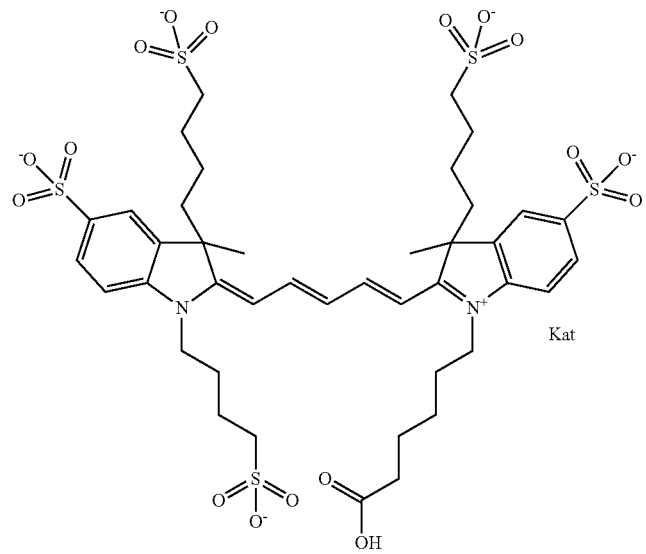
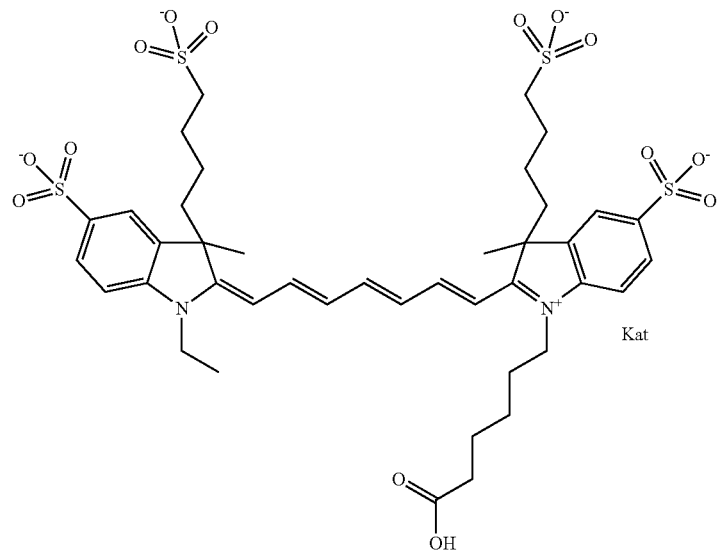

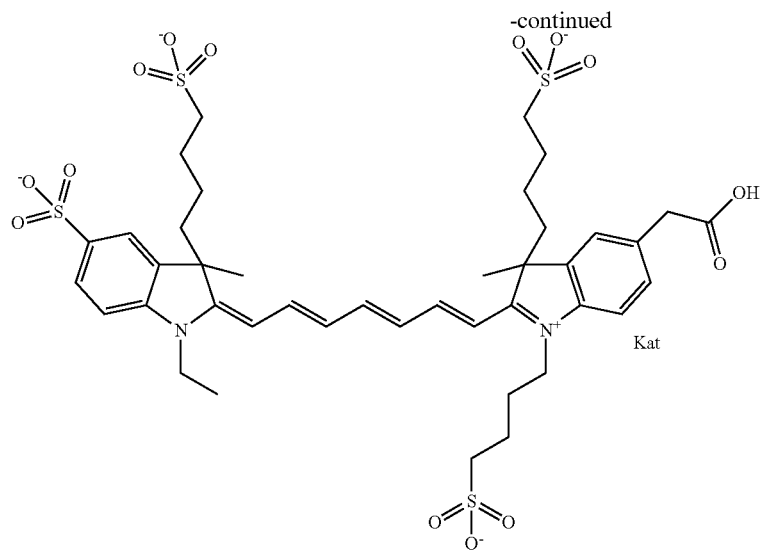

Synthesis of indocyanines with mixed C-carboxyalkyl and C-sulfoalkyl were described in EP 1792949 and U.S. Pat. No. 7,745,640.

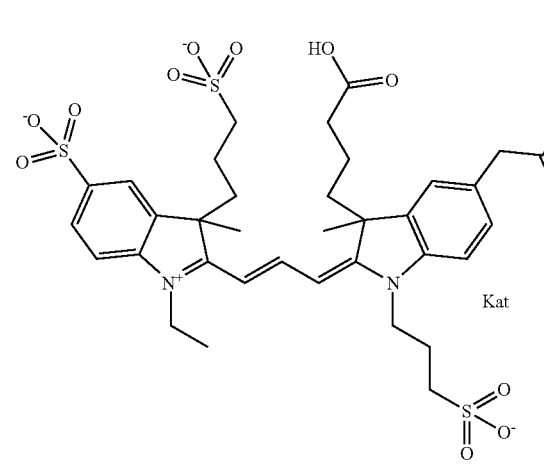

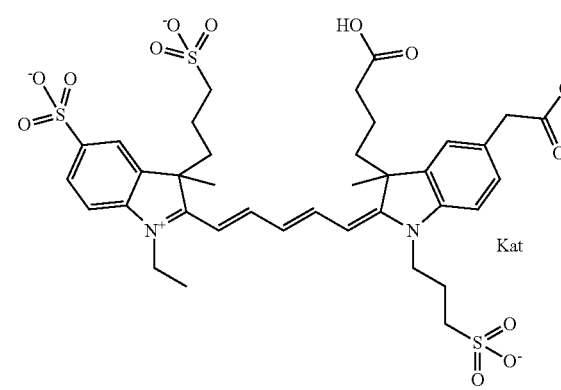

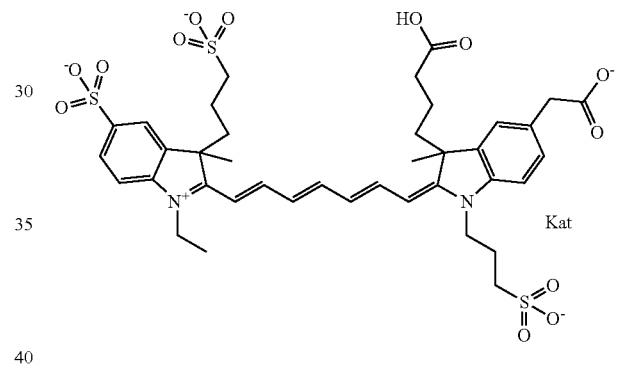

Synthesis of indocyanaines having a PEG-containing, N-carboxyalkyl spacer were described in U.S. Pat. No. 6,939,532.

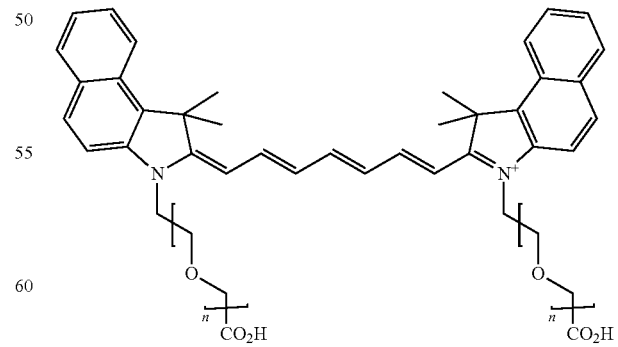

Functionalization of the N-carboxyalkyl with an amino-functionalized PEG-alkyl chain, and N- and C-substituted PEG-alkyl chains, were described in U.S. Publication No. 2009/0305410.

187 188
-continued
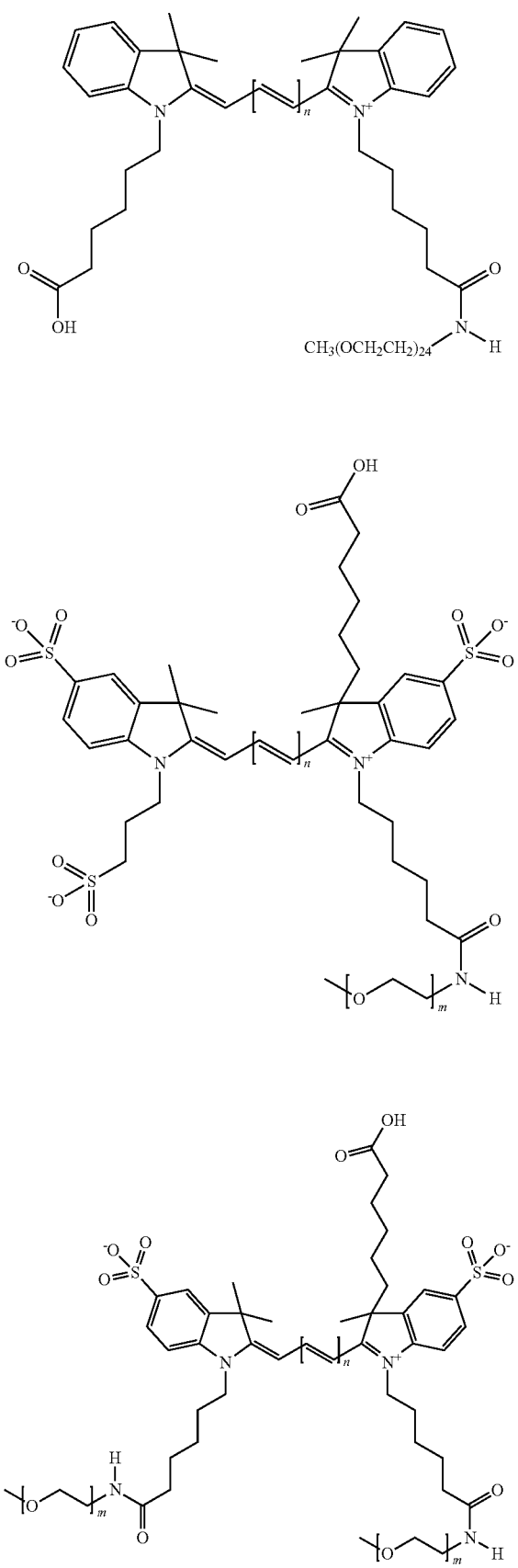
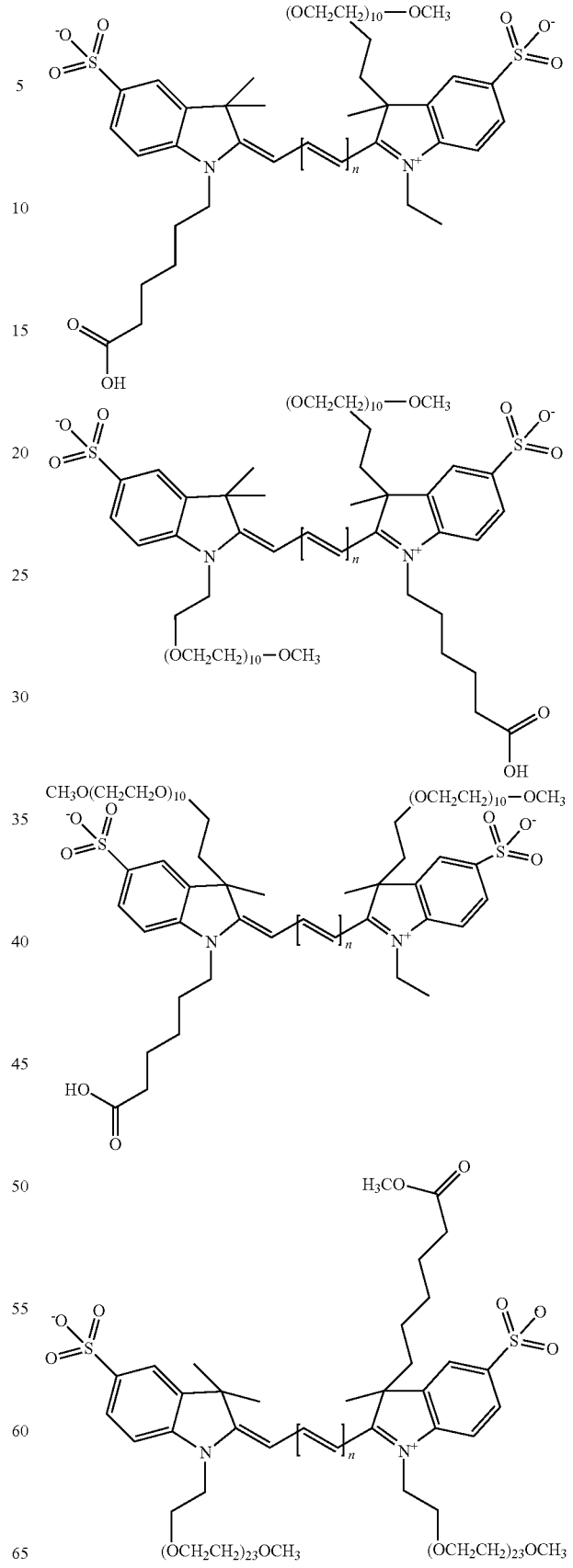

Synthesis of various polymethine bridge substitutions, and other functionalizations of indocyanines, were described in Strekowski, Heterocyclic Polymethine Dyes: Synthesis, Properties and Applications, (2008) Springer-Verlag, Berlin Heidelberg; Gragg, "Synthesis of Near-Infrared Heptamethine Cyanine Dyes" (2010). Chemistry Theses. Paper 28; Patonay et al. (2004) Noncovalent Labeling of Biomolecules with Red and Near-Infrared Dyes. Molecules 9 (2004) 40-49; and U.S. Pat. No. 7,172,907. Examples 1-5 disclose synthesis reactions for the compounds.

In one embodiment, the compound is synthesized by a condensation reaction, known to one skilled in the art, of the two differently substituted indole heterocycles separated by a (poly)methine linker or bridge, e.g., C1, C3, or C5. Other synthesis methods are possible. As only one example, one of the indole heterocycles is first reacted with the C1, C3, or C5 linker. The 1:1 condensation product is isolated, and then condensed with the second indole heterocycle to result in the cyanine compound. The sequence of reacting the indole heterocycles is irrelevant. Thus, a plurality of differently functionalized, strongly hydrophilic, diastereomeric compounds, that differ in total charge and specificity/reactivity of the active groups used for their immobilization, can be easily prepared.

Conjugates of the compounds are prepared by covalently coupling the compounds to a biomolecule using the functional substituent on the N-position of the indole ring. This functional substituent is activated by routine protein chemistry reaction methods known to one skilled in the art. The activated compound may be converted to, without limitation, an N-hydroxysuccinimide (NHS)-ester, an acid fluoride, a tetrafluorophenyl (TFP)- or sulfotetrafluorophenyl (STP)-ester, an iodoacetyl group, a maleimide, a hydrazide, a sulfonyl chloride, a phenylazide. Methods for preparing such compounds are known to one skilled in the art. In one embodiment, the activated substituent is then reacted with an amino group on the biomolecule under conditions to form the linkage. In one embodiment, a non-activated carboxyl group on the N-position of the indole in the compound is coupled to an amine using a carbodimide.

In one embodiment, a N-hydroxysuccinimidyl ester (X=—NHS) of a compound was formed as follows: 20 μmol dye with X=OH (carboxyalkyl group), 8 mg (40 μmol) dicyclohexylcarbodiimide, and 5 mg (40 μmol) N-hydroxysuccinimide were dissolved in 2 ml of DMF and 100 μl water. Six μl (40 μmol) triethylamine was then added. The reaction mixture was stirred at room temperature (about 20° C. to about 22° C.) for 24 hours and then filtered. The solvent was removed and the residue was washed with diethylether. The reaction proceeded quantitatively.

In one embodiment, a maleimide (X=—NH—CH$_2$CH$_2$-maleimide) of a compound was formed as follows: 20 μmol dye with X=—NHS (N-hydroxysuccinimid-ester) was dissolved in 2 ml DMF and 100 μl water and mixed with 7.6 mg (30 μmol) 2-maleimidoethylamine-trifluoracetate and 5 μl (30 μmol) N-ethyldiisopropyl-amine. The reaction mixture was stirred for three hours at room temperature (about 20° C. to about 22° C.). The solvent was evaporated under reduced pressure. The residue was washed with diethylether and acetone and dried in vacuum. The reaction proceeded quantitatively.

In one embodiment, a iodoacetamide (X=—NH—CH$_2$CH$_2$—NH—CO—CH$_2$-1) of a compound was formed as follows: 20 μmol dye with X=—NHS (N-hydroxysuccinimid-ester) was dissolved in 2 ml DMF and 100 μl water, followed by the addition of 40 mg (300 μmol) ethylendiamindihydrochloride and 26 μl (150 μmol) N-ethyldiisopropyl-amine. The reaction mixture was stirred for three hours at room temperature (about 20° C. to about 22° C.). The solvent was then evaporated under reduced pressure, the residue was dissolved in methanol, and the ethylendiamin-dihydrochloride was removed by filtration. The methanol was evaporated under reduced pressure. The residue was dissolved in 2 ml dry DMF, followed by then addition of 7 mg (25 μmol) N-succinimidyl iodoacetate and 4 μl (25 μmol) N-ethyldiisopropyl-amine. The reaction mixture was stirred for three hours at room temperature. The solvent was evaporated under reduced pressure and the residue was purified via reverse phase HPLC.

In one embodiment, a hydroxyl group, such as a terminal hydroxyl group, can be subsequently activated to a reactive derivative able to link with, for example, proteins and other molecules. Examples of activating groups include tosyl chloride (TsCl), tresyl chloride (TrCl), disuccinimidyl carbonate (DSC), divinyl sulfone, bis-epoxy compounds, carbonyl diimidazole (CDI), 2-fluoro-1-methylpyridinium (FMP), and trichloro-s-triazine (TsT). In one embodiment, the hydroxyl group is activated to a succinimidyl carbonate, which is reactive with amines. For example, disuccinimidyl carbonate (DSC) can be used to create amine-reactive groups from hydroxyls in a single step, as described in Wilchek, M. and Miron, T. (1985) (Activation of Sepharose with N,N'-disuccinimidyl carbonate. Applied Biochemistry and Biotechnology 11, 191-193). DSC reacts with a hydroxyl group, such as at the end of a PEG chain of the described compounds, to directly form a reactive ester with loss of one molecule of NHS. This reactive group, which is an NHS carbonate, can be used to couple a described compound to amine-containing molecules, such as proteins. For example, a reaction of an NHS carbonate with an amine creates a carbamate linkage (a urethane bond), which is as stable as the amide bonds formed from the reaction of an NHS ester with an amine. In one embodiment, a terminal hydroxyl group of a PEG-containing compound can be activated with DSC to provide an NHS carbonate reactive group for coupling to amine-containing molecules. In one embodiment, the group X, as described in the disclosed general formulas, is a spacer arm that terminates in a hydroxyl group, such as a PEG group, which also can be activated with DSC to create the NHS carbonate, i.e., when X=—NR-L-O—CO—NHS.

Coupling between the compound and the biomolecule may be performed as follows. The compound is reacted with the biomolecule in an organic or aqueous solution at a pH between pH 5 and pH 12, inclusive. The compound need not be dissolved in an organic solvent, such as dimethyl formamide (DMF) or dimethyl sulfoxide (DMSO) prior to adding the biomolecule. In one embodiment, coupling reaction may be performed in a 100% aqueous solution. In one embodiment, the coupling reaction occurs at room temperature (about 20° C. to about 22° C.).

To form a dye composition, at least one biocompatible excipient is added to the compound, as known to one of ordinary skill in the art. Excipients include but are not limited to buffers, solubility enhancing agents, stabilizing agents, etc.

In one embodiment, a kit for performing an assay method comprises a disclosed compound, and instructions for performing the method using the compound.

The disclosed activated compounds (i.e., the compound modified with a reactive group) are useful to label macromolecules (e.g., antibodies, streptavidin, etc) using methods known to one skilled in the art, e.g., as disclosed in Hermanson, Bioconjugate Techniques, 2nd Ed., London, Elsevier Inc. 2008. The reaction is carried out for one hour to two hours at room temperature (about 20° C. to about 22° C.), and then desalted by dialyzing against several changes of phosphate buffered saline (pH 7.2) or purified by gel filtration to remove the unreacted fluorescent dye. The resulting compound-biomolecule conjugate is useful in applications such as detection of specific proteins in immunoassays, sugars in glycoproteins with lectins, protein-protein interactions, oligonucleotides in nucleic acid, hybridization, and in electrophoretic mobility shift assays (EMSA).

The resulting compound-biomolecule conjugates exhibit fluorescent properties. They may be used in optical, including fluorescence optical, qualitative and quantitative determination methods. Examples of such methods include, but are not limited to, microscopy, immunoassays, hybridization methods, chromatographic and electrophoretic methods, fluorescence resonance energy transfer (FRET) systems, high throughput screenings, analysis of receptor-ligand interactions on a microarray, etc.

Compounds of any of the embodiments can be used as dyes for optical labelling of organic or inorganic biomolecules, also referred to as recognition units. Recognition units are molecules having specificity and/or affinity for a specific group of molecules. Examples of recognition units include, but are not limited to, antibodies that have affinity for antigens, enzymes that bind and/or react with a specific bond or bonds within a sequence of amino acids in a peptide or react with a substrate, cofactors such as metals that enhance or inhibit specific interactions, lectins that bind specific sugars or sugar sequences (e.g., oligosaccharides, polysaccharides, dextrans, etc.), biotin binding proteins such as avidin and streptavidin that bind biotin and biotinylated molecules, antibody binding proteins such as Protein A, Protein G, Protein A/G and Protein L, sequences of amino acids or metals that have affinity for each other (e.g., histidine sequences bind nickel or copper, phosphate containing proteins that bind gallium, aluminium, etc.), specific sequences of nucleic acids such as DNA and/or RNA oligonucleotides that have affinity for proteins, specific sequences of amino acids that have affinity for DNA and/or RNA, haptens, carotenoids, hormones (e.g., neurohormone), neurotransmitters, growth factors, toxins, biological cells, lipids, receptor binding drugs or organic or inorganic polymeric carrier materials, fluorescent proteins such as phycobilliproteins (e.g., phycoethrin, allophycocyanin), etc. The ionic interactions between these recognition units and the disclosed compounds results in labeling of the recognition units. The recognition unit and compound can be covalently bound. The result is a conjugate for qualitative or quantitative determination of various biomaterials or other organic or inorganic materials using optical methods.

The inventive compounds and/or conjugates are useful in optical, including fluorescence optical, qualitative and/or quantitative determination methods to diagnose properties of cells (molecular imaging), in biosensors (point of care measurements), for investigation of the genome, and in miniaturizing technologies. Microscopy, cytometry, cell sorting, fluorescence correlation spectroscopy (FCS), ultra high throughput screening (uHTS), multicolor fluorescence in situ hybridization (mc-FISH), FRET-systems and microarrays (DNA- and protein chips) are exemplary application fields. As known to one skilled in the art, a microarray, a grid-like arrangement where more than two different molecules are immobilized in a known predefined region on at least one surface, is useful to evaluate receptor ligand interactions. As known to one skilled in the art, a receptor is a naturally occurring or synthetic molecule that exhibits an affinity to a given ligand. Receptors can be used in a pure form or bound to another specie. Receptors can be coupled covalently or noncovalently to a binding partner either directly or indirectly (e.g., through a coupling mediator). Receptor examples include, but are not limited to, agonists and antagonists for cell membrane receptors, toxins and other poisons, viral epitopes, hormone like opiates and steroids, hormone receptors, peptides, enzymes, enzyme substrates, drugs acting as cofactors, lectins, sugars, oligonucleotides, nucleic acids, oligosaccharides, cells, cell fragments, tissue fragments, proteins, antibodies, etc. As known to one skilled in the art, a ligand is a molecule that is recognized by a certain receptor. Ligand examples include, but are not limited to, agonists and antagonists for cell membrane receptors, toxins and other poisons, viral epitopes, hormones like opiates and steroids, hormone receptors, peptides, enzymes, enzyme substrates, drugs acting as cofactors, lectins, sugars, oligonucleotides, nucleic acids, oligosaccharides, proteins, antibodies, etc.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 11 tabulates functional assay results with some commercial dyes and inventive compounds in one embodiment.

FIG. 13 tabulates functional assay results with some commercial dyes and inventive compounds in one embodiment.

Figure 1:
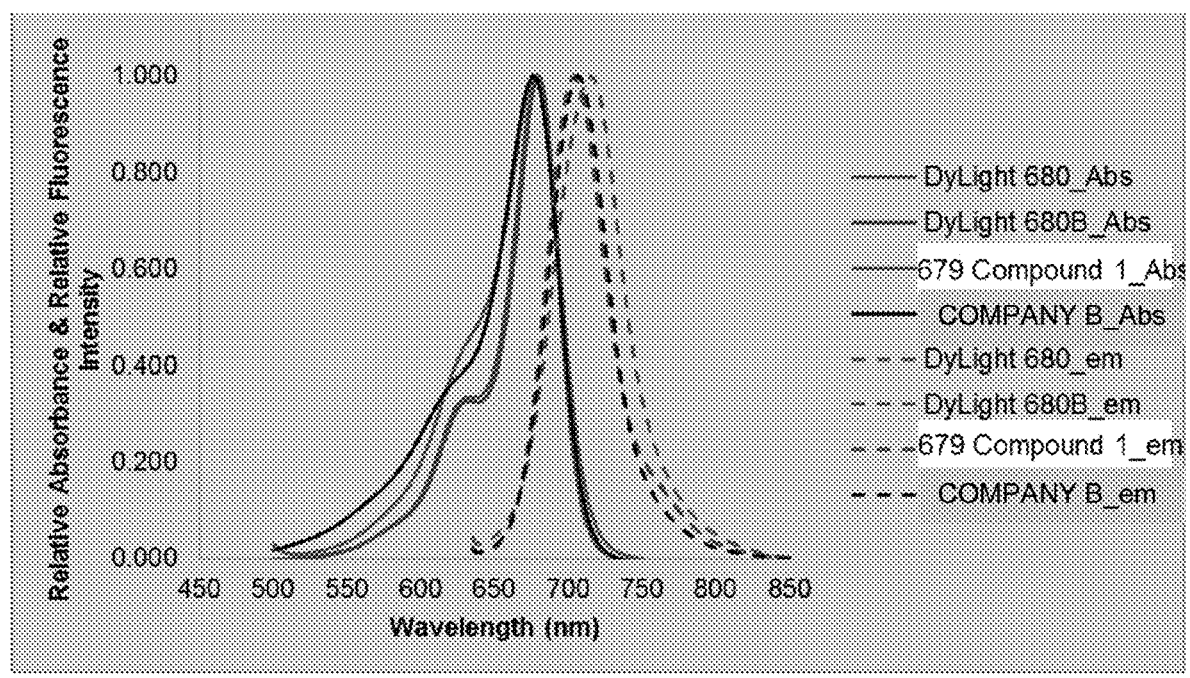
FIG. 1 shows absorption/emission profiles of some inventive compounds and commercial dyes.

The following non-limiting examples further describe the compounds, methods, compositions, uses, and embodiments. They demonstrate that the inventive compounds exhibited desirable properties relative to commercially available fluorescent dyes. Signal to noise ratio (S/N) is the ratio between the desired signal and the mean of the blank, accounting for the standard deviation of the signal and the blank. Signal to background ratio (S/B) is the ratio between the desired average signal and the average blank.

EXAMPLE 1

Synthesis of 1,2-Dimethyl-1-(3-sulfopropyl)-1H-benzo[e]indole-6,8-disulfonic acid tri potassium salt

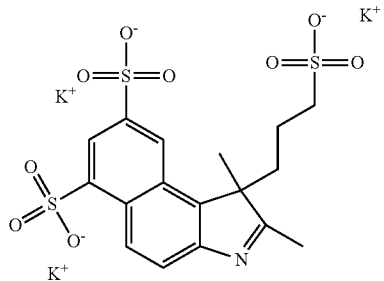 [SMILES: [K+] ; CC1=Nc2ccc3c(S(=O)(=O)[O-])cc(S(=O)(=O)[O-])cc3c2C1(C)CCCS(=O)(=O)[O-] ; [K+] ; [K+]]

Five g (15.7 mmol) 6-hydrazino-naphthalene-1,3-disulfonic acid and 4.93 g (25 mmol) 4-methyl-5-oxohexane sulfonic acid were dissolved in 50 ml acetic acid. The solution was heated at 140° C. for four hours. The solvent was evaporated in vacuum. The oily residue was dissolved in 20 ml methanol, then 50 ml of a saturated solution of KOH in 2-propanol were added to yield a yellow precipitate. The solid was filtered off and dried in vacuum. Yield 4.1 g, MS (ESI−): 158.2 [M]$^{3-}$

EXAMPLE 2

Synthesis of 3-(2-Methoxy-ethyl)-1,2-dimethyl-6,8-disulfo-1-(3-sulfopropyl)-1H-benzo[e]indolium

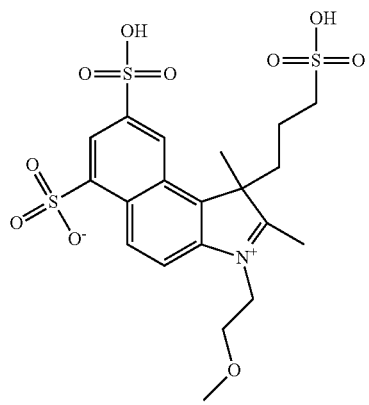 [SMILES: COCC[N+]1=C(C)C(C)(CCCS(=O)(=O)O)c2c1ccc1c(S(=O)(=O)[O-])cc(S(=O)(=O)O)cc21]

A mixture of 7.56 g (12.8 mmol) 1,2-dimethyl-1-(3-sulfopropyl)-1H-benzo[e]indole-6,8-disulfonic acid tri potassium salt and 5.89 g (25.6 mmol) 2-methoxyethyl-p-toluene sulfonate was heated under argon for 24 h. The residue was purified by column chromatography (reversed phase silica, methanol/water, TFA). Yield 3.2 g, MS (ESI−): 266.5 [M−2H]$^{2-}$

EXAMPLE 3

Synthesis of 3-(5-Carboxypentyl)-1,1,2-trimethyl-6,8-disulfo-1H-benzo[e]indolium

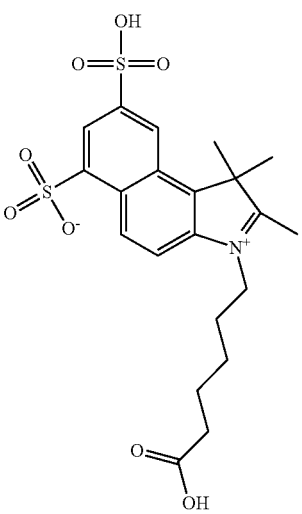 [SMILES: CC1=[N+](CCCCCC(=O)O)c2ccc3c(S(=O)(=O)[O-])cc(S(=O)(=O)O)cc3c2C1(C)C]

A mixture of 5.7 g (12.8 mmol) 1,1,2-trimethyl-1H-benzo[e]indole-6,8-disulfonic acid dipotassium salt and 5 g (25.6 mmol) 6-bromohexanoic acid was heated under argon for 24 h. The residue was purified by column chromatography (reversed phase silica, methanol/water, TFA). Yield 1.4 g, MS (ESI−): 482.1 [M−H]$^-$

EXAMPLE 4

Synthesis of 3-(5-Carboxypentyl)-1,1-dimethyl-2-((1E,3E)-4-phenylamino-buta-1,3-dienyl)-6,8-disulfo-1H-benzo[e]indolium

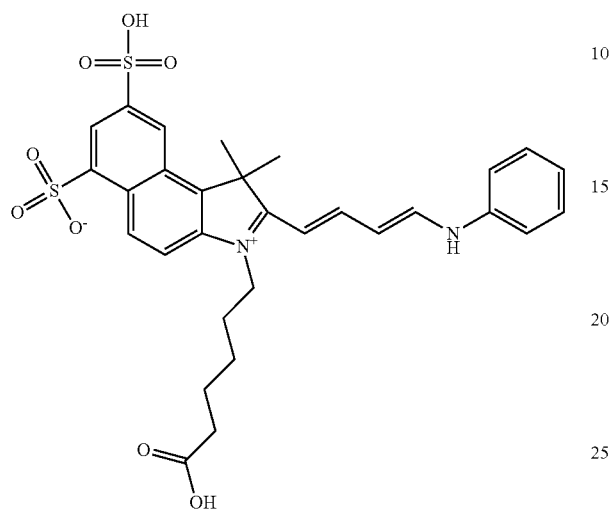

0.97 g (2 mmol) 3-(5-carboxypentyl)-1,1,2-trimethyl-6,8-disulfo-1H-benzo[e]indolium and 0.57 g (2.2 mmol) malonaldehyde-bisphenylimine-hydrochlorid were dissolved in 10 ml acetic acid and 10 ml acetic anhydride and stirred for four hours at 120° C. The solvent was removed under vacuum. The residue was washed carefully with ethyl acetate. A dark brown solid was obtained which was processed without further purification. MS (ESI−): 611.2 [M-H]⁻.

EXAMPLE 5

Synthesis of 679 Compound 1/1 (2-{(1E,3E)-5-[3-(5-Carboxypentyl)-1,1-dimethyl-6,8-disulfo-1,3-dihydro-benzo[e]indol-(2E)-ylidene]-penta-1,3-dienyl}-3-(2-methoxy-ethyl)-1-methyl-6,8-disulfo-1-(3-sulfopropyl)-1H-benzo[e]indolium)

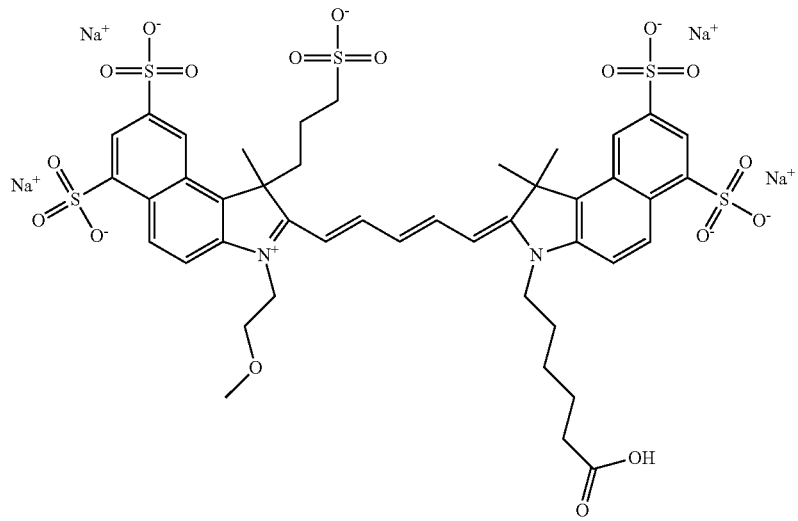

612 mg (1 mmol) 3-(5-carboxypentyl)-1,1-dimethyl-2-((1E,3E)-4-phenylamino-buta-1,3-dienyl)-6,8-disulfo-1H-benzo[e]indolium and 533 mg (1 mmol) 3-(2-Methoxyethyl)-1,2-dimethyl-6,8-disulfo-1-(3-sulfopropyl)-1H-benzo[e]indolium were dissolved in 20 ml acetic acid/acetic anhydride (1/1) followed by the addition of 200 mg of sodium acetate. The solution was stirred under reflux for 15 min. After cooling to room temperature, 20 ml diethylether was added. The resulting precipitate (mixture of the diastereomers 679 Compound 1/1 (isomer 1) and 679 Compound 1/1 (isomer 2)) was extracted by suction, washed with ether, and dried.

The residue was purified by column chromatography (RP-18, acetonitrile/water and concentrated HCl) to separate the diastereomers from each other. The diastereomer that first eluted from the column was termed diastereomer 1 (679 Compound 1/1 (isomer 1)). The diastereomer that eluted second from the column was termed diastereomer 2 (679 Compound 1/1 (isomer 2)). The diastereomers were separated, followed by neutralization and evaporation. Purification of the single diastereomeric compound was completed on a RP-18 column, acetonitrile/water. The corresponding fractions were pooled and the solvent was removed by distillation. The two products (diastereomers 679 Compound 1/1 (isomer 1) and 679 Compound 1/1 (isomer 2)) were dried in high vacuum. 679 Compound 1/1 (isomer 1)
yield: 10%
UV-vis (PBS): $\lambda_{max}$=679 nm
$\lambda_{em}$=698 nm
MS (ESI−) [M/z]: 262.5 $[M]^{4-}$; 357.7 $[M+Na]^{3-}$
679 Compound 1/1 (isomer 2)
yield: 23%
UV-vis (PBS): $\lambda_{max}$=679 nm
$\lambda_{em}$=698 nm
MS (ESI−) [M/z]: 262.5 $[M]^{4-}$; 357.7 $[M+Na]^{3-}$

EXAMPLE 6

The following properties of 679 Compound 1-NHS were compared with commercially available dyes.

|  | DyLight 680-NHS | DyLight 680B-NHS | 679 Compound 1-NHS | Company B Compound-NHS | Cy5.5 Mono Ester |
|---|---|---|---|---|---|
| MW (g/mol) | 950 | 1196.16 | 1240.21 | ~1150 | 1128.42 |
| Ex (nm) | 682 | 679 | 679 | 679 | 675 |
| Em (nm) | 715 | 698 | 698 | 702 | 694 |
| ε (M−1 cm−1) (theoretical) | 140,000 | 180,000 | 180,000 | 184,000 | 250,000 |

Emission/excitation profiles for inventive and commercial compounds was determined by reconstituting the compounds in DMF at 10 mg/ml and then diluting in PBS buffer pH 7.2 to 10 μg/ml. Absorbance spectra were collected on Cary UV spectrophotometer and emission spectra were collected on Tecan Safire, shown in FIG. 1 where solid lines represent absorbance spectra and dashed lines represent emission spectra, for DyLight 680-NHS (purple), DyLight 680B-NHS (blue), 679 Compound 1-NHS (red), and Company B Compound-NHS (black). The maximum absorbance and emission for each compound is shown below.

|  | Max Abs (nm) | Max E nm) |
|---|---|---|
| DyLight 680 | 677 | 715 |
| DyLight 680B | 680 | 704 |
| 679 Compound 1 | 679 | 704 |
| Company B Compound | 676 | 706 |

The following properties of 679 Compound 1-NHS, 679 Compound 4/4-NHS (V08-15173), and 679 Compound 4/4-NHS (V10-04152) were compared with commercially available dyes.

|  | DyLight 680B-NHS | 679 Compound 1-NHS | V08-15173 NHS | V10-04152 NHS | Company B Compound-NHS | Company A Compound-NHS |
|---|---|---|---|---|---|---|
| MW (g/mol) | 1196.16 | 1240.21 | 1728.8 | 1524.75 | ~1150 | 3241 |
| Ex (nm) | 679 | 679 | 684 | 689 | 679 | 681 |
| Em (nm) | 698 | 698 | 706 | 721 | 702 | 698 |
| ε (M−1cm−1) (theoretical) | 180,000 | 180,000 | 180,000 | 180,000 | 184,000 | 210,000 |
| PEG (length/ # of chain) | 0 | 1/1 | 4/4 | 4/4 | N/A | ? |
| Sulfonate | 5 | 5 | 4 | 2 | 3 | ? |

EXAMPLE 7

Inventive and commercial compounds, each as the NHS ester, were conjugated to goat anti-mouse (GAM) antibodies, goat anti-rabbit (GAR) antibodies, and streptavidin (SA). GAM, GAR, and SA, at a concentration of 10 mg/ml in phosphate buffered saline (PBS), were dialyzed against 50 mM borate buffer, pH 8.5. The compounds were reconstituted in dimethylformamide (DMF) at 10 mg/ml and combined at 2×, 4×, 5×, 7.5×, or 10× molar excess with GAM, GAR, or SA for two hours at room temperature to label the antibodies or SA.

The labeled compounds, also termed dyes or labels, were subjected to Pierce Dye Removal Resin (PDDR) to remove the unlabeled (free) compound; 100 μl of the packed resin was used per mg of protein purified. The purified antibody-labeled dyes were then diluted 1:50 in PBS and scanned for absorbance from 700 nm to 230 nm to determine the protein concentration, and to determine the mole dye to mole protein ratio. Each conjugate was diluted 1:10 in 50% glycerol and heated in the presence of 10 mM dithiothreitol (DTT) for 5 min at 95° C., then separated by electrophoresis on polyacrylamide gels in the presence of sodium dodecyl sulfate (SDS-PAGE). The gels were scanned using the Typhoon 9400 Imager to verify removal of the unconjugated compound. Labeling efficiency was compared, with results showing degree of labeling below.

|  | DyLight 680 | DyLight 680B | 679 Compound 1 | Company B Compound | Cy5.5 |
|---|---|---|---|---|---|
| GAM-2X | 0.9 | 1.9 | 2.0 | — | 1.6 |
| GAM-3X | 1.3 | 2.7 | 3.0 | — | 2.2 |
| GAM-4X | 2.0, 1.9 | 3.6, 3.6 | 3.6, 3.7 | 2.8 | 2.6 |
| GAM-6X | 2.3 | 5.0 | 5.1 | 3.9 | — |
| GAM-8X | 2.4 | 5.6 | 5.0 | 4.3 | — |
| GAM-10X | 3.0 | 6.5 | 6.8 | 5.4 | — |
| GAM-12X | 3.0 | 7.4 | 7.2 | 6.2 | — |
| GAR-1X | 0.5 | 0.9 | 1.0 | | 0.7 |
| GAR-2X | 1.0 | 1.5 | 1.6 | | 1.2 |
| GAR-3X | 1.3 | 2.1 | 2.4 | | 1.7 |
| GAR-4X | 1.7, 1.8 | 2.6, 3.1 | 3.1, 3.1 | 2.3 | 2.2 |
| GAR-6X | 2.2 | 4.4 | — | — | — |
| GAR-8X | 2.4 | 5.5 | 5.6 | 4.2 | — |
| GAR-10X | 3.5 | 6.0 | 6.7 | 5.3 | — |
| GAR-12X | 3.4 | 6.6 | 6.7 | 6.2 | — |
| SA-6X | 2.9 | 4.1 | 4.0 | 4.1 | — |
| SA-8X | 3.4 | 4.7 | 5.0 | 4.8 | — |

Labeling efficiency of GAM, GAR and SA was equivalent for 679 compound 1-NHS compared to DyLight 680B-NHS and higher compared to DyLight 680 and Company B compound. The antibodies were labeled, purified, and evaluated by SDS-PAGE as described above. Antibodies were also labeled with Company A compound, which was reconstituted in dimethylsulfoxide (DMSO) and combined at 2×, 5×, 7.5×, 10×, and 15× molar excess with GAM or GAR for sixty-five minutes at room temperature to label the antibodies.

Inventive and commercial compounds, each as the NHS ester, were conjugated to goat anti-rat (GARat) antibodies. GARat, at a concentration of 10 mg/ml in phosphate buffered saline (PBS), was spiked with 10% v/v with 0.67 M borate buffer. The compounds were combined at 5× or 10× molar excess with GAR at for 65 minutes at room temperature to label the antibody. The antibodies were labeled, purified and evaluated by SDS-PAGE as described above.

Labeling efficiency of GARat was slightly higher for 679 Compound 1-NHS compared to DyLight 680B-NHS, V08-15173-NHS and Company B compound-NHS.

In another set of experiments, the labeling of GAM with the inventive and commercial compounds is shown below.

|  | Mole Dye/Mole Protein Ratio @ 2.5 X | Mole Dye/Mole Protein Ratio @ 5 X | Mole Dye/Mole Protein Ratio @ 7.5 X | Mole Dye/Mole Protein Ratio @ 10 X | Mole Dye/Mole Protein Ratio @ 15 X |
|---|---|---|---|---|---|
| V08-15173 | 2.5 | 4.9 | 7.1 | 8.9 | 12.4 |
| V10-04152 | 2.8 | 5.1 | 7.4 | 10.0 | 13.9 |
| DY679P1 | 1.8 | 4.1 | 6.6 | 8.5 | 12.9 |
| Company A compound | 1.1 | 5.3 | 7.4 | 9.4 | 12.6 |
| Company B compound | 1.8 | 4.0 | 6.3 | 8.3 | 13.1 |

Labeling efficiency of GAM was similar for all the dyes at all molar excesses.

In another set of experiments, the labeling of GAR with the inventive and commercial compounds is shown below, at a molar excess of 5×, 15×, and 25×.

|  | Mole Dye/Mole Protein Ratio @ 5 X | Mole Dye/Mole Protein Ratio @ 15 X | Mole Dye/Mole Protein Ratio @ 25 X |
|---|---|---|---|
| V08-15173 | 4.6 | 12.7 | 19.6 |
| V10-04152 | 2.2 | 10.1 | 13.9 |
| DY679P1 | 4.8 | 10.6 | 14.4 |
| Company A Compound | 3.4 | 9.8 | 15.4 |
| Company B Compound | 4.1 | 15.2* | 46.7* |

At 5×, the labeling efficiency of GAR for all the dyes was similar except for V10-04152. At 15× and 25×, the labeling efficiency was similar except for Company B compound. *Company B compound conjugates precipitated in the Slide-A-Lyzer at molar excesses greater than 10×, indicating this method of purification was not suitable for Company B dyes.

EXAMPLE 8

Performance of the dye-GAM conjugates, dye-GAR conjugates, and dye-SA conjugates was evaluated in a functional assay. Wells of a 96 white opaque plate or black clear-bottom plate were coated with target proteins mouse IgG immunoglobulin, rabbit IgG immunoglobulin, or biotinylated bovine serum albumin (BBSA). One hundred µl mouse or rabbit IgG, or BBSA at a concentration of 10 µg/ml was applied to the corresponding wells in columns 1 and 2. The target proteins were serially diluted 1:1 from the wells in columns 2 to 11 using 100 µl PBS. One hundred µl of the samples from the wells in column 11 were discarded. One hundred µl PBS was added to the wells in column 12. The plates were incubated overnight at 4° C. and then blocked 2×200 µl with Thermo Scientific SuperBlock® Blocking Buffer. The coated plates were washed 2×200 µl with PBS-Tween and 1×200 µl with PBS. Based on the calculated concentrations, conjugates were diluted 1:250 in PBS, added to the corresponding plates (100 µl/well) and then incubated for one hour in the dark. The plates were washed with 2×200 µl with PBS-Tween and 1×200 µl with PBS and filled with PBS buffer (100 µl/well) prior to scanning the white opaque plates on Tecan Safire using 679 $nm_{excitation}$/702 $nm_{emission}$ or scanning the black clear-bottom plates on LiCor Odyssey at 700 channel, to detect fluorescence intensity.

As shown in FIGS. 2-7, RFU and/or signal to background ratio (S/B) of the dyes were compared at various concentrations, using the indicated conjugation conditions.

Figure 2:
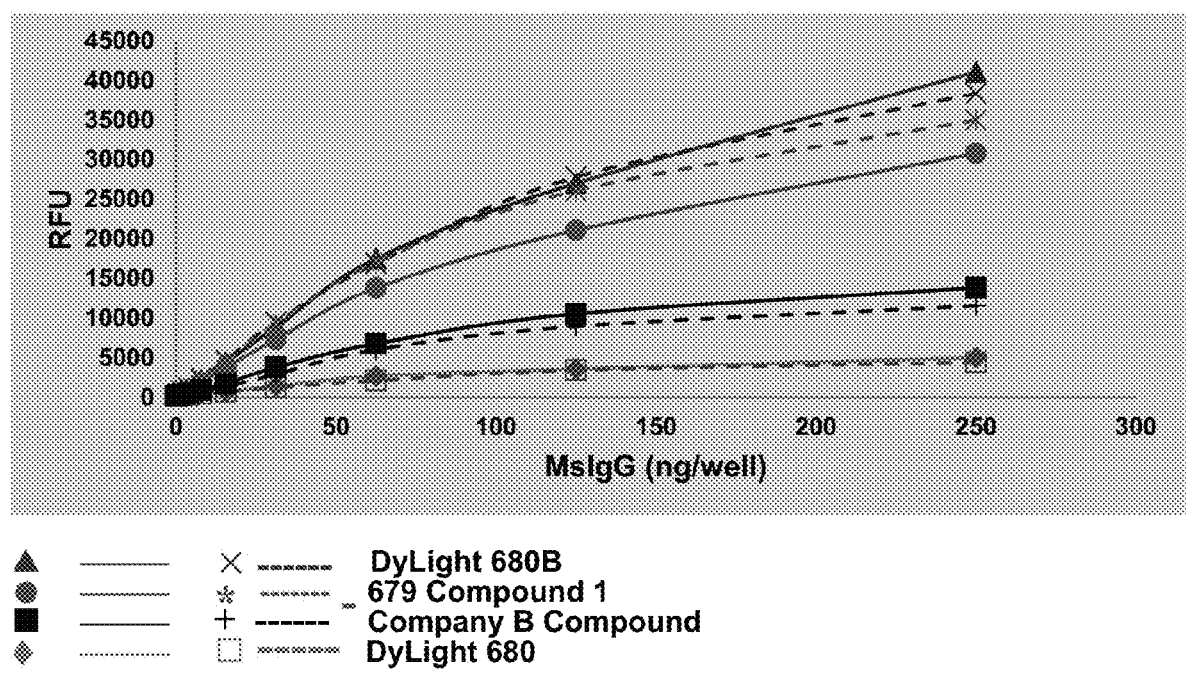
FIG. 2 graphs functional assay results with some commercial dyes and inventive compounds with one conjugate produced in one embodiment.

FIG. 2 shows Tecan Safire results of a functional assay using GAM conjugated with either 8× molar excess of the dyes (solid lines) or 10× molar excess of the dyes (dashed lines) of DyLight 680 (purple filled diamond/open square); DyLight 680B (blue filled triangle/X); 679 Compound 1 (red filled circle/asterisk); and Company B Compound (black filled square/+ sign). DyLight 680B-GAM (8×) showed higher binding fluorescence compared to corresponding 679 Compound 1-GAM (8×). At 10× molar excess, 679 Compound 1-GAM showed similar performance to DyLight 680B-GAM. Both DyLight 680 and Company B compound showed much lower intensity compared to DyLight 680B and 679 Compound 1 conjugates. Signal/Background (S/B) was higher for DyLight 680B-GAM conjugates than 679 Compound 1-GAM conjugates. Similar results were generally obtained for GAR conjugates.

Figure 3:
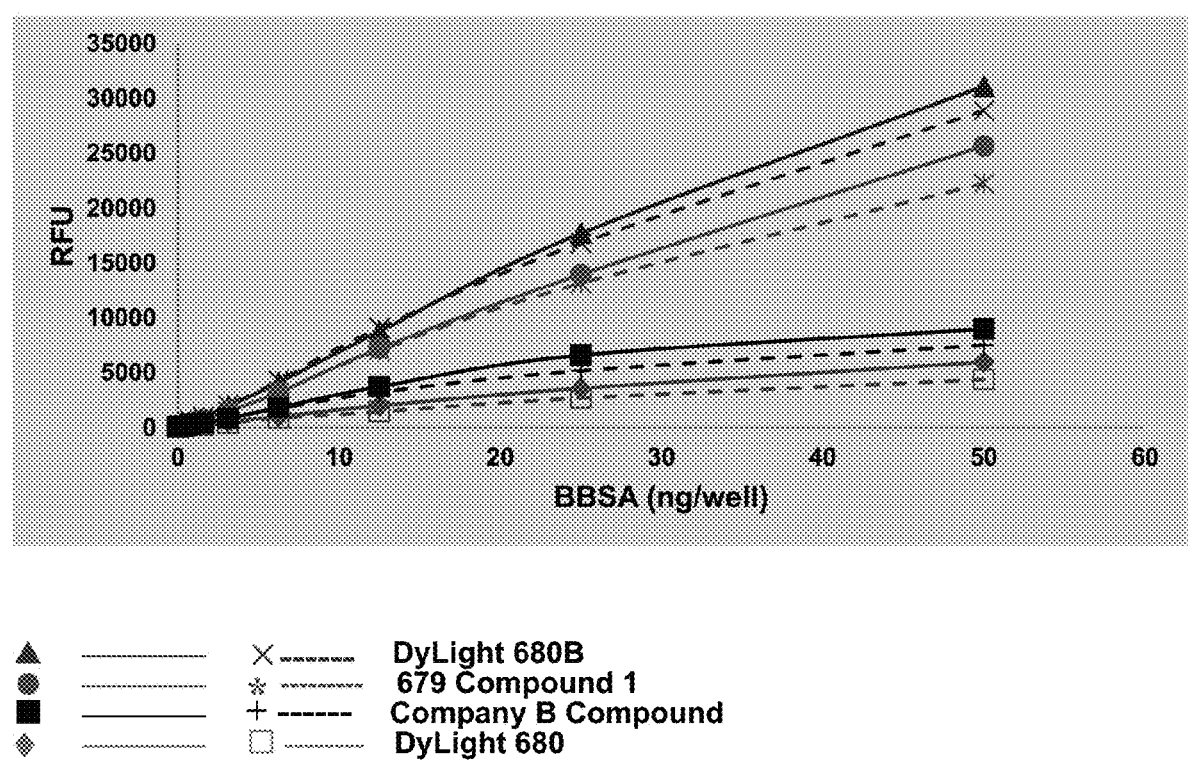
FIG. 3 graphs functional assay results with some commercial dyes and inventive compounds with another conjugate produced in one embodiment.

FIG. 3 shows Tecan Safire results of a functional assay using SA conjugated with either 6× molar excess of the dyes (solid lines) or 8× molar excess of the dyes (dashed lines) of DyLight 680 (purple filled diamond/open square); DyLight 680B (blue filled triangle/X); 679 Compound 1 (red filled circle/asterisk); and Company B Compound (black filled square/+ sign). 679 Compound 1-SA (6×, 8×) showed slightly lower binding fluorescence compared to corresponding DyLight 680B-SA (6×, 8×). There was no quenching trend with the conjugates at higher molar excesses. The S/B was slightly lower for 679 Compound 1-SA conjugates than for DyLight 680B-SA conjugates.

Figure 4:
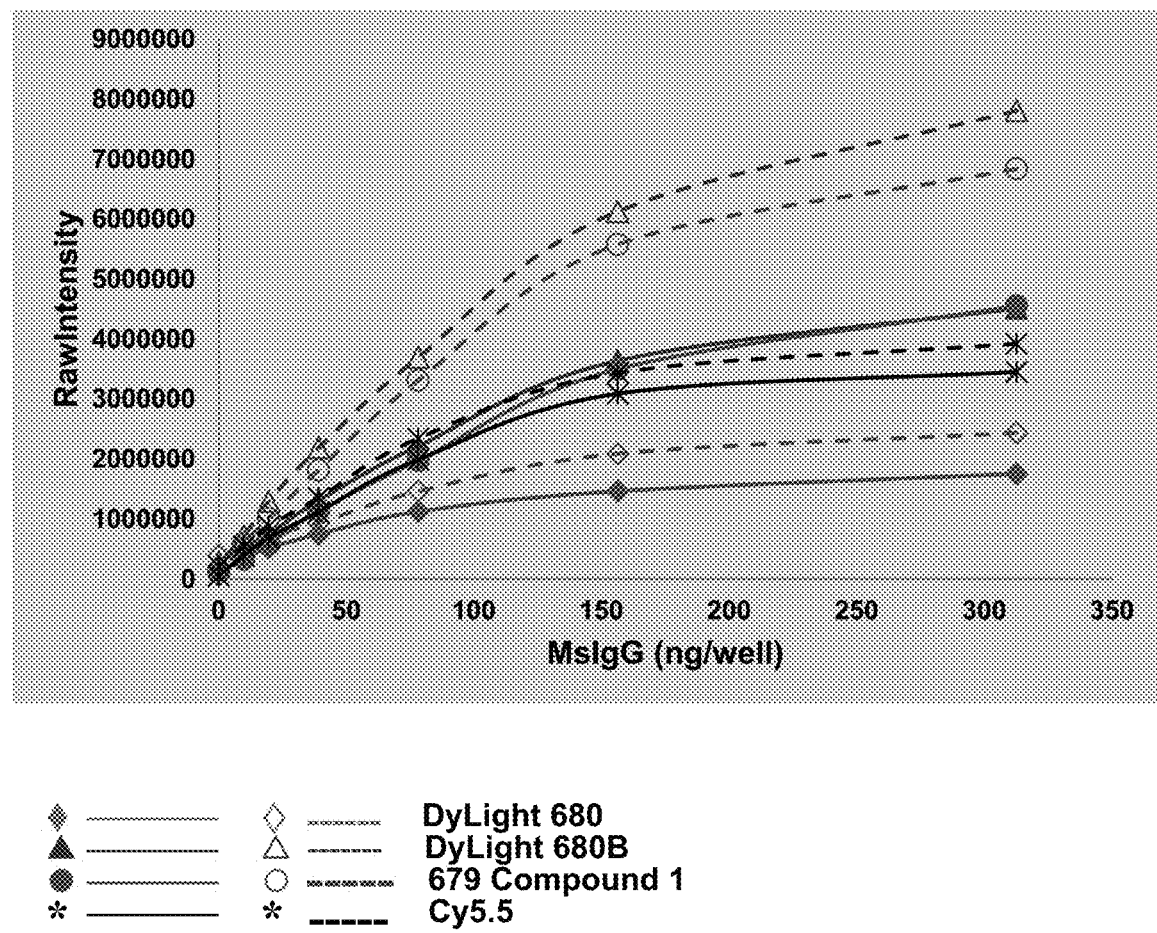
FIG. 4 graphs functional assay results with some commercial dyes and inventive compounds with another conjugate produced in one embodiment.

FIG. 4 shows LiCor Odyssey results of a functional assay using GAM conjugated with either 2× molar excess of the dyes (solid lines) or 4× molar excess of the dyes (dashed lines) of DyLight 680 (purple diamond); DyLight 680B (blue triangle); 679 Compound 1 (red circle); and Cy5.5 (black asterisk). The following table compared S/B and raw intensity data.

| S/B | @ 1250 ng coating | @ 39 ng coating | @ 0 (blank) |
| --- | --- | --- | --- |
| DyLight 680-GAM-2X | 25.3 | 9.8 | 1.0 |
| DyLight 680-GAM-4X | 6.4 | 2.3 | 1.0 |
| DyLight 680B-GAM-2X | 18.2 | 4.6 | 1.0 |
| DyLight 680B-GAM-4X | 31.9 | 8.1 | 1.0 |
| 679 Compound 1-GAM-2X | 36.1 | 7.9 | 1.0 |
| 679 Compound 1-GAM-4X | 65.2 | 15.9 | 1.0 |
| Cy5.5-GAM-2X | 62.3 | 17.7 | 1.0 |
| Cy5.5-GAM-4X | 19.6 | 6.1 | 1.0 |

| Raw Intensity | @ 1250 ng coating | @ 39 ng coating | @ 0 (blank) |
| --- | --- | --- | --- |
| DyLight 680-GAM-2X | 1941300 | 751514 | 76795 |
| DyLight 680-GAM-4X | 2596363 | 937396 | 403405 |
| DyLight 680B-GAM-2X | 5179777 | 1311798 | 284501 |
| DyLight 680B-GAM-4X | 8614438 | 2190343 | 270357 |
| DY679P1-GAM-2X | 5180336 | 1135001 | 143352 |
| DY679P1-GAM-4X | 7482510 | 1820225 | 114807 |
| Cy5.5-GAM-2X | 3957169 | 1124788 | 63513 |
| Cy5.5-GAM-4X | 4379901 | 1358039 | 223585 |

Figure 5:
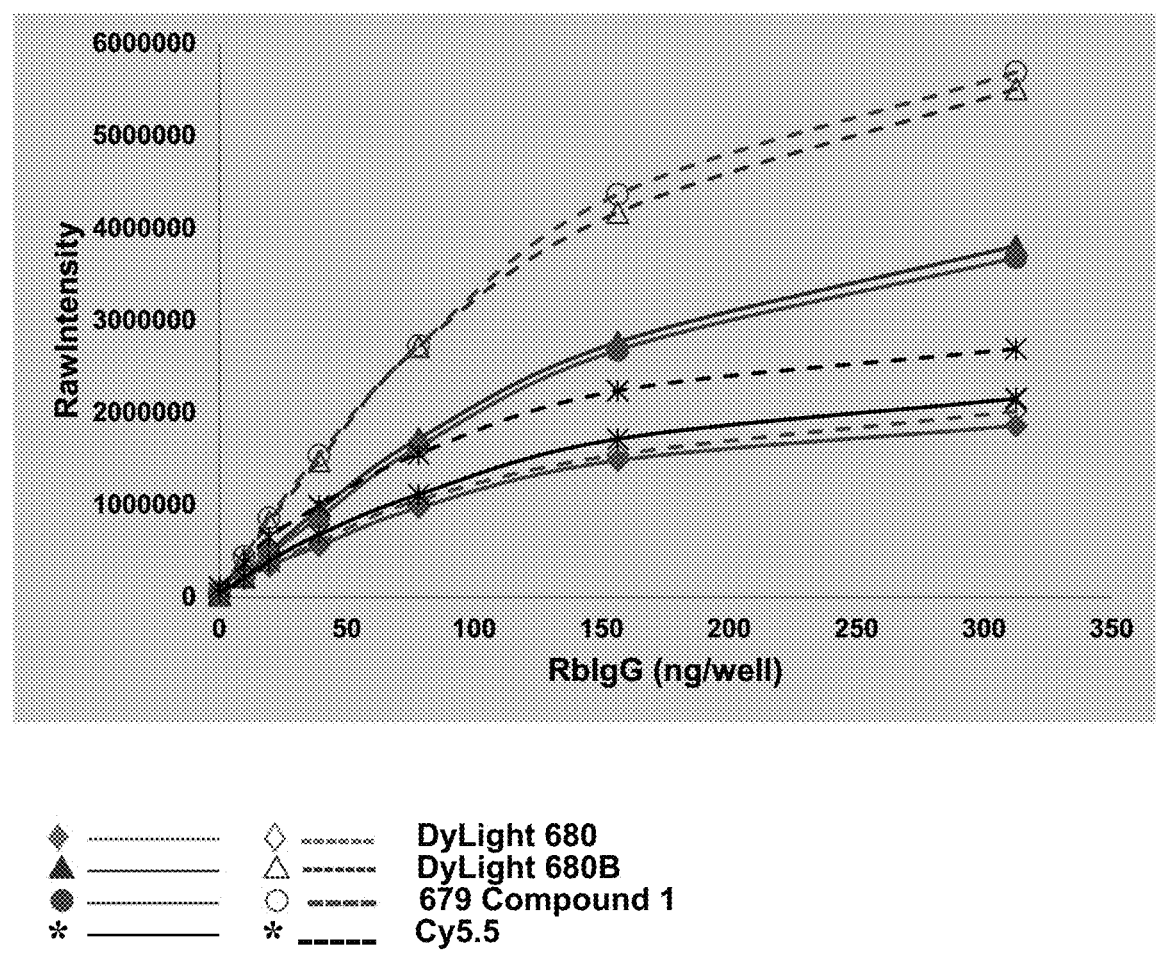
FIG. 5 graphs functional assay results with some commercial dyes and inventive compounds with one conjugate produced in one embodiment.

FIG. 5 shows LiCor Odyssey results of a functional assay using GAR conjugated with either 2× molar excess of the dyes (solid lines) or 4× molar excess of the dyes (dashed lines) of DyLight 680 (purple diamond); DyLight 680B (blue triangle); 679 Compound 1 (red circle); and Cy5.5 (black asterisk). The following table compared S/B and raw intensity data.

| S/B | @ 1250 ng coating | @ 39 ng coating | @ 0 (blank) |
| --- | --- | --- | --- |
| DyLight 680-GAR-2X | 66.7 | 19.8 | 1.0 |
| DyLight 680-GAR-4X | 62.2 | 17.4 | 1.0 |
| DyLight 680B-GAR-2X | 210.6 | 47.5 | 1.0 |
| DyLight 680B-GAR-4X | 167.2 | 39.3 | 1.0 |
| DY679P1-GAR-2X | 184.0 | 39.2 | 1.0 |
| DY679P1-GAR-4X | 141.9 | 33.4 | 1.0 |
| Cy5.5-GAR-2X | 57.3 | 16.1 | 1.0 |
| Cy5.5-GAR-4X | 26.7 | 9.0 | 1.0 |

| Raw Intensity | @ 1250 ng coating | @ 39 ng coating | @ 0 (blank) |
| --- | --- | --- | --- |
| DyLight 680-GAR-2X | 1868227 | 554324 | 28015 |
| DyLight 680-GAR-4X | 2140077 | 597726 | 34391 |
| DyLight 680B-GAR-2X | 4178812 | 943008 | 19839 |
| DyLight 680B-GAR-4X | 6285439 | 1476347 | 37592 |
| DY679P1-GAR-2X | 4039443 | 860737 | 21950 |
| DY679P1-GAR-4X | 6527381 | 1537020 | 46001 |
| Cy5.5-GAR-2X | 2408459 | 675886 | 42049 |
| Cy5.5-GAR-4X | 2929556 | 988970 | 109613 |

Figure 6:
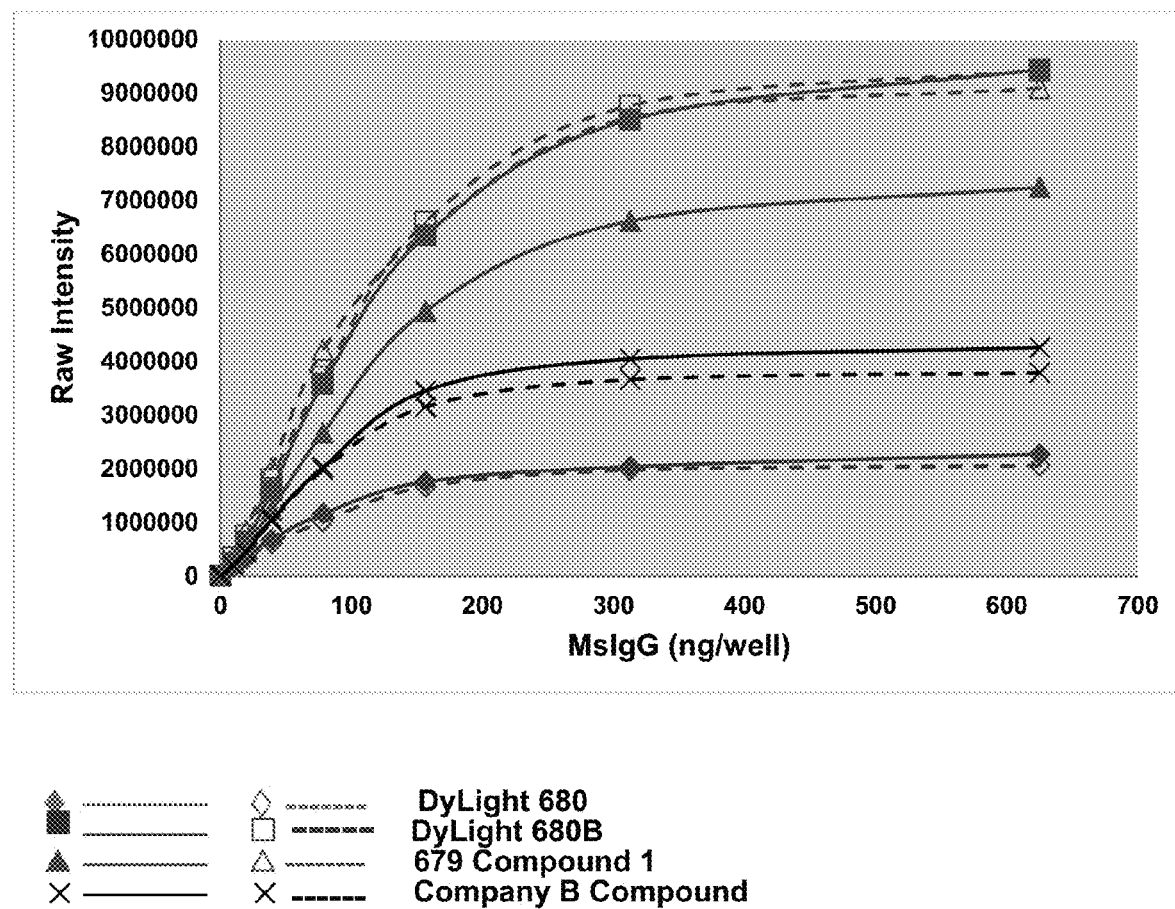
FIG. 6 graphs functional assay results with some commercial dyes and inventive compounds with one conjugate produced in one embodiment.

FIG. 6 shows LiCor Odyssey results of a functional assay using GAM conjugated with either 8× molar excess of the dyes (solid lines) or 10× molar excess of the dyes (dashed lines) of DyLight 680 (purple diamond); DyLight 680B (blue square); 679 Compound 1 (red triangle); and Company B Compound (black X). The following table compared S/B data.

| | 2500 ng mouse IgG/well | 39.1 ng mouse IgG/well |
| --- | --- | --- |
| DyLight 680-GAM-8X | 173.6 | 48.9 |
| DyLight 680-GAM-10X | 137.2 | 37.6 |
| DyLight 680B-GAM-8X | 929.3 | 142.4 |
| DyLight 680B-GAM-10X | 914.5 | 165.6 |
| DY679P1-GAM-8X | 675.2 | 110.5 |
| DY679P1-GAM-10X | 871.5 | 183.5 |
| Company B Compound-GAM-8X | 459.9 | 112.4 |
| Company B Compound-GAM-10X | 374.0 | 96.1 |

679 Compound 1-GAM (10×) showed equivalent bound fluorescence compared to corresponding DyLight 680B-GAM (10×). S/B was lower for 679 Compound 1-GAM (8×,10×) compared to DyLight 680B-GAM (8×,10×). In general, similar results were obtained for GAR conjugates.

Figure 7:
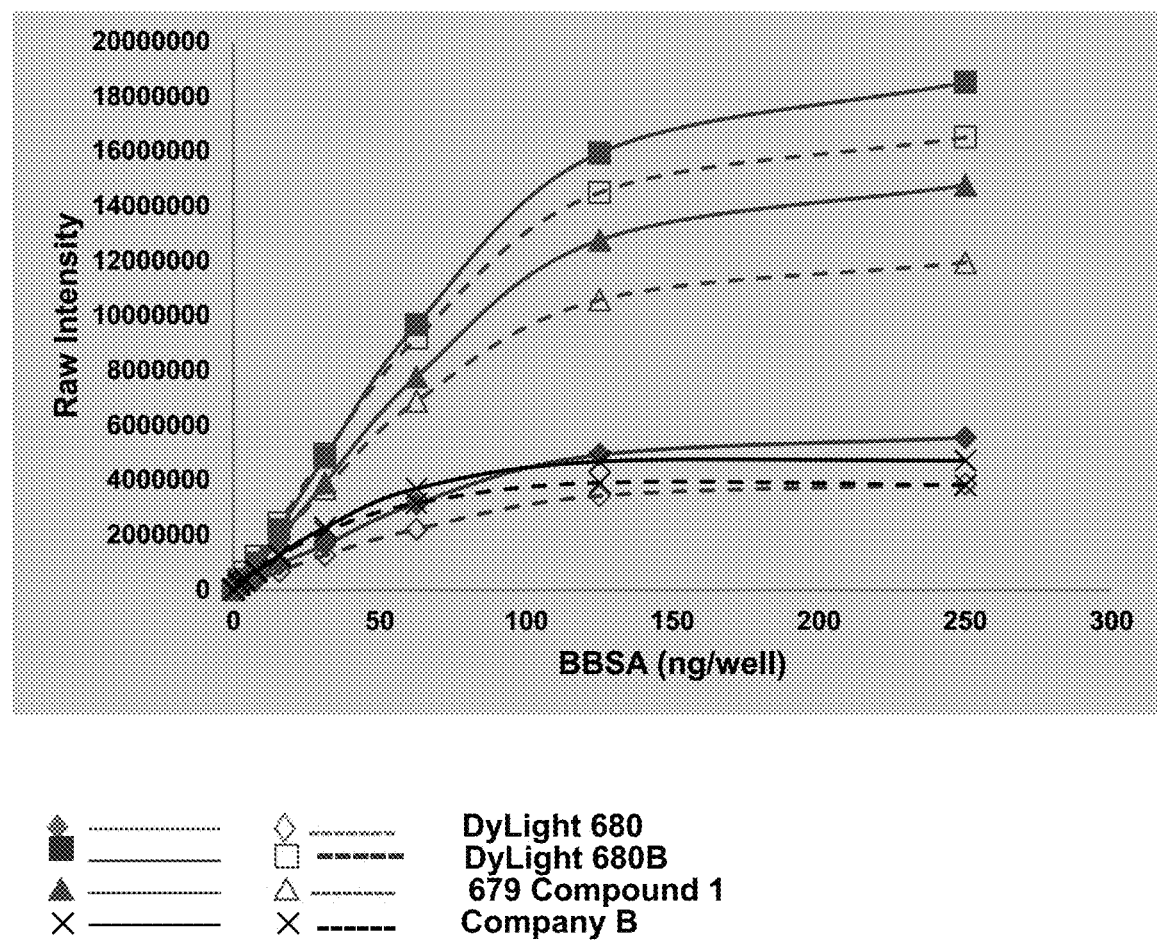
FIG. 7 graphs functional assay results with some commercial dyes and inventive compounds with one conjugate produced in one embodiment.

FIG. 7 shows LiCor Odyssey results of a functional assay using SA conjugated with either 6× molar excess of the dyes (solid lines) or 8× molar excess of the dyes (dashed lines) of DyLight 680 (purple diamond); DyLight 680B (blue square); 679 Compound 1 (red triangle); and Company B Compound (black X). The following table compared S/B data.

| | 250 ng BBSA/well | 3.9 ng BBSA/well |
| --- | --- | --- |
| DyLight 680-SA-6X | 614.5 | 33.1 |
| DyLight 680-SA-8X | 436.3 | 25.1 |
| DyLight 680B-SA-6X | 2196.7 | 43.8 |
| DyLight 680B-SA-8X | 1969.5 | 75.6 |
| DY679P1-SA-6X | 1742.1 | 58.5 |
| DY679P1-SA-8X | 1406.0 | 54.7 |
| Company B Compound-SA-6X | 570.2 | 49.7 |
| Company B Compound-SA-8X | 427.7 | 36.1 |

679 Compound 1-SA (6×, 8×) showed lower bound fluorescence and S/B compared to corresponding DyLight 680B-SA (6×, 8×).

Figure 8:
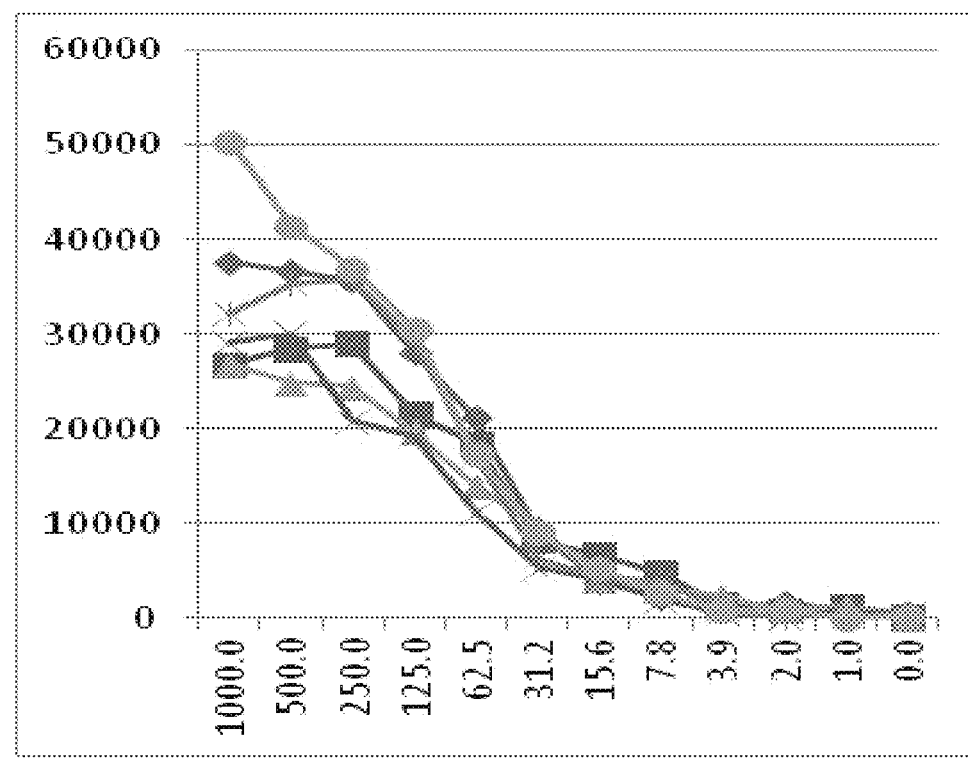
FIG. 8 shows functional assay results with some commercial dyes and inventive compounds in one embodiment.

679 Compound 1 and Company Compound were conjugated to GAR at high molar excesses, and evaluated in a functional assay, as described above. FIG. 8 shows results expressed as RFU of a functional assay using GAR conjugated with 679 Compound 1 at either a 7.5× molar excess (blue diamond), 15× molar excess (red square), or 22.5× molar excess (green triangle), and Company A Compound at either 7.5× molar excess (purple X), 15× molar excess (turquoise asterisk), or 22.5× molar excess (orange circle).

Figure 9:
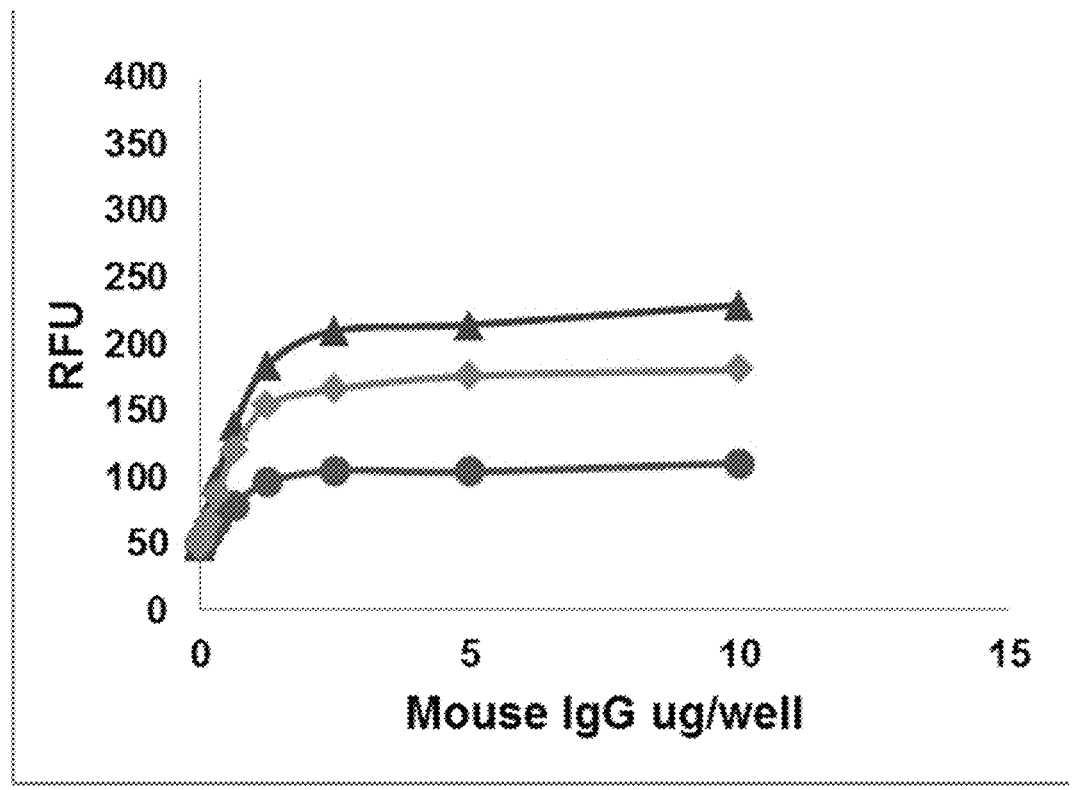
FIG. 9 graphs functional assay results with some commercial dyes and inventive compounds in one embodiment.

FIG. 9 shows VarioSkan Flash results with excitation and emission of 679 nm/702 nm, expressed as RFU of a functional assay using GAM conjugated with 5× molar excess of Company B compound (orange diamond), V08-15173 (blue triangle), and V10-04152 (red circle). Based on the data, V08-15173-GAM (5×) showed higher binding fluorescence compared to Company B Compound-GAM (5×).

Figure 10:
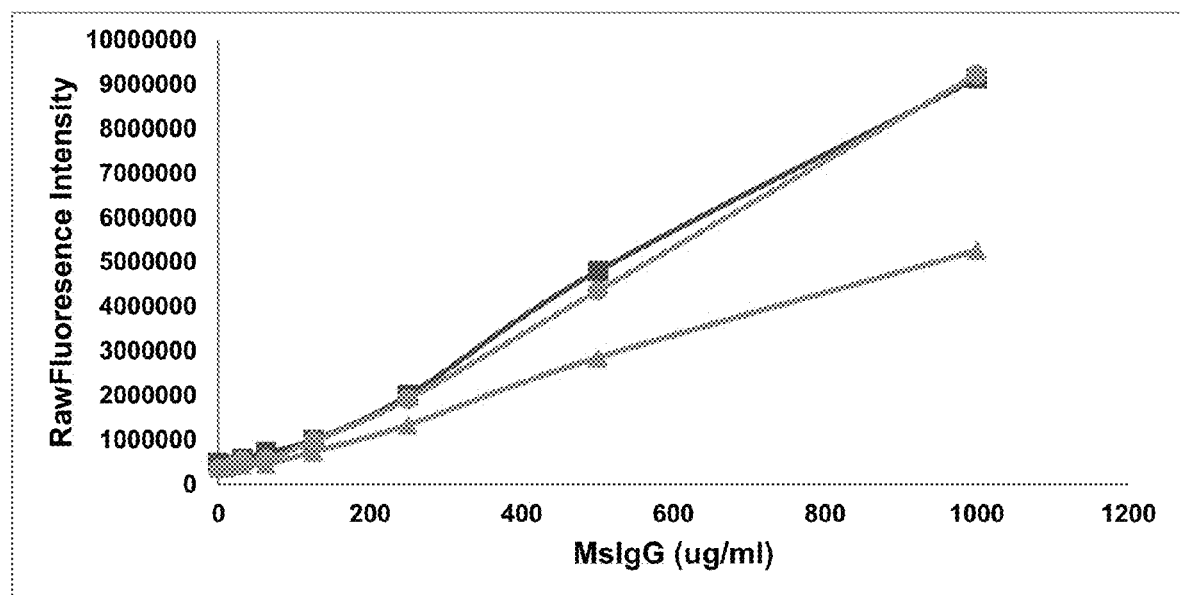
FIG. 10 graphs functional assay results with some commercial dyes and inventive compounds in one embodiment.

FIG. 10 shows LiCOR Odyssey results, using the 700 channel, expressed as Raw Fluorescence Intensity of a functional assay using GAM conjugated with 5× molar excess of 679 Compound 1/1 (green triangle), Company A Compound (purple circle), and V08-15173 (blue square). FIG. 11 shows LiCOR Odyssey results expressed as S/B of a functional assay using GAM conjugated at 2.5×, 5×, 10×, or 15× molar excess of 679 Compound 1/1, Company A Compound, and V08-15173. V08-15173-GAM (5×) showed similar binding fluorescence to Company A Compound-GAM (5×). 679 Compound 1/1-GAM (5×) binding fluorescence was lower compared to the other two conjugates.

Figure 12:
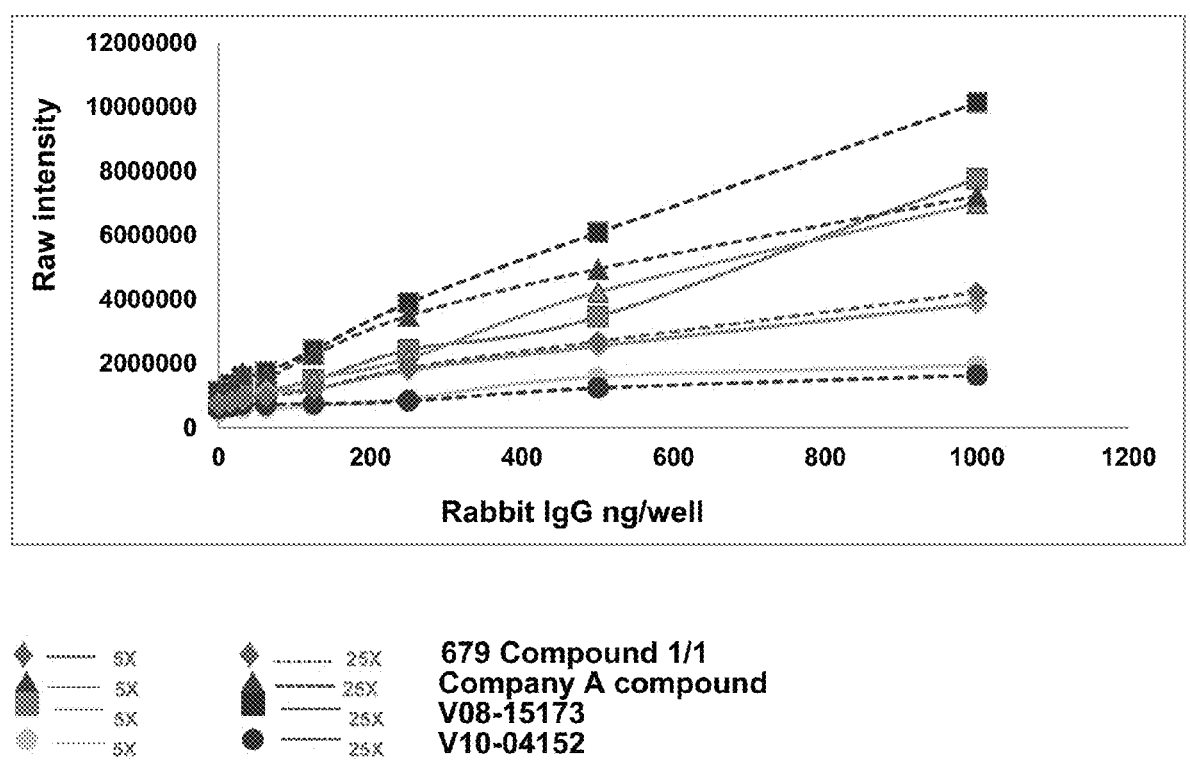
FIG. 12 graphs functional assay results with some some commercial dyes and inventive compounds in one embodiment.
Figure 14:
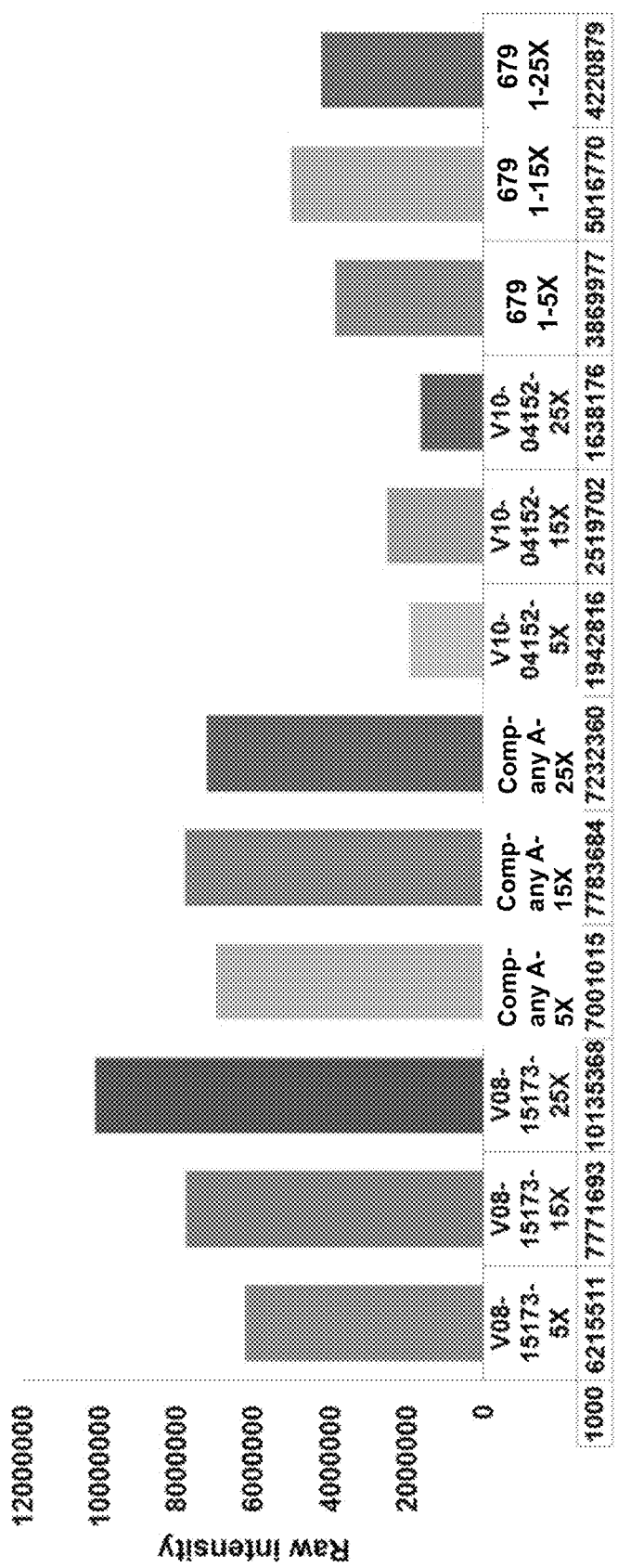
FIG. 14 is a histogram showing functional assay results with some commercial dyes and inventive compounds in one embodiment.

FIG. 12 shows LiCOR Odyssey results, using the 700 channel, expressed as Raw Fluorescence Intensity of a functional assay using GAR conjugated with 5× and 25× molar excess of 679 Compound 1/1 (green 5×, diamond, solid line; green 25×, diamond, dashed line), Company A Compound (purple 5×, triangle, solid line; purple 25×, triangle, dashed line), V08-15173 (light blue 5×, square, solid line; dark blue 25×, square, dashed line), and V10-04152 (yellow 5×, circle, solid line; red 25×, circle, dashed line). FIG. 13 shows LiCOR Odyssey results expressed as S/B of a functional assay using GAR conjugated at 5×, 15×, or 25× molar excess of 679 Compound 1/1, Company A Compound, V08-15173, and V10-04152. Based on the Raw Fluorescence Intensity data, there was no apparent quenching for the V08-15173-GAR at 25× molar excess. 679 Compound 1/1, V10-04152, and Company A Compound were saturating at 25×. FIG. 14 shows summary Raw Fluorescence Intensity data, and apparent quenching at 1000 ng/well at 25× for 679 Compound 1/1 (679 1), V10-04152, and Company A Compound, but no apparent quenching at 25× for V08-15173.

EXAMPLE 9

The inventive compounds were evaluated for immunofluorescence in cell based assays using the following protocol. Frozen A549 cell plates stored at −20° C. were placed for 30 min 50° C. Storage buffer (PBS) was removed and the cells were permeabilized for 15 min (100 µl/well) with 0.1% Triton-X100 in 1×PBS buffer. Plates were blocked for 30 min in 2% BSA in 1×PBS-0.1% Trion-X100. Primary antibodies diluted in 2% BSA in 1×PBS-0.1% Trion-X100 were added to the plates (column 1-11; column 12 included only blocker) and incubated three hours at room temperature. Mouse anti-lamin A was added at 1 µg/ml and rabbit anti-lamin B1 was added at 3 µg/ml. After overnight incubation, the antibody solution was removed from the plates and the plates were washed with PBS-0.5% Tween-20 (2×100 µl/well). GAM and GAR secondary antibodies labeled with DyLight 680-NHS, DyLight 680B-NHS, 679 Compound 1-NHS and Company B Compound-NHS were diluted to 4 µg/ml in PBS, added and incubated for one hour at room temperature. The plates were then washed three times with 100 µl/well PBS, and Hoechst stain diluted to 0.1 µg/ml in PBS was added to each well (100 µl/well). The plates were scanned on ArrayScan Plate Reader for imaging and quantitation.

Figures 15A, 15B, 15C, 15D:
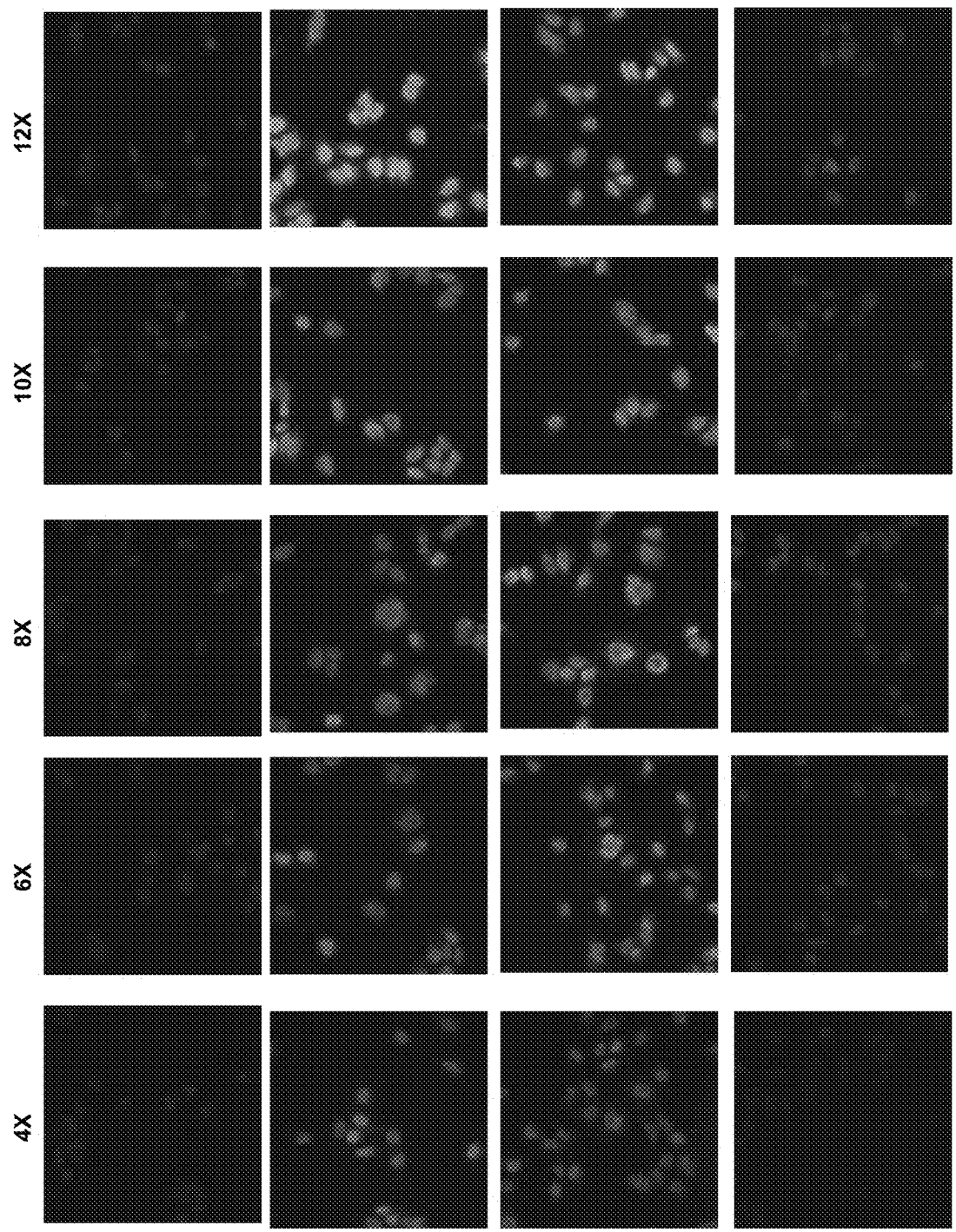
FIGS. 15A-D show immunofluorescence data with some commercial dyes and inventive compounds forming a conjugate in one embodiment.
Figure 16A:
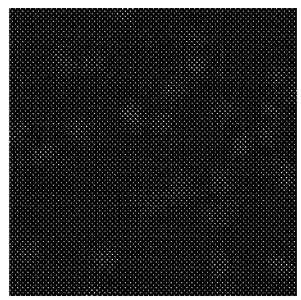
FIGS. 16A-D show immunofluorescence data with some commercial dyes and inventive compounds forming a conjugate in one embodiment.
Figure 16A:
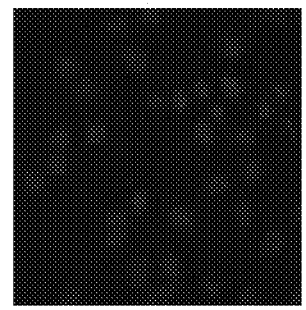
Figure 16A:
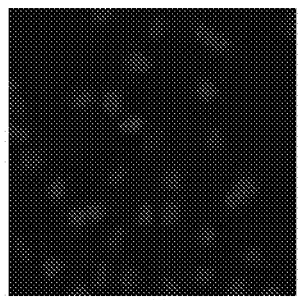
Figure 16B:
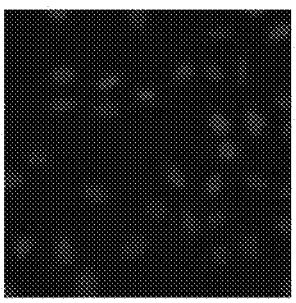
Figure 16B:
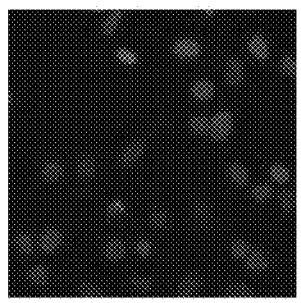
Figure 16B:
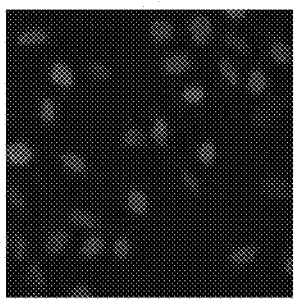
Figure 16C:
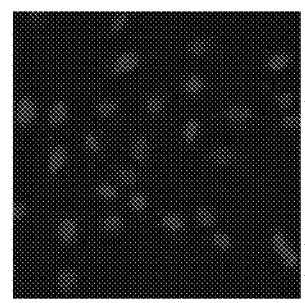
Figure 16C:
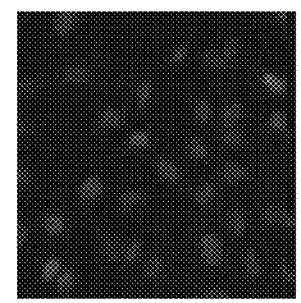
Figure 16C:
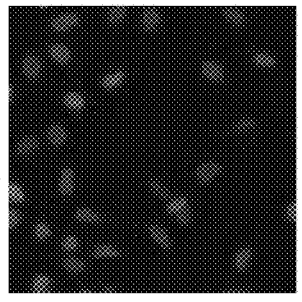
Figure 16D:
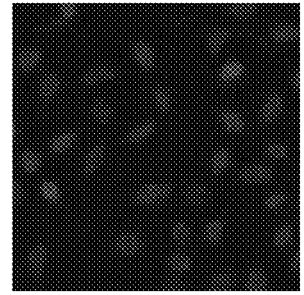
Figure 16D:
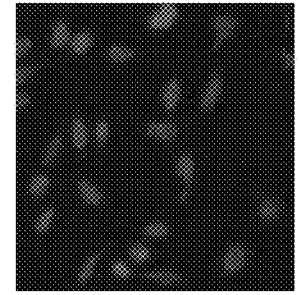
Figure 16D:
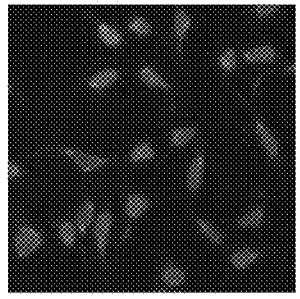
Figure 17A:
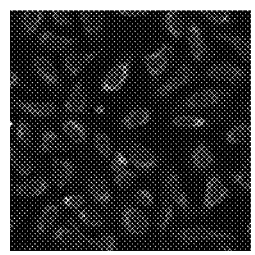
FIGS. 17A-D show immunofluorescence data with some commercial dyes and inventive compounds in one embodiment.
Figure 17A:
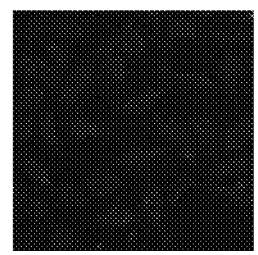
Figure 17B:
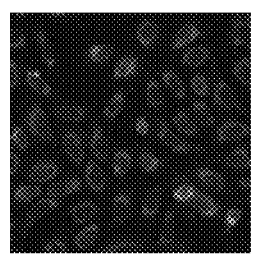
Figure 17B:
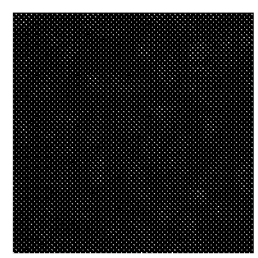
Figure 17C:
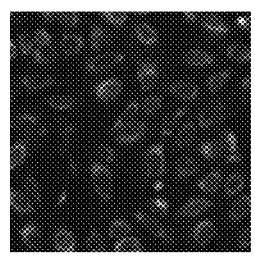
Figure 17C:
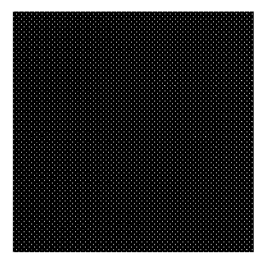
Figure 17D:
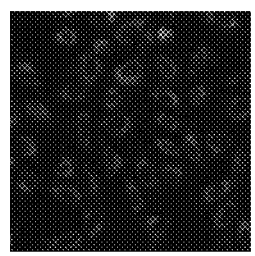
Figure 17D:
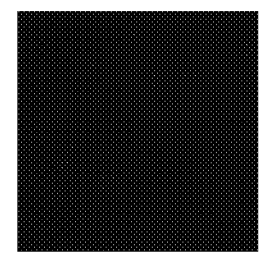
Figure 18A:
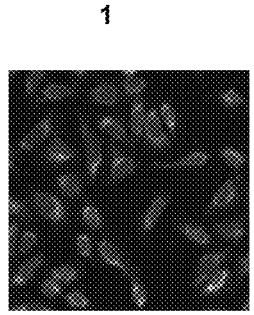
FIGS. 18A-D show immunofluorescence data with some commercial dyes and inventive compounds in one embodiment.
Figure 18A:
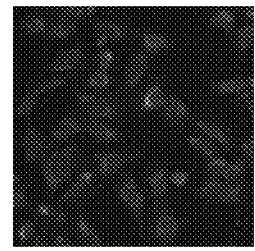
Figure 18B:
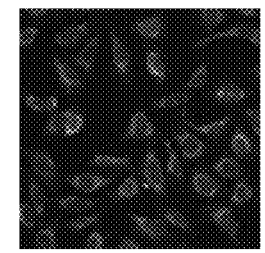
Figure 18B:
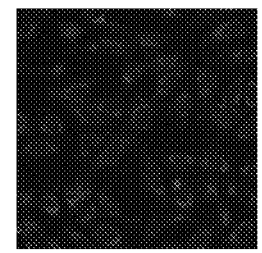
Figure 18C:
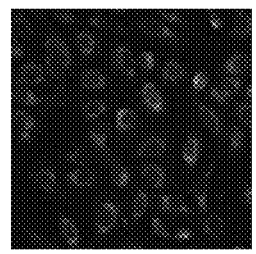
Figure 18C:
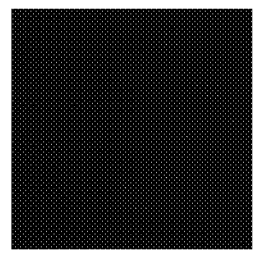
Figure 18D:
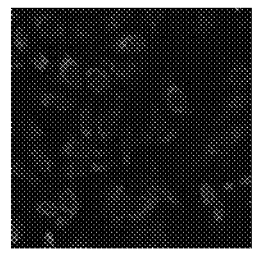
Figure 18D:
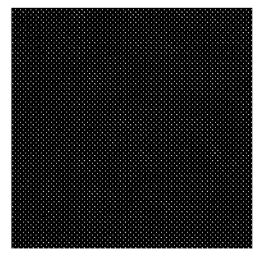

FIG. 15 shows results of an immunofluorescence assay using mouse anti-lamin A as a primary antibody, and DyLight 680-GAM (FIG. 15A), DyLight 680B-GAM (FIG. 15B), 679 Compound 1-GAM (FIG. 15C), or Company B Compound-GAM (FIG. 15D) as secondary antibody, where the compound was conjugated to GAM (secondary antibody) at 4× molar excess (column 1), 6× molar excess (column 2), 8× molar excess (column 3), 10× molar excess (column 4), or 12× molar excess (column 5). 679 Compound 1 conjugated to GAM showed very similar performance to corresponding DyLight 680B conjugates.

The inventive compounds and commercial dye were evaluated for immunofluorescence in a second cell based assay using the following protocol. Frozen U20S cell plates stored at −20° C. were placed overnight at 4° C. Storage buffer (PBS) was removed and the cells were permeabilized for 15 min (100 µl/well) with 0.1% Triton-X100 in 1×PBS buffer. Plates were blocked for 30 min in 2% BSA in 1×PBS-0.1% Trion-X100. Primary antibodies diluted in 2% BSA in 1×PBS-0.1% Trion-X100 were added to the plates (column 1-11; column 12 included only blocker) and incubated five hours at room temperature. Mouse anti-lamin A was added at 2 µg/ml and rabbit anti-lamin B1 was added at 4 µg/ml. After incubation, the antibody solution was removed from the plates and the plates were washed PBS-0.5% Tween-20 (2×100 µl/well). Next, GAM and GAR secondary antibodies labeled with DyLight 680-NHS, DyLight 680B-NHS, 679 Compound 1-NHS, and Cy5.5 Mono Ester were diluted to 4 µg/ml in PBS and incubated with the cells for one hour at room temperature. GAM and GAR conjugated to DyLight 680-NHS, DyLight 680B-NHS, 679 Compound 1-NHS, and Company B Compound at 10× molar excess were diluted to 4 µg/ml in PBS and then serially diluted 1:1 in the plate to the following concentrations: 2 µg/ml, 1 µg/ml, 0.5 µg/ml, 0.25 µg/ml, 0.125 µg/ml and/or 0.0625 µg/ml. The plates were washed 3× with 100 µl/well PBS, and Hoechst stain diluted to 0.1 µg/ml in PBS was added to each well (100 µl/well). The plates were scanned on ArrayScan Plate Reader for imaging and quantitation.

FIG. 16 shows results of an immunofluorescence assay using mouse anti-lamin A as a primary antibody, and either DyLight 680-GAM (FIG. 16A), DyLight 680B-GAM (FIG. 16B), 679 Compound 1-GAM (FIG. 16C), or Cy5.5-GAM (FIG. 16D) as secondary antibody, where the compound was conjugated to GAM (secondary antibody) at 2× molar excess (column 1), 3× molar excess (column 2), or 4× molar excess (column 3). Performance in immunofluorescence of 679 Compound 1 conjugate was similar to the performance of corresponding DyLight 680B conjugates. Quantitative analysis of FIG. 16 data, expressed as Mean Total Intensity, which is the average total intensity of all pixels within a defined area or defined primary object such as a nucleus, is shown below.

| | Mean Total Intensity | | |
| --- | --- | --- | --- |
| | 2X | 3X | 4X |
| DyLight 680 | 91899 | 122829 | 144792 |
| DyLight 680B | 150542 | 228678 | 305700 |

-continued

| Mean Total Intensity | | | |
|---|---|---|---|
| | 2X | 3X | 4X |
| DY679P1 | 232482 | 263580 | 330865 |
| Cy5.5 | 211945 | 342208 | 451111 |

Fluorescence signal intensity for DyLight 680B and 679 Compound 1 GAM conjugates was 2-4 times higher, depending on the molar excess, compared to DyLight 680 or Cy5.5 GAM conjugates, and S/B for DyLight 680B & 679 Compound 1 GAM conjugates at the low molar excesses was comparable to each other and to DyLight 680. Overall fluorescence signal intensity for DyLight 680B and 679 Compound 1 GAR conjugates was about two times higher compared to DyLight 680. The S/B for DyLight 680B and 679 Compound 1 GAR labeled at 2×, 3× or 4× molar excess were comparable to each other and to DyLight 680 conjugates.

In the indicated experiments, the inventive compounds were evaluated for immunofluorescence in cell based assays using the following protocol. Frozen A549 cell plates stored at −20 C were placed for 30 min 50° C. Storage buffer (PBS) was removed and the cells were permeabilized for 15 min (100 μl/well) with 0.1% Triton-X100 in 1×PBS buffer. Plates were blocked for 30 min in 2% BSA in 1×PBS-0.1% Trion-X100. Primary antibodies diluted in 2% BSA in 1×PBS-0.1% Trion-X100 were added to the plates (column 1-11; column 12 included only blocker) and incubated three hours at room temperature. Mouse anti-lamin A was added at 1 μg/ml and rabbit anti-lamin B1 was added at 3 μg/ml. After overnight incubation, the antibody solution was removed from the plates and the plates were washed with PBS-0.5% Tween-20 (2×100 μl/well). GAM and GAR secondary antibodies labeled with DyLight 680-NHS, DyLight 680B-NHS, 679 Compound 1-NHS and Company B Compound-NHS were diluted to 4 μg/ml in PBS, added and incubated for one hour at room temperature. The plates were then washed three times with 100 μl/well PBS, and Hoechst stain diluted to 0.1 μg/ml in PBS was added to each well (100 μl/well). The plates were scanned on ArrayScan Plate Reader for imaging and quantitation.

In the indicated experiments, the inventive compounds and commercial dye were evaluated for immunofluorescence in a cell based assay using the following protocol. Frozen U2OS cell plates which were stored at −80° C. were thawed for 45 minutes at 50° C. Storage buffer (PBS) was removed and the cells were permeabilized for 15 minutes with 0.1% Triton-X100 in 1×PBS buffer (100 μl/well). The cell plate was blocked for 60 minutes in 2% BSA/PBS-0.1% Triton-X100. Primary antibody, either rat anti-Grp94 (5 μg/ml), mouse anti-lamin A (10 μg/ml), or rabbit anti-lamin B1 (10 μg/ml), diluted in 2% BSA/PBS-0.1% Triton-X100 was added to the plate and incubated for 1 hour at room temperature. Control wells contained only 2% BSA/PBS-0.1% Triton-X100 blocker. After incubation, the antibody solution was removed from the plate and the plate was washed three times with 100 μl/well of PBS-0.5% Tween-20 and one time with 100 μl/well PBS. GARat, GAM, or GAR secondary antibodies labeled with various molar excess of the inventive or commercial compound were diluted to 4 μg/ml in PBS and incubated for 1 hour at room temperature. The plates were washed three times with 100 μl/well of PBST and once with 100 μl/well PBS, and Hoechst (diluted to 0.1 μg/ml in PBS) was added to each well (100 μl/well). The plates were scanned on ArrayScan Plate Reader or ToxInsight Instrument.

FIG. 17 shows detection of Grp94 in U2OS cells (column 1) with 679 Compound 1-GARat (FIG. 17A), DyLight 680B-GARat (FIG. 17B), V08-15173-GARat (FIG. 17C), and Company B Compound-GARat (FIG. 17D) conjugated at a 5× molar excess; and associated controls (column 2).

FIG. 18 shows detection of Grp94 in U2OS cells (column 1) with 679 Compound 1-GARat (FIG. 18A), DyLight 680B-GARat (FIG. 18B), V08-15173-GARat (FIG. 18C), and Company B Compound-GARat (FIG. 18D) conjugated at a 10× molar excess; and associated controls (column 2).

As shown in FIGS. 17-18, no non-specific binding was observed with V08-15173-GARat and Compound B Compound-GARat conjugates but there was with DY679P1 and DyLight 680B-GARat conjugates.

Quantitative analysis of the data of FIGS. 17-18, expressed as Mean Total Intensity, which is the average total intensity of all pixels within a defined area or defined primary object such as a nucleus, is shown below.

| | | | Negative Controls | | | |
|---|---|---|---|---|---|---|
| | 5X | 10X | 5X | 10X | S/B (5X) | S/B (10X) |
| 679 Compound 1 - GARat | 81221 | 97162 | 36744 | 70585 | 2.2 | 1.4 |
| DyLight 680B-GARat | 77855 | 91720 | 34773 | 61355 | 2.2 | 1.5 |
| V08-15173-GARat | 76825 | 70881 | 28190 | 26341 | 2.7 | 2.7 |
| Company B Compound-GARat | 64881 | 56119 | 26762 | 30379 | 2.4 | 1.8 |

S/B was slightly better for V08-15173-GARat conjugates (5×, 10×) compared to the corresponding 679 Compound 1-GARat, DyLight 680B-GARat, and Company B Compound-GARat conjugates.

Figure 19A:
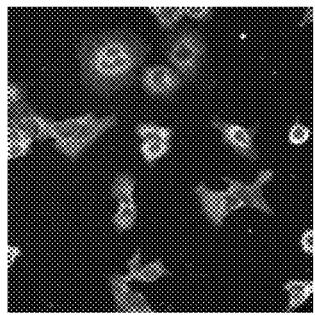
FIGS. 19A-C show immunofluorescence data with commercial dyes and inventive compounds in one embodiment.
Figure 19B:
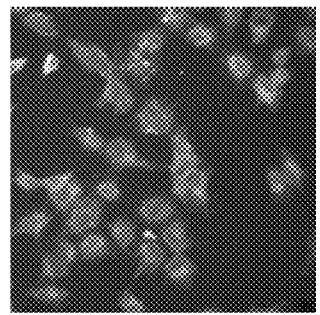
Figure 19C:
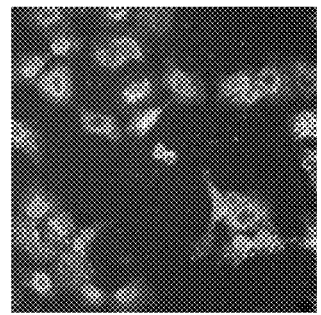

679 Compound 1-GAM, Company A Compound-GAM, and Company A Compound R-GAM were evaluated for immunofluorescence in a cell based assay using detection of PDI in cells with a mouse anti-PDI antibody. FIG. 19 shows results of 679 Compound 1-GAM at a 15× molar excess (FIG. 19A), Company A Compound-GAM at a 15× molar excess (FIG. 19B), and Company A Compound R-GAM at a 15× molar excess (FIG. 19C). As FIG. 19 shows, 679 Compound 1-GAM exhibited proper staining of PDI in the ER while Company A Compound-GAM and Company A Compound R-GAM exhibited non-specific staining with staining found throughout the cell. Similar results were obtained for 679 Compound 1-GAM at 7.5× and 22.5× molar excesses, as well as Company A Compound-GAM and Company A Compound R-GAM at 7.5× molar excess (data not shown).

Figure 20A:
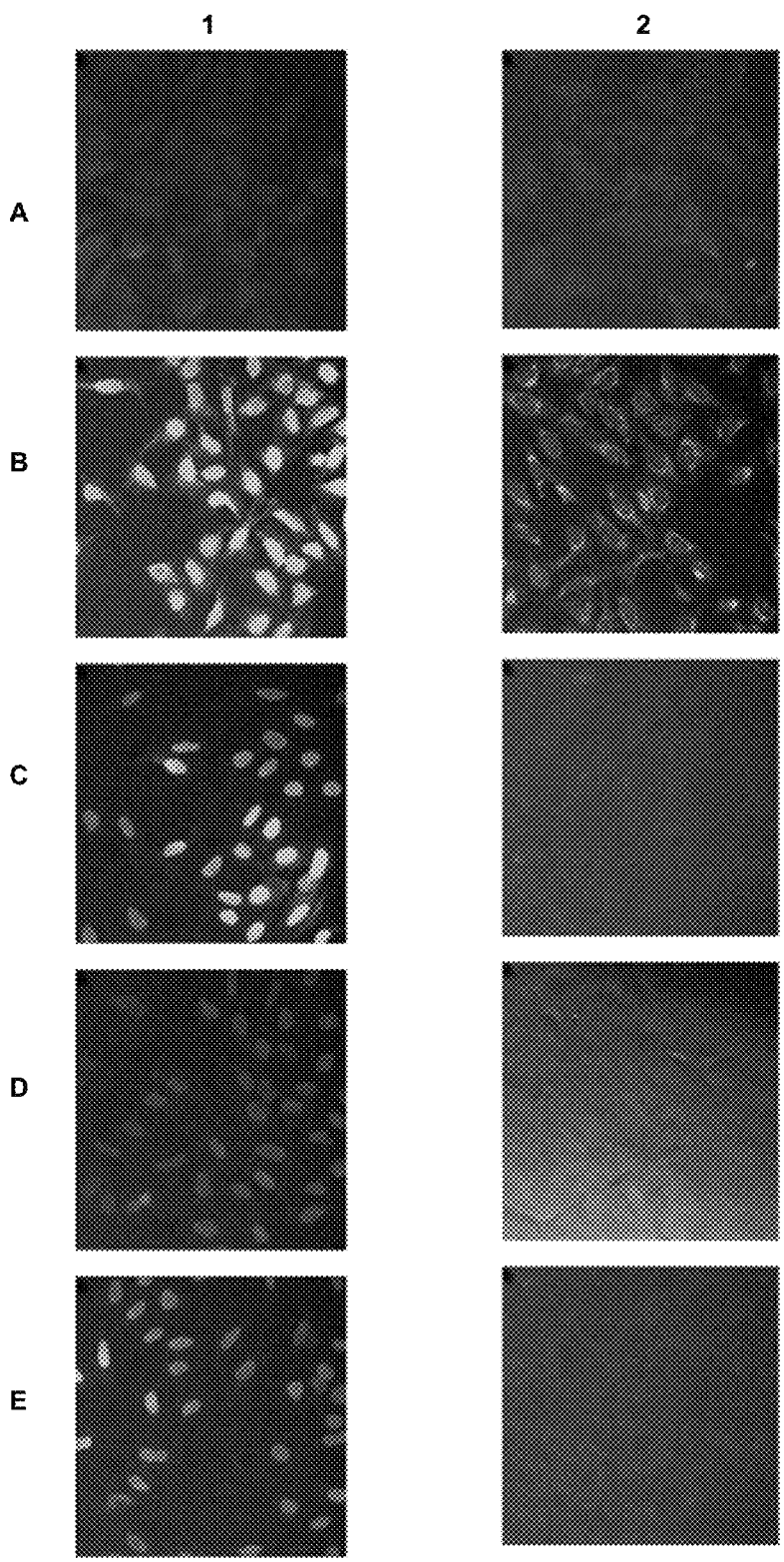
FIG. 20A, column 1 A-E and column 2 A-E show immunofluorescence data with commercial dyes and inventive compounds in one embodiment.
Figure 20B:
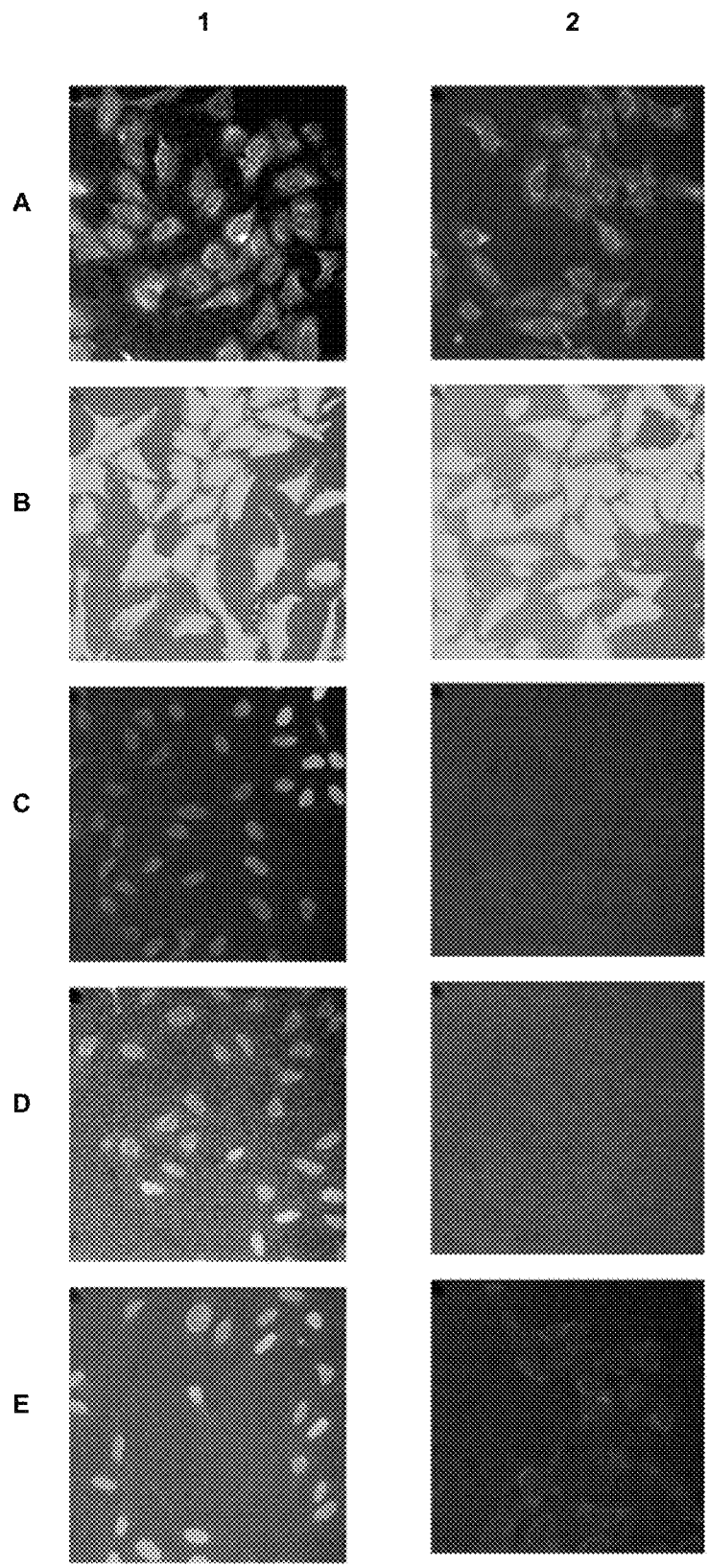
FIG. 20B, column 1 A-E and column 2 A-E show immunofluorescence data with commercial dyes and inventive compounds in one embodiment.
Figure 20C:
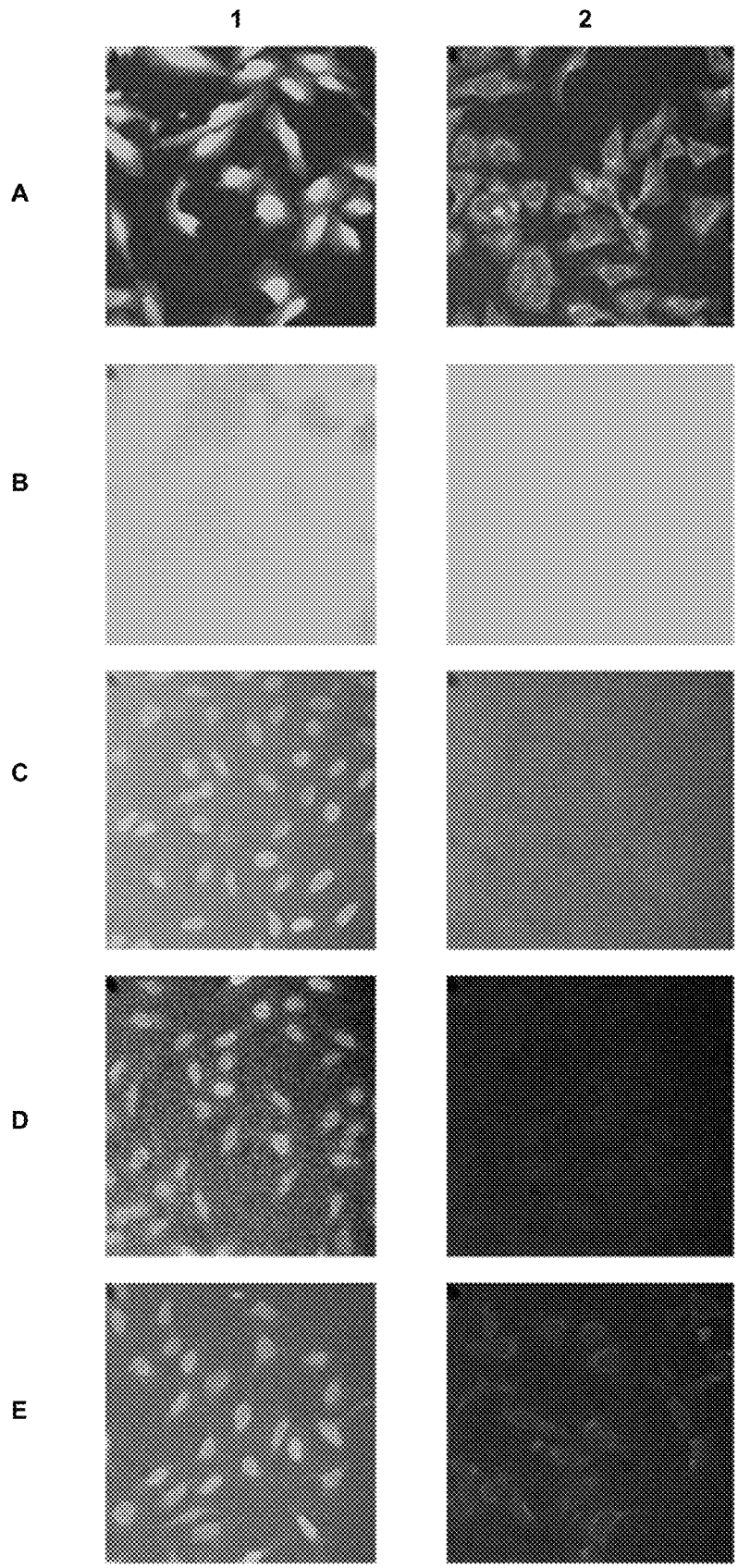
FIG. 20C, column 1 A-E and column 2 A-E show immunofluorescence data with commercial dyes and inventive compounds in one embodiment.

FIG. 20A-C shows detection of lamin A in U2OS cells (column 1) with V08-15173-GAM, V10-04152-GAM, 679

Compound 1/1-GAM, Company A Compound-GAM, and Company B Compound-GAM conjugates (4 μg/ml) at 5× molar excess (FIG. 20A), 10× molar excess (FIG. 20B), and 15× molar excess (FIG. 20C) with V08-15173-GAM (row A FIGS. 20A, 20B, 20C), V10-04152-GAM (row B FIGS. 20A, 20B, 20C), 679 Compound 1/1-GAM (row C FIGS. 20A, 20B, and 20C), Company A Compound-GAM (row D FIGS. 20A, 20B, 20C), Company B Compound-GAM (row E FIGS. 20A, 20B, 20C), and associated negative controls (column 2). There was very little non-specific binding observed with V08-15173-GAM and 679 Compound 1/1-GAM. Company A Compound-GAM and Company B Compound-GAM conjugates showed high non-specific binding starting from 5× molar excess. At low molar excess, Company A Compound-GAM exhibited staining of the nucleus, which was greater than the other dyes. V10-04152-GAM exhibited good specificity but was not very bright. Staining of the nucleus with Company B Compound-GAM was greatly improved at 15× molar excess, but there was an increase in non-specific binding.

The following table shows quantitative analysis of the FIGS. 20A-C data expressed as Mean Total Intensity, which is the average total intensity of all pixels within a defined area or defined primary object such as a nucleus, and S/B ratios.

| Average | V08-15173 | | V10-04152 | | 679 Compound 1/1 | | Company A Compound | | Company B Compound | |
|---|---|---|---|---|---|---|---|---|---|---|
| | | Negative control | | Negative control | | Negative control | | Negative control | | Negative control |
| 2.5 X | 17366 | 5966 | 11946 | 6085 | 29229 | 5628 | 54496 | 9107 | 7092 | 6329 |
| 5.0 X | 32820 | 6643 | 12788 | 7357 | 49279 | 5859 | 72289 | 20303 | 11922 | 8360 |
| 7.5 X | 42876 | 7100 | 12513 | 6503 | 28782 | | 152502 | 51104 | 18894 | 13351 |
| 10 X | 47756 | 9690 | 21147 | 6266 | 30098 | 6115 | 188505 | 136044 | 25020 | 18330 |
| 15 X | 49060 | 10779 | 15942 | 6746 | 48071 | 7277 | 679693 | 665370 | 67705 | 24350 |

| S/B | V08-15173 | V10-04152 | 679 Compound 1/1P1 | Company A Compound | Company B Compound |
|---|---|---|---|---|---|
| 2.5 X | 2.9 | 2.0 | 5.2 | 6.0 | 1.1 |
| 5.0 X | 4.9 | 1.7 | 8.4 | 3.6 | 1.4 |
| 7.5 X | 6.0 | 1.9 | 4.9 | 3.0 | 1.4 |
| 10 X | 4.9 | 3.4 | 4.9 | 1.4 | 1.4 |
| 15 X | 4.6 | 2.4 | 6.6 | 1.0 | 2.8 |

Lamin A, a nuclear protein, should show staining specific to the nucleus. Any lamin A staining outside the nucleus is non-specific staining. In addition, negative control conditions that lack a primary antibody are also used to determine the antibody staining specificity. Company A and Company B Compounds showed no non-specific binding. V08-15173 and 679 Compound 1/1 exhibited a minimal amount of non-specific binding. Due to the strong non-specific binding at higher molar excesses, Company A and Company B Compounds exhibited decreased signal to background (S/B) levels.

Quantitative analysis of a repeat experiment of FIG. 20A-C are shown below.

| Average | V08-15173 | | Company A Compound | | 679 Compound 1/1 | |
|---|---|---|---|---|---|---|
| | | Negative control | | Negative control | | Negative control |
| 2.5 X | 118440 | 12053 | 198471 | 24758 | 77195 | 8711 |
| 5 X | 183078 | 9441 | 351666 | 84270 | 140772 | 8674 |
| 10 X | 391473 | 13094 | 638569 | 330337 | 159948 | 20481 |
| 15 X | 211270 | 17260 | 560119 | 632936 | 199626 | 16277 |

| S/B | V08-15173 | Company A Compound | 679 Compound 1/1 |
|---|---|---|---|
| 2.5 X | 9.8 | 8.0 | 8.9 |
| 5 X | 19.4 | 4.2 | 16.2 |
| 10 X | 29.9 | 1.9 | 7.8 |
| 15 X | 12.2 | 0.9 | 12.3 |

Company A Compound showed much higher non-specific binding compared to V08-15173 and 679 Compound 1/1, with the non specific binding appearing at the 2.5× condition for Company A Compound-GAM.

679 Compound 1/1-NHS and V08-15173-NHS showed on average a 20% lower intensity compared to Company A Compound-NHS. V10-04152 intensity was about 50% lower than V08-15173, and about 65% lower than Company A Compound. GAM labeling efficiency was similar for all dyes at all molar excesses. At 5× molar excess, the GAR labeling efficiency for all dyes was similar, except for V10-04152. At 15× and 25× molar excesses, the GAR labeling efficiency similar for all compounds except Company B Compound. In immunofluorescence studies, Company A Compound, 679 Compound 1/1, and Company B Compound GAM conjugates showed high non-specific binding. V08-15173 and V10-04152 GAM conjugates showed little non-specific binding. Performance of conjugates in immunofluorescence appeared to be highly dependent on the performance of the primary antibody.

EXAMPLE 10

The inventive compounds are used for in vivo imaging to obtain information about biological tissues that are primarily accessible. The compounds are responsive to light in the near infrared region of the spectrum, a part of the spectrum that has minimal interference from the absorbance of biological materials. In one embodiment, the compounds are used for fluorescent imaging of targets within animals. For example, in vivo imaging information can be obtained using methods such as X-ray, magnetic resonance imaging, positron emission tomography, ultrasound imaging and probing, and other non-invasive methods used for diagnosing and treating disease. Light in the near infrared range (NIR), from about 650 nm to about 1000 nm wavelength, can permeate through several centimeters of tissue and thus can be used for in vivo imaging. Fluorescent dyes, such as the inventive compounds that are responsive to light in these longer wavelengths, can be used as conjugates with targeting molecules such as antibodies to bind and accumulate in, e.g., diseased tissue such as tumors, and may be used to distinguish healthy from diseased tissue. In some methods, the inventive compound may be attached to a biomolecule, such as a protein, peptide, or a drug, which is localized or retained in the desired tissue environment. Fluorescent in vivo imaging using NIR dyes such as the inventive compounds are diagnostic agents to discretely target disease tissue directly within animals or humans.

For in-vivo imaging, the compound, an isomer of the compound, or a conjugate of the compound or isomer with a targeting agent, is administered to a tissue (e.g., intravenously), permitted to accumulate with excess compound removed by the circulatory system, then the tissue is irradiated with light at an appropriate wavelength. The NIR fluorescent light is recorded and/or an image is generated from the data obtained to specifically detect and visualize the targeted cells or tissues. The dose of compound administered can differ and would be known by one skilled in the art depending upon the specific tissue, application, etc., as long as the method achieves a detectable concentration of the compound in the tissue to be assessed.

EXAMPLE 11

In Vivo Imaging Using an Inventive Compound Conjugated to Anti-HER2 Antibody

779 Compound 1-NHS is conjugated to a rabbit anti-HER2 antibody (Genscript USA, Piscataway N.J.) by reconstituting the compound in dimethylformamide (DMF) at 10 mg/ml, then incubating at 10× molar excess with rabbit anti-HER2 antibody (0.1 mg) for one hour at room temperature to result in 779 Compound 1-anti-HER2 conjugate. The conjugation reaction is then subjected to PDDR to remove unlabeled (free) 779 Compound 1. Ten microgram of conjugate is injected intravenously to athymic mice bearing BT474 tumors. The animals are imaged overtime at 1, 24, 48, 72, 96, and 120 hours post-injection using Pearl Imager, LI-COR Biosciences (LI-COR Instruments, Lincoln Nebr.).

Upon whole body imaging, fluorescence intensity is observed to be distributed over the whole animal during the first hour imagining and diminishes significantly at 72 hours. After 96 hours, the signal is localized and specific to the tumor.

679 Compound 4/4-NHS is conjugated to a rabbit anti-HER2 antibody (Genscript USA, Piscataway N.J.) by reconstituting the compound in dimethylformamide (DMF) at 10 mg/ml, then incubating at 10× molar excess with rabbit anti-HER2 antibody (0.1 mg) for one hour at room temperature to result in 679 Compound 4/4-anti-HER2 conjugate. The conjugation reaction is then subjected to PDDR to remove unlabeled (free) 679 Compound 4/4. Ten microgram of conjugate is injected intravenously to athymic mice bearing BT474 tumors. The animals are imaged over time at 1, 24, 48, 72, 96, and 120 hours post-injection using Pearl Imager, LI-COR Biosciences (LI-COR Instruments, Lincoln Nebr.).

Upon whole body imaging, fluorescence intensity is observed to be distributed over the whole animal during the first hour imagining and diminishes significantly at 72 hours. After 96 hours, the signal is localized and specific to the tumor.

EXAMPLE 12

In Vivo Imaging Using Either Monosulfonated or Disulfonated Inventive Compound

The compound may be rendered less hydrophilic, i.e., more hydrophobic, by altering the number of sulfonate groups. The fewer sulfonates, the more hydrophobic the compound becomes. In this embodiment, the compound may be more readily retained in a desired tissue or location if the appropriate number of sulfonates is determined; e.g., compound penetration into cells is more efficient if fewer sulfonates are present on the molecule. The compound may contain one, two, three, or four sulfonate groups. Hydrophobic compounds are also known to more efficiently cross the cell membrane, and thus are more desirable when the target of interest is located within the cell.

Alendronate, a compound that binds to, and is retained in, LNCap prostate cancer cells, is conjugated with disulfonated or monosulfonated benzo 779 Compound 1 by incubating a solution containing 1 mM disulfonated or monosulfonated 779 Compound 1-NHS in 1 ml of PBS and 0.5 ml tetrahydrofuran (THF) with 0.1 mM alendronate and 0.2 mM diisopropylethylamine at room temperature overnight. The conjugate is purified using reverse phase HPLC with 0-50% methanol against a 0.1 M ammonium acetate buffer, and is then lyophilized.

LNCap cells are grown orthotopically in nude mice. 779 Compound 1-alendronate (5 nmole) is injected into the tumor. Control mice are injected with free 779 Compound 1 containing a carboxylic acid residue instead of the reactive NHS ester. X-ray and near infra-red fluorescence images are captured.

Upon imaging the whole mouse, 779 Compound 1-alendroneate conjugate is retained in mouse tissue greater than the unconjugated compound; the conjugate is retained in the LNCap cell-induced tumor for at least 18 hrs.

Alendronate, a compound that binds to, and is retained in, LNCap prostate cancer cells, is conjugated with disulfonated or monosulfonated 679 Compound 4/4 by incubating a solution containing 1 mM disulfonated or monosulfonated 679 Compound 4/4-NHS in 1 ml of PBS and 0.5 ml tetrahydrofuran (THF) with 0.1 mM alendronate and 0.2 mM diisopropylethylamine at room temperature overnight. The conjugate is purified using reverse phase HPLC with 0-50% methanol against a 0.1 M ammonium acetate buffer, and is then lyophilized.

LNCap cells are grown orthotopically in nude mice. 679 Compound 4/4-alendronate (5 nmole) is injected into the tumor. Control mice are injected with free 679 Compound 4/4 containing a carboxylic acid residue instead of the reactive NHS ester. X-ray and near infra-red fluorescence images are captured.

Upon imaging the whole mouse, 679 Compound 4/4-alendroneate conjugate is retained in mouse tissue greater than the unconjugated compound; the conjugate is retained in the LNCap cell-induced tumor for at least 18 hrs.

EXAMPLE 13

In Vivo Imaging Using Either Monosulfonated or Disulfonated Inventive Compound

A drug delivery nanoparticle system conjugated with disulfonated or monosulfonated 779 Compound 1 is prepared as follows. A solution containing 1 mM disulfonated or monosulfonated 779 Compound 1-NHS in 1 ml of PBS is incubated overnight at room temperature with 0.1 mM of an anti-cancer drug conjugated with transferrin in the form of a nanoparticle. The resulting 779 Compound 1-nanoparticle conjugate is purified by centrifugation and then lyophilized.

The 779 Compound 1 (isomer 1)-nanoparticle conjugate (1 nmole) is injected intravenously into a mouse tail vein. Control mice are injected with free 779 Compound 1 dye. X-ray and near infra-red fluorescence images of mouse brain are captured.

779 Compound 1-nanoparticle conjugate localizes in the mouse brain for greater than about 24 hours after injection. Tumor size progressively decreases after injection of 779 Compound 1-nanoparticle conjugate, compared to 779 Compound 1-nanoparticle without the anti-cancer drug.

A drug delivery nanoparticle system conjugated with disulfonated or monosulfonated 679 Compound 4/4 is prepared as follows. A solution containing 1 mM disulfonated or monosulfonated 679 Compound 4/4-NHS in 1 ml of PBS is incubated overnight at room temperature with 0.1 mM of an anti-cancer drug conjugated with transferrin in the form of a nanoparticle. The resulting 679 Compound 4/4-nanoparticle conjugate is purified by centrifugation and then lyophilized.

The 679 Compound 4/4 (isomer 1)-nanoparticle conjugate (1 nmole) is injected intravenously into a mouse tail vein. Control mice are injected with free 679 Compound 4/4 dye. X-ray and near infra-red fluorescence images of mouse brain are captured.

679 Compound 4/4-nanoparticle conjugate localizes in the mouse brain for greater than about 24 hours after injection. Tumor size progressively decreases after injection of 679 Compound 4/4-nanoparticle conjugate, compared to 679 Compound 4/4-nanoparticle without the anti-cancer drug.

EXAMPLE 14

The mono-sulfonated derivative is on any one of eight possible positions on the 579, 679, or 779 compound, accounting for the stereochemistry around the carbon positions on the rings as well as the non-symmetrical nature of the two ends of each dye. Similarly, the di- and tri-substituted sulfonates can be on multiple possible positions on the inventive compounds.

EXAMPLE 15

The inventive compounds are used for in vivo imaging as described in J. Gastrointest Surg (2008) 12:1938-1950. Briefly, human pancreatic cell lines are maintained in media supplemented with penicillin/streptomycin at 37° C. with 5% $CO_2$. Mouse anti-CEA antibody and Control Mouse IgG (in PBS with 0.20% sodium azide) are conjugated to V08-15173. The dye is reconstituted at 10 mg/ml in DMF and then added to the antibody at a 10 molar excess. The reaction is carried out for one hour at room temperature. The samples are then dialyzed against 3×2 L of PBS. The cell lines are plated in 96-well plates at $5 \times 10^4$ cells per well. After 48 hours culture in appropriate media, the cells are incubated with 1 µg of V08-15173 labeled anti-CEA antibody or V08-15173-labeled control mouse IgG for four hours at 37° C. The cells are then washed three times with PBS and then imaged with an inverted Nikon De-485 microscope and Spot camera RD.

Surgical procedures and intravital imaging are performed with the animals anesthesized by intramuscular injection of 0.02 ml of 50% ketamine, 38% xylazine and 12 acepromazine maleate. Human pancreatic and colorectal cancer cell lines are harvested by trypsinization and washed twice with serum free medium and washed twice with serum-free medium. Cells ($1 \times 10^6$ in 100 µl of serum-free media) are injected subcutaneously within 30 minutes of harvesting over the right flank in female nu/nu mice between 4-6 weeks of age. Subcutaneous tumors are allowed to grow for 7-14 days until they reached diameter of 1-2 mm prior to the delivery of conjugated antibody. For ASPC-1 implants, the cells are harvested by trypsinization and washed 3× in serum-free media. The cells are resuspended in serum-free media. The cells are resuspended in serum-free media at $5 \times 10^6$/ml. A volume of 200 µl of the cell suspension is then injected directly into the peritoneal cavity within 30 minutes of harvesting.

For antibody delivery, one to two weeks after subcutaneous, orthotopic, or intraperitoneal tumor implantation, animals are given intravenous (i.v.) injection of either conjugated anti-CEA or conjugated control IgG antibody diluted in PBS to a final volume of 100 µl. All i.v. injections are done via the tail vein. For the dose-response experiment, the antibody dose is 75 µg. For the in vivo time course, the animals are anesthesized and imaged at 30 min, 1, 2, 6, 24 hours and 8 and 15 days after systemic antibody delivery.

Predicted in vivo and ex vivo analysis results are that post-experiment surgical exposure reveals accumulation of dye in the liver, bladder, and a region of inflammation in the subcutaneous tissue. Ex vivo analysis of the vital organs confirms the presence of dye predominantly in the liver with some signal detected in the spleen intestines and lungs.

EXAMPLE 16

The inventive compounds are used for in vivo imaging as described in J. Gastrointest Surg (2008) 12:1938-1950. Briefly, human pancreatic cell lines are maintained in media supplemented with penicillin/streptomycin at 37° C. with 5% $CO_2$. Mouse anti-CEA antibody and Control Mouse IgG (in PBS with 0.20% sodium azide) are conjugated to 779 Compound 1. The dye is reconstituted at 10 mg/ml in DMF and then added to the antibody at a 10 molar excess. The reaction is carried out for one hour at room temperature. The samples are then dialyzed against 3×2 L of PBS. The cell lines are plated in 96-well plates at $5 \times 10^4$ cells per well. After 48 hours culture in appropriate media, the cells are incubated with 1 µg of V08-15173 labeled anti-CEA antibody or V08-15173-labeled control mouse IgG for four hours at 37° C. The cells are then washed three times with PBS and then imaged with an inverted Nikon De-485 microscope and Spot camera RD.

Surgical procedures and intravital imaging are performed with the animals anesthesized by intramuscular injection of 0.02 ml of 50% ketamine, 38% xylazine and 12 acepromazine maleate. Human pancreatic and colorectal cancer cell lines are harvested by trypsinization and washed twice with serum free medium and washed twice with serum-free medium. Cells ($1 \times 10^6$ in 100 µl of serum-free media) are injected subcutaneously within 30 minutes of harvesting over the right flank in female nu/nu mice between 4-6 weeks of age. Subcutaneous tumors are allowed to grow for 7-14 days until they reached diameter of 1-2 mm prior to the delivery of conjugated antibody. For ASPC-1 implants, the cells are harvested by trypsinization and washed 3× in serum-free media. The cells are resuspended in serum-free media. The cells are resuspended in serum-free media at 5×10⁶/ml. A volume of 200 µl of the cell suspension is then injected directly into the peritoneal cavity within 30 minutes of harvesting.

For antibody delivery, one to two weeks after subcutaneous, orthotopic or intraperitoneal tumor implantation, animals are given intravenous (i.v.) injection of either conjugated anti-CEA or conjugated control IgG antibody diluted in PBS to a final volume of 100 µl. All i.v. injections are done by tail vein. For the dose-response experiment, the antibody dose is 75 µg. For the in vivo time course, the animals are anesthesized and imaged at 30 min, 1, 2, 6, 24 hours and 8 and 15 days after systemic antibody delivery.

Predicted in vivo and ex vivo analysis results are that post-experiment surgical exposure reveals accumulation of dye in the liver, bladder, and a region of inflammation in the subcutaneous tissue. Ex vivo analysis of the vital organs confirms the presence of dye predominantly in the liver with some signal detected in the spleen intestines and lungs.

The embodiments shown and described in the specification are only specific embodiments of inventors who are skilled in the art and are not limiting in any way. Therefore, various changes, modifications, or alterations to those embodiments may be made without departing from the spirit of the invention or the scope of the following claims. The references cited are expressly incorporated by reference herein in their entirety.

What is claimed is:
1. A method of detecting at least one biomolecule, the method comprising combining at least one biomolecule with a composition comprising at least one excipient and a compound in an effective concentration to detect at least one biomolecule under conditions sufficient for binding the compound to the biomolecule, and detecting the biomolecule-bound compound, where the compound is selected from the group consisting of

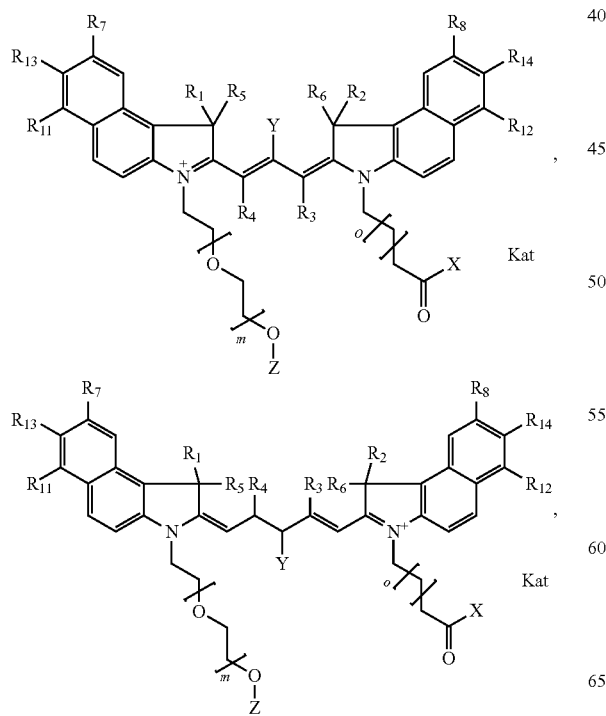

-continued
and

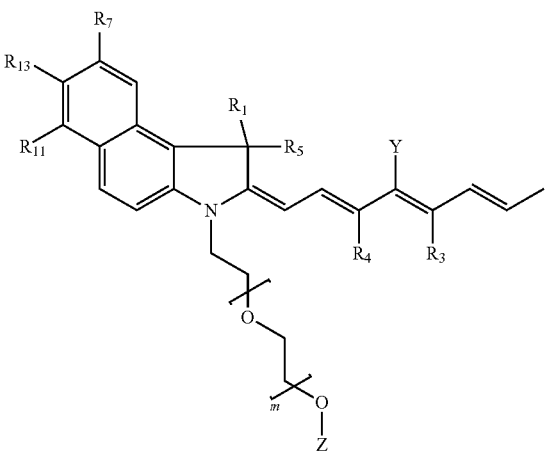

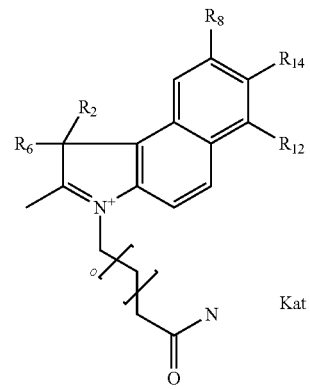

where
each of $R_1$, $R_2$, $R_5$, and $R_6$ is the same or different and is independently selected from the group consisting of an aliphatic, heteroaliphatic, sulfoalkyl, heteroaliphatic with terminal $SO_3$—, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -L-$SO_2$NH—P—Z, and a carboxamide group -LCONH—P—Z, where Z is selected from H, $CH_3$, a $CH_3$ group, an alkyl group, or a heteroalkyl group;
each of $R_7$, $R_8$, $R_{11}$, $R_{12}$, $R_{13}$, and $R_{14}$ is the same or different and is independently selected from the group consisting of H, $SO_3$—, a PEG group P—Z where P is selected from an ethylene glycol group, a diethylene glycol group, and a polyethylene glycol group, where the polyethylene glycol group is $(CH_2CH_2O)s$, where s is an integer from 3-6 inclusive, a sulfonamide-containing group -L-$SO_2$NH—P—Z, and a carboxamide-containing group —CONH—PZ, where Z is selected from H, $CH_3$, a $CH_3$ group, an alkyl group, or a heteroalkyl group;
X is selected from —OH, —SH, —$NH_2$, —NH—$NH_2$, —F, —Cl, —Br, —I, —NHS (hydroxysuccinimidyl-/ sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, NR-L-CO-TFP, —NR-L-CO-benzotriazole, —NR-L-CHO, —NR-L-maleimide, —NR-L-NH—CO—CH$_2$—I, or —NR-LNH—CO—CH$_2$—Br wherein R is —H or an aliphatic or heteroaliphatic group;

L is selected from a divalent linear (—(CH$_2$)$_t$—, t=0 to 15), crossed, or cyclic alkyl group optionally substituted by at least one oxygen atom and/or sulfur atom;

Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive;

each of R$_3$ and R$_4$ is the same or different and is independently hydrogen, an aliphatic group, a heteroaliphatic group, or a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, and Z is selected from H, CH$_3$, a CH$_3$ group, an alkyl group, or a heteroalkyl group; or R$_3$ and R$_4$ together form a cyclic structure where R$_3$ and R$_4$ are joined using a divalent structural element selected from the group consisting of —(CH$_2$)$_q$—, —(CH$_2$)$_q$O(CH$_2$)$_{q'}$—, —(CH$_2$)$_q$S(CH$_2$)$_{q'}$—, —(CH$_2$)$_g$CH=CH—, —OCH=CH— where each of q and q' is the same or different and is a integer from 2 to 6 inclusive; and Y is selected from the group consisting of hydrogen, alkyl, sulfoalkyl, fluorine, chlorine, bromine, a substituted or unsubstituted aryl, phenylmercapto function, and a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, and Z is selected from H, CH$_3$, a CH$_3$ group, an alkyl group, or a heteroalkyl group.

2. The method of claim 1 wherein the biomolecule is selected from a protein, antibody, enzyme, nucleoside triphosphate, oligonucleotide, biotin, hapten, cofactor, lectin, antibody binding protein, carotenoid, carbohydrate, hormone, neurotransmitter, growth factors, toxin, biological cell, lipid, receptor binding drug, fluorescent proteins, organic polymer carrier material, inorganic polymeric carrier material, and combinations thereof.

3. The method of claim 1 wherein the at least one biomolecule is detected in an assay selected from fluorescence microscopy, flow cytometry, immunoassay, hybridization, chromatographic assay, electrophoretic assay, microwell plate based assay, fluorescence resonance energy transfer (FRET) system, high throughput screening, or microarray.

4. The method of claim 1 wherein the biomolecule is detected by in vivo imaging comprising providing the biomolecule-bound compound to at least one of a biological sample, tissue, or organism, and detecting the biomolecule within the at least one of a biological sample, tissue, or organism.

5. A method of labeling at least one biomolecule, the method comprising combining at least one biomolecule with a composition comprising at least one excipient and a compound in an effective concentration to label the at least one biomolecule under conditions sufficient for labeling the biomolecule with the compound, where the compound is selected from the group consisting of

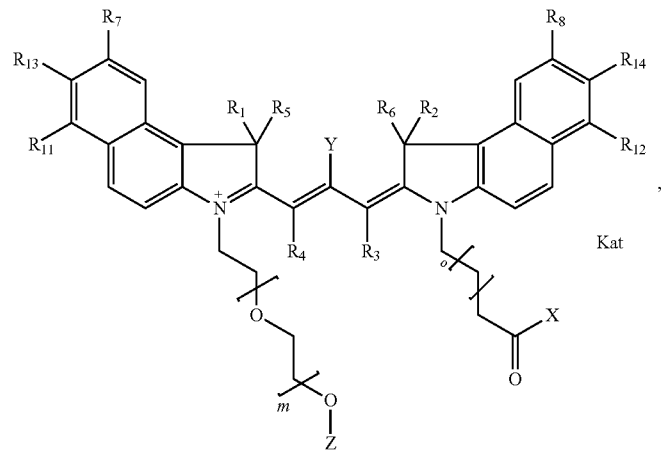

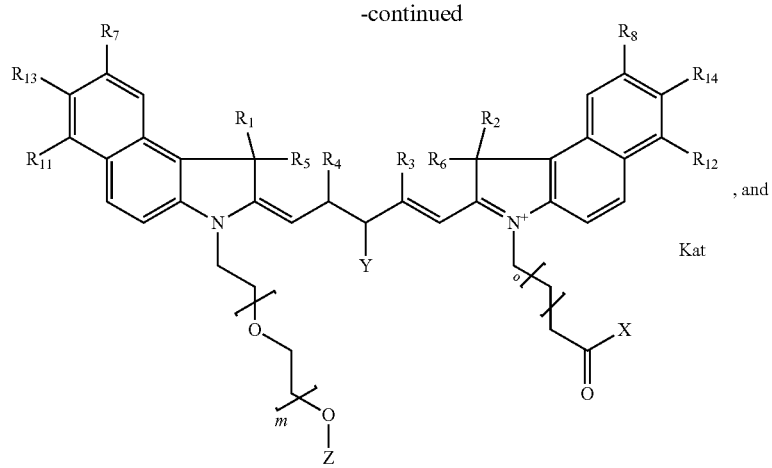

, and

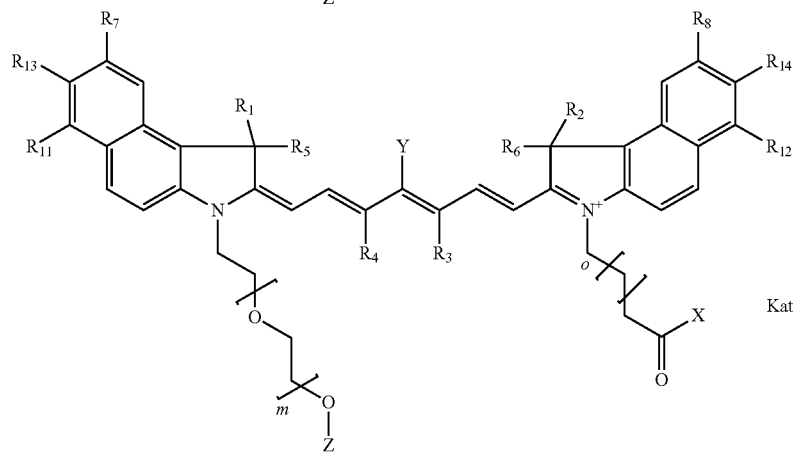

X is selected from —OH, —SH, —NH$_2$, —NH—NH$_2$, —F, —Cl, —Br, —I, -NETS (hydroxysuccinimidyl-/sulfosuccinimidyl), —O-TFP (2,3,5,6-tetrafluorophenoxy), —O-STP (4-sulfo-2,3,5,6-tetrafluorophenoxy), —O-benzotriazole, -benzotriazole, imidazole, azide, —O-carbodiimide, —NR-L-OH, —NR-L-O-phosphoramidite, —NR-L-SH, —NR-L-NH$_2$, —NR-L-NH—NH$_2$, —NR-L-CO$_2$H, —NR-L-CO—NHS, —NR-L-CO-STP, NR-L-CO-TFP, —NR-L-CO-benzotriazole, —NR-L-CHO, —NR-L-maleimide, —NR-L-NH—CO—CH$_2$—I, or —NR-LNH—CO—CH$_2$—Br wherein R is —H or an aliphatic or heteroaliphatic group;

L is selected from a divalent linear (—(CH$_2$)$_t$—, t=0 to 15), crossed, or cyclic alkyl group optionally substituted by at least one oxygen atom and/or sulfur atom;

Kat is a number of Na$^+$, K$^+$, Ca$^{2+}$, ammonia, or other cation(s) needed to compensate the negative charge brought by the cyanine; m is an integer from 0 to 5 inclusive; o is an integer from 0 to 12 inclusive;

each of R$_3$ and R$_4$ is the same or different and is independently hydrogen, an aliphatic group, a heteroaliphatic group, or a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, and Z is selected from H, CH$_3$, a CH$_3$ group, an alkyl group, or a heteroalkyl group; or R$_3$ and R$_4$ together form a cyclic structure where R$_3$ and R$_4$ are joined using a divalent structural element selected from the group consisting of —(CH$_2$)$_q$—, —(CH$_2$)$_q$O(CH$_2$)$_q'$—, —(CH$_2$)$_q$S(CH$_2$)$_q'$—, —(CH$_2$)$_g$CH=CH—, —OCH=CH— where each of q and q' is the same or different and is an integer from 2 to 6 inclusive; and Y is selected from the group consisting of hydrogen, alkyl, sulfoalkyl, fluorine, chlorine, bromine, a substituted or unsubstituted aryl, phenylmercapto function, and a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, and Z is selected from H, CH$_3$, a CH$_3$ group, an alkyl group, or a heteroalkyl group.

6. The method of claim 5 wherein the biomolecule is selected from the group consisting of a protein, antibody, enzyme, nucleoside triphosphate, oligonucleotide, biotin, hapten, cofactor, lectin, antibody binding protein, carotenoid, where each of R$_1$, R$_2$, R$_5$, and R$_6$ is the same or different and is independently selected from the group consisting of an aliphatic, heteroaliphatic, sulfoalkyl, heteroaliphatic with terminal SO$_3$—, a PEG group P—Z where P is selected from an ethylene glycol group, a diethylene glycol group, and a polyethylene glycol group, where the polyethylene glycol group is (CH$_2$CH$_2$O)$_s$, where s is an integer from 3-6 inclusive, a sulfonamide group -L-SO$_2$NH—P—Z, and a carboxamide group -LCONH—P—Z, where Z is selected from H, $CH_3$, a $CH_3$ group, an alkyl group, or a heteroalkyl group;

each of $R_7$, $R_8$, $R_{11}$, $R_{12}$, $R_{13}$, and $R_{14}$ is the same or different and is independently selected from the group consisting of H, $SO_3$—, a PEG group P—Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide-containing group -L-$SO_2$NH—P—Z, and a carboxamide-containing group —CONH—PZ, where Z is selected from H, $CH_3$, a $CH_3$ group, an alkyl group, or a heteroalkyl group;

carbohydrate, hormone, neurotransmitter, growth factors, toxin, biological cell, lipid, receptor binding drug, fluorescent proteins, organic polymer carrier material, inorganic polymeric carrier material, and combinations thereof.

\* \* \* \* \*

UNITED STATES PATENT AND TRADEMARK OFFICE
CERTIFICATE OF CORRECTION

| | | |
|---|---|---|
| PATENT NO. | : 10,730,857 B2 | Page 1 of 2 |
| APPLICATION NO. | : 16/141534 | |
| DATED | : August 4, 2020 | |
| INVENTOR(S) | : Greg Hermanson et al. | |

It is certified that error appears in the above-identified patent and that said Letters Patent is hereby corrected as shown below:

In the Claims

In Claim 1, Column 214, the compound should read:

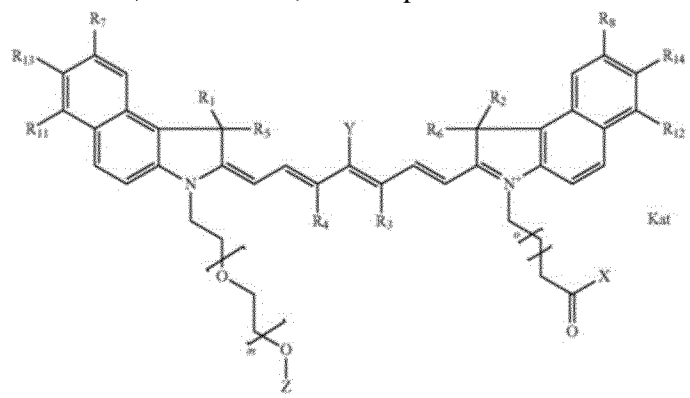

In Claim 1, Column 215, Lines 34-35 should read:
-$(CH_2)_q$-, -$(CH_2)_qO(CH_2)_{q'}$-, -$(CH_2)_qS(CH_2)_{q'}$-, -$(CH_2)_qCH=CH$-, -$OCH=CH$-

In Claim 5, Column 217, please insert the following after the last compound:
--where
    each of $R_1$, $R_2$, $R_5$, and $R_6$ is the same or different and is independently selected from the group consisting of an aliphatic, heteroaliphatic, sulfoalkyl, heteroaliphatic with terminal $SO_3$-, a PEG group P-Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide group -L-$SO_2$NH-P-Z, and a carboxamide group -LCONH-P-Z, where Z is selected from H, $CH_3$, a $CH_3$ group, an alkyl group, or a heteroalkyl group;
    each of $R_7$, $R_8$, $R_{11}$, $R_{12}$, $R_{13}$, and $R_{14}$ is the same or different and is independently selected from the group consisting of H, $SO_3$-, a PEG group P-Z where P is selected from an ethylene glycol group, a diethylene glycol group, and a polyethylene glycol group, where the polyethylene glycol group is $(CH_2CH_2O)_s$, where s is an integer from 3-6 inclusive, a sulfonamide-containing group Signed and Sealed this
Sixth Day of October, 2020

Andrei Iancu
*Director of the United States Patent and Trademark Office*

CERTIFICATE OF CORRECTION (continued)
U.S. Pat. No. 10,730,857 B2

-L-SO$_2$NH-P-Z, and a carboxamide-containing group -CONH-PZ, where Z is selected from H, CH$_3$, a CH$_3$ group, an alkyl group, or a heteroalkyl group;--

In Claim 5, Column 217, Line 39 should read:
-F, -Cl, -Br, -I, -NHS (hydroxysuccinimidyl-/

In Claim 5, Column 218, Lines 39-40 should read:
-(CH$_2$)$_q$-, -(CH$_2$)$_q$O(CH$_2$)$_{q'}$-, -(CH$_2$)$_q$S(CH$_2$)$_{q'}$-, -(CH$_2$)$_q$CH=CH-, -OCH=CH- In Claim 6, Column 218, Line 53-Column 219, Line 17, (approx.) should read in its entirety:
The method of claim 5 wherein the biomolecule is selected from the group consisting of a protein, antibody, enzyme, nucleoside triphosphate, oligonucleotide, biotin, hapten, cofactor, lectin, antibody binding protein, carotenoid, carbohydrate, hormone, neurotransmitter, growth factors, toxin, biological cell, lipid, receptor binding drug, fluorescent proteins, organic polymer carrier material, inorganic polymeric carrier material, and combinations thereof.